United States Patent
Shibuya et al.

(10) Patent No.: US 7,414,066 B2
(45) Date of Patent: Aug. 19, 2008

(54) AMIDE COMPOUNDS AND MEDICATIONS CONTAINING THE SAME TECHNICAL FIELD

(75) Inventors: Kimiyuki Shibuya, Tokorozawa (JP); Toru Miura, Omiya (JP); Katsumi Kawamine, Higashimurayama (JP); Yukihiro Sato, Higashimurayama (JP); Tadaaki Ohgiya, Tokorozawa (JP); Takahiro Kitamura, Higashimurayama (JP); Chiyoka Ozaki, Tokyo (JP); Toshiyuki Edano, Kawagoe (JP); Mitsuteru Hirata, Tsurugashima (JP)

(73) Assignee: Kowa Company Ltd., Aichi (JP)

( * ) Notice: Subject to any disclaimer, the term of this patent is extended or adjusted under 35 U.S.C. 154(b) by 0 days.

(21) Appl. No.: 10/985,915

(22) Filed: Nov. 9, 2004

(65) Prior Publication Data

US 2005/0131001 A1    Jun. 16, 2005

Related U.S. Application Data

(60) Division of application No. 09/666,152, filed on Sep. 20, 2000, now Pat. No. 6,849,647, which is a continuation of application No. 09/358,083, filed on Jul. 21, 1999, now abandoned.

(51) Int. Cl.
*A61K 31/4439* (2006.01)
*C07D 401/12* (2006.01)

(52) U.S. Cl. .................. 514/341; 546/273.1; 546/273.7
(58) Field of Classification Search .............. 546/273.7, 546/273.1; 514/341
See application file for complete search history.

(56) References Cited

U.S. PATENT DOCUMENTS

| 5,290,801 A | 3/1994 | Higley et al. |
| 5,358,946 A | 10/1994 | Wilde |

FOREIGN PATENT DOCUMENTS

| EP | 0 807 627 A2 | 11/1997 |
| JP | 4-139172 | 5/1992 |

OTHER PUBLICATIONS

Abdel et al., "Synthesis and Biological Activities of Some New 2-(N-Heterocyclo Caboxamidomethyl Thio) Naphth[1,2-d]Oxazoles. Part VI," J. Indian Chem. Soc. LVIII:171-173 (1981).
Bellemin et al., "New Indole Derivatives as ACAT Inhibitors: Synthesis and Structure-Activity Relationships," Eur. J. Med. Chem. 31:123-132 (1996).
Brandstrom et al., "Structure activity relationships of substituted benzimidazoles," Scand. J. Gastroenterol., 20(Suppl.108)15-22 (1985).
Lindberg et al., "The Mechanisms of Action of the Gastric Acid Secretion Inhibitor Omeprazole," Journal of Medicinal Chemistry 29(8):1327-1329 (1986).
Mahmoud et al., "Synthesis and biological activities of some new 2-(N-heterocyclic carboxamidomethyl thio) benzoxazoles, benzthiazoles and benzimidazoles. Part VIII," Eur. J. Med. Chem. 16(4):383-384 (1981).
Mahmoud et al., "Synthesis of Some New Aryl-and Aralkyl-Mercaptobenzoxazoles,-Benzimidazoles and -Benzothioazoles of Potential Biological Interest," Gazetta Chimica Italiana 112:55-56 (1982).
Matsuda et al., "ACAT Inhibitors as Antiatherosclerotic Agents: Compounds and Mechanisms," Medicinal Research Reviews 14(3):271-305 (1994).
Wilde et al., "ACYL CoA:Cholesterol Acyltransferase (ACAT) Inhibitors: Ureas Bearing Heterocyclic Groups Bioisosteric for an Imidazole," Biorganic & Medicinal Chemistry Letters 5(2):167-172 (1995).
Wilde et al., "ACYL CoA:Cholesterol Acyltransferase (ACAT) Inhibitors: Ureas Bearing Two Heterocyclic Head Groups," Biorganic & Medicinal Chemistry Letters 5(2):173-176 (1995).

*Primary Examiner*—Patricia L Morris
(74) *Attorney, Agent, or Firm*—Edwards Angell Palmer & Dodge LLP; Peter F. Corless; Christine C. O'Day

(57) ABSTRACT

The present invention provides to a novel compound having an ACAT inhibiting activity.

The present invention relates to compounds represented by formula (I)

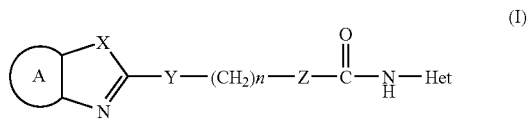

wherein
represents an optionally substituted divalent residue such as benzene, pyridine, cyclohexane or naphthalene, or a group,
Het represents a 5- to 8-membered, substituted or unsubstituted heterocyclic group containing at least one heteroatom selected from the group consisting of a nitrogen atom, an oxygen atom and a sulfur atom, such as a monocyclic group, a polycyclic group or a group of a fused ring,
X represents —NH—, an oxygen atom or a sulfur atom,
Y represents —NR$_4$—, an oxygen atom, a sulfur atom, a sulfoxide or a sulfone,
Z represents a single bond or —NR$_5$—,
R$_4$ represents a hydrogen atom, a lower alkyl group, an aryl group or an optionally substituted silyl lower alkyl group,
R$_5$ represents a hydrogen atom, a lower alkyl group, an aryl group or an optionally substituted silyl lower alkyl group, and
n is an integer of from 1 to 15, or salts or solvates thereof, and a pharmaceutical composition containing at least one of these compounds.

6 Claims, No Drawings

AMIDE COMPOUNDS AND MEDICATIONS CONTAINING THE SAME TECHNICAL FIELD

CROSS-REFERENCE TO RELATED APPLICATION(S)

This application is a divisional application of U.S. Ser. No. 09/666,152, filed on Sep. 20, 2000 (now U.S. Pat. No. 6,849,647), which application was a continuation application of U.S. Ser. No. 09/358,083 filed Jul. 21, 1999 (abandoned), each of which is incorporated by reference.

TECHNICAL FIELD

The present invention relates to novel amide compounds and medications containing the same. More specifically, the present invention relates to compounds represented by the the formula (I)

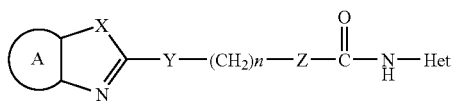

wherein

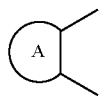

represents an optionally substituted divalent residue such as benzene, pyridine, cyclohexane or naphthalene, or a group,

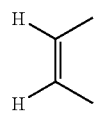

Het represents a 5- to 8-membered, substituted or unsubstituted heterocyclic group containing at least one heteroatom selected from the group consisting of a nitrogen atom, an oxygen atom and a sulfur atom, such as a monocyclic group, a polycyclic group or a group of a fused ring, X represents —NH—, an oxygen atom or a sulfur atom, Y represents —$NR_4$—, an oxygen atom, a sulfur atom, a sulfoxide or a sulfone, Z represents a single bond or —$NR_5$—, $R_4$ represents a hydrogen atom, a lower alkyl group, an aryl group or an optionally substituted silyl lower alkyl group, $R_5$ represents a hydrogen atom, a lower alkyl group, an aryl group or an optionally substituted silyl lower alkyl group, and n is an integer of from 1 to 15, or salts or solvates thereof, and a pharmaceutical composition containing these compounds.

Specifically, the prent invention relates to compounds represented by the the formula (IA)

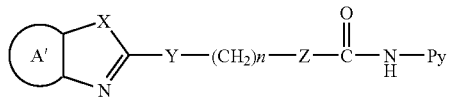

wherein

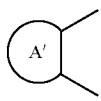

represents an optionally substituted divalent residue such as benzen or pyridine, Py represents an optionally substituted pyridyl or pyrimidyl group, Y represents —$NR_4$—, an oxygen atom, a sulfur atom, a sulfoxide or a sulfone, Z represents a single bond or —$NR_5$—, $R_4$ represents a hydrogen atom, a lower alkyl group, an aryl group or an optionally substituted silyl lower alkyl group, $R_5$ represents a hydrogen atom, a lower alkyl group, an aryl group or an optionally substituted silyl lower alkyl group, and n is an integer of from 1 to 15, or salts or solvates thereof, and a pharmaceutical composition containing these compounds.

More specifically, the present invention relates to compounds represented by the formula (II)

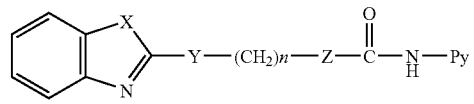

wherein

X represents —NH—, an oxygen atom or a sulfur atom,

Y represents —$NR_4$—, an oxygen atom, a sulfur atom, a sulfoxide or a sulfone,

Z represents a single bond or —$NR_5$—, $R_4$ represents a hydrogen atom, a lower alkyl group, an aryl group or an optionally substituted silyl lower alkyl group, $R_5$ represents a hydrogen atom, a lower alkyl group, an aryl group or an optionally substituted silyl lower alkyl group, Py represents an optionally substituted pyridyl or pyrimidyl group, and n is an integer of from 1 to 15, or salts or solvates thereof, and a pharmaceutical composition containing these compounds.

BACKGROUND ART

In recent years, hyperlipemia and arteriosclerosis derived therefrom have been rapidly increased with the change to western eating habits with high-calory and high-cholesterol foods based on the higher level of life and with the advance of age of the population, and this has been one of social problems. The conventional pharmacotherapy of hyperlipemia and arteriosclerosis has mainly put stress on the decrease in blood lipid that causes these diseases, and the lesion of the arteriosclerosis itself has not been treated as a target. Acyl coenzyme A cholesterol acyltransferase (ACAT) is an enzyme that catalyzes synthesis from cholesterol to cholesterol ester, and plays a vital role in metabolism of cholesterol and absorption thereof in digestive organs. Inhibition of the ACAT enzyme that catalyzes esterification of free cholesterol in epithelial cells of the small intestine results in inhibition of absorption of cholesterol from the intestine, and inhibition of synthesis of cholesterol ester in the liver based on the ACAT inhibition results in suppression of secretion of VLDL from the liver to the blood. These results are considered to lead to an activity of decreasing blood cholesterol. Most of conventional ACAT inhibitors have been expected to exhibit an activity of decreasing blood cholesterol as an antihyperlipemic agent by acting on the ACAT enzymes in the small intestine and the liver.

For example, as an ACAT inhibitor, the specification of U.S. Pat. No. 4,716,175 describes 2,2-dimethyl-N-(2,4,6-trimethoxyphenyl)dodecanamide, and European Patent No. 372,445 describes N'-(2,4-difluorophenyl)-N-[5-(4,5-diphenyl-1H-imidazol-2-ylthio)pentyl]-N-heptylurea. However, most of the conventional ACAT inhibitors have put stress on an activity of decreasing blood cholesterol as an antihyperlipemic agent, and the administration thereof at a high dose for exhibiting its activity has often caused side effects such as intestinal bleeding, intestinal disorders, diarrhea, hepatopathy and the like at the stage of a clinical test, making difficult the clinical development thereof.

The arteriosclerosis is inherently a characteristic lesion such as intima hypertrophy and lipidosis of the blood vessel. According to the recent studies, suppression of foamation of macrophages that play a main role in formation of the arteriosclerosis lesion has been expected to lead to regression of the arteriosclerosis lesion itself. Foam cells derived from macrophages (cholesterol ester is stored in cells as fat droplets) have been observed in the gruel arteriosclerosis lesion, and the foamation of macrophages is deemed to deeply participate in the progression of the lesion. Further, it has been reported that the ACAT activity in the blood vessel wall in the arteriosclerosis lesion site is increased and cholesterol ester is stored in the blood vessel wall [refer to Gillease, J. et al., Exp. Mole. Pathol., 44, 329-339 (1986)].

The inhibition of esterification of cholesterol with an ACAT inhibitor results in formation of free cholesterol in cells, and this free cholesterol is removed with high-density lipoprotein (HDL), transferred to the liver (inversely transferred with HDL), and metabolized. Accordingly, suppression of storage of cholesterol ester in the lesion site is expected. As a result, it is considered to provide a direct anti-arteriosclerotic activity. There is a report that ACAT includes two types, a type present in the small intestine and a type present in the blood vessel wall [Kinunen M. et al., Biochemistry, 27, 7344-7350 (1988)]. However, many of the past researches on the ACAT inhibitor have been conducted using an enzyme of a type present in the small intestine and the liver [Tomoda Eiichi et al., J. Antibiotics, 47, 148-153 (1994)].

The present inventors considered that medications which selectively inhibit an ACAT enzyme of a type present in the blood vessel wall can be those for treating arteriosclerosis that give less side effects, and have conducted synthesis and researches of such inhibitors.

The present inventors continued studies for achieving this object, and found in advance that compounds represented by the formula (IV)

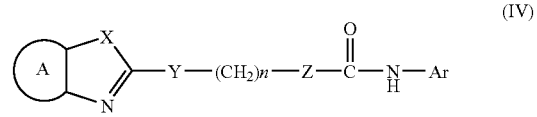

wherein

represents an optionally substituted divalent residue such as benzene, pyridine, cyclohexane or naphthalene or a group,

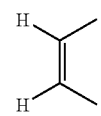

Ar represents an optionally substituted aryl group
X represents —NH—, an oxygen atom or a sulfur atom,
Y represents —NR$_4$—, an oxygen atom, a sulfur atom, a sulfoxide or a sulfone,
Z represents a single bond or —NR$_5$—,
R$_4$ represents a hydrogen atom, a lower alkyl group, an aryl group or an optionally substituted silyl lower alkyl group,
R$_5$ represents a hydrogen atom, a lower alkyl group, an aryl group or an optionally substituted silyl lower alkyl group, and
n is an integer of from 0 to 15, or salts or solvates thereof, and compounds represented by the formula (V)

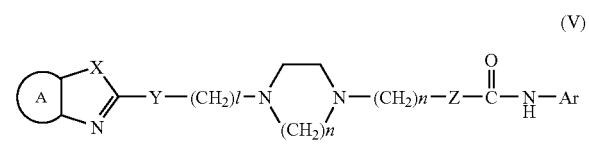

wherein

represents an optionally substituted divalent residue such as benzene, pyridine, cyclohexane or naphthalene, or a group,

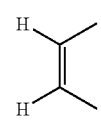

Ar represents an optionally substituted aryl group,
X represents —NH—, an oxygen atom or a sulfur atom, Y represents —NR₄—, an oxygen atom, a sulfur atom, a sulfoxide or a sulfone, Z represents a single bond or —NR₅—, R₄ represents a hydrogen atom, a lower alkyl group, an aryl group or an optionally substituted silyl lower alkyl group, R₅ represents a hydrogen atom, a lower alkyl group, an aryl group or an optionally substituted silyl lower alkyl group, l is an integer of from 0 to 15, m is an integer of 2 or 3, and n is integer of from 0 to 3, or salts or solvates thereof have an excellent ACAT inhibitory activity, and they applied the same for patents (Japanese Patent Application Nos. 88,660/1997, 90,146/1997 and 149,892/1997).

Further, as compounds similar to the compounds represented by the formula (I), 3-(benzothiazol-2-ylthio)-N-(phenyl)propanamide is disclosed in J. Chem. Eng. Data, 27, 207 (1982), and 3-(benzoxazol-2-ylthio)-N-(phenyl)propanamide in Fungitsidy, Ed. Melnikov, N. N. Izd. Fan Uzb. SSR: Tashkent, USSR. 82-88 (1980). However, these compounds are not only those in which an amide moiety is a phenyl group, but also these documents are totally devoid of the description that the compounds have an ACAT inhibitory activity.

Thus, the present inventors found that the compounds represented by the formula (IV) or (V) have an organ-selective ACAT inhibitory activity and an intracellular cholesterol transfer inhibitory activity, and that these are useful as an antihyperlipemic agent having an activity of decreasing blood cholesterol and as an agent for preventing and treating arteriosclerosis having a macrophage foamation inhibitory activity.

However, the compounds represented by these formulas (IV) and (V) did not necessarily have a sufficient activity, nor was the organ-selectivity satisfactory.

Under these circumstances, the present inventors have conducted further investigations to develop an ACAT inhibitor having a superior ACAT inhibitory activity, and have consequently found that the compounds represented by the formula (I) are useful ACAT inhibitors which conquer the above-mentioned defects. This finding has led to the completion of the present invention.

DISCLOSURE OF INVENTION

The present invention is to provide compounds represented by the formula (I)

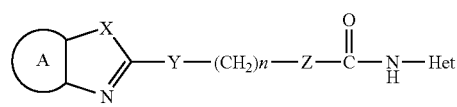

wherein

represents an optionally substituted divalent residue such as benzene, pyridine, cyclohexane or naphthalene, or a group

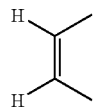

Het represents a 5- to 8-membered, substituted or unsubstituted heterocyclic group containing at least one heteroatom selected from the group consisting of a nitrogen atom, an oxygen atom and a sulfur atom, such as a monocyclic group, a polycyclic group or a group of a fused ring, X represents —NH—, an oxygen atom or a sulfur atom, Y represents —NR₄—, an oxygen atom, a sulfur atom, a sulfoxide or a sulfone, Z represents a single bond or —NR₅—, R₄ represents a hydrogen atom, a lower alkyl group, an aryl group or an optionally substituted silyl lower alkyl group, R₅ represents a hydrogen atom, a lower alkyl group, an aryl group or an optionally substituted silyl lower alkyl group, and n is an integer of from 1 to 15, or salts or solvates thereof.

Further, the present invention is to provide a pharmaceutical composition containing at least one type selected from the compounds represented by the formula (I), and the salts and the solvates thereof in a therapeutically effective amount, and a pharmaceutically acceptable carrier.

Still further, the present invention is to provide an ACAT inhibitor, an intracellular cholesterol transfer inhibitor, a blood cholesterol depressant or a macrophage foamation suppressant containing at least one type selected from the compounds represented by the formula (I), and the salts and the solvates thereof in a therapeutically effective amount, and a pharmaceutically acceptable carrier. That is, the present invention is to provide a medication for treating or preventing diseases such as hyperlipemia, arteriosclerosis, cervical and cerebral arteriosclerosis, cerebrovascular accidents, ischemic heart disease, coronary arteriosclerosis, nephrosclerosis, arteriosclerotic nephrosclerosis, arteriolonephrosclerosis, malignant nephrosclerosis, ischemic intestinal disease, acute occlusion of mesenteric vessel, chronic mesenteric angina, ischemic colitis, aortic aneurysm and arteriosclerosis obliterans (ASO), this medication containing at least one type selected from the compounds represented by the formula (I), and the salts and the solvates thereof, and a pharmaceutically acceptable carrier, as well as a therapeutic method using the same.

BEST MODE FOR CARRYING OUT THE INVENTION

As preferable examples of the compounds represented by the the formula (IA)

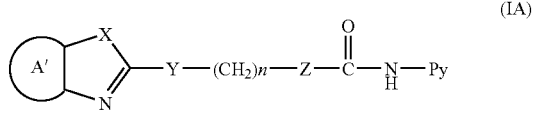

wherein

represents an optionally substituted divalent residue such as benzen or pyridine, Py represents an optionally substituted pyridyl or pyrimidyl group, X represents —NH—, an oxygen atom or a sulfur atom, Y represents —NR$_4$—, an oxygen atom, a sulfur atom, a sulfoxide or a sulfone, Z represents a single bond or —NR$_5$—, R$_4$ represents a hydrogen atom, a lower alkyl group, an aryl group or an optionally substituted silyl lower alkyl group, R$_5$ represents a hydrogen atom, a lower alkyl group, an aryl group or an optionally substituted silyl lower alkyl group, and n is an integer of from 1 to 15, or salts or solvates thereof, and a pharmaceutical composition containing these compounds can be mentioned.

As more preferable examples of the compounds represented by the formula (I) in the present invention, the compounds represented by the formula (II)

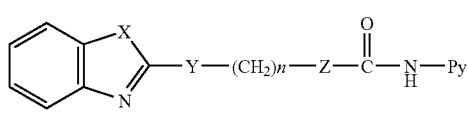

(II)

wherein Py represents an optionally substituted pyridyl or pyrimidyl group, and the other substituents are the same as described in the above-mentioned the formula (I), and the salts or the solvates thereof can be mentioned.

As further preferable examples of the compounds represented by the formula (I) in the present invention, the compounds represented by the formula (III)

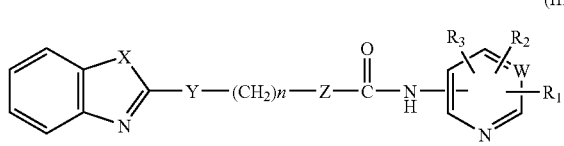

(III)

wherein

W represents =CH— or =N—, and

R$_1$, R$_2$ and R$_3$ are the same or different, and each represents a hydrogen atom, a lower alkyl group, a lower alkoxy group, a halogen atom, a hydroxyl group, a phosphate group, a sulfonamide group, a lower alkylthio group or an optionally substituted amino group, or two of R$_1$, R$_2$ and R$_3$ together form an alkylenedioxide group.

The substituent Het of the compounds represented by the formula (I) in the present invention is a 5- to 8-membered, substituted or unsubstituted heterocyclic group containing at least one heteroatom selected from the group consisting of a nitrogen atom, an oxygen atom and a sulfur atom. This cyclic group may be a monocyclic group, a polycyclic group in which the heterocyclic groups are bound to each other or bound to a carbon ring such as a 6-membered aromatic ring either directly or through a carbon chain, or a group of a fused ring in which the heterocyclic groups are fused to each other or to a carbon ring such as a 6-membered aromatic ring. Among these heterocyclic groups, a 5- to 8-membered heterocyclic group, preferably a 5- or 6-membered heterocyclic group, containing one or two nitrogen atoms is preferable. Preferable examples of the substituent Het include a substituted or unsubstituted pyridyl group, a substituted or unsubstituted pyrimidyl group, a substituted or unsubstituted indolyl group, and a substituted or unsubstituted quinolyl group. A substituted or unsubstituted pyridyl group, and a substituted or unsubstituted pyrimidyl group are further preferable.

These heterocyclic groups may be unsubstituted, but have preferably one or more substituents. The substituent of these heterocyclic groups is not particularly limited unless the ACAT inhibitory activity of the present invention is impaired. Preferable examples thereof include an amino group substituted with a lower alkyl group, a lower alkoxy group, a lower alkylthio group, a lower alkylcarbonyl group, a halogen atom, an amino group or a lower alkyl group; a substituted or unsubstituted aryl group such as a phenyl group or a naphthyl group; and a substituted or unsubstituted aralkyl group such as a benzyl group or a phenetyl group. Further, two substituents may be bound to form an alkylenedioxy group such as a methylenedioxy group.

As the lower alkyl group, a linear or branched alkyl group having from 1 to 10 carbon atoms, preferably from 1 to 6 carbon atoms is preferable. Especially preferable examples thereof include methyl, ethyl, n-propyl, iso-propyl, n-butyl, iso-butyl, tert-butyl, n-pentyl and n-hexyl groups.

As the lower alkyl group in the lower alkoxy group, the lower alkylthio group and the lower alkylcarbonyl group, the above-mentioned linear or branched alkyl group having from 1 to 10 carbon atoms, preferably from 1 to 6 carbon atoms is preferable. Examples thereof include methoxy, ethoxy, n-propoxy, iso-propoxy, n-butoxy, iso-butoxy, tert-butoxy, n-pentyloxy, n-hexyloxy, methylthio, ethylthio, n-propylthio, iso-propylthio, n-butylthio, iso-butylthio, tert-butylthio, n-pentylthio, n-hexylthio, methylcarbonyl, ethylcarbonyl, n-propylcarbonyl, iso-propylcarbonyl, n-butylcarbonyl, iso-butylcarbonyl, tert-butylcarbonyl, n-pentylcarbonyl and n-hexylcarbonyl groups.

Preferable examples of the halogen atom include fluorine, chlorine, bromine and iodine atoms.

As the aryl group, an aryl group having from 6 to 20 carbon atoms, preferably from 6 to 10 carbon atoms is mentioned. This aryl group may be unsubstituted or substituted with the above-mentioned lower alkyl group, lower alkoxy group, lower alkylthio group, lower alkylcarbonyl group, halogen atom, amino group or amino group substituted with the lower alkyl group. Preferable examples of the aryl group include phenyl, naphthyl, 2-methoxyphenyl and 4-methylthiophenyl groups.

The aralkyl group is an aralkyl group having from 7 to 20 carbon atoms, preferably from 7 to 12 carbon atoms. This aralkyl group may be unsubstituted or substituted with the above-mentioned lower alkyl group, lower alkoxy group, lower alkylthio group, lower alkylcarbonyl group, halogen atom, amino group or amino group substituted with the lower alkyl group. Preferable examples of the aralkyl group include benzyl, phenetyl and 4-methylbenzyl groups.

Examples of the substituent in the substituted amino group include the above-mentioned lower alkyl, lower alkylcarbonyl, aryl and aralkyl groups, and the number of the substituent in the amino group may be 1 or 2. Preferable examples of the substituted amino group include methylamino, ethylamino, dimethylamino, diethylamino, acetylamino and benzylamino groups.

The alkylene group of the alkylenedioxy group is a linear or branched alkylene group having from 1 to 10 carbon atoms, preferably from 1 to 5 carbon atoms. Preferable examples thereof include methylenedioxy and ethylenedioxy groups.

As the preferable Het group, a group represented by the formula (VI) is mentioned.

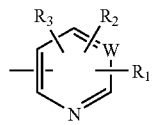

wherein W, $R_1$, $R_2$ and $R_3$ are as defined above.

Preferable examples of the Het group include
2-methylthio-3-pyridyl,
2-ethylthio-3-pyridyl,
2-(iso-propylthio)-3-pyridyl,
2-methoxy-3-pyridyl,
2-chloro-3-pyridyl,
2-methylthio-4-methyl-3-pyridyl,
2-ethylthio-4-methyl-3-pyridyl,
2-(iso-propylthio)-4-methyl-3-pyridyl,
2-methoxy-4-methyl-3-pyridyl,
2,6-bis(methylthio)-3-pyridyl,
2,6-bis(ethylthio)-3-pyridyl,
2,6-bis(iso-propylthio)-3-pyridyl,
2-methylthio-6-methoxy-3-pyridyl,
2-ethylthio-6-methoxy-3-pyridyl,
2-(iso-propylthio)-6-methoxy-3-pyridyl,
2-methylthio-6-methyl-3-pyridyl,
2-ethylthio-6-methyl-3-pyridyl,
2-(iso-propylthio)-6-methyl-3-pyridyl
2,6-dimethoxy-3-pyridyl,
2-methoxy-6-methyl-3-pyridyl,
2-methyl-6-methylthio-3-pyridyl,
2-methyl-6-ethylthio-3-pyridyl,
2-methyl-6-(iso-propylthio)-3-pyridyl,
2-methyl-6-methoxy-3-pyridyl,
2,6-dimehtyl-3-pyridyl,
2,6-diethyl-3-pyridyl,
2,4-bismethylthio-6-methyl-3-pyridyl,
2,4-bisethylthio-6-methyl-3-pyridyl,
2,4-bis(iso-propylthio)-6-methyl-3-pyridyl,
2,4-dimethoxy-6-methyl-3-pyridyl,
2,4,6-trimethyl-3-pyridyl,
4-ethyl-2,6-dimethyl-3-pyridyl,
2,4-dichloro-6-methyl-3-pyridyl,
4,6-bis(methylthio)-5-pyrimidyl,
4,6-bis(ethylthio)-5-pyrimidyl,
4,6-bis(iso-propylthio)-5-pyrimidyl,
4,6-dimethoxy-5-pyrimidyl,
4,6-dichloro-2-methyl-5-pyrimidyl,
4,6-bis(dimethylamino)-5-pyrimidyl,
4,6-bismethylthio-2-methyl-5-pyrimidyl,
2,4,6-trimethoxy-5-pyrimidyl
4-methyl-6-methyltio-3-pyridyl,
5-methylthio-2-pyridyl,
2,4,6-tris(methylthio)-5-pyrimidyl groups and so on.
The substituent

in the compounds represented by the the formula (I) in the present invention is a divalent group adjacent the azole ring which is formed with two carbon atoms constituting the azole ring. It is preferably an optionally substituted divalent group such as benzene, pyridine, cyclohexane or naphthalene, or a group as follows.

An optionally substituted divalent residue such as benzen or pyridine is preferable. These divalent groups may have a substituent. Examples of the substituent include the above-mentioned lower alkyl group, lower alkoxy group, lower alkylsulfonyl group lower alkylthio group, lower alkylcarbonyl group, halogen atom, amino group, amino group substituted with the lower alkyl group, substituted or unsubstituted aryl group such as the phenyl group or the naphthyl group, and substituted or unsubstituted aralkyl group such as the benzyl group or the phenetyl group. Further, the two substituents may be bound to form an alkylenedioxy group such as a methylenedioxy group.

The substituent X in the compounds represented by the formula (I) in the present invention represents —NH—, an oxygen atom or a sulfur atom, and forms, together with the above-mentioned substituent, an azole ring such as imidazole, oxazole or thiazole.

Further, the substituent Y in the compounds represented by the formula (I) of the present invention represents —$NR_4$—, an oxygen atom, a sulfur atom, a sulfoxide or a sulfone, and the substituent $R_4$ of the nitrogen atom represents a hydrogen atom, a lower alkyl group, an aryl group or an optionally substituted silyl lower alkyl group. The lower alkyl group or the aryl group as the substituent $R_4$ is as mentioned above. Examples thereof include methyl, ethyl and phenyl groups. The lower alkyl group of the optionally substituted silyl lower alkyl group as the substituent $R_4$ may be the above-mentioned group. Examples of the substituent of the silyl lower alkyl group include the above-mentioned lower alkyl, aryl and aralkyl groups. Preferable examples thereof include trimethylsilylmethyl and dimethylphenylsilylmethyl groups.

As the substituent Y, a sulfur atom is preferable.

The substituent Z in the compounds represented by the formula (I) of the present invention represents a single bond or —$NR_5$—, and the substituent $R_5$ of the nitrogen atom represents a hydrogen atom, a lower alkyl group, an aryl group or an optionally substituted silyl lower alkyl group. Examples of these substituents are the above-mentioned groups.

The number n of recurring units in the compounds represented by the formula (I) in the present invention is an integer of from 1 to 15, preferably an integer of from 1 to 9. As the recurring unit, a methylene group is mentioned in the formula (I). The methylene group may have a substituent or one or more methylene units may be substituted with a heteroatom such as a nitrogen atom, an oxygen atom or a sulfur atom unless the ACAT inhibitory activity of the present invention is impaired.

The substituents X, Y, Z and the recurring unit in the compounds represented by the formula (II) in the present invention are the above-mentioned ones. The substituent Py represents an optionally substituted pyridyl or pyrimidyl group. The substituent of the pyridyl or pyrimidyl group is not particularly limited unless the ACAT inhibitory activity of the present invention is impaired. The group represented by the formula (VI) is preferable.

The substituents X, Y, Z and the recurring unit in the compounds represented by the formula (III) in the present invention are the above-mentioned ones. The substituent W represents a carbon atom or a nitrogen atom, and forms a pyridine or pyrimidine ring. Further, the substituents $R_1$, $R_2$ and $R_3$ are the same or different, and each represents a hydrogen atom, a lower alkyl group, a lower alkoxy group, a halogen atom, a hydroxyl group, a phosphate group, a sulfonamide group, a lower alkylthio group or an optionally substituted amino group, or two of $R_1$, $R_2$ and $R_3$ together form an alkylenedioxy group. Of these groups, the lower alkyl group, the lower alkoxy group, the halogen atom, the lower alkylthio group, the optionally substituted amino group and the alkylenedioxy group are the above-mentioned ones. Preferable examples of $R_1$, $R_2$ and $R_3$ include methyl, ethyl, iso-propyl, methoxy, ethoxy and iso-propoxy groups, chlorine, and methylthio, ethylthio, iso-propylthio and dimethylamino groups. The site of the pyridine ring or the pyrimidine ring bound to the adjacent nitrogen atom is not particularly limited either unless the ACAT inhibitory activity of the present invention is impaired.

The salts of the compounds represented by the formula (I), (II) or (III) in the present invention are not particularly limited unless the ACAT inhibitory activity of the present invention is impaired. Acid addition salts or base addition salts can be used as required. Preferable examples of the acid addition salts include inorganic acid salts such as a hydrochloride, a sulfate, a nitrate and a phosphate; and organic acid salts such as a methanesulfonate, a maleate, a fumarate and a citrate.

Further, the solvates of the compounds represented by the formula (I), (II) or (III) in the present invention are products to which solvents used in the production, the purification or the like, such as water, alcohol and the like are added, and are not particularly limited unless they have an adverse effect on the ACAT inhibitory activity. As the solvates, hydrides are preferable.

A process for producing the compounds of the present invention is described below.

Compounds (I) can be produced by various known processes, and the process is not particularly limited. For example, compounds (I) can be produced according to the following reaction steps.

1. Process for Producing Compounds of the Formula (I) when the Substituent Z is a Single Bond:

A carboxylic acid represented by the formula (VII) or its reactive derivative, for example, an acid halide, is reacted with a heterocyclic amine represented by the formula (VIII) according to the following reaction formulae

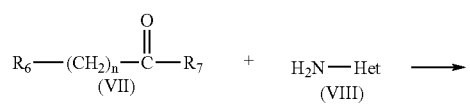

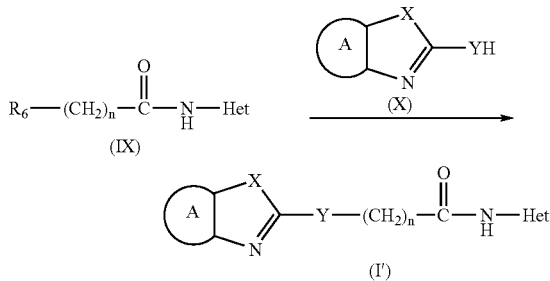

wherein $R_6$ represents a leaving group, and $R_7$ represents a reactive derivative residue of a hydroxyl group or a carboxylate group, to form an amide derivative represented by the formula (IX). When the resulting compound of the formula (IX) is reacted with an azole derivative represented by the formula (X), a desired compound (I') in which the substituent Z in the formula (I) is a single bond can be produced.

An ordinary method used in peptide synthesis can be applied to the reaction between compounds (VII) and (VIII). Examples of the leaving group $R_6$ in the formula (VII) include halogen atoms such as chlorine and bromine atoms. Preferable examples of the reactive derivative residue $R_7$ include acid anhydride residues with mesylic acid, tosylic acid, acetic acid, pivaloylic acid and the like. This reaction is described more specifically below. The desired compound can be obtained by reacting both of the compounds in a solvent in the presence of a condensation agent.

As the condensation agent, for example, 1-(3'-dimethylaminopropyl)-3-ethylcarbodiimide (WSC) and 1,3-dicyclohexylcarbodiimide (DCC) may be used singly, and a combination of 1-hydroxybenzotriazole (HOBt) and N-hydroxysuccinimide (HOSu) is also available. The solvent is not particularly limited. For example, dimethylformamide, methylene chloride, chloroform, tetrahydrofuran and toluene can be used either singly or in combination. The reaction conditions vary depending on a starting material to be used. Generally, the reaction is conducted at from 0 to 100° C., preferably at a temperature close to room temperature, for from 1 to 30 hours, preferably for from 10 to 20 hours. In this manner, the reaction is completed. Further, when a carbonyl halide having a high reactivity is used as compound (VII), for example, compounds (VII) and (VIII) can be reacted in the presence of a base, for example, triethylamine, 4-dimethylaminopyridine or N-methylmorpholine in a usual manner.

With respect to starting compounds (VII) and (VIII), for example, compound (VII) can be produced by a method in which a haloalkyl alcohol is oxidized into a carboxylic acid with a Jones' reagent or the like, and compound (VIII) by a method in which a nitrated heterocyclic compound is subjected to a reduction reaction such as a catalytic reduction or the like to obtain a corresponding amino heterocyclic compound, respectively.

The reaction between compounds (IX) and (X) obtained by the above-mentioned methods can be conducted in a solvent in the presence or absence of a base. As the solvent, the above-mentioned various types can be used. The base includes inorganic bases, for example, alkali metal hydroxides such as sodium hydroxide and potassium hydroxide, alkali metal carbonates such as sodium carbonate and potassium carbonate, and alkali metal hydrogencarbonates such as sodium hydrogencarbonate and potassium hydrogencarbonate; and organic bases such as pyridine, triethylamine, N,N-diisopropylethylamine, N-methylmorpholine and N,N-dimethylaniline.

Further, with respect to the desired compound represented by the formula (I'), according to the reaction shown by the following formula

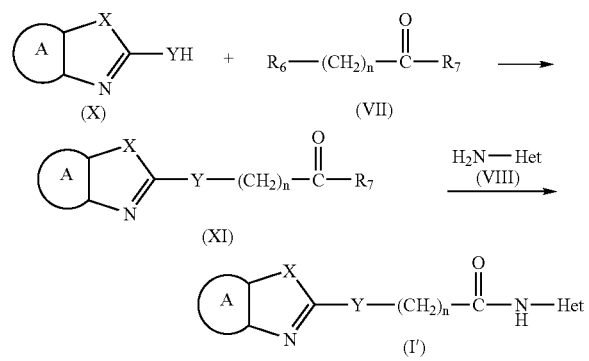

wherein $R_6$ represents a leaving group, and $R_7$ represents a reactive derivative residue of a hydroxyl group or a carboxylate group, an azole derivative represented by the formula (X) is reacted with a free carboxylic acid or an inactive substance of a carboxylic acid as the compound represented by the formula (VII) to obtain a carboxylic acid derivative represented by the formula (XI). When the resulting compound represented by the formula (XI) or its reactive derivative, for example, an acid halide, is reacted with a heterocyclic amine derivative represented by the formula (VIII), the desired compound (I') in which the substituent Z in the formula (I) is a single bond can be produced.

The reaction between compounds (X) and (VII) can be conducted according to the second step of the above-mentioned reaction formula. The reaction in which potassium hydroxide is used as a base and ethanol as a solvent respectively is especially preferable. The reaction between the resulting compounds (XI) and (VIII) can be conducted according to the first step of the above-mentioned reaction formula.

2. Process for Producing Compounds of the Formula (I) when the Substituent Z is —NH—:

The compound represented by the formula (I) in which Z is —NH— can be produced by various processes. It is preferable to produce the same by the process shown by the following reaction formula.

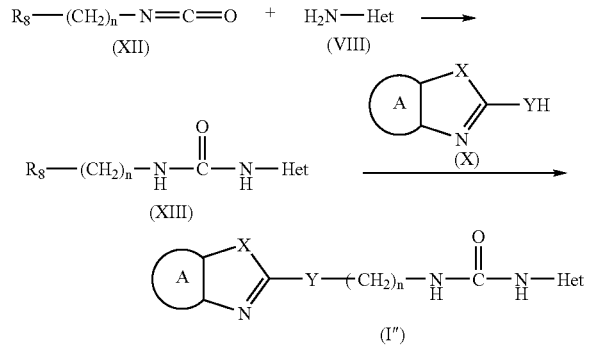

wherein $R_8$ represents a leaving group.

The isocyanate derivative represented by the formula (XII) is reacted with the heterocyclic amine represented by the formula (VIII) to obtain an urea derivative represented by the formula (XIII). The resulting urea derivative is reacted with compound (X) to form desired compound (I'') in which the substituent Z in the formula (I) is —NH—.

With respect to the reaction between compounds (XII) and (VIII) in the first step of this reaction formula, compound (XII) is reacted with compound (VIII) in an amount of from 1 to 2 equivalents in a solvent to obtain compound (XIII). At this time, the solvent is not particularly limited. Preferable examples thereof include methylene chloride, chloroform, ether, tetrahydrofuran, toluene, xylene and dimethylformamide. The reaction proceeds in a boiling point of a solvent used from 0° C. for a reaction time of from 1 to 24 hours.

The isocyanate derivative represented by the formula (XII) is a known compound, and it can be produced by, for example, a method in which the above-mentioned carboxylic acid as compound (VII) is reacted with diphenylphospholyl azide in the presence of a base (method of Shioiri et al.), a method via an acid azide by reacting the acid halide of compound (VII) with sodium azide.

The reaction between compounds (XIII) and (X) can be conducted according to the second step of the above-mentioned reaction formula.

Further, when the substituent Z in the formula (I) is —$NR_5$— (wherein $R_5$ represents the above-mentioned groups except a hydrogen atom), the compound can be produced by replacing a nitrogen atom with the substituent $R_5$ at an appropriate stage.

The intermediate and the desired compound obtained in each of the above-mentioned reactions can be isolated and purified by a purification method which is ordinarily used in the synthetic organic chemistry, such as filtration, extraction, washing, drying, concentration, recrystallization and various chromatographies. Further, each intermediate is subjected to the subsequent step without any purification unless any trouble is caused, which is well known to those skilled in the art.

The resulting compounds (I) can be formed into salts of the present invention in a usual manner.

Further, compounds (I) can be formed into solvates with solvents such as a reaction solvent, a recrystallization solvent and the like, especially hydrides in a usual manner, which is well known to those skilled in the art.

The compounds represented by the formula (I), (II) or (III), which are obtained by the process of the present invention are shown in Tables 1 to 63 below.

TABLE 1

| Compound No. | A | X | Y | Z | n | Het |
|---|---|---|---|---|---|---|
| 1 | (benzo) | O | S | * | 1 | 2-methylthio-3-pyridyl |
| 2 | " | O | S | * | 2 | 2-methylthio-3-pyridyl |
| 3 | " | O | S | * | 3 | 2-methylthio-3-pyridyl |
| 4 | " | O | S | * | 4 | 2-methylthio-3-pyridyl |
| 5 | " | O | S | * | 5 | 2-methylthio-3-pyridyl |
| 6 | " | O | S | * | 6 | 2-methylthio-3-pyridyl |
| 7 | " | O | S | * | 7 | 2-methylthio-3-pyridyl |
| 8 | " | O | S | * | 8 | 2-methylthio-3-pyridyl |

TABLE 1-continued

| Compound No. | A | X | Y | Z | n | Het |
|---|---|---|---|---|---|---|
| 9 | " | O | S | * | 9 | 2-methylthio-3-pyridyl |
| 10 | " | O | S | * | 14 | 2-methylthio-3-pyridyl |
| 11 | " | S | S | * | 1 | 2-methylthio-3-pyridyl |
| 12 | " | S | S | * | 2 | 2-methylthio-3-pyridyl |
| 13 | " | S | S | * | 3 | 2-methylthio-3-pyridyl |
| 14 | " | S | S | * | 4 | 2-methylthio-3-pyridyl |
| 15 | " | S | S | * | 5 | 2-methylthio-3-pyridyl |
| 16 | " | S | S | * | 6 | 2-methylthio-3-pyridyl |
| 17 | " | S | S | * | 7 | 2-methylthio-3-pyridyl |
| 18 | " | S | S | * | 8 | 2-methylthio-3-pyridyl |
| 19 | " | S | S | * | 9 | 2-methylthio-3-pyridyl |
| 20 | " | S | S | * | 14 | 2-methylthio-3-pyridyl |

*: Single Bond

TABLE 2

| Compound No. | A | X | Y | Z | n | Het |
|---|---|---|---|---|---|---|
| 21 | (ortho-disubstituted benzene) | NH | S | * | 1 | 2-methylthio-3-pyridyl |
| 22 | " | NH | S | * | 2 | 2-methylthio-3-pyridyl |
| 23 | " | NH | S | * | 3 | 2-methylthio-3-pyridyl |
| 24 | " | NH | S | * | 4 | 2-methylthio-3-pyridyl |
| 25 | " | NH | S | * | 5 | 2-methylthio-3-pyridyl |
| 26 | " | NH | S | * | 6 | 2-methylthio-3-pyridyl |
| 27 | " | NH | S | * | 7 | 2-methylthio-3-pyridyl |
| 28 | " | NH | S | * | 8 | 2-methylthio-3-pyridyl |
| 29 | " | NH | S | * | 9 | 2-methylthio-3-pyridyl |
| 30 | " | NH | S | * | 14 | 2-methylthio-3-pyridyl |
| 31 | " | O | S | * | 1 | 2-ethylthio-3-pyridyl |
| 32 | " | O | S | * | 2 | 2-ethylthio-3-pyridyl |
| 33 | " | O | S | * | 3 | 2-ethylthio-3-pyridyl |
| 34 | " | O | S | * | 4 | 2-ethylthio-3-pyridyl |
| 35 | " | O | S | * | 5 | 2-ethylthio-3-pyridyl |
| 36 | " | O | S | * | 6 | 2-ethylthio-3-pyridyl |
| 37 | " | O | S | * | 7 | 2-ethylthio-3-pyridyl |
| 38 | " | O | S | * | 8 | 2-ethylthio-3-pyridyl |
| 39 | " | O | S | * | 9 | 2-ethylthio-3-pyridyl |
| 40 | " | O | S | * | 14 | 2-ethylthio-3-pyridyl |

*: Single Bond

TABLE 3

| Compound No. | A | X | Y | Z | n | Het |
|---|---|---|---|---|---|---|
| 41 | (ortho-disubstituted benzene) | S | S | * | 1 | 2-ethylthio-3-pyridyl |
| 42 | " | S | S | * | 2 | 2-ethylthio-3-pyridyl |
| 43 | " | S | S | * | 3 | 2-ethylthio-3-pyridyl |
| 44 | " | S | S | * | 4 | 2-ethylthio-3-pyridyl |
| 45 | " | S | S | * | 5 | 2-ethylthio-3-pyridyl |
| 46 | " | S | S | * | 6 | 2-ethylthio-3-pyridyl |
| 47 | " | S | S | * | 7 | 2-ethylthio-3-pyridyl |

TABLE 3-continued

| Compound No. | A | X | Y | Z | n | Het |
|---|---|---|---|---|---|---|
| 48 | " | S | S | * | 8 | 2-ethylthio-3-pyridyl |
| 49 | " | S | S | * | 9 | 2-ethylthio-3-pyridyl |
| 50 | " | S | S | * | 14 | 2-ethylthio-3-pyridyl |
| 51 | " | NH | S | * | 1 | 2-ethylthio-3-pyridyl |
| 52 | " | NH | S | * | 2 | 2-ethylthio-3-pyridyl |
| 53 | " | NH | S | * | 3 | 2-ethylthio-3-pyridyl |
| 54 | " | NH | S | * | 4 | 2-ethylthio-3-pyridyl |
| 55 | " | NH | S | * | 5 | 2-ethylthio-3-pyridyl |
| 56 | " | NH | S | * | 6 | 2-ethylthio-3-pyridyl |
| 57 | " | NH | S | * | 7 | 2-ethylthio-3-pyridyl |
| 58 | " | NH | S | * | 8 | 2-ethylthio-3-pyridyl |
| 59 | " | NH | S | * | 9 | 2-ethylthio-3-pyridyl |
| 60 | " | NH | S | * | 14 | 2-ethylthio-3-pyridyl |

*: Single Bond

TABLE 4

| Compound No. | A | X | Y | Z | n | Het |
|---|---|---|---|---|---|---|
| 61 | (ortho-disubstituted benzene) | O | S | * | 1 | 2-(iso-propylthio)-3-pyridyl |
| 62 | " | O | S | * | 2 | 2-(iso-propylthio)-3-pyridyl |
| 63 | " | O | S | * | 3 | 2-(iso-propylthio)-3-pyridyl |
| 64 | " | O | S | * | 4 | 2-(iso-propylthio)-3-pyridyl |
| 65 | " | O | S | * | 5 | 2-(iso-propylthio)-3-pyridyl |
| 66 | " | O | S | * | 6 | 2-(iso-propylthio)-3-pyridyl |
| 67 | " | O | S | * | 7 | 2-(iso-propylthio)-3-pyridyl |
| 68 | " | O | S | * | 8 | 2-(iso-propylthio)-3-pyridyl |
| 69 | " | O | S | * | 9 | 2-(iso-propylthio)-3-pyridyl |
| 70 | " | O | S | * | 14 | 2-(iso-propylthio)-3-pyridyl |
| 71 | " | S | S | * | 1 | 2-(iso-propylthio)-3-pyridyl |
| 72 | " | S | S | * | 2 | 2-(iso-propylthio)-3-pyridyl |
| 73 | " | S | S | * | 3 | 2-(iso-propylthio)-3-pyridyl |
| 74 | " | S | S | * | 4 | 2-(iso-propylthio)-3-pyridyl |
| 75 | " | S | S | * | 5 | 2-(iso-propylthio)-3-pyridyl |
| 76 | " | S | S | * | 6 | 2-(iso-propylthio)-3-pyridyl |
| 77 | " | S | S | * | 7 | 2-(iso-propylthio)-3-pyridyl |
| 78 | " | S | S | * | 8 | 2-(iso-propylthio)-3-pyridyl |
| 79 | " | S | S | * | 9 | 2-(iso-propylthio)-3-pyridyl |
| 80 | " | S | S | * | 14 | 2-(iso-propylthio)-3-pyridyl |

*: Single Bond

TABLE 5

| Compound No. | A | X | Y | Z | n | Het |
|---|---|---|---|---|---|---|
| 81 | (2-methylphenyl, o-tolyl) | NH | S | * | 1 | 2-(iso-propylthio)-3-pyridyl |
| 82 | " | NH | S | * | 2 | 2-(iso-propylthio)-3-pyridyl |
| 83 | " | NH | S | * | 3 | 2-(iso-propylthio)-3-pyridyl |
| 84 | " | NH | S | * | 4 | 2-(iso-propylthio)-3-pyridyl |
| 85 | " | NH | S | * | 5 | 2-(iso-propylthio)-3-pyridyl |
| 86 | " | NH | S | * | 6 | 2-(iso-propylthio)-3-pyridyl |
| 87 | " | NH | S | * | 7 | 2-(iso-propylthio)-3-pyridyl |
| 88 | " | NH | S | * | 8 | 2-(iso-propylthio)-3-pyridyl |
| 89 | " | NH | S | * | 9 | 2-(iso-propylthio)-3-pyridyl |
| 90 | " | NH | S | * | 14 | 2-(iso-propylthio)-3-pyridyl |
| 91 | " | O | S | * | 1 | 2-methoxy-3-pyridyl |
| 92 | " | O | S | * | 2 | 2-methoxy-3-pyridyl |
| 93 | " | O | S | * | 3 | 2-methoxy-3-pyridyl |
| 94 | " | O | S | * | 4 | 2-methoxy-3-pyridyl |
| 95 | " | O | S | * | 5 | 2-methoxy-3-pyridyl |
| 96 | " | O | S | * | 6 | 2-methoxy-3-pyridyl |
| 97 | " | O | S | * | 7 | 2-methoxy-3-pyridyl |
| 98 | " | O | S | * | 8 | 2-methoxy-3-pyridyl |
| 99 | " | O | S | * | 9 | 2-methoxy-3-pyridyl |
| 100 | " | O | S | * | 14 | 2-methoxy-3-pyridyl |

*: Single Bond

TABLE 6

| Compound No. | A | X | Y | Z | n | Het |
|---|---|---|---|---|---|---|
| 101 | (2-methylphenyl, o-tolyl) | S | * | 1 | 1 | 2-methoxy-3-pyridyl |
| 102 | " | S | S | * | 2 | 2-methoxy-3-pyridyl |
| 103 | " | S | S | * | 3 | 2-methoxy-3-pyridyl |
| 104 | " | S | S | * | 4 | 2-methoxy-3-pyridyl |
| 105 | " | S | S | * | 5 | 2-methoxy-3-pyridyl |
| 106 | " | S | S | * | 6 | 2-methoxy-3-pyridyl |
| 107 | " | S | S | * | 7 | 2-methoxy-3-pyridyl |
| 108 | " | S | S | * | 8 | 2-methoxy-3-pyridyl |
| 109 | " | S | S | * | 9 | 2-methoxy-3-pyridyl |
| 110 | " | S | S | * | 14 | 2-methoxy-3-pyridyl |
| 111 | " | NH | S | * | 1 | 2-methoxy-3-pyridyl |
| 112 | " | NH | S | * | 2 | 2-methoxy-3-pyridyl |
| 113 | " | NH | S | * | 3 | 2-methoxy-3-pyridyl |
| 114 | " | NH | S | * | 4 | 2-methoxy-3-pyridyl |
| 115 | " | NH | S | * | 5 | 2-methoxy-3-pyridyl |
| 116 | " | NH | S | * | 6 | 2-methoxy-3-pyridyl |
| 117 | " | NH | S | * | 7 | 2-methoxy-3-pyridyl |
| 118 | " | NH | S | * | 8 | 2-methoxy-3-pyridyl |
| 119 | " | NH | S | * | 9 | 2-methoxy-3-pyridyl |
| 120 | " | NH | S | * | 14 | 2-methoxy-3-pyridyl |

*: Single Bond

TABLE 7

| Compound No. | A | X | Y | Z | n | Het |
|---|---|---|---|---|---|---|
| 121 | (2-methylphenyl, o-tolyl) | O | S | * | 1 | 2-chloro-3-pyridyl |
| 122 | " | O | S | * | 2 | 2-chloro-3-pyridyl |
| 123 | " | O | S | * | 3 | 2-chloro-3-pyridyl |
| 124 | " | O | S | * | 4 | 2-chloro-3-pyridyl |
| 125 | " | O | S | * | 5 | 2-chloro-3-pyridyl |
| 126 | " | O | S | * | 6 | 2-chloro-3-pyridyl |
| 127 | " | O | S | * | 7 | 2-chloro-3-pyridyl |
| 128 | " | O | S | * | 8 | 2-chloro-3-pyridyl |
| 129 | " | O | S | * | 9 | 2-chloro-3-pyridyl |
| 130 | " | O | S | * | 14 | 2-chloro-3-pyridyl |
| 131 | " | S | S | * | 1 | 2-chloro-3-pyridyl |
| 132 | " | S | S | * | 2 | 2-chloro-3-pyridyl |
| 133 | " | S | S | * | 3 | 2-chloro-3-pyridyl |
| 134 | " | S | S | * | 4 | 2-chloro-3-pyridyl |
| 135 | " | S | S | * | 5 | 2-chloro-3-pyridyl |
| 136 | " | S | S | * | 6 | 2-chloro-3-pyridyl |
| 137 | " | S | S | * | 7 | 2-chloro-3-pyridyl |
| 138 | " | S | S | * | 8 | 2-chloro-3-pyridyl |
| 139 | " | S | S | * | 9 | 2-chloro-3-pyridyl |
| 140 | " | S | S | * | 14 | 2-chloro-3-pyridyl |

*: Single Bond

TABLE 8

| Compound No. | A | X | Y | Z | n | Het |
|---|---|---|---|---|---|---|
| 141 | (2-methylphenyl, o-tolyl) | NH | S | * | 1 | 2-chloro-3-pyridyl |
| 142 | " | NH | S | * | 2 | 2-chloro-3-pyridyl |
| 143 | " | NH | S | * | 3 | 2-chloro-3-pyridyl |
| 144 | " | NH | S | * | 4 | 2-chloro-3-pyridyl |
| 145 | " | NH | S | * | 5 | 2-chloro-3-pyridyl |
| 146 | " | NH | S | * | 6 | 2-chloro-3-pyridyl |
| 147 | " | NH | S | * | 7 | 2-chloro-3-pyridyl |
| 148 | " | NH | S | * | 8 | 2-chloro-3-pyridyl |
| 149 | " | NH | S | * | 9 | 2-chloro-3-pyridyl |
| 150 | " | NH | S | * | 14 | 2-chloro-3-pyridyl |
| 151 | " | O | S | * | 1 | 2-methylthio-4-methyl-3-pyridyl |
| 152 | " | O | S | * | 2 | 2-methylthio-4-methyl-3-pyridyl |

TABLE 8-continued

| Compound No. | A | X | Y | Z | n | Het |
|---|---|---|---|---|---|---|
| 153 | " | O | S | * | 3 | 2-methylthio-4-methyl-3-pyridyl |
| 154 | " | O | S | * | 4 | 2-methylthio-4-methyl-3-pyridyl |
| 155 | " | O | S | * | 5 | 2-methylthio-4-methyl-3-pyridyl |
| 156 | " | O | S | * | 6 | 2-methylthio-4-methyl-3-pyridyl |
| 157 | " | O | S | * | 7 | 2-methylthio-4-methyl-3-pyridyl |
| 158 | " | O | S | * | 8 | 2-methylthio-4-methyl-3-pyridyl |
| 159 | " | O | S | * | 9 | 2-methylthio-4-methyl-3-pyridyl |
| 160 | " | O | S | * | 14 | 2-methylthio-4-methyl-3-pyridyl |

*: Single Bond

TABLE 9

| Compound No. | A | X | Y | Z | n | Het |
|---|---|---|---|---|---|---|
| 161 | (o-dimethylphenyl) | S | S | * | 1 | 2-methylthio-4-methyl-3-pyridyl |
| 162 | " | S | S | * | 2 | 2-methylthio-4-methyl-3-pyridyl |
| 163 | " | S | S | * | 3 | 2-methylthio-4-methyl-3-pyridyl |
| 164 | " | S | S | * | 4 | 2-methylthio-4-methyl-3-pyridyl |
| 165 | " | S | S | * | 5 | 2-methylthio-4-methyl-3-pyridyl |
| 166 | " | S | S | * | 6 | 2-methylthio-4-methyl-3-pyridyl |
| 167 | " | S | S | * | 7 | 2-methylthio-4-methyl-3-pyridyl |
| 168 | " | S | S | * | 8 | 2-methylthio-4-methyl-3-pyridyl |
| 169 | " | S | S | * | 9 | 2-methylthio-4-methyl-3-pyridyl |
| 170 | " | S | S | * | 14 | 2-methylthio-4-methyl-3-pyridyl |
| 171 | " | NH | S | * | 1 | 2-methylthio-4-methyl-3-pyridyl |
| 172 | " | NH | S | * | 2 | 2-methylthio-4-methyl-3-pyridyl |
| 173 | " | NH | S | * | 3 | 2-methylthio-4-methyl-3-pyridyl |
| 174 | " | NH | S | * | 4 | 2-methylthio-4-methyl-3-pyridyl |
| 175 | " | NH | S | * | 5 | 2-methylthio-4-methyl-3-pyridyl |
| 176 | " | NH | S | * | 6 | 2-methylthio-4-methyl-3-pyridyl |
| 177 | " | NH | S | * | 7 | 2-methylthio-4-methyl-3-pyridyl |
| 178 | " | NH | S | * | 8 | 2-methylthio-4-methyl-3-pyridyl |
| 179 | " | NH | S | * | 9 | 2-methylthio-4-methyl-3-pyridyl |
| 180 | " | NH | S | * | 14 | 2-methylthio-4-methyl-3-pyridyl |

*: Single Bond

TABLE 10

| Compound No. | A | X | Y | Z | n | Het |
|---|---|---|---|---|---|---|
| 181 | (o-dimethylphenyl) | O | S | * | 1 | 2-ethylthio-4-methyl-3-pyridyl |
| 182 | " | O | S | * | 2 | 2-ethylthio-4-methyl-3-pyridyl |
| 183 | " | O | S | * | 3 | 2-ethylthio-4-methyl-3-pyridyl |
| 184 | " | O | S | * | 4 | 2-ethylthio-4-methyl-3-pyridyl |
| 185 | " | O | S | * | 5 | 2-ethylthio-4-methyl-3-pyridyl |
| 186 | " | O | S | * | 6 | 2-ethylthio-4-methyl-3-pyridyl |
| 187 | " | O | S | * | 7 | 2-ethylthio-4-methyl-3-pyridyl |
| 188 | " | O | S | * | 8 | 2-ethylthio-4-methyl-3-pyridyl |
| 189 | " | O | S | * | 9 | 2-ethylthio-4-methyl-3-pyridyl |
| 190 | " | O | S | * | 14 | 2-ethylthio-4-methyl-3-pyridyl |
| 191 | " | S | S | * | 1 | 2-ethylthio-4-methyl-3-pyridyl |
| 192 | " | S | S | * | 2 | 2-ethylthio-4-methyl-3-pyridyl |
| 193 | " | S | S | * | 3 | 2-ethylthio-4-methyl-3-pyridyl |
| 194 | " | S | S | * | 4 | 2-ethylthio-4-methyl-3-pyridyl |
| 195 | " | S | S | * | 5 | 2-ethylthio-4-methyl-3-pyridyl |
| 196 | " | S | S | * | 6 | 2-ethylthio-4-methyl-3-pyridyl |
| 197 | " | S | S | * | 7 | 2-ethylthio-4-methyl-3-pyridyl |
| 198 | " | S | S | * | 8 | 2-ethylthio-4-methyl-3-pyridyl |
| 199 | " | S | S | * | 9 | 2-ethylthio-4-methyl-3-pyridyl |
| 200 | " | S | S | * | 14 | 2-ethylthio-4-methyl-3-pyridyl |

*: Single Bond

TABLE 11

| Compound No. | A | X | Y | Z | n | Het |
|---|---|---|---|---|---|---|
| 201 | (o-dimethylphenyl) | NH | S | * | 1 | 2-ethylthio-4-methyl-3-pyridyl |
| 202 | " | NH | S | * | 2 | 2-ethylthio-4-methyl-3-pyridyl |
| 203 | " | NH | S | * | 3 | 2-ethylthio-4-methyl-3-pyridyl |
| 204 | " | NH | S | * | 4 | 2-ethylthio-4-methyl-3-pyridyl |
| 205 | " | NH | S | * | 5 | 2-ethylthio-4-methyl-3-pyridyl |
| 206 | " | NH | S | * | 6 | 2-ethylthio-4-methyl-3-pyridyl |
| 207 | " | NH | S | * | 7 | 2-ethylthio-4-methyl-3-pyridyl |

TABLE 11-continued

| Compound No. | A | X | Y | Z | n | Het |
|---|---|---|---|---|---|---|
| 208 | " | NH | S | * | 8 | 2-ethylthio-4-methyl-3-pyridyl |
| 209 | " | NH | S | * | 9 | 2-ethylthio-4-methyl-3-pyridyl |
| 210 | " | NH | S | * | 14 | 2-ethylthio-4-methyl-3-pyridyl |
| 211 | " | O | S | * | 1 | 2-(iso-propylthio)-4-methyl-3-pyridyl |
| 212 | " | O | S | * | 2 | 2-(iso-propylthio)-4-methyl-3-pyridyl |
| 213 | " | O | S | * | 3 | 2-(iso-propylthio)-4-methyl-3-pyridyl |
| 214 | " | O | S | * | 4 | 2-(iso-propylthio)-4-methyl-3-pyridyl |
| 215 | " | O | S | * | 5 | 2-(iso-propylthio)-4-methyl-3-pyridyl |
| 216 | " | O | S | * | 6 | 2-(iso-propylthio)-4-methyl-3-pyridyl |
| 217 | " | O | S | * | 7 | 2-(iso-propylthio)-4-methyl-3-pyridyl |
| 218 | " | O | S | * | 8 | 2-(iso-propylthio)-4-methyl-3-pyridyl |
| 219 | " | O | S | * | 9 | 2-(iso-propylthio)-4-methyl-3-pyridyl |
| 220 | " | O | S | * | 14 | 2-(iso-propylthio)-4-methyl-3-pyridyl |

*: Single Bond

TABLE 12

| Compound No. | A | X | Y | Z | n | Het |
|---|---|---|---|---|---|---|
| 221 | (dimethylbenzene) | S | S | * | 1 | 2-(iso-propylthio)-4-methyl-3-pyridyl |
| 222 | " | S | S | * | 2 | 2-(iso-propylthio)-4-methyl-3-pyridyl |
| 223 | " | S | S | * | 3 | 2-(iso-propylthio)-4-methyl-3-pyridyl |
| 224 | " | S | S | * | 4 | 2-(iso-propylthio)-4-methyl-3-pyridyl |
| 225 | " | S | S | * | 5 | 2-(iso-propylthio)-4-methyl-3-pyridyl |
| 226 | " | S | S | * | 6 | 2-(iso-propylthio)-4-methyl-3-pyridyl |
| 227 | " | S | S | * | 7 | 2-(iso-propylthio)-4-methyl-3-pyridyl |
| 228 | " | S | S | * | 8 | 2-(iso-propylthio)-4-methyl-3-pyridyl |
| 229 | " | S | S | * | 9 | 2-(iso-propylthio)-4-methyl-3-pyridyl |
| 230 | " | S | S | * | 14 | 2-(iso-propylthio)-4-methyl-3-pyridyl |
| 231 | " | NH | S | * | 1 | 2-(iso-propylthio)-4-methyl-3-pyridyl |
| 232 | " | NH | S | * | 2 | 2-(iso-propylthio)-4-methyl-3-pyridyl |
| 233 | " | NH | S | * | 3 | 2-(iso-propylthio)-4-methyl-3-pyridyl |
| 234 | " | NH | S | * | 4 | 2-(iso-propylthio)-4-methyl-3-pyridyl |
| 235 | " | NH | S | * | 5 | 2-(iso-propylthio)-4-methyl-3-pyridyl |
| 236 | " | NH | S | * | 6 | 2-(iso-propylthio)-4-methyl-3-pyridyl |

TABLE 12-continued

| Compound No. | A | X | Y | Z | n | Het |
|---|---|---|---|---|---|---|
| 237 | " | NH | S | * | 7 | 2-(iso-propylthio)-4-methyl-3-pyridyl |
| 238 | " | NH | S | * | 8 | 2-(iso-propylthio)-4-methyl-3-pyridyl |
| 239 | " | NH | S | * | 9 | 2-(iso-propylthio)-4-methyl-3-pyridyl |
| 240 | " | NH | S | * | 14 | 2-(iso-propylthio)-4-methyl-3-pyridyl |

*: Single Bond

TABLE 13

| Compound No. | A | X | Y | Z | n | Het |
|---|---|---|---|---|---|---|
| 241 | (dimethylbenzene) | O | S | * | 1 | 2-methoxy-4-methyl-3-pyridyl |
| 242 | " | O | S | * | 2 | 2-methoxy-4-methyl-3-pyridyl |
| 243 | " | O | S | * | 3 | 2-methoxy-4-methyl-3-pyridyl |
| 244 | " | O | S | * | 4 | 2-methoxy-4-methyl-3-pyridyl |
| 245 | " | O | S | * | 5 | 2-methoxy-4-methyl-3-pyridyl |
| 246 | " | O | S | * | 6 | 2-methoxy-4-methyl-3-pyridyl |
| 247 | " | O | S | * | 7 | 2-methoxy-4-methyl-3-pyridyl |
| 248 | " | O | S | * | 8 | 2-methoxy-4-methyl-3-pyridyl |
| 249 | " | O | S | * | 9 | 2-methoxy-4-methyl-3-pyridyl |
| 250 | " | O | S | * | 14 | 2-methoxy-4-methyl-3-pyridyl |
| 251 | " | S | S | * | 1 | 2-methoxy-4-methyl-3-pyridyl |
| 252 | " | S | S | * | 2 | 2-methoxy-4-methyl-3-pyridyl |
| 253 | " | S | S | * | 3 | 2-methoxy-4-methyl-3-pyridyl |
| 254 | " | S | S | * | 4 | 2-methoxy-4-methyl-3-pyridyl |
| 255 | " | S | S | * | 5 | 2-methoxy-4-methyl-3-pyridyl |
| 256 | " | S | S | * | 6 | 2-methoxy-4-methyl-3-pyridyl |
| 257 | " | S | S | * | 7 | 2-methoxy-4-methyl-3-pyridyl |
| 258 | " | S | S | * | 8 | 2-methoxy-4-methyl-3-pyridyl |
| 259 | " | S | S | * | 9 | 2-methoxy-4-methyl-3-pyridyl |
| 260 | " | S | S | * | 14 | 2-methoxy-4-methyl-3-pyridyl |

*: Single Bond

TABLE 14

| Compound No. | A | X | Y | Z | n | Het |
|---|---|---|---|---|---|---|
| 261 | 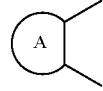 | NH | S | * | 1 | 2-methoxy-4-methyl-3-pyridyl |
| 262 | " | NH | S | * | 2 | 2-methoxy-4-methyl-3-pyridyl |
| 263 | " | NH | S | * | 3 | 2-methoxy-4-methyl-3-pyridyl |
| 264 | " | NH | S | * | 4 | 2-methoxy-4-methyl-3-pyridyl |
| 265 | " | NH | S | * | 5 | 2-methoxy-4-methyl-3-pyridyl |
| 266 | " | NH | S | * | 6 | 2-methoxy-4-methyl-3-pyridyl |
| 267 | " | NH | S | * | 7 | 2-methoxy-4-methyl-3-pyridyl |
| 268 | " | NH | S | * | 8 | 2-methoxy-4-methyl-3-pyridyl |
| 269 | " | NH | S | * | 9 | 2-methoxy-4-methyl-3-pyridyl |
| 270 | " | NH | S | * | 14 | 2-methoxy-4-methyl-3-pyridyl |
| 271 | " | O | S | * | 1 | 2,6-bismethylthio-3-pyridyl |
| 272 | " | O | S | * | 2 | 2,6-bismethylthio-3-pyridyl |
| 273 | " | O | S | * | 3 | 2,6-bismethylthio-3-pyridyl |
| 274 | " | O | S | * | 4 | 2,6-bismethylthio-3-pyridyl |
| 275 | " | O | S | * | 5 | 2,6-bismethylthio-3-pyridyl |
| 276 | " | O | S | * | 6 | 2,6-bismethylthio-3-pyridyl |
| 277 | " | O | S | * | 7 | 2,6-bismethylthio-3-pyridyl |
| 278 | " | O | S | * | 8 | 2,6-bismethylthio-3-pyridyl |
| 279 | " | O | S | * | 9 | 2,6-bismethylthio-3-pyridyl |
| 280 | " | O | S | * | 14 | 2,6-bismethylthio-3-pyridyl |

*: Single Bond

TABLE 15

| Compound No. | A | X | Y | Z | n | Het |
|---|---|---|---|---|---|---|
| 281 | 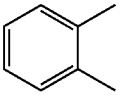 | S | S | * | 1 | 2,6-bismethylthio-3-pyridyl |
| 282 | " | S | S | * | 2 | 2,6-bismethylthio-3-pyridyl |
| 283 | " | S | S | * | 3 | 2,6-bismethylthio-3-pyridyl |
| 284 | " | S | S | * | 4 | 2,6-bismethylthio-3-pyridyl |
| 285 | " | S | S | * | 5 | 2,6-bismethylthio-3-pyridyl |
| 286 | " | S | S | * | 6 | 2,6-bismethylthio-3-pyridyl |
| 287 | " | S | S | * | 7 | 2,6-bismethylthio-3-pyridyl |
| 288 | " | S | S | * | 8 | 2,6-bismethylthio-3-pyridyl |
| 289 | " | S | S | * | 9 | 2,6-bismethylthio-3-pyridyl |
| 290 | " | S | S | * | 14 | 2,6-bismethylthio-3-pyridyl |
| 291 | " | NH | S | * | 1 | 2,6-bismethylthio-3-pyridyl |
| 292 | " | NH | S | * | 2 | 2,6-bismethylthio-3-pyridyl |
| 293 | " | NH | S | * | 3 | 2,6-bismethylthio-3-pyridyl |
| 294 | " | NH | S | * | 4 | 2,6-bismethylthio-3-pyridyl |
| 295 | " | NH | S | * | 5 | 2,6-bismethylthio-3-pyridyl |
| 296 | " | NH | S | * | 6 | 2,6-bismethylthio-3-pyridyl |
| 297 | " | NH | S | * | 7 | 2,6-bismethylthio-3-pyridyl |
| 298 | " | NH | S | * | 8 | 2,6-bismethylthio-3-pyridyl |
| 299 | " | NH | S | * | 9 | 2,6-bismethylthio-3-pyridyl |
| 300 | " | NH | S | * | 14 | 2,6-bismethylthio-3-pyridyl |

*: Single Bond

TABLE 16

| Compound No. | A | X | Y | Z | n | Het |
|---|---|---|---|---|---|---|
| 301 | 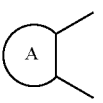 | O | S | * | 1 | 2,6-bisethylthio-3-pyridyl |
| 302 | " | O | S | * | 2 | 2,6-bisethylthio-3-pyridyl |
| 303 | " | O | S | * | 3 | 2,6-bisethylthio-3-pyridyl |
| 304 | " | O | S | * | 4 | 2,6-bisethylthio-3-pyridyl |
| 305 | " | O | S | * | 5 | 2,6-bisethylthio-3-pyridyl |
| 306 | " | O | S | * | 6 | 2,6-bisethylthio-3-pyridyl |
| 307 | " | O | S | * | 7 | 2,6-bisethylthio-3-pyridyl |
| 308 | " | O | S | * | 8 | 2,6-bisethylthio-3-pyridyl |
| 309 | " | O | S | * | 9 | 2,6-bisethylthio-3-pyridyl |
| 310 | " | O | S | * | 14 | 2,6-bisethylthio-3-pyridyl |
| 311 | " | S | S | * | 1 | 2,6-bisethylthio-3-pyridyl |
| 312 | " | S | S | * | 2 | 2,6-bisethylthio-3-pyridyl |
| 313 | " | S | S | * | 3 | 2,6-bisethylthio-3-pyridyl |
| 314 | " | S | S | * | 4 | 2,6-bisethylthio-3-pyridyl |
| 315 | " | S | S | * | 5 | 2,6-bisethylthio-3-pyridyl |
| 316 | " | S | S | * | 6 | 2,6-bisethylthio-3-pyridyl |
| 317 | " | S | S | * | 7 | 2,6-bisethylthio-3-pyridyl |
| 318 | " | S | S | * | 8 | 2,6-bisethylthio-3-pyridyl |
| 319 | " | S | S | * | 9 | 2,6-bisethylthio-3-pyridyl |
| 320 | " | S | S | * | 14 | 2,6-bisethylthio-3-pyridyl |

*: Single Bond

TABLE 17

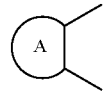

| Compound No. | A | X | Y | Z | n | Het |
|---|---|---|---|---|---|---|
| 321 | (benzene) | NH | S | * | 1 | 2,6-bisethylthio-3-pyridyl |
| 322 | " | NH | S | * | 2 | 2,6-bisethylthio-3-pyridyl |
| 323 | " | NH | S | * | 3 | 2,6-bisethylthio-3-pyridyl |
| 324 | " | NH | S | * | 4 | 2,6-bisethylthio-3-pyridyl |
| 325 | " | NH | S | * | 5 | 2,6-bisethylthio-3-pyridyl |
| 326 | " | NH | S | * | 6 | 2,6-bisethylthio-3-pyridyl |
| 327 | " | NH | S | * | 7 | 2,6-bisethylthio-3-pyridyl |
| 328 | " | NH | S | * | 8 | 2,6-bisethylthio-3-pyridyl |
| 329 | " | NH | S | * | 9 | 2,6-bisethylthio-3-pyridyl |
| 330 | " | NH | S | * | 14 | 2,6-bisethylthio-3-pyridyl |
| 331 | " | O | S | * | 1 | 2,6-bis(iso-propylthio)-3-pyridyl |
| 332 | " | O | S | * | 2 | 2,6-bis(iso-propylthio)-3-pyridyl |
| 333 | " | O | S | * | 3 | 2,6-bis(iso-propylthio)-3-pyridyl |
| 334 | " | O | S | * | 4 | 2,6-bis(iso-propylthio)-3-pyridyl |
| 335 | " | O | S | * | 5 | 2,6-bis(iso-propylthio)-3-pyridyl |
| 336 | " | O | S | * | 6 | 2,6-bis(iso-propylthio)-3-pyridyl |
| 337 | " | O | S | * | 7 | 2,6-bis(iso-propylthio)-3-pyridyl |
| 338 | " | O | S | * | 8 | 2,6-bis(iso-propylthio)-3-pyridyl |
| 339 | " | O | S | * | 9 | 2,6-bis(iso-propylthio)-3-pyridyl |
| 340 | " | O | S | * | 14 | 2,6-bis(iso-propylthio)-3-pyridyl |

*: Single Bond

TABLE 18

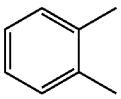

| Compound No. | A | X | Y | Z | n | Het |
|---|---|---|---|---|---|---|
| 341 | (benzene) | S | S | * | 1 | 2,6-bis(iso-propylthio)-3-pyridyl |
| 342 | " | S | S | * | 2 | 2,6-bis(iso-propylthio)-3-pyridyl |
| 343 | " | S | S | * | 3 | 2,6-bis(iso-propylthio)-3-pyridyl |
| 344 | " | S | S | * | 4 | 2,6-bis(iso-propylthio)-3-pyridyl |
| 345 | " | S | S | * | 5 | 2,6-bis(iso-propylthio)-3-pyridyl |
| 346 | " | S | S | * | 6 | 2,6-bis(iso-propylthio)-3-pyridyl |
| 347 | " | S | S | * | 7 | 2,6-bis(iso-propylthio)-3-pyridyl |
| 348 | " | S | S | * | 8 | 2,6-bis(iso-propylthio)-3-pyridyl |
| 349 | " | S | S | * | 9 | 2,6-bis(iso-propylthio)-3-pyridyl |
| 350 | " | S | S | * | 14 | 2,6-bis(iso-propylthio)-3-pyridyl |
| 351 | " | NH | S | * | 1 | 2,6-bis(iso-propylthio)-3-pyridyl |
| 352 | " | NH | S | * | 2 | 2,6-bis(iso-propylthio)-3-pyridyl |
| 353 | " | NH | S | * | 3 | 2,6-bis(iso-propylthio)-3-pyridyl |
| 354 | " | NH | S | * | 4 | 2,6-bis(iso-propylthio)-3-pyridyl |
| 355 | " | NH | S | * | 5 | 2,6-bis(iso-propylthio)-3-pyridyl |
| 356 | " | NH | S | * | 6 | 2,6-bis(iso-propylthio)-3-pyridyl |
| 357 | " | NH | S | * | 7 | 2,6-bis(iso-propylthio)-3-pyridyl |
| 358 | " | NH | S | * | 8 | 2,6-bis(iso-propylthio)-3-pyridyl |
| 359 | " | NH | S | * | 9 | 2,6-bis(iso-propylthio)-3-pyridyl |
| 360 | " | NH | S | * | 14 | 2,6-bis(iso-propylthio)-3-pyridyl |

*: Single Bond

TABLE 19

| Compound No. | A | X | Y | Z | n | Het |
|---|---|---|---|---|---|---|
| 361 | (benzene) | O | S | * | 1 | 2-methylthio-6-methoxy-3-pyridyl |
| 362 | " | O | S | * | 2 | 2-methylthio-6-methoxy-3-pyridyl |
| 363 | " | O | S | * | 3 | 2-methylthio-6-methoxy-3-pyridyl |
| 364 | " | O | S | * | 4 | 2-methylthio-6-methoxy-3-pyridyl |
| 365 | " | O | S | * | 5 | 2-methylthio-6-methoxy-3-pyridyl |
| 366 | " | O | S | * | 6 | 2-methylthio-6-methoxy-3-pyridyl |
| 367 | " | O | S | * | 7 | 2-methylthio-6-methoxy-3-pyridyl |
| 368 | " | O | S | * | 8 | 2-methylthio-6-methoxy-3-pyridyl |
| 369 | " | O | S | * | 9 | 2-methylthio-6-methoxy-3-pyridyl |
| 370 | " | O | S | * | 14 | 2-methylthio-6-methoxy-3-pyridyl |
| 371 | " | S | S | * | 1 | 2-methylthio-6-methoxy-3-pyridyl |
| 372 | " | S | S | * | 2 | 2-methylthio-6-methoxy-3-pyridyl |
| 373 | " | S | S | * | 3 | 2-methylthio-6-methoxy-3-pyridyl |
| 374 | " | S | S | * | 4 | 2-methylthio-6-methoxy-3-pyridyl |
| 375 | " | S | S | * | 5 | 2-methylthio-6-methoxy-3-pyridyl |
| 376 | " | S | S | * | 6 | 2-methylthio-6-methoxy-3-pyridyl |
| 377 | " | S | S | * | 7 | 2-methylthio-6-methoxy-3-pyridyl |
| 378 | " | S | S | * | 5 | 2-methylthio-6-methoxy-3-pyridyl |
| 379 | " | S | S | * | 9 | 2-methylthio-6-methoxy-3-pyridyl |
| 380 | " | S | S | * | 14 | 2-methylthio-6-methoxy-3-pyridyl |

*: Single Bond

TABLE 20

| Compound No. | A | X | Y | Z | n | Het |
|---|---|---|---|---|---|---|
| 381 | ortho-disubstituted benzene | NH | S | * | 1 | 2-methylthio-6-methoxy-3-pyridyl |
| 382 | " | NH | S | * | 2 | 2-methylthio-6-methoxy-3-pyridyl |
| 383 | " | NH | S | * | 3 | 2-methylthio-6-methoxy-3-pyridyl |
| 384 | " | NH | S | * | 4 | 2-methylthio-6-methoxy-3-pyridyl |
| 385 | " | NH | S | * | 5 | 2-methylthio-6-methoxy-3-pyridyl |
| 386 | " | NH | S | * | 6 | 2-methylthio-6-methoxy-3-pyridyl |
| 387 | " | NH | S | * | 7 | 2-methylthio-6-methoxy-3-pyridyl |
| 388 | " | NH | S | * | 8 | 2-methylthio-6-methoxy-3-pyridyl |
| 389 | " | NH | S | * | 9 | 2-methylthio-6-methoxy-3-pyridyl |
| 390 | " | NH | S | * | 14 | 2-methylthio-6-methoxy-3-pyridyl |
| 391 | " | O | S | * | 1 | 2-ethylthio-6-methoxy-3-pyridyl |
| 392 | " | O | S | * | 2 | 2-ethylthio-6-methoxy-3-pyridyl |
| 393 | " | O | S | * | 3 | 2-ethylthio-6-methoxy-3-pyridyl |
| 394 | " | O | S | * | 4 | 2-ethylthio-6-methoxy-3-pyridyl |
| 395 | " | O | S | * | 5 | 2-ethylthio-6-methoxy-3-pyridyl |
| 396 | " | O | S | * | 6 | 2-ethylthio-6-methoxy-3-pyridyl |
| 397 | " | O | S | * | 7 | 2-ethylthio-6-methoxy-3-pyridyl |
| 398 | " | O | S | * | 8 | 2-ethylthio-6-methoxy-3-pyridyl |
| 399 | " | O | S | * | 9 | 2-ethylthio-6-methoxy-3-pyridyl |
| 400 | " | O | S | * | 14 | 2-ethylthio-6-methoxy-3-pyridyl |

*: Single Bond

TABLE 21

| Compound No. | A | X | Y | Z | n | Het |
|---|---|---|---|---|---|---|
| 401 | ortho-disubstituted benzene | S | S | * | 1 | 2-ethylthio-6-methoxy-3-pyridyl |
| 402 | " | S | S | * | 2 | 2-ethylthio-6-methoxy-3-pyridyl |
| 403 | " | S | S | * | 3 | 2-ethylthio-6-methoxy-3-pyridyl |
| 404 | " | S | S | * | 4 | 2-ethylthio-6-methoxy-3-pyridyl |
| 405 | " | S | S | * | 5 | 2-ethylthio-6-methoxy-3-pyridyl |
| 406 | " | S | S | * | 6 | 2-ethylthio-6-methoxy-3-pyridyl |
| 407 | " | S | S | * | 7 | 2-ethylthio-6-methoxy-3-pyridyl |
| 408 | " | S | S | * | 8 | 2-ethylthio-6-methoxy-3-pyridyl |
| 409 | " | S | S | * | 9 | 2-ethylthio-6-methoxy-3-pyridyl |
| 410 | " | S | S | * | 14 | 2-ethylthio-6-methoxy-3-pyridyl |
| 411 | " | NH | S | * | 1 | 2-ethylthio-6-methoxy-3-pyridyl |
| 412 | " | NH | S | * | 2 | 2-ethylthio-6-methoxy-3-pyridyl |
| 413 | " | NH | S | * | 3 | 2-ethylthio-6-methoxy-3-pyridyl |
| 414 | " | NH | S | * | 4 | 2-ethylthio-6-methoxy-3-pyridyl |
| 415 | " | NH | S | * | 5 | 2-ethylthio-6-methoxy-3-pyridyl |
| 416 | " | NH | S | * | 6 | 2-ethylthio-6-methoxy-3-pyridyl |
| 417 | " | NH | S | * | 7 | 2-ethylthio-6-methoxy-3-pyridyl |
| 418 | " | NH | S | * | 8 | 2-ethylthio-6-methoxy-3-pyridyl |
| 419 | " | NH | S | * | 9 | 2-ethylthio-6-methoxy-3-pyridyl |
| 420 | " | NH | S | * | 14 | 2-ethylthio-6-methoxy-3-pyridyl |

*: Single Bond

TABLE 22

| Compound No. | A | X | Y | Z | n | Het |
|---|---|---|---|---|---|---|
| 421 | (2-methylphenyl) | O | S | * | 1 | 2-(iso-propylthio)-6-methoxy-3-pyridyl |
| 422 | " | O | S | * | 2 | 2-(iso-propylthio)-6-methoxy-3-pyridyl |
| 423 | " | O | S | * | 3 | 2-(iso-propylthio)-6-methoxy-3-pyridyl |
| 424 | " | O | S | * | 4 | 2-(iso-propylthio)-6-methoxy-3-pyridyl |
| 425 | " | O | S | * | 5 | 2-(iso-propylthio)-6-methoxy-3-pyridyl |
| 426 | " | O | S | * | 6 | 2-(iso-propylthio)-6-methoxy-3-pyridyl |
| 427 | " | O | S | * | 7 | 2-(iso-propylthio)-6-methoxy-3-pyridyl |
| 428 | " | O | S | * | 8 | 2-(iso-propylthio)-6-methoxy-3-pyridyl |
| 429 | " | O | S | * | 9 | 2-(iso-propylthio)-6-methoxy-3-pyridyl |
| 430 | " | O | S | * | 14 | 2-(iso-propylthio)-6-methoxy-3-pyridyl |
| 431 | " | S | S | * | 1 | 2-(iso-propylthio)-6-methoxy-3-pyridyl |
| 432 | " | S | S | * | 2 | 2-(iso-propylthio)-6-methoxy-3-pyridyl |
| 433 | " | S | S | * | 3 | 2-(iso-propylthio)-6-methoxy-3-pyridyl |
| 434 | " | S | S | * | 4 | 2-(iso-propylthio)-6-methoxy-3-pyridyl |
| 435 | " | S | S | * | 5 | 2-(iso-propylthio)-6-methoxy-3-pyridyl |
| 436 | " | S | S | * | 6 | 2-(iso-propylthio)-6-methoxy-3-pyridyl |
| 437 | " | S | S | * | 7 | 2-(iso-propylthio)-6-methoxy-3-pyridyl |
| 438 | " | S | S | * | 8 | 2-(iso-propylthio)-6-methoxy-3-pyridyl |
| 439 | " | S | S | * | 9 | 2-(iso-propylthio)-6-methoxy-3-pyridyl |
| 440 | " | S | S | * | 14 | 2-(iso-propylthio)-6-methoxy-3-pyridyl |

*: Single Bond

TABLE 23

| Compound No. | A | X | Y | Z | n | Het |
|---|---|---|---|---|---|---|
| 441 | (2-methylphenyl) | NH | S | * | 1 | 2-(iso-propylthio)-6-methoxy-3-pyridyl |
| 442 | " | NH | S | * | 2 | 2-(iso-propylthio)-6-methoxy-3-pyridyl |
| 443 | " | NH | S | * | 3 | 2-(iso-propylthio)-6-methoxy-3-pyridyl |
| 444 | " | NH | S | * | 4 | 2-(iso-propylthio)-6-methoxy-3-pyridyl |
| 445 | " | NH | S | * | 5 | 2-(iso-propylthio)-6-methoxy-3-pyridyl |
| 446 | " | NH | S | * | 6 | 2-(iso-propylthio)-6-methoxy-3-pyridyl |
| 447 | " | NH | S | * | 7 | 2-(iso-propylthio)-6-methoxy-3-pyridyl |
| 448 | " | NH | S | * | 8 | 2-(iso-propylthio)-6-methoxy-3-pyridyl |
| 449 | " | NH | S | * | 9 | 2-(iso-propylthio)-6-methoxy-3-pyridyl |
| 450 | " | NH | S | * | 14 | 2-(iso-propylthio)-6-methoxy-3-pyridyl |
| 451 | " | O | S | * | 1 | 2-methylthio-6-methyl-3-pyridyl |
| 452 | " | O | S | * | 2 | 2-methylthio-6-methyl-3-pyridyl |
| 453 | " | O | S | * | 3 | 2-methylthio-6-methyl-3-pyridyl |
| 454 | " | O | S | * | 4 | 2-methylthio-6-methyl-3-pyridyl |
| 455 | " | O | S | * | 5 | 2-methylthio-6-methyl-3-pyridyl |
| 456 | " | O | S | * | 6 | 2-methylthio-6-methyl-3-pyridyl |
| 457 | " | O | S | * | 7 | 2-methylthio-6-methyl-3-pyridyl |
| 458 | " | O | S | * | 8 | 2-methylthio-6-methyl-3-pyridyl |
| 459 | " | O | S | * | 9 | 2-methylthio-6-methyl-3-pyridyl |
| 460 | " | O | S | * | 14 | 2-methylthio-6-methyl-3-pyridyl |

*: Single Bond

TABLE 24

| Compound No. | A | X | Y | Z | n | Het |
|---|---|---|---|---|---|---|
| 461 |  | S | S | * | 1 | 2-methylthio-6-methyl-3-pyridyl |
| 462 | " | S | S | * | 2 | 2-methylthio-6-methyl-3-pyridyl |
| 463 | " | S | S | * | 3 | 2-methylthio-6-methyl-3-pyridyl |
| 464 | " | S | S | * | 4 | 2-methylthio-6-methyl-3-pyridyl |
| 465 | " | S | S | * | 5 | 2-methylthio-6-methyl-3-pyridyl |
| 466 | " | S | S | * | 6 | 2-methylthio-6-methyl-3-pyridyl |
| 467 | " | S | S | * | 7 | 2-methylthio-6-methyl-3-pyridyl |
| 468 | " | S | S | * | 8 | 2-methylthio-6-methyl-3-pyridyl |
| 469 | " | S | S | * | 9 | 2-methylthio-6-methyl-3-pyridyl |
| 470 | " | S | S | * | 14 | 2-methylthio-6-methyl-3-pyridyl |
| 471 | " | NH | S | * | 1 | 2-methylthio-6-methyl-3-pyridyl |
| 472 | " | NH | S | * | 2 | 2-methylthio-6-methyl-3-pyridyl |
| 473 | " | NH | S | * | 3 | 2-methylthio-6-methyl-3-pyridyl |
| 474 | " | NH | S | * | 4 | 2-methylthio-6-methyl-3-pyridyl |
| 475 | " | NH | S | * | 5 | 2-methylthio-6-methyl-3-pyridyl |
| 476 | " | NH | S | * | 6 | 2-methylthio-6-methyl-3-pyridyl |
| 477 | " | NH | S | * | 7 | 2-methylthio-6-methyl-3-pyridyl |
| 478 | " | NH | S | * | 8 | 2-methylthio-6-methyl-3-pyridyl |
| 479 | " | NH | S | * | 9 | 2-methylthio-6-methyl-3-pyridyl |
| 480 | " | NH | S | * | 14 | 2-methylthio-6-methyl-3-pyridyl |

*: Single Bond

TABLE 25

| Compound No. | A | X | Y | Z | n | Het |
|---|---|---|---|---|---|---|
| 481 |  | O | S | * | 1 | 2-ethylthio-6-methyl-3-pyridyl |
| 482 | " | O | S | * | 2 | 2-ethylthio-6-methyl-3-pyridyl |
| 483 | " | O | S | * | 3 | 2-ethylthio-6-methyl-3-pyridyl |
| 484 | " | O | S | * | 4 | 2-ethylthio-6-methyl-3-pyridyl |
| 485 | " | O | S | * | 5 | 2-ethylthio-6-methyl-3-pyridyl |
| 486 | " | O | S | * | 6 | 2-ethylthio-6-methyl-3-pyridyl |
| 487 | " | O | S | * | 7 | 2-ethylthio-6-methyl-3-pyridyl |
| 488 | " | O | S | * | 8 | 2-ethylthio-6-methyl-3-pyridyl |
| 489 | " | O | S | * | 9 | 2-ethylthio-6-methyl-3-pyridyl |
| 490 | " | O | S | * | 14 | 2-ethylthio-6-methyl-3-pyridyl |
| 491 | " | S | S | * | 1 | 2-ethylthio-6-methyl-3-pyridyl |
| 492 | " | S | S | * | 2 | 2-ethylthio-6-methyl-3-pyridyl |
| 493 | " | S | S | * | 3 | 2-ethylthio-6-methyl-3-pyridyl |
| 494 | " | S | S | * | 4 | 2-ethylthio-6-methyl-3-pyridyl |
| 495 | " | S | S | * | 5 | 2-ethylthio-6-methyl-3-pyridyl |
| 496 | " | S | S | * | 6 | 2-ethylthio-6-methyl-3-pyridyl |
| 497 | " | S | S | * | 7 | 2-ethylthio-6-methyl-3-pyridyl |
| 498 | " | S | S | * | 8 | 2-ethylthio-6-methyl-3-pyridyl |
| 499 | " | S | S | * | 9 | 2-ethylthio-6-methyl-3-pyridyl |
| 500 | " | S | S | * | 14 | 2-ethylthio-6-methyl-3-pyridyl |

*: Single Bond

TABLE 26

| Compound No. | A | X | Y | Z | n | Het |
|---|---|---|---|---|---|---|
| 501 |  | NH | S | * | 1 | 2-ethylthio-6-methyl-3-pyridyl |
| 502 | " | NH | S | * | 2 | 2-ethylthio-6-methyl-3-pyridyl |
| 503 | " | NH | S | * | 3 | 2-ethylthio-6-methyl-3-pyridyl |
| 504 | " | NH | S | * | 4 | 2-ethylthio-6-methyl-3-pyridyl |
| 505 | " | NH | S | * | 5 | 2-ethylthio-6-methyl-3-pyridyl |
| 506 | " | NH | S | * | 6 | 2-ethylthio-6-methyl-3-pyridyl |
| 507 | " | NH | S | * | 7 | 2-ethylthio-6-methyl-3-pyridyl |
| 508 | " | NH | S | * | 8 | 2-ethylthio-6-methyl-3-pyridyl |
| 509 | " | NH | S | * | 9 | 2-ethylthio-6-methyl-3-pyridyl |
| 510 | " | NH | S | * | 14 | 2-ethylthio-6-methyl-3-pyridyl |
| 511 | " | O | S | * | 1 | 2-(iso-propylthio)-6-methyl-3-pyridyl |
| 512 | " | O | S | * | 2 | 2-(iso-propylthio)-6-methyl-3-pyridyl |
| 513 | " | O | S | * | 3 | 2-(iso-propylthio)-6-methyl-3-pyridyl |
| 514 | " | O | S | * | 4 | 2-(iso-propylthio)-6-methyl-3-pyridyl |
| 515 | " | O | S | * | 5 | 2-(iso-propylthio)-6-methyl-3-pyridyl |
| 516 | " | O | S | * | 6 | 2-(iso-propylthio)-6-methyl-3-pyridyl |
| 517 | " | O | S | * | 7 | 2-(iso-propylthio)-6-methyl-3-pyridyl |
| 518 | " | O | S | * | 8 | 2-(iso-propylthio)-6-methyl-3-pyridyl |
| 519 | " | O | S | * | 9 | 2-(iso-propylthio)-6-methyl-3-pyridyl |
| 520 | " | O | S | * | 14 | 2-(iso-propylthio)-6-methyl-3-pyridyl |

*: Single Bond

TABLE 27

| Compound No. | A | X | Y | Z | n | Het |
|---|---|---|---|---|---|---|
| 521 | 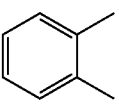 | S | S | * | 1 | 2-(iso-propylthio)-6-methyl-3-pyridyl |
| 522 | " | S | S | * | 2 | 2-(iso-propylthio)-6-methyl-3-pyridyl |
| 523 | " | S | S | * | 3 | 2-(iso-propylthio)-6-methyl-3-pyridyl |
| 524 | " | S | S | * | 4 | 2-(iso-propylthio)-6-methyl-3-pyridyl |
| 525 | " | S | S | * | 5 | 2-(iso-propylthio)-6-methyl-3-pyridyl |
| 526 | " | S | S | * | 6 | 2-(iso-propylthio)-6-methyl-3-pyridyl |
| 527 | " | S | S | * | 7 | 2-(iso-propylthio)-6-methyl-3-pyridyl |
| 528 | " | S | S | * | 8 | 2-(iso-propylthio)-6-methyl-3-pyridyl |
| 529 | " | S | S | * | 9 | 2-(iso-propylthio)-6-methyl-3-pyridyl |
| 530 | " | S | S | * | 14 | 2-(iso-propylthio)-6-methyl-3-pyridyl |
| 531 | " | NH | S | * | 1 | 2-(iso-propylthio)-6-methyl-3-pyridyl |
| 532 | " | NH | S | * | 2 | 2-(iso-propylthio)-6-methyl-3-pyridyl |
| 533 | " | NH | S | * | 3 | 2-(iso-propylthio)-6-methyl-3-pyridyl |
| 534 | " | NH | S | * | 4 | 2-(iso-propylthio)-6-methyl-3-pyridyl |
| 535 | " | NH | S | * | 5 | 2-(iso-propylthio)-6-methyl-3-pyridyl |
| 536 | " | NH | S | * | 6 | 2-(iso-propylthio)-6-methyl-3-pyridyl |
| 537 | " | NH | S | * | 7 | 2-(iso-propylthio)-6-methyl-3-pyridyl |
| 538 | " | NH | S | * | 8 | 2-(iso-propylthio)-6-methyl-3-pyridyl |
| 539 | " | NH | S | * | 9 | 2-(iso-propylthio)-6-methyl-3-pyridyl |
| 540 | " | NH | S | * | 14 | 2-(iso-propylthio)-6-methyl-3-pyridyl |

*: Single Bond

TABLE 28

| Compound No. | A | X | Y | Z | n | Het |
|---|---|---|---|---|---|---|
| 541 |  | O | S | * | 1 | 2,6-dimethoxyl-3-pyridyl |
| 542 | " | O | S | * | 2 | 2,6-dimethoxyl-3-pyridyl |
| 543 | " | O | S | * | 3 | 2,6-dimethoxyl-3-pyridyl |
| 544 | " | O | S | * | 4 | 2,6-dimethoxyl-3-pyridyl |
| 545 | " | O | S | * | 5 | 2,6-dimethoxyl-3-pyridyl |
| 546 | " | O | S | * | 6 | 2,6-dimethoxyl-3-pyridyl |
| 547 | " | O | S | * | 7 | 2,6-dimethoxyl-3-pyridyl |
| 548 | " | O | S | * | 8 | 2,6-dimethoxyl-3-pyridyl |
| 549 | " | O | S | * | 9 | 2,6-dimethoxyl-3-pyridyl |
| 550 | " | O | S | * | 14 | 2,6-dimethoxyl-3-pyridyl |
| 551 | " | S | S | * | 1 | 2,6-dimethoxyl-3-pyridyl |
| 552 | " | S | S | * | 2 | 2,6-dimethoxyl-3-pyridyl |
| 553 | " | S | S | * | 3 | 2,6-dimethoxyl-3-pyridyl |
| 554 | " | S | S | * | 4 | 2,6-dimethoxyl-3-pyridyl |
| 555 | " | S | S | * | 5 | 2,6-dimethoxyl-3-pyridyl |
| 556 | " | S | S | * | 6 | 2,6-dimethoxyl-3-pyridyl |
| 557 | " | S | S | * | 7 | 2,6-dimethoxyl-3-pyridyl |
| 558 | " | S | S | * | 8 | 2,6-dimethoxyl-3-pyridyl |
| 559 | " | S | S | * | 9 | 2,6-dimethoxyl-3-pyridyl |
| 560 | " | S | S | * | 14 | 2,6-dimethoxyl-3-pyridyl |

*: Single Bond

TABLE 29

| Compound No. | A | X | Y | Z | n | Het |
|---|---|---|---|---|---|---|
| 561 |  | NH | S | * | 1 | 2,6-dimethoxyl-3-pyridyl |
| 562 | " | NH | S | * | 2 | 2,6-dimethoxyl-3-pyridyl |
| 563 | " | NH | S | * | 3 | 2,6-dimethoxyl-3-pyridyl |
| 564 | " | NH | S | * | 4 | 2,6-dimethoxyl-3-pyridyl |
| 565 | " | NH | S | * | 5 | 2,6-dimethoxyl-3-pyridyl |
| 566 | " | NH | S | * | 6 | 2,6-dimethoxyl-3-pyridyl |
| 567 | " | NH | S | * | 7 | 2,6-dimethoxyl-3-pyridyl |
| 568 | " | NH | S | * | 8 | 2,6-dimethoxyl-3-pyridyl |
| 569 | " | NH | S | * | 9 | 2,6-dimethoxyl-3-pyridyl |
| 570 | " | NH | S | * | 14 | 2,6-dimethoxyl-3-pyridyl |
| 571 | " | O | S | * | 1 | 2-methoxy-6-methyl-3-pyridyl |
| 572 | " | O | S | * | 2 | 2-methoxy-6-methyl-3-pyridyl |
| 573 | " | O | S | * | 3 | 2-methoxy-6-methyl-3-pyridyl |
| 574 | " | O | S | * | 4 | 2-methoxy-6-methyl-3-pyridyl |
| 575 | " | O | S | * | 5 | 2-methoxy-6-methyl-3-pyridyl |
| 576 | " | O | S | * | 6 | 2-methoxy-6-methyl-3-pyridyl |
| 577 | " | O | S | * | 7 | 2-methoxy-6-methyl-3-pyridyl |
| 578 | " | O | S | * | 8 | 2-methoxy-6-methyl-3-pyridyl |
| 579 | " | O | S | * | 9 | 2-methoxy-6-methyl-3-pyridyl |
| 580 | " | O | S | * | 14 | 2-methoxy-6-methyl-3-pyridyl |

*: Single Bond

TABLE 30

| Compound No. | A | X | Y | Z | n | Het |
|---|---|---|---|---|---|---|
| 581 | benzene (ortho-disubstituted) | S | S | * | 1 | 2-methoxy-6-methyl-3-pyridyl |
| 582 | " | S | S | * | 2 | 2-methoxy-6-methyl-3-pyridyl |
| 583 | " | S | S | * | 3 | 2-methoxy-6-methyl-3-pyridyl |
| 584 | " | S | S | * | 4 | 2-methoxy-6-methyl-3-pyridyl |
| 585 | " | S | S | * | 5 | 2-methoxy-6-methyl-3-pyridyl |
| 586 | " | S | S | * | 6 | 2-methoxy-6-methyl-3-pyridyl |
| 587 | " | S | S | * | 7 | 2-methoxy-6-methyl-3-pyridyl |
| 588 | " | S | S | * | 8 | 2-methoxy-6-methyl-3-pyridyl |
| 589 | " | S | S | * | 9 | 2-methoxy-6-methyl-3-pyridyl |
| 590 | " | S | S | * | 14 | 2-methoxy-6-methyl-3-pyridyl |
| 591 | " | NH | S | * | 1 | 2-methoxy-6-methyl-3-pyridyl |
| 592 | " | NH | S | * | 2 | 2-methoxy-6-methyl-3-pyridyl |
| 593 | " | NH | S | * | 3 | 2-methoxy-6-methyl-3-pyridyl |
| 594 | " | NH | S | * | 4 | 2-methoxy-6-methyl-3-pyridyl |
| 595 | " | NH | S | * | 5 | 2-methoxy-6-methyl-3-pyridyl |
| 596 | " | NH | S | * | 6 | 2-methoxy-6-methyl-3-pyridyl |
| 597 | " | NH | S | * | 7 | 2-methoxy-6-methyl-3-pyridyl |
| 598 | " | NH | S | * | 8 | 2-methoxy-6-methyl-3-pyridyl |
| 599 | " | NH | S | * | 9 | 2-methoxy-6-methyl-3-pyridyl |
| 600 | " | NH | S | * | 14 | 2-methoxy-6-methyl-3-pyridyl |

*: Single Bond

TABLE 31

| Compound No. | A | X | Y | Z | n | Het |
|---|---|---|---|---|---|---|
| 601 | benzene (ortho-disubstituted) | O | S | * | 1 | 2-methyl-6-methythio-3-pyridyl |
| 602 | " | O | S | * | 2 | 2-methyl-6-methythio-3-pyridyl |
| 603 | " | O | S | * | 3 | 2-methyl-6-methythio-3-pyridyl |
| 604 | " | O | S | * | 4 | 2-methyl-6-methythio-3-pyridyl |
| 605 | " | O | S | * | 5 | 2-methyl-6-methythio-3-pyridyl |
| 606 | " | O | S | * | 6 | 2-methyl-6-methythio-3-pyridyl |
| 607 | " | O | S | * | 7 | 2-methyl-6-methythio-3-pyridyl |
| 608 | " | O | S | * | 8 | 2-methyl-6-methythio-3-pyridyl |
| 609 | " | O | S | * | 9 | 2-methyl-6-methythio-3-pyridyl |
| 610 | " | O | S | * | 14 | 2-methyl-6-methythio-3-pyridyl |
| 611 | " | S | S | * | 1 | 2-methyl-6-methythio-3-pyridyl |
| 612 | " | S | S | * | 2 | 2-methyl-6-methythio-3-pyridyl |
| 613 | " | S | S | * | 3 | 2-methyl-6-methythio-3-pyridyl |
| 614 | " | S | S | * | 4 | 2-methyl-6-methythio-3-pyridyl |
| 615 | " | S | S | * | 5 | 2-methyl-6-methythio-3-pyridyl |
| 616 | " | S | S | * | 6 | 2-methyl-6-methythio-3-pyridyl |
| 617 | " | S | S | * | 7 | 2-methyl-6-methythio-3-pyridyl |
| 618 | " | S | S | * | 8 | 2-methyl-6-methythio-3-pyridyl |
| 619 | " | S | S | * | 9 | 2-methyl-6-methythio-3-pyridyl |
| 620 | " | S | S | * | 14 | 2-methyl-6-methythio-3-pyridyl |

*: Single Bond

TABLE 32

| Compound No. | A | X | Y | Z | n | Het |
|---|---|---|---|---|---|---|
| 621 | benzene (ortho-disubstituted) | NH | S | * | 1 | 2-methyl-6-methythio-3-pyridyl |
| 622 | " | NH | S | * | 2 | 2-methyl-6-methythio-3-pyridyl |
| 623 | " | NH | S | * | 3 | 2-methyl-6-methythio-3-pyridyl |
| 624 | " | NH | S | * | 4 | 2-methyl-6-methythio-3-pyridyl |
| 625 | " | NH | S | * | 5 | 2-methyl-6-methythio-3-pyridyl |
| 626 | " | NH | S | * | 6 | 2-methyl-6-methythio-3-pyridyl |

TABLE 32-continued

| Compound No. | A | X | Y | Z | n | Het |
|---|---|---|---|---|---|---|
| 627 | " | NH | S | * | 7 | 2-methyl-6-methythio-3-pyridyl |
| 628 | " | NH | S | * | 8 | 2-methyl-6-methythio-3-pyridyl |
| 629 | " | NH | S | * | 9 | 2-methyl-6-methythio-3-pyridyl |
| 630 | " | NH | S | * | 14 | 2-methyl-6-methythio-3-pyridyl |
| 631 | " | O | S | * | 1 | 2-methyl-6-ethythio-3-pyridyl |
| 632 | " | O | S | * | 2 | 2-methyl-6-ethythio-3-pyridyl |
| 633 | " | O | S | * | 3 | 2-methyl-6-ethythio-3-pyridyl |
| 634 | " | O | S | * | 4 | 2-methyl-6-ethythio-3-pyridyl |
| 635 | " | O | S | * | 5 | 2-methyl-6-ethythio-3-pyridyl |
| 636 | " | O | S | * | 6 | 2-methyl-6-ethythio-3-pyridyl |
| 637 | " | O | S | * | 7 | 2-methyl-6-ethythio-3-pyridyl |
| 638 | " | O | S | * | 8 | 2-methyl-6-ethythio-3-pyridyl |
| 639 | " | O | S | * | 9 | 2-methyl-6-ethythio-3-pyridyl |
| 640 | " | O | S | * | 14 | 2-methyl-6-ethythio-3-pyridyl |

*: Single Bond

TABLE 33

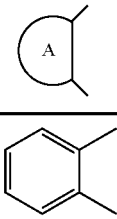

| Compound No. | A | X | Y | Z | n | Het |
|---|---|---|---|---|---|---|
| 641 | (2,3-dimethylphenyl) | S | S | * | 1 | 2-methyl-6-ethythio-3-pyridyl |
| 642 | " | S | S | * | 2 | 2-methyl-6-ethythio-3-pyridyl |
| 643 | " | S | S | * | 3 | 2-methyl-6-ethythio-3-pyridyl |
| 644 | " | S | S | * | 4 | 2-methyl-6-ethythio-3-pyridyl |
| 645 | " | S | S | * | 5 | 2-methyl-6-ethythio-3-pyridyl |
| 646 | " | S | S | * | 6 | 2-methyl-6-ethythio-3-pyridyl |
| 647 | " | S | S | * | 7 | 2-methyl-6-ethythio-3-pyridyl |
| 648 | " | S | S | * | 8 | 2-methyl-6-ethythio-3-pyridyl |
| 649 | " | S | S | * | 9 | 2-methyl-6-ethythio-3-pyridyl |
| 650 | " | S | S | * | 14 | 2-methyl-6-ethythio-3-pyridyl |
| 651 | " | NH | S | * | 1 | 2-methyl-6-ethythio-3-pyridyl |
| 652 | " | NH | S | * | 2 | 2-methyl-6-ethythio-3-pyridyl |
| 653 | " | NH | S | * | 3 | 2-methyl-6-ethythio-3-pyridyl |
| 654 | " | NH | S | * | 4 | 2-methyl-6-ethythio-3-pyridyl |
| 655 | " | NH | S | * | 5 | 2-methyl-6-ethythio-3-pyridyl |
| 656 | " | NH | S | * | 6 | 2-methyl-6-ethythio-3-pyridyl |
| 657 | " | NH | S | * | 7 | 2-methyl-6-ethythio-3-pyridyl |
| 658 | " | NH | S | * | 8 | 2-methyl-6-ethythio-3-pyridyl |
| 659 | " | NH | S | * | 9 | 2-methyl-6-ethythio-3-pyridyl |
| 660 | " | NH | S | * | 14 | 2-methyl-6-ethythio-3-pyridyl |

*: Single Bond

TABLE 34

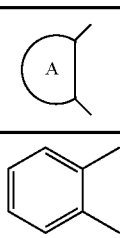

| Compound No. | A | X | Y | Z | n | Het |
|---|---|---|---|---|---|---|
| 661 | (2,3-dimethylphenyl) | O | S | * | 1 | 2-methyl-6-(iso-propylthio)-3-pyridyl |
| 662 | " | O | S | * | 2 | 2-methyl-6-(iso-propylthio)-3-pyridyl |
| 663 | " | O | S | * | 3 | 2-methyl-6-(iso-propylthio)-3-pyridyl |
| 664 | " | O | S | * | 4 | 2-methyl-6-(iso-propylthio)-3-pyridyl |
| 665 | " | O | S | * | 5 | 2-methyl-6-(iso-propylthio)-3-pyridyl |
| 666 | " | O | S | * | 6 | 2-methyl-6-(iso-propylthio)-3-pyridyl |
| 667 | " | O | S | * | 7 | 2-methyl-6-(iso-propylthio)-3-pyridyl |
| 668 | " | O | S | * | 8 | 2-methyl-6-(iso-propylthio)-3-pyridyl |
| 669 | " | O | S | * | 9 | 2-methyl-6-(iso-propylthio)-3-pyridyl |
| 670 | " | O | S | * | 14 | 2-methyl-6-(iso-propylthio)-3-pyridyl |
| 671 | " | S | S | * | 1 | 2-methyl-6-(iso-propylthio)-3-pyridyl |
| 672 | " | S | S | * | 2 | 2-methyl-6-(iso-propylthio)-3-pyridyl |
| 673 | " | S | S | * | 3 | 2-methyl-6-(iso-propylthio)-3-pyridyl |
| 674 | " | S | S | * | 4 | 2-methyl-6-(iso-propylthio)-3-pyridyl |
| 675 | " | S | S | * | 5 | 2-methyl-6-(iso-propylthio)-3-pyridyl |
| 676 | " | S | S | * | 6 | 2-methyl-6-(iso-propylthio)-3-pyridyl |
| 677 | " | S | S | * | 7 | 2-methyl-6-(iso-propylthio)-3-pyridyl |
| 678 | " | S | S | * | 8 | 2-methyl-6-(iso-propylthio)-3-pyridyl |
| 679 | " | S | S | * | 9 | 2-methyl-6-(iso-propylthio)-3-pyridyl |
| 680 | " | S | S | * | 14 | 2-methyl-6-(iso-propylthio)-3-pyridyl |

*: Single Bond

TABLE 35

| Compound No. | A | X | Y | Z | n | Het |
|---|---|---|---|---|---|---|
| 681 | (o-disubstituted benzene) | NH | S | * | 1 | 2-methyl-6-(iso-propylthio)-3-pyridyl |
| 682 | " | NH | S | * | 2 | 2-methyl-6-(iso-propylthio)-3-pyridyl |
| 683 | " | NH | S | * | 3 | 2-methyl-6-(iso-propylthio)-3-pyridyl |
| 684 | " | NH | S | * | 4 | 2-methyl-6-(iso-propylthio)-3-pyridyl |
| 685 | " | NH | S | * | 5 | 2-methyl-6-(iso-propylthio)-3-pyridyl |
| 686 | " | NH | S | * | 6 | 2-methyl-6-(iso-propylthio)-3-pyridyl |
| 687 | " | NH | S | * | 7 | 2-methyl-6-(iso-propylthio)-3-pyridyl |
| 688 | " | NH | S | * | 8 | 2-methyl-6-(iso-propylthio)-3-pyridyl |
| 689 | " | NH | S | * | 9 | 2-methyl-6-(iso-propylthio)-3-pyridyl |
| 690 | " | NH | S | * | 14 | 2-methyl-6-(iso-propylthio)-3-pyridyl |
| 691 | " | O | S | * | 1 | 2-methyl-6-mehoxy-3-pyridyl |
| 692 | " | O | S | * | 2 | 2-methyl-6-mehoxy-3-pyridyl |
| 693 | " | O | S | * | 3 | 2-methyl-6-mehoxy-3-pyridyl |
| 694 | " | O | S | * | 4 | 2-methyl-6-mehoxy-3-pyridyl |
| 695 | " | O | S | * | 5 | 2-methyl-6-mehoxy-3-pyridyl |
| 696 | " | O | S | * | 6 | 2-methyl-6-mehoxy-3-pyridyl |
| 697 | " | O | S | * | 7 | 2-methyl-6-mehoxy-3-pyridyl |
| 698 | " | O | S | * | 8 | 2-methyl-6-mehoxy-3-pyridyl |
| 699 | " | O | S | * | 9 | 2-methyl-6-mehoxy-3-pyridyl |
| 700 | " | O | S | * | 14 | 2-methyl-6-mehoxy-3-pyridyl |

*: Single Bond

TABLE 36

| Compound No. | A | X | Y | Z | n | Het |
|---|---|---|---|---|---|---|
| 701 | (o-disubstituted benzene) | S | S | * | 1 | 2-methyl-6-mehoxy-3-pyridyl |
| 702 | " | S | S | * | 2 | 2-methyl-6-mehoxy-3-pyridyl |
| 703 | " | S | S | * | 3 | 2-methyl-6-mehoxy-3-pyridyl |
| 704 | " | S | S | * | 4 | 2-methyl-6-mehoxy-3-pyridyl |
| 705 | " | S | S | * | 5 | 2-methyl-6-mehoxy-3-pyridyl |
| 706 | " | S | S | * | 6 | 2-methyl-6-mehoxy-3-pyridyl |
| 707 | " | S | S | * | 7 | 2-methyl-6-mehoxy-3-pyridyl |
| 708 | " | S | S | * | 8 | 2-methyl-6-mehoxy-3-pyridyl |
| 709 | " | S | S | * | 9 | 2-methyl-6-mehoxy-3-pyridyl |
| 710 | " | S | S | * | 14 | 2-methyl-6-mehoxy-3-pyridyl |
| 711 | " | NH | S | * | 1 | 2-methyl-6-mehoxy-3-pyridyl |
| 712 | " | NH | S | * | 2 | 2-methyl-6-mehoxy-3-pyridyl |
| 713 | " | NH | S | * | 3 | 2-methyl-6-mehoxy-3-pyridyl |
| 714 | " | NH | S | * | 4 | 2-methyl-6-mehoxy-3-pyridyl |
| 715 | " | NH | S | * | 5 | 2-methyl-6-mehoxy-3-pyridyl |
| 716 | " | NH | S | * | 6 | 2-methyl-6-mehoxy-3-pyridyl |
| 717 | " | NH | S | * | 7 | 2-methyl-6-mehoxy-3-pyridyl |
| 718 | " | NH | S | * | 8 | 2-methyl-6-mehoxy-3-pyridyl |
| 719 | " | NH | S | * | 9 | 2-methyl-6-mehoxy-3-pyridyl |
| 720 | " | NH | S | * | 14 | 2-methyl-6-mehoxy-3-pyridyl |

*: Single Bond

TABLE 37

| Compound No. | A | X | Y | Z | n | Het |
|---|---|---|---|---|---|---|
| 721 | (o-disubstituted benzene) | O | S | * | 1 | 2, 6-dimethyl-3-pyridyl |
| 722 | " | O | S | * | 2 | 2, 6-dimethyl-3-pyridyl |
| 723 | " | O | S | * | 3 | 2, 6-dimethyl-3-pyridyl |
| 724 | " | O | S | * | 4 | 2, 6-dimethyl-3-pyridyl |
| 725 | " | O | S | * | 5 | 2, 6-dimethyl-3-pyridyl |
| 726 | " | O | S | * | 6 | 2, 6-dimethyl-3-pyridyl |
| 727 | " | O | S | * | 7 | 2, 6-dimethyl-3-pyridyl |
| 728 | " | O | S | * | 8 | 2, 6-dimethyl-3-pyridyl |
| 729 | " | O | S | * | 9 | 2, 6-dimethyl-3-pyridyl |

TABLE 37-continued

| Compound No. | A | X | Y | Z | n | Het |
|---|---|---|---|---|---|---|
| 730 | " | O | S | * | 14 | 2,6-dimethyl-3-pyridyl |
| 731 | " | S | S | * | 1 | 2,6-dimethyl-3-pyridyl |
| 732 | " | S | S | * | 2 | 2,6-dimethyl-3-pyridyl |
| 733 | " | S | S | * | 3 | 2,6-dimethyl-3-pyridyl |
| 734 | " | S | S | * | 4 | 2,6-dimethyl-3-pyridyl |
| 735 | " | S | S | * | 5 | 2,6-dimethyl-3-pyridyl |
| 736 | " | S | S | * | 6 | 2,6-dimethyl-3-pyridyl |
| 737 | " | S | S | * | 7 | 2,6-dimethyl-3-pyridyl |
| 738 | " | S | S | * | 8 | 2,6-dimethyl-3-pyridyl |
| 739 | " | S | S | * | 9 | 2,6-dimethyl-3-pyridyl |
| 740 | " | S | S | * | 14 | 2,6-dimethyl-3-pyridyl |

*: Single Bond

TABLE 38

| Compound No. | A | X | Y | Z | n | Het |
|---|---|---|---|---|---|---|
| 741 | (o-xylyl) | NH | S | * | 1 | 2,6-dimethyl-3-pyridyl |
| 742 | " | NH | S | * | 2 | 2,6-dimethyl-3-pyridyl |
| 743 | " | NH | S | * | 3 | 2,6-dimethyl-3-pyridyl |
| 744 | " | NH | S | * | 4 | 2,6-dimethyl-3-pyridyl |
| 745 | " | NH | S | * | 5 | 2,6-dimethyl-3-pyridyl |
| 746 | " | NH | S | * | 6 | 2,6-dimethyl-3-pyridyl |
| 747 | " | NH | S | * | 7 | 2,6-dimethyl-3-pyridyl |
| 748 | " | NH | S | * | 8 | 2,6-dimethyl-3-pyridyl |
| 749 | " | NH | S | * | 9 | 2,6-dimethyl-3-pyridyl |
| 750 | " | NH | S | * | 14 | 2,6-dimethyl-3-pyridyl |
| 751 | " | O | S | * | 1 | 2,6-diethyl-3-pyridyl |
| 752 | " | O | S | * | 2 | 2,6-diethyl-3-pyridyl |
| 753 | " | O | S | * | 3 | 2,6-diethyl-3-pyridyl |
| 754 | " | O | S | * | 4 | 2,6-diethyl-3-pyridyl |
| 755 | " | O | S | * | 5 | 2,6-diethyl-3-pyridyl |
| 756 | " | O | S | * | 6 | 2,6-diethyl-3-pyridyl |
| 757 | " | O | S | * | 7 | 2,6-diethyl-3-pyridyl |
| 758 | " | O | S | * | 8 | 2,6-diethyl-3-pyridyl |
| 759 | " | O | S | * | 9 | 2,6-diethyl-3-pyridyl |
| 760 | " | O | S | * | 14 | 2,6-diethyl-3-pyridyl |

*: Single Bond

TABLE 39

| Compound No. | A | X | Y | Z | n | Het |
|---|---|---|---|---|---|---|
| 761 | (o-xylyl) | S | S | * | 1 | 2,6-diethyl-3-pyridyl |
| 762 | " | S | S | * | 2 | 2,6-diethyl-3-pyridyl |
| 763 | " | S | S | * | 3 | 2,6-diethyl-3-pyridyl |
| 764 | " | S | S | * | 4 | 2,6-diethyl-3-pyridyl |
| 765 | " | S | S | * | 5 | 2,6-diethyl-3-pyridyl |
| 766 | " | S | S | * | 6 | 2,6-diethyl-3-pyridyl |
| 767 | " | S | S | * | 7 | 2,6-diethyl-3-pyridyl |
| 768 | " | S | S | * | 8 | 2,6-diethyl-3-pyridyl |
| 769 | " | S | S | * | 9 | 2,6-diethyl-3-pyridyl |
| 770 | " | S | S | * | 14 | 2,6-diethyl-3-pyridyl |
| 771 | " | NH | S | * | 1 | 2,6-diethyl-3-pyridyl |
| 772 | " | NH | S | * | 2 | 2,6-diethyl-3-pyridyl |
| 773 | " | NH | S | * | 3 | 2,6-diethyl-3-pyridyl |
| 774 | " | NH | S | * | 4 | 2,6-diethyl-3-pyridyl |
| 775 | " | NH | S | * | 5 | 2,6-diethyl-3-pyridyl |
| 776 | " | NH | S | * | 6 | 2,6-diethyl-3-pyridyl |
| 777 | " | NH | S | * | 7 | 2,6-diethyl-3-pyridyl |
| 778 | " | NH | S | * | 8 | 2,6-diethyl-3-pyridyl |
| 779 | " | NH | S | * | 9 | 2,6-diethyl-3-pyridyl |
| 780 | " | NH | S | * | 14 | 2,6-diethyl-3-pyridyl |

*: Single Bond

TABLE 40

| Compound No. | A | X | Y | Z | n | Het |
|---|---|---|---|---|---|---|
| 781 | (o-xylyl) | O | S | * | 1 | 2,4-bismethylthio-6-methyl-3-pyridyl |
| 782 | " | O | S | * | 2 | 2,4-bismethylthio-6-methyl-3-pyridyl |
| 783 | " | O | S | * | 3 | 2,4-bismethylthio-6-methyl-3-pyridyl |
| 784 | " | O | S | * | 4 | 2,4-bismethylthio-6-methyl-3-pyridyl |
| 785 | " | O | S | * | 5 | 2,4-bismethylthio-6-methyl-3-pyridyl |
| 786 | " | O | S | * | 6 | 2,4-bismethylthio-6-methyl-3-pyridyl |
| 787 | " | O | S | * | 7 | 2,4-bismethylthio-6-methyl-3-pyridyl |
| 788 | " | O | S | * | 8 | 2,4-bismethylthio-6-methyl-3-pyridyl |
| 789 | " | O | S | * | 9 | 2,4-bismethylthio-6-methyl-3-pyridyl |
| 790 | " | O | S | * | 14 | 2,4-bismethylthio-6-methyl-3-pyridyl |
| 791 | " | S | S | * | 1 | 2,4-bismethylthio-6-methyl-3-pyridyl |
| 792 | " | S | S | * | 2 | 2,4-bismethylthio-6-methyl-3-pyridyl |
| 793 | " | S | S | * | 3 | 2,4-bismethylthio-6-methyl-3-pyridyl |
| 794 | " | S | S | * | 4 | 2,4-bismethylthio-6-methyl-3-pyridyl |
| 795 | " | S | S | * | 5 | 2,4-bismethylthio-6-methyl-3-pyridyl |

TABLE 40-continued

| Compound No. | A | X | Y | Z | n | Het |
|---|---|---|---|---|---|---|
| 796 | " | S | S | * | 6 | 2, 4-bismethylthio-6-methyl-3-pyridyl |
| 797 | " | S | S | * | 7 | 2, 4-bismethylthio-6-methyl-3-pyridyl |
| 798 | " | S | S | * | 8 | 2, 4-bismethylthio-6-methyl-3-pyridyl |
| 799 | " | S | S | * | 9 | 2, 4-bismethylthio-6-methyl-3-pyridyl |
| 800 | " | S | S | * | 14 | 2, 4-bismethylthio-6-methyl-3-pyridyl |

*: Single Bond

TABLE 41

| Compound No. | A | X | Y | Z | n | Het |
|---|---|---|---|---|---|---|
| 801 | (ortho-phenylene) | NH | S | * | 1 | 2, 4-bismethylthio-6-methyl-3-pyridyl |
| 802 | " | NH | S | * | 2 | 2, 4-bismethylthio-6-methyl-3-pyridyl |
| 803 | " | NH | S | * | 3 | 2, 4-bismethylthio-6-methyl-3-pyridyl |
| 804 | " | NH | S | * | 4 | 2, 4-bismethylthio-6-methyl-3-pyridyl |
| 805 | " | NH | S | * | 5 | 2, 4-bismethylthio-6-methyl-3-pyridyl |
| 806 | " | NH | S | * | 6 | 2, 4-bismethylthio-6-methyl-3-pyridyl |
| 807 | " | NH | S | * | 7 | 2, 4-bismethylthio-6-methyl-3-pyridyl |
| 808 | " | NH | S | * | 8 | 2, 4-bismethylthio-6-methyl-3-pyridyl |
| 809 | " | NH | S | * | 9 | 2, 4-bismethylthio-6-methyl-3-pyridyl |
| 810 | " | NH | S | * | 14 | 2, 4-bismethylthio-6-methyl-3-pyridyl |
| 811 | " | O | S | * | 1 | 2, 4-bisethylthio-6-methyl-3-pyridyl |
| 812 | " | O | S | * | 2 | 2, 4-bisethylthio-6-methyl-3-pyridyl |
| 813 | " | O | S | * | 3 | 2, 4-bisethylthio-6-methyl-3-pyridyl |
| 814 | " | O | S | * | 4 | 2, 4-bisethylthio-6-methyl-3-pyridyl |
| 815 | " | O | S | * | 5 | 2, 4-bisethylthio-6-methyl-3-pyridyl |
| 816 | " | O | S | * | 6 | 2, 4-bisethylthio-6-methyl-3-pyridyl |
| 817 | " | O | S | * | 7 | 2, 4-bisethylthio-6-methyl-3-pyridyl |
| 818 | " | O | S | * | 8 | 2, 4-bisethylthio-6-methyl-3-pyridyl |
| 819 | " | O | S | * | 9 | 2, 4-bisethylthio-6-methyl-3-pyridyl |
| 820 | " | O | S | * | 14 | 2, 4-bisethylthio-6-methyl-3-pyridyl |

*: Single Bond

TABLE 42

| Compound No. | A | X | Y | Z | n | Het |
|---|---|---|---|---|---|---|
| 821 | (ortho-phenylene) | S | S | * | 1 | 2, 4-bisethylthio-6-methyl-3-pyridyl |
| 822 | " | S | S | * | 2 | 2, 4-bisethylthio-6-methyl-3-pyridyl |
| 823 | " | S | S | * | 3 | 2, 4-bisethylthio-6-methyl-3-pyridyl |
| 824 | " | S | S | * | 4 | 2, 4-bisethylthio-6-methyl-3-pyridyl |
| 825 | " | S | S | * | 5 | 2, 4-bisethylthio-6-methyl-3-pyridyl |
| 826 | " | S | S | * | 6 | 2, 4-bisethylthio-6-methyl-3-pyridyl |
| 827 | " | S | S | * | 7 | 2, 4-bisethylthio-6-methyl-3-pyridyl |
| 828 | " | S | S | * | 8 | 2, 4-bisethylthio-6-methyl-3-pyridyl |
| 829 | " | S | S | * | 9 | 2, 4-bisethylthio-6-methyl-3-pyridyl |
| 830 | " | S | S | * | 14 | 2, 4-bisethylthio-6-methyl-3-pyridyl |
| 831 | " | NH | S | * | 1 | 2, 4-bisethylthio-6-methyl-3-pyridyl |
| 832 | " | NH | S | * | 2 | 2, 4-bisethylthio-6-methyl-3-pyridyl |
| 833 | " | NH | S | * | 3 | 2, 4-bisethylthio-6-methyl-3-pyridyl |
| 834 | " | NH | S | * | 4 | 2, 4-bisethylthio-6-methyl-3-pyridyl |

TABLE 42-continued

| Compound No. | A | X | Y | Z | n | Het |
|---|---|---|---|---|---|---|
| 835 | " | NH | S | * | 5 | 2, 4-bisethylthio-6-methyl-3-pyridyl |
| 836 | " | NH | S | * | 6 | 2, 4-bisethylthio-6-methyl-3-pyridyl |
| 837 | " | NH | S | * | 7 | 2, 4-bisethylthio-6-methyl-3-pyridyl |
| 838 | " | NH | S | * | 8 | 2, 4-bisethylthio-6-methyl-3-pyridyl |
| 839 | " | NH | S | * | 9 | 2, 4-bisethylthio-6-methyl-3-pyridyl |
| 840 | " | NH | S | * | 14 | 2, 4-bisethylthio-6-methyl-3-pyridyl |

*: Single Bond

TABLE 43

| Compound No. | A | X | Y | Z | n | Het |
|---|---|---|---|---|---|---|
| 841 | (2-methylphenyl) | O | S | * | 1 | 2, 4-bis(iso-propylthio)-6-methyl-3-pyridyl |
| 842 | " | O | S | * | 2 | 2, 4-bis(iso-propylthio)-6-methyl-3-pyridyl |
| 843 | " | O | S | * | 3 | 2, 4-bis(iso-propylthio)-6-methyl-3-pyridyl |
| 844 | " | O | S | * | 4 | 2, 4-bis(iso-propylthio)-6-methyl-3-pyridyl |
| 845 | " | O | S | * | 5 | 2, 4-bis(iso-propylthio)-6-methyl-3-pyridyl |
| 846 | " | O | S | * | 6 | 2, 4-bis(iso-propylthio)-6-methyl-3-pyridyl |
| 847 | " | O | S | * | 7 | 2, 4-bis(iso-propylthio)-6-methyl-3-pyridyl |
| 848 | " | O | S | * | 8 | 2, 4-bis(iso-propylthio)-6-methyl-3-pyridyl |
| 849 | " | O | S | * | 9 | 2, 4-bis(iso-propylthio)-6-methyl-3-pyridyl |
| 850 | " | O | S | * | 14 | 2, 4-bis(iso-propylthio)-6-methyl-3-pyridyl |
| 851 | " | S | S | * | 1 | 2, 4-bis(iso-propylthio)-6-methyl-3-pyridyl |
| 852 | " | S | S | * | 2 | 2, 4-bis(iso-propylthio)-6-methyl-3-pyridyl |
| 853 | " | S | S | * | 3 | 2, 4-bis(iso-propylthio)-6-methyl-3-pyridyl |
| 854 | " | S | S | * | 4 | 2, 4-bis(iso-propylthio)-6-methyl-3-pyridyl |
| 855 | " | S | S | * | 5 | 2, 4-bis(iso-propylthio)-6-methyl-3-pyridyl |
| 856 | " | S | S | * | 6 | 2, 4-bis(iso-propylthio)-6-methyl-3-pyridyl |
| 857 | " | S | S | * | 7 | 2, 4-bis(iso-propylthio)-6-methyl-3-pyridyl |
| 858 | " | S | S | * | 8 | 2, 4-bis(iso-propylthio)-6-methyl-3-pyridyl |
| 859 | " | S | S | * | 9 | 2, 4-bis(iso-propylthio)-6-methyl-3-pyridyl |
| 860 | " | S | S | * | 14 | 2, 4-bis(iso-propylthio)-6-methyl-3-pyridyl |

*: Single Bond

TABLE 44

| Compound No. | A | X | Y | Z | n | Het |
|---|---|---|---|---|---|---|
| 861 | (2-methylphenyl) | NH | S | * | 1 | 2, 4-bis(iso-propylthio)-6-methyl-3-pyridyl |
| 862 | " | NH | S | * | 2 | 2, 4-bis(iso-propylthio)-6-methyl-3-pyridyl |
| 863 | " | NH | S | * | 3 | 2, 4-bis(iso-propylthio)-6-methyl-3-pyridyl |
| 864 | " | NH | S | * | 4 | 2, 4-bis(iso-propylthio)-6-methyl-3-pyridyl |
| 865 | " | NH | S | * | 5 | 2, 4-bis(iso-propylthio)-6-methyl-3-pyridyl |
| 866 | " | NH | S | * | 6 | 2, 4-bis(iso-propylthio)-6-methyl-3-pyridyl |
| 867 | " | NH | S | * | 7 | 2, 4-bis(iso-propylthio)-6-methyl-3-pyridyl |
| 868 | " | NH | S | * | 8 | 2, 4-bis(iso-propylthio)-6-methyl-3-pyridyl |
| 869 | " | NH | S | * | 9 | 2, 4-bis(iso-propylthio)-6-methyl-3-pyridyl |
| 870 | " | NH | S | * | 14 | 2, 4-bis(iso-propylthio)-6-methyl-3-pyridyl |
| 871 | " | O | S | * | 1 | 2, 4-dimethoxy-6-methyl-3-pyridyl |
| 872 | " | O | S | * | 2 | 2, 4-dimethoxy-6-methyl-3-pyridyl |
| 873 | " | O | S | * | 3 | 2, 4-dimethoxy-6-methyl-3-pyridyl |

TABLE 44-continued

| Compound No. |  A | X | Y | Z | n | Het |
|---|---|---|---|---|---|---|
| 874 | " | O | S | * | 4 | 2, 4-dimethoxy-6-methyl-3-pyridyl |
| 875 | " | O | S | * | 5 | 2, 4-dimethoxy-6-methyl-3-pyridyl |
| 876 | " | O | S | * | 6 | 2, 4-dimethoxy-6-methyl-3-pyridyl |
| 877 | " | O | S | * | 7 | 2, 4-dimethoxy-6-methyl-3-pyridyl |
| 878 | " | O | S | * | 8 | 2, 4-dimethoxy-6-methyl-3-pyridyl |
| 879 | " | O | S | * | 9 | 2, 4-dimethoxy-6-methyl-3-pyridyl |
| 880 | " | O | S | * | 14 | 2, 4-dimethoxy-6-methyl-3-pyridyl |

*: Single Bond

TABLE 45

| Compound No. | A | X | Y | Z | n | Het |
|---|---|---|---|---|---|---|
| 881 | o-dimethylphenyl | S | S | * | 1 | 2, 4-dimethoxy-6-methyl-3-pyridyl |
| 882 | " | S | S | * | 2 | 2, 4-dimethoxy-6-methyl-3-pyridyl |
| 883 | " | S | S | * | 3 | 2, 4-dimethoxy-6-methyl-3-pyridyl |
| 884 | " | S | S | * | 4 | 2, 4-dimethoxy-6-methyl-3-pyridyl |
| 885 | " | S | S | * | 5 | 2, 4-dimethoxy-6-methyl-3-pyridyl |
| 886 | " | S | S | * | 6 | 2, 4-dimethoxy-6-methyl-3-pyridyl |
| 887 | " | S | S | * | 7 | 2, 4-dimethoxy-6-methyl-3-pyridyl |
| 888 | " | S | S | * | 8 | 2, 4-dimethoxy-6-methyl-3-pyridyl |
| 889 | " | S | S | * | 9 | 2, 4-dimethoxy-6-methyl-3-pyridyl |
| 890 | " | S | S | * | 14 | 2, 4-dimethoxy-6-methyl-3-pyridyl |
| 891 | " | NH | S | * | 1 | 2, 4-dimethoxy-6-methyl-3-pyridyl |
| 892 | " | NH | S | * | 2 | 2, 4-dimethoxy-6-methyl-3-pyridyl |
| 893 | " | NH | S | * | 3 | 2, 4-dimethoxy-6-methyl-3-pyridyl |
| 894 | " | NH | S | * | 4 | 2, 4-dimethoxy-6-methyl-3-pyridyl |
| 895 | " | NH | S | * | 5 | 2, 4-dimethoxy-6-methyl-3-pyridyl |
| 896 | " | NH | S | * | 6 | 2, 4-dimethoxy-6-methyl-3-pyridyl |
| 897 | " | NH | S | * | 7 | 2, 4-dimethoxy-6-methyl-3-pyridyl |
| 898 | " | NH | S | * | 8 | 2, 4-dimethoxy-6-methyl-3-pyridyl |
| 899 | " | NH | S | * | 9 | 2, 4-dimethoxy-6-methyl-3-pyridyl |
| 900 | " | NH | S | * | 14 | 2, 4-dimethoxy-6-methyl-3-pyridyl |

*: Single Bond

TABLE 46

| Compound No. | A | X | Y | Z | n | Het |
|---|---|---|---|---|---|---|
| 901 | o-dimethylphenyl | O | S | * | 1 | 2, 4, 6-trimethyl-3-pyridyl |
| 902 | " | O | S | * | 2 | 2, 4, 6-trimethyl-3-pyridyl |
| 903 | " | O | S | * | 3 | 2, 4, 6-trimethyl-3-pyridyl |
| 904 | " | O | S | * | 4 | 2, 4, 6-trimethyl-3-pyridyl |
| 905 | " | O | S | * | 5 | 2, 4, 6-trimethyl-3-pyridyl |
| 906 | " | O | S | * | 6 | 2, 4, 6-trimethyl-3-pyridyl |
| 907 | " | O | S | * | 7 | 2, 4, 6-trimethyl-3-pyridyl |
| 908 | " | O | S | * | 8 | 2, 4, 6-trimethyl-3-pyridyl |
| 909 | " | O | S | * | 9 | 2, 4, 6-trimethyl-3-pyridyl |
| 910 | " | O | S | * | 14 | 2, 4, 6-trimethyl-3-pyridyl |
| 911 | " | S | S | * | 1 | 2, 4, 6-trimethyl-3-pyridyl |
| 912 | " | S | S | * | 2 | 2, 4, 6-trimethyl-3-pyridyl |
| 913 | " | S | S | * | 3 | 2, 4, 6-trimethyl-3-pyridyl |
| 914 | " | S | S | * | 4 | 2, 4, 6-trimethyl-3-pyridyl |
| 915 | " | S | S | * | 5 | 2, 4, 6-trimethyl-3-pyridyl |
| 916 | " | S | S | * | 6 | 2, 4, 6-trimethyl-3-pyridyl |
| 917 | " | S | S | * | 7 | 2, 4, 6-trimethyl-3-pyridyl |
| 918 | " | S | S | * | 8 | 2, 4, 6-trimethyl-3-pyridyl |
| 919 | " | S | S | * | 9 | 2, 4, 6-trimethyl-3-pyridyl |
| 920 | " | S | S | * | 14 | 2, 4, 6-trimethyl-3-pyridyl |

*: Single Bond

TABLE 47

| Compound No. | A | X | Y | Z | n | Het |
|---|---|---|---|---|---|---|
| 921 |  (2-methylphenyl) | NH | S | * | 1 | 2, 4, 6-trimethyl-3-pyridyl |
| 922 | " | NH | S | * | 2 | 2, 4, 6-trimethyl-3-pyridyl |
| 923 | " | NH | S | * | 3 | 2, 4, 6-trimethyl-3-pyridyl |
| 924 | " | NH | S | * | 4 | 2, 4, 6-trimethyl-3-pyridyl |
| 925 | " | NH | S | * | 5 | 2, 4, 6-trimethyl-3-pyridyl |
| 926 | " | NH | S | * | 6 | 2, 4, 6-trimethyl-3-pyridyl |
| 927 | " | NH | S | * | 7 | 2, 4, 6-trimethyl-3-pyridyl |
| 928 | " | NH | S | * | 8 | 2, 4, 6-trimethyl-3-pyridyl |
| 929 | " | NH | S | * | 9 | 2, 4, 6-trimethyl-3-pyridyl |
| 930 | " | NH | S | * | 14 | 2, 4, 6-trimethyl-3-pyridyl |
| 931 | " | O | S | * | 1 | 4-ethyl-2, 6-dimethyl-3-pyridyl |
| 932 | " | O | S | * | 2 | 4-ethyl-2, 6-dimethyl-3-pyridyl |
| 933 | " | O | S | * | 3 | 4-ethyl-2, 6-dimethyl-3-pyridyl |
| 934 | " | O | S | * | 4 | 4-ethyl-2, 6-dimethyl-3-pyridyl |
| 935 | " | O | S | * | 5 | 4-ethyl-2, 6-dimethyl-3-pyridyl |
| 936 | " | O | S | * | 6 | 4-ethyl-2, 6-dimethyl-3-pyridyl |
| 937 | " | O | S | * | 7 | 4-ethyl-2, 6-dimethyl-3-pyridyl |
| 938 | " | O | S | * | 8 | 4-ethyl-2, 6-dimethyl-3-pyridyl |
| 939 | " | O | S | * | 9 | 4-ethyl-2, 6-dimethyl-3-pyridyl |
| 940 | " | O | S | * | 14 | 4-ethyl-2, 6-dimethyl-3-pyridyl |

*: Single Bond

TABLE 48

| Compound No. | A | X | Y | Z | n | Het |
|---|---|---|---|---|---|---|
| 941 | 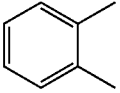 (2-methylphenyl) | S | S | * | 1 | 4-ethyl-2, 6-dimethyl-3-pyridyl |
| 942 | " | S | S | * | 2 | 4-ethyl-2, 6-dimethyl-3-pyridyl |
| 943 | " | S | S | * | 3 | 4-ethyl-2, 6-dimethyl-3-pyridyl |
| 944 | " | S | S | * | 4 | 4-ethyl-2, 6-dimethyl-3-pyridyl |
| 945 | " | S | S | * | 5 | 4-ethyl-2, 6-dimethyl-3-pyridyl |
| 946 | " | S | S | * | 6 | 4-ethyl-2, 6-dimethyl-3-pyridyl |
| 947 | " | S | S | * | 7 | 4-ethyl-2, 6-dimethyl-3-pyridyl |
| 948 | " | S | S | * | 8 | 4-ethyl-2, 6-dimethyl-3-pyridyl |
| 949 | " | S | S | * | 9 | 4-ethyl-2, 6-dimethyl-3-pyridyl |
| 950 | " | S | S | * | 14 | 4-ethyl-2, 6-dimethyl-3-pyridyl |
| 951 | " | NH | S | * | 1 | 4-ethyl-2, 6-dimethyl-3-pyridyl |
| 952 | " | NH | S | * | 2 | 4-ethyl-2, 6-dimethyl-3-pyridyl |
| 953 | " | NH | S | * | 3 | 4-ethyl-2, 6-dimethyl-3-pyridyl |
| 954 | " | NH | S | * | 4 | 4-ethyl-2, 6-dimethyl-3-pyridyl |
| 955 | " | NH | S | * | 5 | 4-ethyl-2, 6-dimethyl-3-pyridyl |
| 956 | " | NH | S | * | 6 | 4-ethyl-2, 6-dimethyl-3-pyridyl |
| 957 | " | NH | S | * | 7 | 4-ethyl-2, 6-dimethyl-3-pyridyl |
| 958 | " | NH | S | * | 8 | 4-ethyl-2, 6-dimethyl-3-pyridyl |
| 959 | " | NH | S | * | 9 | 4-ethyl-2, 6-dimethyl-3-pyridyl |
| 960 | " | NH | S | * | 14 | 4-ethyl-2, 6-dimethyl-3-pyridyl |

*: Single Bond

TABLE 49

| Compound No. | A | X | Y | Z | n | Het |
|---|---|---|---|---|---|---|
| 961 |  (2-methylphenyl) | O | S | * | 1 | 2, 4-dichloro-6-methyl-3-pyridyl |
| 962 | " | O | S | * | 2 | 2, 4-dichloro-6-methyl-3-pyridyl |
| 963 | " | O | S | * | 3 | 2, 4-dichloro-6-methyl-3-pyridyl |
| 964 | " | O | S | * | 4 | 2, 4-dichloro-6-methyl-3-pyridyl |
| 965 | " | O | S | * | 5 | 2, 4-dichloro-6-methyl-3-pyridyl |
| 966 | " | O | S | * | 6 | 2, 4-dichloro-6-methyl-3-pyridyl |
| 967 | " | O | S | * | 7 | 2, 4-dichloro-6-methyl-3-pyridyl |
| 968 | " | O | S | * | 8 | 2, 4-dichloro-6-methyl-3-pyridyl |
| 969 | " | O | S | * | 9 | 2, 4-dichloro-6-methyl-3-pyridyl |
| 970 | " | O | S | * | 14 | 2, 4-dichloro-6-methyl-3-pyridyl |
| 971 | " | S | S | * | 1 | 2, 4-dichloro-6-methyl-3-pyridyl |
| 972 | " | S | S | * | 2 | 2, 4-dichloro-6-methyl-3-pyridyl |
| 973 | " | S | S | * | 3 | 2, 4-dichloro-6-methyl-3-pyridyl |
| 974 | " | S | S | * | 4 | 2, 4-dichloro-6-methyl-3-pyridyl |
| 975 | " | S | S | * | 5 | 2, 4-dichloro-6-methyl-3-pyridyl |

TABLE 49-continued

| Compound No. | A | X | Y | Z | n | Het |
|---|---|---|---|---|---|---|
| 976 | " | S | S | * | 6 | 2,4-dichloro-6-methyl-3-pyridyl |
| 977 | " | S | S | * | 7 | 2,4-dichloro-6-methyl-3-pyridyl |
| 978 | " | S | S | * | 8 | 2,4-dichloro-6-methyl-3-pyridyl |
| 979 | " | S | S | * | 9 | 2,4-dichloro-6-methyl-3-pyridyl |
| 980 | " | S | S | * | 14 | 2,4-dichloro-6-methyl-3-pyridyl |

*: Single Bond

TABLE 50

| Compound No. | A | X | Y | Z | n | Het |
|---|---|---|---|---|---|---|
| 981 | (2-methylphenyl) | NH | S | * | 1 | 2,4-dichloro-6-methyl-3-pyridyl |
| 982 | " | NH | S | * | 2 | 2,4-dichloro-6-methyl-3-pyridyl |
| 983 | " | NH | S | * | 3 | 2,4-dichloro-6-methyl-3-pyridyl |
| 984 | " | NH | S | * | 4 | 2,4-dichloro-6-methyl-3-pyridyl |
| 985 | " | NH | S | * | 5 | 2,4-dichloro-6-methyl-3-pyridyl |
| 986 | " | NH | S | * | 6 | 2,4-dichloro-6-methyl-3-pyridyl |
| 987 | " | NH | S | * | 7 | 2,4-dichloro-6-methyl-3-pyridyl |
| 988 | " | NH | S | * | 8 | 2,4-dichloro-6-methyl-3-pyridyl |
| 989 | " | NH | S | * | 9 | 2,4-dichloro-6-methyl-3-pyridyl |
| 990 | " | NH | S | * | 14 | 2,4-dichloro-6-methyl-3-pyridyl |
| 991 | " | O | S | * | 1 | 4,6-bismethylthio-5-pyrimidyl |
| 992 | " | O | S | * | 2 | 4,6-bismethylthio-5-pyrimidyl |
| 993 | " | O | S | * | 3 | 4,6-bismethylthio-5-pyrimidyl |
| 994 | " | O | S | * | 4 | 4,6-bismethylthio-5-pyrimidyl |
| 995 | " | O | S | * | 5 | 4,6-bismethylthio-5-pyrimidyl |
| 996 | " | O | S | * | 6 | 4,6-bismethylthio-5-pyrimidyl |
| 997 | " | O | S | * | 7 | 4,6-bismethylthio-5-pyrimidyl |
| 998 | " | O | S | * | 8 | 4,6-bismethylthio-5-pyrimidyl |
| 999 | " | O | S | * | 9 | 4,6-bismethylthio-5-pyrimidyl |
| 1000 | " | O | S | * | 14 | 4,6-bismethylthio-5-pyrimidyl |

*: Single Bond

TABLE 51

| Compound No. | A | X | Y | Z | n | Het |
|---|---|---|---|---|---|---|
| 1001 | (2-methylphenyl) | S | S | * | 1 | 4,6-bismethylthio-5-pyrimidyl |
| 1002 | " | S | S | * | 2 | 4,6-bismethylthio-5-pyrimidyl |
| 1003 | " | S | S | * | 3 | 4,6-bismethylthio-5-pyrimidyl |
| 1004 | " | S | S | * | 4 | 4,6-bismethylthio-5-pyrimidyl |
| 1005 | " | S | S | * | 5 | 4,6-bismethylthio-5-pyrimidyl |
| 1006 | " | S | S | * | 6 | 4,6-bismethylthio-5-pyrimidyl |
| 1007 | " | S | S | * | 7 | 4,6-bismethylthio-5-pyrimidyl |
| 1008 | " | S | S | * | 8 | 4,6-bismethylthio-5-pyrimidyl |
| 1009 | " | S | S | * | 9 | 4,6-bismethylthio-5-pyrimidyl |
| 1010 | " | S | S | * | 14 | 4,6-bismethylthio-5-pyrimidyl |
| 1011 | " | NH | S | * | 1 | 4,6-bismethylthio-5-pyrimidyl |
| 1012 | " | NH | S | * | 2 | 4,6-bismethylthio-5-pyrimidyl |
| 1013 | " | NH | S | * | 3 | 4,6-bismethylthio-5-pyrimidyl |
| 1014 | " | NH | S | * | 4 | 4,6-bismethylthio-5-pyrimidyl |
| 1015 | " | NH | S | * | 5 | 4,6-bismethylthio-5-pyrimidyl |
| 1016 | " | NH | S | * | 6 | 4,6-bismethylthio-5-pyrimidyl |
| 1017 | " | NH | S | * | 7 | 4,6-bismethylthio-5-pyrimidyl |
| 1018 | " | NH | S | * | 8 | 4,6-bismethylthio-5-pyrimidyl |
| 1019 | " | NH | S | * | 9 | 4,6-bismethylthio-5-pyrimidyl |
| 1020 | " | NH | S | * | 14 | 4,6-bismethylthio-5-pyrimidyl |

*: Single Bond

TABLE 52

| Compound No. | A | X | Y | Z | n | Het |
|---|---|---|---|---|---|---|
| 1021 | (2-methylphenyl) | O | S | * | 1 | 4,6-bisethylthio-5-pyrimidyl |
| 1022 | " | O | S | * | 2 | 4,6-bnisethylthio-5-pyrimidyl |
| 1023 | " | O | S | * | 3 | 4,6-bnisethylthio-5-pyrimidyl |
| 1024 | " | O | S | * | 4 | 4,6-bnisethylthio-5-pyrimidyl |
| 1025 | " | O | S | * | 5 | 4,6-bnisethylthio-5-pyrimidyl |
| 1026 | " | O | S | * | 6 | 4,6-bnisethylthio-5-pyrimidyl |
| 1027 | " | O | S | * | 7 | 4,6-bnisethylthio-5-pyrimidyl |

TABLE 52-continued

| Compound No. | A | X | Y | Z | n | Het |
|---|---|---|---|---|---|---|
| 1028 | " | O | S | * | 8 | 4,6-bnisethylthio-5-pyrimidyl |
| 1029 | " | O | S | * | 9 | 4,6-bnisethylthio-5-pyrimidyl |
| 1030 | " | O | S | * | 14 | 4,6-bnisethylthio-5-pyrimidyl |
| 1031 | " | S | S | * | 1 | 4,6-bnisethylthio-5-pyrimidyl |
| 1032 | " | S | S | * | 2 | 4,6-bnisethylthio-5-pyrimidyl |
| 1033 | " | S | S | * | 3 | 4,6-bnisethylthio-5-pyrimidyl |
| 1034 | " | S | S | * | 4 | 4,6-bnisethylthio-5-pyrimidyl |
| 1035 | " | S | S | * | 5 | 4,6-bnisethylthio-5-pyrimidyl |
| 1036 | " | S | S | * | 6 | 4,6-bnisethylthio-5-pyrimidyl |
| 1037 | " | S | S | * | 7 | 4,6-bnisethylthio-5-pyrimidyl |
| 1038 | " | S | S | * | 8 | 4,6-bnisethylthio-5-pyrimidyl |
| 1039 | " | S | S | * | 9 | 4,6-bnisethylthio-5-pyrimidyl |
| 1040 | " | S | S | * | 14 | 4,6-bnisethylthio-5-pyrimidyl |

*: Single Bond

TABLE 53

| Compound No. | A | X | Y | Z | n | Het |
|---|---|---|---|---|---|---|
| 1041 | (o-dimethylphenyl) | NH | S | * | 1 | 4,6-bisethylthio-5-pyrimidyl |
| 1042 | " | NH | S | * | 2 | 4,6-bisethylthio-5-pyrimidyl |
| 1043 | " | NH | S | * | 3 | 4,6-bisethylthio-5-pyrimidyl |
| 1044 | " | NH | S | * | 4 | 4,6-bisethylthio-5-pyrimidyl |
| 1045 | " | NH | S | * | 5 | 4,6-bisethylthio-5-pyrimidyl |
| 1046 | " | NH | S | * | 6 | 4,6-bisethylthio-5-pyrimidyl |
| 1047 | " | NH | S | * | 7 | 4,6-bisethylthio-5-pyrimidyl |
| 1048 | " | NH | S | * | 8 | 4,6-bisethylthio-5-pyrimidyl |
| 1049 | " | NH | S | * | 9 | 4,6-bisethylthio-5-pyrimidyl |
| 1050 | " | NH | S | * | 14 | 4,6-bisethylthio-5-pyrimidyl |
| 1051 | " | O | S | * | 1 | 4,6-bis(iso-propylthio)-5-pyrimidyl |
| 1052 | " | O | S | * | 2 | 4,6-bis(iso-propylthio)-5-pyrimidyl |
| 1053 | " | O | S | * | 3 | 4,6-bis(iso-propylthio)-5-pyrimidyl |
| 1054 | " | O | S | * | 4 | 4,6-bis(iso-propylthio)-5-pyrimidyl |
| 1055 | " | O | S | * | 5 | 4,6-bis(iso-propylthio)-5-pyrimidyl |
| 1056 | " | O | S | * | 6 | 4,6-bis(iso-propylthio)-5-pyrimidyl |
| 1057 | " | O | S | * | 7 | 4,6-bis(iso-propylthio)-5-pyrimidyl |
| 1058 | " | O | S | * | 8 | 4,6-bis(iso-propylthio)-5-pyrimidyl |
| 1059 | " | O | S | * | 9 | 4,6-bis(iso-propylthio)-5-pyrimidyl |
| 1060 | " | O | S | * | 14 | 4,6-bis(iso-propylthio)-5-pyrimidyl |

*: Single Bond

TABLE 54

| Compound No. | A | X | Y | Z | n | Het |
|---|---|---|---|---|---|---|
| 1061 | (o-dimethylphenyl) | S | S | * | 1 | 4,6-bis(iso-propylthio)-5-pyrimidyl |
| 1062 | " | S | S | * | 2 | 4,6-bis(iso-propylthio)-5-pyrimidyl |
| 1063 | " | S | S | * | 3 | 4,6-bis(iso-propylthio)-5-pyrimidyl |
| 1064 | " | S | S | * | 4 | 4,6-bis(iso-propylthio)-54-pyrimidyl |
| 1065 | " | S | S | * | 5 | 4,6-bis(iso-propylthio)-5-pyrimidyl |
| 1066 | " | S | S | * | 6 | 4,6-bis(iso-propylthio)-5-pyrimidyl |
| 1067 | " | S | S | * | 7 | 4,6-bis(iso-propylthio)-5-pyrimidyl |
| 1068 | " | S | S | * | 8 | 4,6-bis(iso-propylthio)-5-pyrimidyl |
| 1069 | " | S | S | * | 9 | 4,6-bis(iso-propylthio)-5-pyrimidyl |
| 1070 | " | S | S | * | 14 | 4,6-bis(iso-propylthio)-5-pyrimidyl |
| 1071 | " | NH | S | * | 1 | 4,6-bis(iso-propylthio)-5-pyrimidyl |
| 1072 | " | NH | S | * | 2 | 4,6-bis(iso-propylthio)-5-pyrimidyl |
| 1073 | " | NH | S | * | 3 | 4,6-bis(iso-propylthio)-5-pyrimidyl |
| 1074 | " | NH | S | * | 4 | 4,6-bis(iso-propylthio)-5-pyrimidyl |
| 1075 | " | NH | S | * | 5 | 4,6-bis(iso-propylthio)-5-pyrimidyl |
| 1076 | " | NH | S | * | 6 | 4,6-bis(iso-propylthio)-5-pyrimidyl |
| 1077 | " | NH | S | * | 7 | 4,6-bis(iso-propylthio)-5-pyrimidyl |
| 1078 | " | NH | S | * | 8 | 4,6-bis(iso-propylthio)-5-pyrimidyl |
| 1079 | " | NH | S | * | 9 | 4,6-bis(iso-propylthio)-5-pyrimidyl |
| 1080 | " | NH | S | * | 14 | 4,6-bis(iso-propylthio)-5-pyrimidyl |

*: Single Bond

TABLE 55

| Compound No. | A | X | Y | Z | n | Het |
|---|---|---|---|---|---|---|
| 1081 | 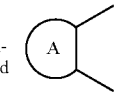 | O | S | * | 1 | 4,6-dimethoxy-5-pyrimidyl |
| 1082 | " | O | S | * | 2 | 4,6-dimethoxy-5-pyrimidyl |
| 1083 | " | O | S | * | 3 | 4,6-dimethoxy-5-pyrimidyl |
| 1084 | " | O | S | * | 4 | 4,6-dimethoxy-5-pyrimidyl |
| 1085 | " | O | S | * | 5 | 4,6-dimethoxy-5-pyrimidyl |
| 1086 | " | O | S | * | 6 | 4,6-dimethoxy-5-pyrimidyl |
| 1087 | " | O | S | * | 7 | 4,6-dimethoxy-5-pyrimidyl |
| 1088 | " | O | S | * | 8 | 4,6-dimethoxy-5-pyrimidyl |
| 1089 | " | O | S | * | 9 | 4,6-dimethoxy-5-pyrimidyl |
| 1090 | " | O | S | * | 14 | 4,6-dimethoxy-5-pyrimidyl |
| 1091 | " | S | S | * | 1 | 4,6-dimethoxy-5-pyrimidyl |
| 1092 | " | S | S | * | 2 | 4,6-dimethoxy-5-pyrimidyl |
| 1093 | " | S | S | * | 3 | 4,6-dimethoxy-5-pyrimidyl |
| 1094 | " | S | S | * | 4 | 4,6-dimethoxy-5-pyrimidyl |
| 1095 | " | S | S | * | 5 | 4,6-dimethoxy-5-pyrimidyl |
| 1096 | " | S | S | * | 6 | 4,6-dimethoxy-5-pyrimidyl |
| 1097 | " | S | S | * | 7 | 4,6-dimethoxy-5-pyrimidyl |
| 1098 | " | S | S | * | 8 | 4,6-dimethoxy-5-pyrimidyl |
| 1099 | " | S | S | * | 9 | 4,6-dimethoxy-5-pyrimidyl |
| 1100 | " | S | S | * | 14 | 4,6-dimethoxy-5-pyrimidyl |

*: Single Bond

TABLE 56

| Compound No. | A | X | Y | Z | n | Het |
|---|---|---|---|---|---|---|
| 1101 | 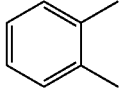 | NH | S | * | 1 | 4,6-dichloro-2-methyl-5-pyrimidyl |
| 1102 | " | NH | S | * | 2 | 4,6-dichloro-2-methyl-5-pyrimidyl |
| 1103 | " | NH | S | * | 3 | 4,6-dichloro-2-methyl-5-pyrimidyl |
| 1104 | " | NH | S | * | 4 | 4,6-dichloro-2-methyl-5-pyrimidyl |
| 1105 | " | NH | S | * | 5 | 4,6-dichloro-2-methyl-5-pyrimidyl |
| 1106 | " | NH | S | * | 6 | 4,6-dichloro-2-methyl-5-pyrimidyl |
| 1107 | " | NH | S | * | 7 | 4,6-dichloro-2-methyl-5-pyrimidyl |
| 1108 | " | NH | S | * | 8 | 4,6-dichloro-2-methyl-5-pyrimidyl |
| 1109 | " | NH | S | * | 9 | 4,6-dichloro-2-methyl-5-pyrimidyl |
| 1110 | " | NH | S | * | 14 | 4,6-dichloro-2-methyl-5-pyrimidyl |
| 1111 | " | O | S | * | 1 | 4,6-dichloro-2-methyl-5-pyrimidyl |
| 1112 | " | O | S | * | 2 | 4,6-dichloro-2-methyl-5-pyrimidyl |
| 1113 | " | O | S | * | 3 | 4,6-dichloro-2-methyl-5-pyrimidyl |
| 1114 | " | O | S | * | 4 | 4,6-dichloro-2-methyl-5-pyrimidyl |
| 1115 | " | O | S | * | 5 | 4,6-dichloro-2-methyl-5-pyrimidyl |
| 1116 | " | O | S | * | 6 | 4,6-dichloro-2-methyl-5-pyrimidyl |
| 1117 | " | O | S | * | 7 | 4,6-dichloro-2-methyl-5-pyrimidyl |
| 1118 | " | O | S | * | 8 | 4,6-dichloro-2-methyl-5-pyrimidyl |
| 1119 | " | O | S | * | 9 | 4,6-dichloro-2-methyl-5-pyrimidyl |
| 1120 | " | O | S | * | 14 | 4,6-dichloro-2-methyl-5-pyrimidyl |

*: Single Bond

TABLE 57

| Compound No. | A | X | Y | Z | n | Het |
|---|---|---|---|---|---|---|
| 1121 | 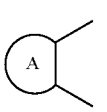 | S | S | * | 1 | 4,6-bis(dimethylamino)-5-pyrimidyl |
| 1122 | " | S | S | * | 2 | 4,6-bis(ddimnethylthio)-5-pyrimidyl |
| 1123 | " | S | S | * | 3 | 4,6-bis(ddimnethylthio)-5-pyrimidyl |
| 1124 | " | S | S | * | 4 | 4,6-bis(ddimnethylthio)-5-pyrimidyl |
| 1125 | " | S | S | * | 5 | 4,6-bis(ddimnethylthio)-5-pyrimidyl |
| 1126 | " | S | S | * | 6 | 4,6-bis(ddimnethylthio)-5-pyrimidyl |
| 1127 | " | S | S | * | 7 | 4,6-bis(ddimnethylthio)-5-pyrimidyl |
| 1128 | " | S | S | * | 8 | 4,6-bis(ddimnethylthio)-5-pyrimidyl |
| 1129 | " | S | S | * | 9 | 4,6-bis(ddimnethylthio)-5-pyrimidyl |
| 1130 | " | S | S | * | 14 | 4,6-bis(ddimnethylthio)-5-pyrimidyl |
| 1131 | " | NH | S | * | 1 | 4,6-bis(ddimnethylthio)-5-pyrimidyl |
| 1122 | " | NH | S | * | 2 | 4,6-bis(ddimnethylthio)-5-pyrimidyl |
| 1133 | " | NH | S | * | 3 | 4,6-bis(ddimnethylthio)-5-pyrimidyl |
| 1134 | " | NH | S | * | 4 | 4,6-bis(ddimnethylthio)-5-pyrimidyl |
| 1135 | " | NH | S | * | 5 | 4,6-bis(ddimnethylthio)-5-pyrimidyl |
| 1136 | " | NH | S | * | 6 | 4,6-bis(ddimnethylthio)-5-pyrimidyl |
| 1137 | " | NH | S | * | 7 | 4,6-bis(ddimnethylthio)-5-pyrimidyl |
| 1138 | " | NH | S | * | 8 | 4,6-bis(ddimnethylthio)-5-pyrimidyl |
| 1139 | " | NH | S | * | 9 | 4,6-bis(ddimnethylthio)-5-pyrimidyl |
| 1140 | " | NH | S | * | 14 | 4,6-bis(ddimnethylthio)-5-pyrimidyl |

*: Single Bond

TABLE 58

| Compound No. | A 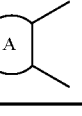 | X | Y | Z | n | Het |
|---|---|---|---|---|---|---|
| 1141 | | O | S | * | 1 | 4,6-bismethylthio-2-methyl-5-pyrimidyl |
| 1142 | " | O | S | * | 2 | 4,6-bismethylthio-2-methyl-5-pyrimidyl |
| 1143 | " | O | S | * | 2 | 4,6-bismethylthio-2-methyl-5-pyrimidyl |
| 1144 | " | O | S | * | 2 | 4,6-bismethylthio-2-methyl-5-pyrimidyl |
| 1145 | " | O | S | * | 2 | 4,6-bismethylthio-2-methyl-5-pyrimidyl |
| 1146 | " | O | S | * | 2 | 4,6-bismethylthio-2-methyl-5-pyrimidyl |
| 1147 | " | O | S | * | 2 | 4,6-bismethylthio-2-methyl-5-pyrimidyl |
| 1148 | " | O | S | * | 2 | 4,6-bismethylthio-2-methyl-5-pyrimidyl |
| 1149 | " | O | S | * | 2 | 4,6-bismethylthio-2-methyl-5-pyrimidyl |
| 1150 | " | O | S | * | 2 | 4,6-bismethylthio-2-methyl-5-pyrimidyl |
| 1151 | " | O | S | * | 2 | 4,6-bismethylthio-2-methyl-5-pyrimidyl |
| 1152 | " | O | S | * | 2 | 4,6-bismethylthio-2-methyl-5-pyrimidyl |
| 1153 | " | O | S | * | 2 | 4,6-bismethylthio-2-methyl-5-pyrimidyl |
| 1154 | " | O | S | * | 2 | 4,6-bismethylthio-2-methyl-5-pyrimidyl |
| 1155 | " | O | S | * | 2 | 4,6-bismethylthio-2-methyl-5-pyrimidyl |
| 1156 | " | O | S | * | 2 | 4,6-bismethylthio-2-methyl-5-pyrimidyl |
| 1157 | " | O | S | * | 2 | 4,6-bismethylthio-2-methyl-5-pyrimidyl |
| 1158 | " | O | S | * | 2 | 4,6-bismethylthio-2-methyl-5-pyrimidyl |
| 1159 | " | O | S | * | 2 | 4,6-bismethylthio-2-methyl-5-pyrimidyl |
| 1160 | " | O | S | * | 2 | 4,6-bismethylthio-2-methyl-5-pyrimidyl |

*: Single Bond

TABLE 59

| Compound No. | A 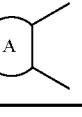 | X | Y | Z | n | Het |
|---|---|---|---|---|---|---|
| 1161 | | NH | S | * | 1 | 4,6-bismethylthio-2-methyl-5-pyrimidyl |
| 1162 | " | NH | S | * | 2 | 4,6-bismethylthio-2-methyl-5-pyrimidyl |
| 1163 | " | NH | S | * | 3 | 4,6-bismethylthio-2-methyl-5-pyrimidyl |
| 1164 | " | NH | S | * | 4 | 4,6-bismethylthio-2-methyl-5-pyrimidyl |
| 1165 | " | NH | S | * | 5 | 4,6-bismethylthio-2-methyl-5-pyrimidyl |
| 1166 | " | NH | S | * | 6 | 4,6-bismethylthio-2-methyl-5-pyrimidyl |
| 1167 | " | NH | S | * | 7 | 4,6-bismethylthio-2-methyl-5-pyrimidyl |

TABLE 59-continued

| Compound No. | A | X | Y | Z | n | Het |
|---|---|---|---|---|---|---|
| 1168 | " | NH | S | * | 8 | 4,6-bismethylthio-2-methyl-5-pyrimidyl |
| 1169 | " | NH | S | * | 9 | 4,6-bismethylthio-2-methyl-5-pyrimidyl |
| 1170 | " | NH | S | * | 14 | 4,6-bismethylthio-2-methyl-5-pyrimidyl |
| 1171 | " | NH | S | * | 1 | 4,6-bismethylthio-2-methyl-5-pyrimidyl |
| 1172 | " | O | S | * | 2 | 4,6-bismethylthio-2-methyl-5-pyrimidyl |
| 1173 | " | O | S | * | 3 | 4,6-bismethylthio-2-methyl-5-pyrimidyl |
| 1174 | " | O | S | * | 4 | 4,6-bismethylthio-2-methyl-5-pyrimidyl |
| 1175 | " | O | S | * | 5 | 4,6-bismethylthio-2-methyl-5-pyrimidyl |
| 1176 | " | O | S | * | 6 | 4,6-bismethylthio-2-methyl-5-pyrimidyl |
| 1177 | " | O | S | * | 7 | 4,6-bismethylthio-2-methyl-5-pyrimidyl |
| 1178 | " | O | S | * | 8 | 4,6-bismethylthio-2-methyl-5-pyrimidyl |
| 1179 | " | O | S | * | 9 | 4,6-bismethylthio-2-methyl-5-pyrimidyl |
| 1180 | " | O | S | * | 14 | 4,6-bismethylthio-2-methyl-5-pyrimidyl |

*: Single Bond

TABLE 60

| Compound No. | A 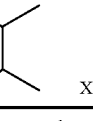 | X | Y | Z | n | Het |
|---|---|---|---|---|---|---|
| 1181 | | S | S | * | 1 | 2,4,6-trimethoxy-5-pyrimidyl |
| 1182 | " | S | S | * | 2 | 2,4,6-trimethoxy-5-pyrimidyl |
| 1183 | " | S | S | * | 3 | 2,4,6-trimethoxy-5-pyrimidyl |
| 1184 | " | S | S | * | 4 | 2,4,6-trimethoxy-5-pyrimidyl |
| 1185 | " | S | S | * | 5 | 2,4,6-trimethoxy-5-pyrimidyl |
| 1186 | " | S | S | * | 6 | 2,4,6-trimethoxy-5-pyrimidyl |
| 1187 | " | S | S | * | 7 | 2,4,6-trimethoxy-5-pyrimidyl |
| 1188 | " | S | S | * | 8 | 2,4,6-trimethoxy-5-pyrimidyl |
| 1189 | " | S | S | * | 9 | 2,4,6-trimethoxy-5-pyrimidyl |
| 1190 | " | S | S | * | 14 | 2,4,6-trimethoxy-5-pyrimidyl |
| 1191 | " | NH | S | * | 1 | 2,4,6-trimethoxy-5-pyrimidyl |
| 1192 | " | NH | S | * | 2 | 2,4,6-trimethoxy-5-pyrimidyl |
| 1193 | " | NH | S | * | 3 | 2,4,6-trimethoxy-5-pyrimidyl |
| 1194 | " | NH | S | * | 4 | 2,4,6-trimethoxy-5-pyrimidyl |
| 1195 | " | NH | S | * | 5 | 2,4,6-trimethoxy-5-pyrimidyl |
| 1196 | " | NH | S | * | 6 | 2,4,6-trimethoxy-5-pyrimidyl |

TABLE 60-continued

| Compound No. | A  | X | Y | Z | n | Het |
|---|---|---|---|---|---|---|
| 1197 | " | NH | S | * | 7 | 2,4,6-trimethoxy-5-pyrimidyl |
| 1198 | " | NH | S | * | 8 | 2,4,6-trimethoxy-5-pyrimidyl |
| 1199 | " | NH | S | * | 9 | 2,4,6-trimethoxy-5-pyrimidyl |
| 1200 | " | NH | S | * | 14 | 2,4,6-trimethoxy-5-pyrimidyl |

*: Single Bond

TABLE 61

| Compound No. | A  | X | Y | Z | n | Het |
|---|---|---|---|---|---|---|
| 1201 | | O | SO | * | 5 | 2-methylthio-3-pyridyl |
| 1202 | " | O | SO$_2$ | * | 5 | 2-methylthio-3-pyridyl |
| 1203 | " | O | NH | * | 5 | 2-methylthio-3-pyridyl |
| 1204 | " | S | SO | * | 5 | 2-methylthio-3-pyridyl |

TABLE 61-continued

| Compound No. | A  | X | Y | Z | n | Het |
|---|---|---|---|---|---|---|
| 1205 | " | S | SO$_2$ | * | 5 | 2-methylthio-3-pyridyl |
| 1206 | " | S | NH | * | 5 | 2-methylthio-3-pyridyl |
| 1207 | " | NH | SO | * | 5 | 2-methylthio-3-pyridyl |
| 1208 | " | NH | SO$_2$ | * | 5 | 2-methylthio-3-pyridyl |
| 1209 | " | NH | NH | * | 5 | 2-methylthio-3-pyridyl |
| 1210 | " | O | SO | NH | 6 | 2-methylthio-3-pyridyl |
| 1211 | " | O | SO$_2$ | NH | 6 | 2-methylthio-3-pyridyl |
| 1212 | " | O | NH | NH | 6 | 2-methylthio-3-pyridyl |
| 1213 | " | S | SO | NH | 6 | 2-methylthio-3-pyridyl |
| 1214 | " | S | SO$_2$ | NH | 6 | 2-methylthio-3-pyridyl |
| 1215 | " | S | NH | NH | 6 | 2-methylthio-3-pyridyl |
| 1216 | " | NH | SO | NH | 6 | 2-methylthio-3-pyridyl |
| 1217 | " | NH | SO$_2$ | NH | 6 | 2-methylthio-3-pyridyl |
| 1218 | " | NH | NH | NH | 6 | 2-methylthio-3-pyridyl |

*: Single Bond

TABLE 62

| Compound No. | A  | X | Y | Z | n | Het |
|---|---|---|---|---|---|---|
| 1219 | | O | SO | * | 5 | 2,4-bismethylthio-6-methyl-3-pyridyl |
| 1220 | " | O | SO$_2$ | * | 5 | 2,4-bismethylthio-6-methyl-3-pyridyl |
| 1221 | " | O | NH | * | 5 | 2,4-bismethylthio-6-methyl-3-pyridyl |
| 1222 | " | S | SO | * | 5 | 2,4-bismethylthio-6-methyl-3-pyridyl |
| 1223 | " | S | SO$_2$ | * | 5 | 2,4-bismethylthio-6-methyl-3-pyridyl |
| 1224 | " | S | NH | * | 5 | 2,4-bismethylthio-6-methyl-3-pyridyl |
| 1225 | " | NH | SO | * | 5 | 2,4-bismethylthio-6-methyl-3-pyridyl |
| 1226 | " | NH | SO$_2$ | * | 5 | 2,4-bismethylthio-6-methyl-3-pyridyl |
| 1227 | " | NH | NH | * | 5 | 2,4-bismethylthio-6-methyl-3-pyridyl |
| 1228 | " | O | SO | NH | 6 | 2,4-bismethylthio-6-methyl-3-pyridyl |
| 1229 | " | O | SO$_2$ | NH | 6 | 2,4-bismethylthio-6-methyl-3-pyridyl |
| 1230 | " | O | NH | NH | 6 | 2,4-bismethylthio-6-methyl-3-pyridyl |
| 1231 | " | S | SO | NH | 6 | 2,4-bismethylthio-6-methyl-3-pyridyl |
| 1232 | " | S | SO$_2$ | NH | 6 | 2,4-bismethylthio-6-methyl-3-pyridyl |
| 1233 | " | S | NH | NH | 6 | 2,4-bismethylthio-6-methyl-3-pyridyl |
| 1234 | " | NH | SO | NH | 6 | 2,4-bismethylthio-6-methyl-3-pyridyl |
| 1235 | " | NH | NH | NH | 6 | 2,4-bismethylthio-6-methyl-3-pyridyl |
| 1236 | " | NH | NH | NH | 6 | 2,4-bismethylthio-6-methyl-3-pyridyl |

*: Single Bond

TABLE 63

| Compound No. | A | X | Y | Z | n | Het |
|---|---|---|---|---|---|---|
| 1237 | pyridine (2,3-dimethyl) | O | S | Single Bond | 5 | 3-Me-2,4-bis(MeS)-6-Me-pyridine |
| 1238 | 2-COOMe-phenyl (2,3-dimethyl) | O | S | Single Bond | 5 | 3-Me-2,4-bis(MeS)-6-Me-pyridine |
| 1239 | pyridine (2,3-dimethyl) | O | S | Single Bond | 8 | 3-Me-2,4-bis(MeS)-6-Me-pyridine |
| 1240 | 2-COOMe-phenyl (2,3-dimethyl) | O | S | Single Bond | 8 | 3-Me-2,4-bis(MeS)-6-Me-pyridine |
| 1241 | pyridine (2,3-dimethyl) | O | S | Single Bond | 5 | 3-Me-2,4-bis(MeS)-pyridine |
| 1242 | 2-COOMe-phenyl (2,3-dimethyl) | O | S | Single Bond | 5 | 3-Me-2,4-bis(MeS)-pyridine |
| 1243 | pyridine (2,3-dimethyl) | O | S | Single Bond | 8 | 3-Me-2,4-bis(MeS)-pyridine |
| 1244 | 2-COOMe-phenyl (2,3-dimethyl) | O | S | Single Bond | 8 | 3-Me-2,4-bis(MeS)-pyridine |

TABLE 63-continued

| Compound No. | A | X | Y | Z | n | Het |
|---|---|---|---|---|---|---|
| 1245 | 2,3-pyridyl | S | S | Single Bond | 1 | 4-EtS, 3-Me, 2-EtS, 6-Me pyridyl |
| 1246 | 2-COOMe phenyl | NH | S | Single Bond | 1 | 4-iPrS, 3-Me, 2-iPrS, 6-Me pyridyl |

TABLE 64

| Compound No. | A | X | Y | Z | n | Het |
|---|---|---|---|---|---|---|
| 1247 | 2-CF₃ phenyl | O | S | Single Bond | 1 | 4-MeS, 3-Me, 2-MeS, 6-Me pyridyl |
| 1248 | 2-CF₃ phenyl | O | S | Single Bond | 2 | 4-MeS, 3-Me, 2-MeS, 6-Me pyridyl |
| 1249 | 2-CF₃ phenyl | O | S | Single Bond | 3 | 4-MeS, 3-Me, 2-MeS, 6-Me pyridyl |
| 1250 | 2-CF₃ phenyl | O | S | Single Bond | 4 | 4-MeS, 3-Me, 2-MeS, 6-Me pyridyl |
| 1251 | 2-CF₃ phenyl | O | S | Single Bond | 5 | 4-MeS, 3-Me, 2-MeS, 6-Me pyridyl |

TABLE 64-continued

| Compound No. | A | X | Y | Z | n | Het |
|---|---|---|---|---|---|---|
| 1252 | CF₃, 2,3-disubstituted phenyl | O | S | Single Bond | 6 | pyridine with 4-MeS, 3-Me, 6-Me, 2-MeS |
| 1253 | CF₃, 2,3-disubstituted phenyl | O | S | Single Bond | 7 | pyridine with 4-MeS, 3-Me, 6-Me, 2-MeS |
| 1254 | CF₃, 2,3-disubstituted phenyl | O | S | Single Bond | 8 | pyridine with 4-MeS, 3-Me, 6-Me, 2-MeS |
| 1255 | CF₃, 2,3-disubstituted phenyl | O | S | Single Bond | 9 | pyridine with 4-MeS, 3-Me, 6-Me, 2-MeS |
| 1256 | CF₃, 2,3-disubstituted phenyl | O | S | Single Bond | 14 | pyridine with 4-MeS, 3-Me, 6-Me, 2-MeS |

TABLE 65

| Compound No. | A | X | Y | Z | n | Het |
|---|---|---|---|---|---|---|
| 1257 | CMe₂ attached to phenyl with Cl, Me, Me substituents | O | S | Single Bond | 1 | pyridine with 4-MeS, 3-Me, 6-Me, 2-MeS |

TABLE 65-continued

| Compound No. | A | X | Y | Z | n | Het |
|---|---|---|---|---|---|---|
| 1258 | 3-Cl, 4-Me, 5-Me, 6-Me, 2-CH(Me)Me-phenyl | O | S | Single Bond | 2 | 3-Me, 4-MeS, 2-MeS, 6-Me-pyridyl |
| 1259 | 3-Cl, 4-Me, 5-Me, 6-Me, 2-CH(Me)Me-phenyl | O | S | Single Bond | 3 | 3-Me, 4-MeS, 2-MeS, 6-Me-pyridyl |
| 1260 | 3-Cl, 4-Me, 5-Me, 6-Me, 2-CH(Me)Me-phenyl | O | S | Single Bond | 4 | 3-Me, 4-MeS, 2-MeS, 6-Me-pyridyl |
| 1261 | 3-Cl, 4-Me, 5-Me, 6-Me, 2-CH(Me)Me-phenyl | O | S | Single Bond | 5 | 3-Me, 4-MeS, 2-MeS, 6-Me-pyridyl |
| 1262 | 3-Cl, 4-Me, 5-Me, 6-Me, 2-CH(Me)Me-phenyl | O | S | Single Bond | 6 | 3-Me, 4-MeS, 2-MeS, 6-Me-pyridyl |
| 1263 | 3-Cl, 4-Me, 5-Me, 6-Me, 2-CH(Me)Me-phenyl | O | S | Single Bond | 7 | 3-Me, 4-MeS, 2-MeS, 6-Me-pyridyl |

TABLE 65-continued
| Compound No. | A | X | Y | Z | n | Het |
|---|---|---|---|---|---|---|
| 1264 |  | O | S | Single Bond | 8 | 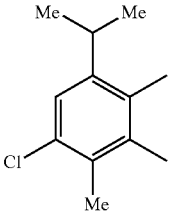 |
| 1265 | 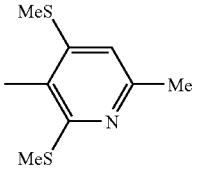 | O | S | Single Bond | 9 | 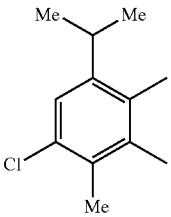 |
| 1266 | 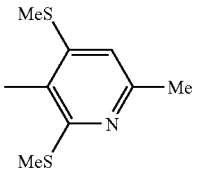 | O | S | Single Bond | 14 | 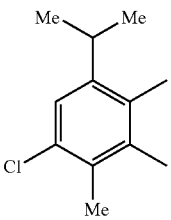 |
TABLE 66
| Compound No. | A | X | Y | Z | n | Het |
|---|---|---|---|---|---|---|
| 1267 | 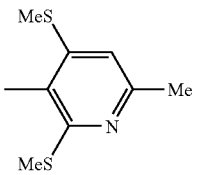 | O | S | Single Bond | 1 | 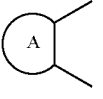 |
| 1268 | 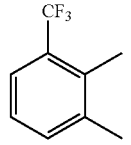 | O | S | Single Bond | 2 | 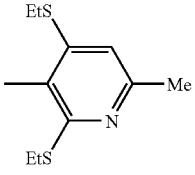 |
| 1269 | 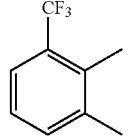 | O | S | Single Bond | 3 | 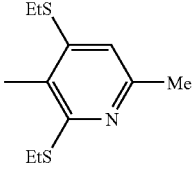 |

TABLE 66-continued

| Compound No. | A | X | Y | Z | n | Het |
|---|---|---|---|---|---|---|
| 1270 | CF₃-phenyl (2,3-disub) | O | S | Single Bond | 4 | 4-EtS, 3-Me, 2-EtS, 6-Me pyridine |
| 1271 | CF₃-phenyl (2,3-disub) | O | S | Single Bond | 5 | 4-EtS, 3-Me, 2-EtS, 6-Me pyridine |
| 1272 | CF₃-phenyl (2,3-disub) | O | S | Single Bond | 6 | 4-EtS, 3-Me, 2-EtS, 6-Me pyridine |
| 1273 | CF₃-phenyl (2,3-disub) | O | S | Single Bond | 7 | 4-EtS, 3-Me, 2-EtS, 6-Me pyridine |
| 1274 | CF₃-phenyl (2,3-disub) | O | S | Single Bond | 8 | 4-EtS, 3-Me, 2-EtS, 6-Me pyridine |
| 1275 | CF₃-phenyl (2,3-disub) | O | S | Single Bond | 9 | 4-EtS, 3-Me, 2-EtS, 6-Me pyridine |
| 1276 | CF₃-phenyl (2,3-disub) | O | S | Single Bond | 14 | 4-EtS, 3-Me, 2-EtS, 6-Me pyridine |

TABLE 67

| Compound No. | A | X | Y | Z | n | Het |
|---|---|---|---|---|---|---|
| 1277 | 5-Cl, 2-CHMe₂, 3,4-diMe-phenyl | O | S | Single Bond | 1 | 4-EtS, 2-EtS, 3,6-diMe-pyridinyl |
| 1278 | 5-Cl, 2-CHMe₂, 3,4-diMe-phenyl | O | S | Single Bond | 2 | 4-EtS, 2-EtS, 3,6-diMe-pyridinyl |
| 1279 | 5-Cl, 2-CHMe₂, 3,4-diMe-phenyl | O | S | Single Bond | 3 | 4-EtS, 2-EtS, 3,6-diMe-pyridinyl |
| 1280 | 5-Cl, 2-CHMe₂, 3,4-diMe-phenyl | O | S | Single Bond | 4 | 4-EtS, 2-EtS, 3,6-diMe-pyridinyl |
| 1281 | 5-Cl, 2-CHMe₂, 3,4-diMe-phenyl | O | S | Single Bond | 5 | 4-EtS, 2-EtS, 3,6-diMe-pyridinyl |
| 1282 | 5-Cl, 2-CHMe₂, 3,4-diMe-phenyl | O | S | Single Bond | 6 | 4-EtS, 2-EtS, 3,6-diMe-pyridinyl |

TABLE 67-continued
| Compound No. | A | X | Y | Z | n | Het |
|---|---|---|---|---|---|---|
| 1283 | 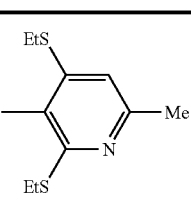 | O | S | Single Bond | 7 | 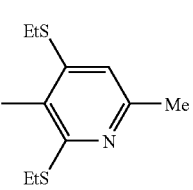 |
| 1284 | 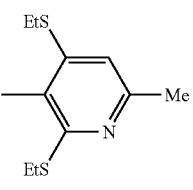 | O | S | Single Bond | 8 | 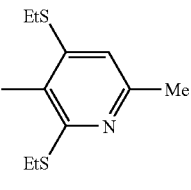 |
| 1285 | 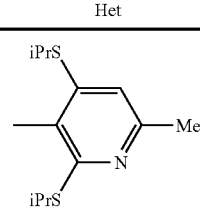 | O | S | Single Bond | 9 | 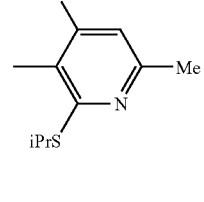 |
| 1286 | Me—Me / Cl, Me, Me | O | S | Single Bond | 14 | EtS, Me, EtS (pyridine) |
TABLE 68
| Compound No. | A | X | Y | Z | n | Het |
|---|---|---|---|---|---|---|
| 1287 | CF₃ (2,3-dimethylphenyl) | O | S | Single Bond | 1 | iPrS, Me, iPrS (pyridine) |
| 1288 | CF₃ (2,3-dimethylphenyl) | O | S | Single Bond | 2 | iPrS, Me, iPrS (pyridine) |

TABLE 68-continued
| Compound No. | A | X | Y | Z | n | Het |
|---|---|---|---|---|---|---|
| 1289 |  CF₃ | O | S | Single Bond | 3 | 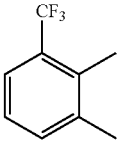 |
| 1290 | 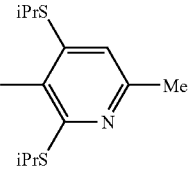 CF₃ | O | S | Single Bond | 4 | 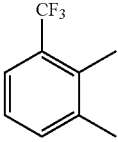 |
| 1291 | 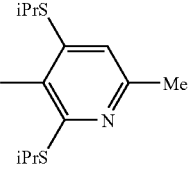 CF₃ | O | S | Single Bond | 5 | 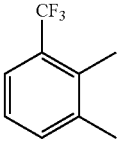 |
| 1292 | 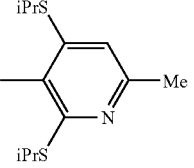 CF₃ | O | S | Single Bond | 6 | 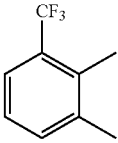 |
| 1293 | 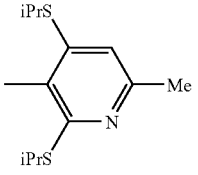 CF₃ | O | S | Single Bond | 7 | 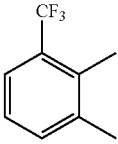 |
| 1294 | 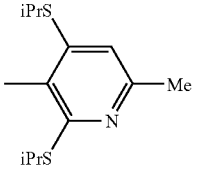 CF₃ | O | S | Single Bond | 8 | 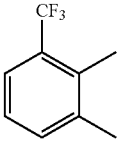 |
| 1295 | 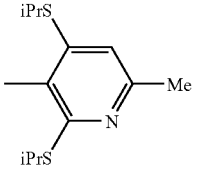 CF₃ | O | S | Single Bond | 9 | 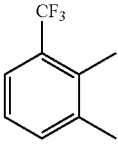 |
| 1296 | 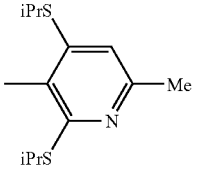 CF₃ | O | S | Single Bond | 14 | 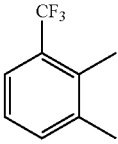 |

TABLE 69

| Compound No. | A | X | Y | Z | n | Het |
|---|---|---|---|---|---|---|
| 1297 | Me-CH(Me)-[3-Cl,5,6-diMe,4-Me-phenyl] | O | S | Single Bond | 1 | 3-Me,4-iPrS,6-Me,2-iPrS-pyridine |
| 1298 | Me-CH(Me)-[3-Cl,5,6-diMe,4-Me-phenyl] | O | S | Single Bond | 2 | 3-Me,4-iPrS,6-Me,2-iPrS-pyridine |
| 1299 | Me-CH(Me)-[3-Cl,5,6-diMe,4-Me-phenyl] | O | S | Single Bond | 3 | 3-Me,4-iPrS,6-Me,2-iPrS-pyridine |
| 1300 | Me-CH(Me)-[3-Cl,5,6-diMe,4-Me-phenyl] | O | S | Single Bond | 4 | 3-Me,4-iPrS,6-Me,2-iPrS-pyridine |
| 1301 | Me-CH(Me)-[3-Cl,5,6-diMe,4-Me-phenyl] | O | S | Single Bond | 5 | 3-Me,4-iPrS,6-Me,2-iPrS-pyridine |
| 1302 | Me-CH(Me)-[3-Cl,5,6-diMe,4-Me-phenyl] | O | S | Single Bond | 6 | 3-Me,4-iPrS,6-Me,2-iPrS-pyridine |

TABLE 69-continued

| Compound No. | A | X | Y | Z | n | Het |
|---|---|---|---|---|---|---|
| 1303 | 5-Cl, 2,3,4-triMe, 6-CH(Me)₂-phenyl | O | S | Single Bond | 7 | 3-Me, 6-Me, 2,4-bis(iPrS)-pyridin-yl |
| 1304 | 5-Cl, 2,3,4-triMe, 6-CH(Me)₂-phenyl | O | S | Single Bond | 8 | 3-Me, 6-Me, 2,4-bis(iPrS)-pyridin-yl |
| 1305 | 5-Cl, 2,3,4-triMe, 6-CH(Me)₂-phenyl | O | S | Single Bond | 9 | 3-Me, 6-Me, 2,4-bis(iPrS)-pyridin-yl |
| 1306 | 5-Cl, 2,3,4-triMe, 6-CH(Me)₂-phenyl | O | S | Single Bond | 14 | 3-Me, 6-Me, 2,4-bis(iPrS)-pyridin-yl |

TABLE 70

| Compound No. | A | X | Y | Z | n | Het |
|---|---|---|---|---|---|---|
| 1307 | 2,3-diMe, 6-SO₂Me-phenyl | O | S | Single Bond | 1 | 3-Me, 6-Me, 2,4-bis(MeS)-pyridin-yl |
| 1308 | 2,3-diMe, 6-SO₂Me-phenyl | O | S | Single Bond | 2 | 3-Me, 6-Me, 2,4-bis(MeS)-pyridin-yl |

TABLE 70-continued

| Compound No. | A | X | Y | Z | n | Het |
|---|---|---|---|---|---|---|
| 1309 | 2,3-dimethylphenyl-SO₂Me | O | S | Single Bond | 3 | pyridine (MeS, MeS, Me) |
| 1310 | 2,3-dimethylphenyl-SO₂Me | O | S | Single Bond | 4 | pyridine (MeS, MeS, Me) |
| 1311 | 2,3-dimethylphenyl-SO₂Me | O | S | Single Bond | 5 | pyridine (MeS, MeS, Me) |
| 1312 | 2,3-dimethylphenyl-SO₂Me | O | S | Single Bond | 6 | pyridine (MeS, MeS, Me) |
| 1313 | 2,3-dimethylphenyl-SO₂Me | O | S | Single Bond | 7 | pyridine (MeS, MeS, Me) |
| 1314 | 2,3-dimethylphenyl-SO₂Me | O | S | Single Bond | 8 | pyridine (MeS, MeS, Me) |
| 1315 | 2,3-dimethylphenyl-SO₂Me | O | S | Single Bond | 9 | pyridine (MeS, MeS, Me) |
| 1316 | 2,3-dimethylphenyl-SO₂Me | O | S | Single Bond | 14 | pyridine (MeS, MeS, Me) |

TABLE 71

| Compound No. | A | X | Y | Z | n | Het |
|---|---|---|---|---|---|---|
| 1317 | SO₂Me (2,3-disubstituted phenyl) | O | S | Single Bond | 1 | 4-EtS, 3-Me, 2-EtS, 6-Me pyridine |
| 1318 | SO₂Me (2,3-disubstituted phenyl) | O | S | Single Bond | 2 | 4-EtS, 3-Me, 2-EtS, 6-Me pyridine |
| 1319 | SO₂Me (2,3-disubstituted phenyl) | O | S | Single Bond | 3 | 4-EtS, 3-Me, 2-EtS, 6-Me pyridine |
| 1320 | SO₂Me (2,3-disubstituted phenyl) | O | S | Single Bond | 4 | 4-EtS, 3-Me, 2-EtS, 6-Me pyridine |
| 1321 | SO₂Me (2,3-disubstituted phenyl) | O | S | Single Bond | 5 | 4-EtS, 3-Me, 2-EtS, 6-Me pyridine |
| 1322 | SO₂Me (2,3-disubstituted phenyl) | O | S | Single Bond | 6 | 4-EtS, 3-Me, 2-EtS, 6-Me pyridine |
| 1323 | SO₂Me (2,3-disubstituted phenyl) | O | S | Single Bond | 7 | 4-EtS, 3-Me, 2-EtS, 6-Me pyridine |
| 1324 | SO₂Me (2,3-disubstituted phenyl) | O | S | Single Bond | 8 | 4-EtS, 3-Me, 2-EtS, 6-Me pyridine |

TABLE 71-continued

| Compound No. | A | X | Y | Z | n | Het |
|---|---|---|---|---|---|---|
| 1325 | SO₂Me (2,3-dimethylphenyl) | O | S | Single Bond | 9 | 3-methyl-4-EtS-2-EtS-6-Me-pyridine |
| 1326 | SO₂Me (2,3-dimethylphenyl) | O | S | Single Bond | 14 | 3-methyl-4-EtS-2-EtS-6-Me-pyridine |

TABLE 72

| Compound No. | A | X | Y | Z | n | Het |
|---|---|---|---|---|---|---|
| 1327 | SO₂Me (2,3-dimethylphenyl) | O | S | Single Bond | 1 | 3-methyl-4-iPrS-2-iPrS-6-Me-pyridine |
| 1328 | SO₂Me (2,3-dimethylphenyl) | O | S | Single Bond | 2 | 3-methyl-4-iPrS-2-iPrS-6-Me-pyridine |
| 1329 | SO₂Me (2,3-dimethylphenyl) | O | S | Single Bond | 3 | 3-methyl-4-iPrS-2-iPrS-6-Me-pyridine |
| 1330 | SO₂Me (2,3-dimethylphenyl) | O | S | Single Bond | 4 | 3-methyl-4-iPrS-2-iPrS-6-Me-pyridine |
| 1331 | SO₂Me (2,3-dimethylphenyl) | O | S | Single Bond | 5 | 3-methyl-4-iPrS-2-iPrS-6-Me-pyridine |

TABLE 72-continued

| Compound No. | A | X | Y | Z | n | Het |
|---|---|---|---|---|---|---|
| 1332 | SO₂Me, 2,3-dimethylphenyl | O | S | Single Bond | 6 | 3,4-bis(iPrS)-6-Me-pyridyl |
| 1333 | SO₂Me, 2,3-dimethylphenyl | O | S | Single Bond | 7 | 3,4-bis(iPrS)-6-Me-pyridyl |
| 1334 | SO₂Me, 2,3-dimethylphenyl | O | S | Single Bond | 8 | 3,4-bis(iPrS)-6-Me-pyridyl |
| 1335 | SO₂Me, 2,3-dimethylphenyl | O | S | Single Bond | 9 | 3,4-bis(iPrS)-6-Me-pyridyl |
| 1336 | SO₂Me, 2,3-dimethylphenyl | O | S | Single Bond | 14 | 3,4-bis(iPrS)-6-Me-pyridyl |

TABLE 73

| Compound No. | A | X | Y | Z | n | Het |
|---|---|---|---|---|---|---|
| 1337 | 2-methylphenyl | O | S | * | 1 | 4-methyl-6-methylthio-3-pyridyl |
| 1338 | " | O | S | * | 2 | 4-methyl-6-methylthio-3-pyridyl |
| 1339 | " | O | S | * | 3 | 4-methyl-6-methylthio-3-pyridyl |
| 1340 | " | O | S | * | 4 | 4-methyl-6-methylthio-3-pyridyl |
| 1341 | " | O | S | * | 5 | 4-methyl-6-methylthio-3-pyridyl |
| 1342 | " | O | S | * | 6 | 4-methyl-6-methylthio-3-pyridyl |
| 1343 | " | O | S | * | 7 | 4-methyl-6-methylthio-3-pyridyl |
| 1344 | " | O | S | * | 8 | 4-methyl-6-methylthio-3-pyridyl |
| 1345 | " | O | S | * | 9 | 4-methyl-6-methylthio-3-pyridyl |
| 1346 | " | O | S | * | 14 | 4-methyl-6-methylthio-3-pyridyl |
| 1347 | " | S | S | * | 1 | 4-methyl-6-methylthio-3-pyridyl |
| 1348 | " | S | S | * | 2 | 4-methyl-6-methylthio-3-pyridyl |
| 1349 | " | S | S | * | 3 | 4-methyl-6-methylthio-3-pyridyl |
| 1350 | " | S | S | * | 4 | 4-methyl-6-methylthio-3-pyridyl |
| 1351 | " | S | S | * | 5 | 4-methyl-6-methylthio-3-pyridyl |

TABLE 73-continued

| Compound No. | | X | Y | Z | n | Het |
|---|---|---|---|---|---|---|
| 1352 | " | S | S | * | 6 | 4-methyl-6-methylthio-3-pyridyl |
| 1353 | " | S | S | * | 7 | 4-methyl-6-methylthio-3-pyridyl |
| 1354 | " | S | S | * | 8 | 4-methyl-6-methylthio-3-pyridyl |
| 1355 | " | S | S | * | 9 | 4-methyl-6-methylthio-3-pyridyl |
| 1356 | " | S | S | * | 14 | 4-methyl-6-methylthio-3-pyridyl |

* = Single Bond

TABLE 74

| Compound No. | | X | Y | Z | n | Het |
|---|---|---|---|---|---|---|
| 1357 | | NH | S | * | 1 | 4-methyl-6-methylthio-3-pyridyl |
| 1358 | " | NH | S | * | 2 | 4-methyl-6-methylthio-3-pyridyl |
| 1359 | " | NH | S | * | 3 | 4-methyl-6-methylthio-3-pyridyl |
| 1360 | " | NH | S | * | 4 | 4-methyl-6-methylthio-3-pyridyl |
| 1361 | " | NH | S | * | 5 | 4-methyl-6-methylthio-3-pyridyl |
| 1362 | " | NH | S | * | 6 | 4-methyl-6-methylthio-3-pyridyl |
| 1363 | " | NH | S | * | 7 | 4-methyl-6-methylthio-3-pyridyl |
| 1364 | " | NH | S | * | 8 | 4-methyl-6-methylthio-3-pyridyl |
| 1365 | " | NH | S | * | 9 | 4-methyl-6-methylthio-3-pyridyl |
| 1366 | " | NH | S | * | 14 | 4-methyl-6-methylthio-3-pyridyl |
| 1367 | " | O | S | * | 1 | 5-methylthio-2-pyridyl |
| 1368 | " | O | S | * | 2 | 5-methylthio-2-pyridyl |
| 1369 | " | O | S | * | 3 | 5-methylthio-2-pyridyl |
| 1370 | " | O | S | * | 4 | 5-methylthio-2-pyridyl |
| 1371 | " | O | S | * | 5 | 5-methylthio-2-pyridyl |
| 1372 | " | O | S | * | 6 | 5-methylthio-2-pyridyl |
| 1373 | " | O | S | * | 7 | 5-methylthio-2-pyridyl |
| 1374 | " | O | S | * | 8 | 5-methylthio-2-pyridyl |
| 1375 | " | O | S | * | 9 | 5-methylthio-2-pyridyl |
| 1376 | " | O | S | * | 14 | 5-methylthio-2-pyridyl |

* = Single Bond

TABLE 75

| Compound No. | | X | Y | Z | n | Het |
|---|---|---|---|---|---|---|
| 1377 | | S | S | * | 1 | 5-methylthio-2-pyridyl |
| 1378 | " | S | S | * | 2 | 5-methylthio-2-pyridyl |
| 1379 | " | S | S | * | 3 | 5-methylthio-2-pyridyl |

TABLE 75-continued

| Compound No. | | X | Y | Z | n | Het |
|---|---|---|---|---|---|---|
| 1380 | " | S | S | * | 4 | 5-methylthio-2-pyridyl |
| 1381 | " | S | S | * | 5 | 5-methylthio-2-pyridyl |
| 1382 | " | S | S | * | 6 | 5-methylthio-2-pyridyl |
| 1383 | " | S | S | * | 7 | 5-methylthio-2-pyridyl |
| 1384 | " | S | S | * | 8 | 5-methylthio-2-pyridyl |
| 1385 | " | S | S | * | 9 | 5-methylthio-2-pyridyl |
| 1386 | " | S | S | * | 14 | 5-methylthio-2-pyridyl |
| 1387 | " | NH | S | * | 1 | 5-methylthio-2-pyridyl |
| 1388 | " | NH | S | * | 2 | 5-methylthio-2-pyridyl |
| 1389 | " | NH | S | * | 3 | 5-methylthio-2-pyridyl |
| 1390 | " | NH | S | * | 4 | 5-methylthio-2-pyridyl |
| 1391 | " | NH | S | * | 5 | 5-methylthio-2-pyridyl |
| 1392 | " | NH | S | * | 6 | 5-methylthio-2-pyridyl |
| 1393 | " | NH | S | * | 7 | 5-methylthio-2-pyridyl |
| 1394 | " | NH | S | * | 8 | 5-methylthio-2-pyridyl |
| 1395 | " | NH | S | * | 9 | 5-methylthio-2-pyridyl |
| 1396 | " | NH | S | * | 14 | 5-methylthio-2-pyridyl |

* = Single Bond

TABLE 76

| Compound No. | | X | Y | Z | n | Het |
|---|---|---|---|---|---|---|
| 1397 | | O | S | * | 1 | 2,4,6-trismethylthio-5-pyrimidyl |
| 1398 | " | O | S | * | 2 | 2,4,6-trismethylthio-5-pyrimidyl |
| 1399 | " | O | S | * | 3 | 2,4,6-trismethylthio-5-pyrimidyl |
| 1400 | " | O | S | * | 4 | 2,4,6-trismethylthio-5-pyrimidyl |
| 1401 | " | O | S | * | 5 | 2,4,6-trismethylthio-5-pyrimidyl |
| 1402 | " | O | S | * | 6 | 2,4,6-trismethylthio-5-pyrimidyl |
| 1403 | " | O | S | * | 7 | 2,4,6-trismethylthio-5-pyrimidyl |
| 1404 | " | O | S | * | 8 | 2,4,6-trismethylthio-5-pyrimidyl |
| 1405 | " | O | S | * | 9 | 2,4,6-trismethylthio-5-pyrimidyl |
| 1406 | " | O | S | * | 14 | 2,4,6-trismethylthio-5-pyrimidyl |
| 1407 | " | S | S | * | 1 | 2,4,6-trismethylthio-5-pyrimidyl |
| 1408 | " | S | S | * | 2 | 2,4,6-trismethylthio-5-pyrimidyl |
| 1409 | " | S | S | * | 3 | 2,4,6-trismethylthio-5-pyrimidyl |
| 1410 | " | S | S | * | 4 | 2,4,6-trismethylthio-5-pyrimidyl |
| 1411 | " | S | S | * | 5 | 2,4,6-trismethylthio-5-pyrimidyl |
| 1412 | " | S | S | * | 6 | 2,4,6-trismethylthio-5-pyrimidyl |
| 1413 | " | S | S | * | 7 | 2,4,6-trismethylthio-5-pyrimidyl |
| 1414 | " | S | S | * | 8 | 2,4,6-trismethylthio-5-pyrimidyl |
| 1415 | " | S | S | * | 9 | 2,4,6-trismethylthio-5-pyrimidyl |
| 1416 | " | S | S | * | 14 | 2,4,6-trismethylthio-5-pyrimidyl |

* = Single Bond

TABLE 77

| Compound No. | A | X | Y | Z | n | Het |
|---|---|---|---|---|---|---|
| 1417 | (o-dimethylphenyl) | NH | S | * | 1 | 2,4,6-trismethylthio-5-pyrimidyl |
| 1418 | " | NH | S | * | 2 | 2,4,6-trismethylthio-5-pyrimidyl |
| 1419 | " | NH | S | * | 3 | 2,4,6-trismethylthio-5-pyrimidyl |
| 1420 | " | NH | S | * | 4 | 2,4,6-trismethylthio-5-pyrimidyl |
| 1421 | " | NH | S | * | 5 | 2,4,6-trismethylthio-5-pyrimidyl |
| 1422 | " | NH | S | * | 6 | 2,4,6-trismethylthio-5-pyrimidyl |
| 1423 | " | NH | S | * | 7 | 2,4,6-trismethylthio-5-pyrimidyl |
| 1424 | " | NH | S | * | 8 | 2,4,6-trismethylthio-5-pyrimidyl |
| 1425 | " | NH | S | * | 9 | 2,4,6-trismethylthio-5-pyrimidyl |
| 1426 | " | NH | S | * | 14 | 2,4,6-trismethylthio-5-pyrimidyl |

* = Single Bond

TABLE 78

| Compound No. | A | X | Y | Z | n | Het |
|---|---|---|---|---|---|---|
| 1427 | (dimethylphenyl) | COOMe | O | S | Single Bond | 1 | EtS, Me, EtS pyridyl |
| 1428 | (methylpyridyl) | | O | S | Single Bond | 1 | EtS, Me, EtS pyridyl |

The compounds represented by the formula (I) in the present invention has an ACAT inhibitory activity and/or an intracellular cholesterol transfer inhibitory activity, and is useful in the medical field as medications for treating hyperlipemia or arteriosclerosis. Especially, the compounds of the present invention exhibit an activity of selectively inhibiting an ACAT enzyme which is present in the blood vessel wall. Accordingly, it is expected to have a less side effect than a non-selective ACAT inhibitor, and is preferable as an active ingredient of a drug.

The pharmaceutical composition of the present invention contains the compounds represented by the formula (I) or acid addition salts or solvates thereof as active ingredients. It comprises at least one type of the active ingredients in a therapeutically effective amount, and a pharmaceutically acceptable carrier.

The pharmaceutical composition of the present invention contains the compounds represented by the formula (I), or the acid addition salts or the solvates thereof as active ingredients. At least one type of the active ingredients is used singly, or can be shaped into an administrable preparation such as a tablet, a capsule, a granule, a powder, an injection or a suppository using a pharmaceutically acceptable carrier well-known to those skilled in the art, such as a excipient, a binder, a support or a diluent. These preparations can be produced by a known method. For example, an orally administrable preparation can be produced by mixing the compound represented by the formula (I) with an excipient such as starch, mannitol or lactose, a binder such as carboxymethylcellulose sodium or hydroxypropyl cellulose, a disintegrant such as crystalline cellulose or carboxymethyl cellulose calcium, a lubricant such as talc or magnesium stearate, and a fluidity improving agent such as light silicic anhydride, which are combined as required.

The pharmaceutical composition of the present invention can be administered either orally or parenterally.

The dose of the pharmaceutical composition of the present invention varies depending on the weight, the age, the sex, the progression of disease and the like of patients. Generally, it is preferably administered to an adult person at a dose of from 1 to 100 mg, preferably from 5 to 200 mg a day, from one to three times a day.

The ACAT inhibitory activity of the compounds represented by the formula (I) in the present invention was tested in the following Experiment Examples.

EXPERIMENT EXAMPLE 1

ACAT Inhibitory Activity

A microsome was prepared from the breast aorta of a rabbit which had been fed with 1% cholesterol food for 8 weeks in a usual manner, and suspended in a 0.15 M phosphate buffer solution (pH 7.4) to form an enzyme solution. An enzyme solution derived from the small intestine was prepared from the small intestine of a rabbit that had eaten a normal food.

The ACAT inhibitory activity was measured by modifying the method of J. G. Heider (J. Lipid Res., 24, 1127-1134, 1983). That is, 2 μl of a test compound dissolved in dimethyl sulfoxide (DMSO) were added to 88 μl of a 0.15 M phosphate buffer solution (pH 7.4)containing $^{14}$C-Oleoyl-CoA (40 μM, 60,000 dpm) and bovine serum albumin (2.4 mg/ml), and the mixture was incubated at 37° C. for 5 minutes.

To this solution were added 10 μl of the enzyme solution, and the mixture was reacted at 37° C. for 5 minutes (for 3 minutes in the case of the small intestine). Then, 3 ml of a chloroform/methanol (2/1) mixture and 0.5 ml of 0.04 N hydrochloric acid were added thereto to stop the reaction. The lipid was then extracted. The solvent layer was concentrated to dryness, and dissolved in hexane. The solution was spotted on a TLC plate(supplied by Merck Co.). The elution was conducted with a hexane:ether:acetic acid (75:25:1) mixture.

The radioactivity of the resulting cholesterol ester fraction was measured using BAS 2000 (supplied by Fuji Photo Film Co., Ltd.). An $IC_{50}$ value was obtained from the calculation in contrast with a control containing only DMSO. The results are shown in Table 79.

TABLE 79

| Test Compound No. | Enzyme from A‡ $IC_{50}$ (μM) | Enzyme from B‡ $IC_{50}$ (μM) | $IC_{50}$ (B‡)/ $IC_{50}$ (A‡) |
|---|---|---|---|
| 795 | 0.028 | 0.016 | 0.6 |
| 811 | 0.014 | 0.38 | 27.1 |
| 815 | 0.014 | 0.017 | 1.2 |
| 818 | 0.0056 | 0.016 | 2.9 |
| 831 | 0.63 | 0.61 | 1.0 |
| Control 1 | 0.45 | 0.87 | 1.9 |
| Control 2 | 0.047 | 0.13 | 2.8 |
| Control 3 | 0.034 | 0.056 | 1.7 |
| Control 4 | 0.026 | 0.037 | 1.4 |
| Control 5 | 0.01 | 0.065 | 6.5 |
| Control 6 | 0.11 | 0.51 | 4.6 |

A‡: the blood vessel wall
B‡: the small intestine

EXPERIMENT EXAMPLE 2

ACAT Inhibitory Activity (Anti-foamation Activity) in J744 Cells and HepG2 Cells J774 cells or HepG2 cells were spread on a 24-well plate. The cells were incubated in a 5% $CO_2$ incubator at 37° C. for 24 hours using DMEM in the case of the J774 cells and a MEM culture solution in the case of the HepG2 cells (both containing 10% fetal calf serum).

The medium was replaced with 0.5 ml of each culture solution containing 10 μg/ml of 25-OH cholesterol and a test piece, and the cells were further incubated for 18 hours.

The medium was removed, and the residue was washed twice with PBS, then extracted with 1.5 ml of a hexane: isopropanol (3:2) mixture, and concentrated to dryness. The extract was dissolved in 0.2 ml of isopropanol containing 10% Triton X-100. Total cholesterol (TC) and free cholesterol (FC) were measured using Cholesterol E Test Wako (supplied by Wako Pure Chemical Industries, Ltd.) and Free Cholesterol E Test Wako (supplied by Wako Pure Chemical Industries, Ltd.).

The cell extract residue was solubilized in 0.25 ml of 2N NaOH at 37° C. for 30 minutes, and the protein amount was measured using BCA Protein Assay Reagent (Pierce).

The amount of cholesterol based on the protein was calculated from the difference between TC and FC, and an $IC_{50}$ value was obtained from the calculation in contrast with the control. The results are shown in Table 80.

TABLE 80

| Test Compound No. | Enzyme (J774) $IC_{50}$ (μM) | Enzyme (HepG2) $IC_{50}$ (μM) | $IC_{50}$ (HepG2)/ $IC_{50}$ (J774) |
|---|---|---|---|
| 795 | 0.050 | 0.35 | 7.0 |
| 797 | 0.0036 | 0.029 | 8.1 |
| 811 | 0.050 | 1.8 | 36.0 |
| 815 | 0.12 | 2.6 | 21.7 |
| 818 | 0.062 | 0.063 | 1.0 |
| 831 | 0.057 | 5.4 | 94.7 |
| 1253 | 0.0041 | 0.0044 | 1.1 |
| 1282 | 0.0032 | 0.0062 | 1.9 |
| 1292 | 0.0027 | 0.030 | 11.1 |
| 1294 | 0.0042 | 0.0024 | 0.6 |
| 1302 | 0.0021 | 0.015 | 7.1 |
| Control 1 | 0.56 | 5.3 | 9.5 |
| Control 2 | 0.58 | 1.1 | 1.9 |
| Control 3 | 0.32 | 1.3 | 4.3 |
| Control 4 | 0.12 | 0.75 | 6.3 |
| Control 5 | 1.9 | 1.6 | 0.8 |
| Control 6 | 0.28 | 9.1 | 32.8 |

As control compounds, the following control compounds (1) to (6) were subjected to the same test, and the results are also shown in Tables 64 and 65. Control Compounds (1) to (6) are as follows.

CONTROL COMPOUND (1)

5-[2-(2-(4-fluorophenyl)ethyl)-3-(1-methyl-1H-imidazol-2-yl)-2H-1-benzopyran-6-yl]oxy-2,2-dimethyl-N-(2,6-diisopropylphenyl)pentanamide (WO 92/09582)

Control compound (2): (+)-(S)-2-[5-(3,5-dimethylpyrazol-1-yl)pentasulfinyl]-4,5-diphenylimidazole (EP 523941)
Control compound (3): N-(2,2,5,5-tetramethyl-1,3-dioxan-4-ylcarbonyl)-β-alanine 2 (S)-[N'-(2,2-dimethylpropyl)-N'-nonylureido]-1(S)-cyclohexyl ester (EP 421441)
Control compound (4): [5-(4,5-diphenyl-1H-imidazol-2-ylthio)pentyl]-N-heptyl-2-benzoxazolamie (WO 93/23392)
Control compound (5): 6-(benzoxazol-2-ylthio)-N-(2,6-diisopropylphenyl)hexanamide (compound of Japanese Patent Application No. 88,660/1997)
Contol compound (6): 2-[4-[2-(benzimidazol-2-ylthio)ethyl]piperazin-1-yl]-N-(2,6-diisopropylphenyl)acetamide (compound of Japanese Patent Application No. 149,892/1997)

EXAMPLES

The present invention is illustrated more specifically by referring to the following Examples. However, the present invention is not limited to these Examples.

Example 1 (Compound No. 5 in Table)

Production of 6-(benzoxazol-2-ylthio)-N-(2-methylthio-3-pyridyl)hexanamide

A methanol (50 ml) solution of 2-chloro-3-nitropyridine (4.30 g, 27.1 mmol) was added dropwise to a methanol (30 ml) solution of sodium thiomethoxide (2.10 g, 28.5 mmol) while being cooled with ice, and the mixed solution was stirred for 17 hours. Water was then added to the reaction mixture, and the resulting mixture was extracted with ethyl acetate. The organic layer was washed with a saturated aqueous solution of sodium chloride, and dried over sodium sulfate. Subsequently, the solvent was distilled off, and the resulting crystals were recrystallized from a mixture of an ethyl acetate-hexane mixture to obtain 2.93 g (yield 64%) of 2-methylthio-3-nitropyridine as a yellow needle crystal.

This nitropyridine (851 mg, 5.0 mmol) was dissolved in a mixed solvent of acetic acid (35 ml) and conc. hydrochloric acid (1.4 ml), and zinc (3.92 g, 60 mmol) was added thereto in small portions while being cooled with ice. After the mixture was stirred for 30 minutes, the reaction mixture was filtered, and the filtrate was neutralized with an aqueous solution of sodium hydrogencarbonate, and extracted with methylene chloride. The organic layer was washed with water and then with a saturated aqueous solution of sodium chloride, and dried over sodium sulfate. Subsequently, the solvent was distilled off to obtain 600 mg (yield 86%) of 3-amino-2-methylthiopyridine as a pale yellow oil.

Triethylamine (520 mg, 5.14 mmol) was added to a THF (7 ml) solution of this aminopyridine (600 mg, 4.28 mmol). Subsequently, 6-bromohexanoyl chloride (1.10 g, 5.14 mmol) was slowly added dropwise thereto while being cooled with ice, and the mixture was stirred at room temperature for 3 hours. The reaction mixture was diluted with water, and extracted with ethyl acetate. The organic layer was washed with water and then with a saturated aqueous solution of sodium chloride, and dried over sodium sulfate. Thereafter, the solvent was distilled off, and the resulting crude product was purified through silica gel chromatography (silica gel 125 g, eluent-hexane:ethyl acetate=6:1→3:1→2:1) to obtain 1.08 g (yield 79%) of 6-bromo-N-(2-methylthio-3-pyridyl) hexanamide as a colorless needle crystal (melting point: 66 to 67° C.).

To a DMF (2 ml) solution of this amide (159 mg, 0.5 mmol) and 2-mercaptobenzoxazole (83 mg, 0.55 mmol) were added 18-crown-6 (13 mg, 0.05 mmol) and potassium carbonate (83 mg, 0.6 mmol). and the mixture was stirred at 80° C. for 3 hours. The reaction mixture was diluted with water, and extracted with ethyl acetate. The organic layer was washed with water and then with a saturated aqueous solution of sodium chloride, and dried over sodium sulfate. Subsequently, the solvent was distilled off, and the resulting crude product was purified through silica gel chromatography (silica gel 20 g, eluent-hexane:ethyl acetate=5:2→2:1) to obtain 156 g (yield 81%) of a desired compound as a colorless needle crystal.

Melting point:127-128° C.

IR (KBr) cm$^{-1}$: 3447, 3265, 1654, 1522, 1508.

$^1$H-NMR (CDCl$_3$) δ: 1.58-1.65 (2H, m), 1.83 (2H, quint, J=7.4 Hz), 1.92 (2H, quint, J=7.4 Hz), 2.46 (2H, t, J=7.4 Hz), 2.62 (3H, s), 3.34 (2H, t, J=7.4 Hz), 7.06 (1H, dd, J=8.1, 4.6 Hz), 7.21-7.30 (3H, m), 7.44 (1H, m), 7.59 (1H, m), 8.26 (1H, d, J=4.6 Hz), 8.28 (1H, d, J=8.1 Hz).

EIMS m/z (relative intensity): 387 (M$^+$), 165 (100).

| Elemental analysis: as C$_{19}$H$_{21}$N$_3$O$_2$S$_2$ | | | |
|---|---|---|---|
| calculated: | C, 58.89; | H, 5.46; | N, 10.84; | S, 16.55. |
| found: | C, 58.92; | H, 5.43; | N, 10.78; | S, 16.55. |

Example 2 (Compound No. 8 in Table)

Production of 9-(benzoxazol-2-ylthio)-N-(2-methylthio-3-pyridiyl)nonanamide

The reaction and the treatment were conducted in the same manner as in Example 1 except that 9-bromononanoyl chloride was used instead of 6-bromohexanoyl chloride to obtain 9-bromo-N-(2-methylthio-3-pyridyl)nonanamide.

To a DMF (5 ml) solution of this amide (90 mg, 0.25 mmol) and 2-mercaptobenzoxazole (38 mg, 0.25 mmol) were added potassium carbonate (42 mg, 0.30 mmol) and 18-crown-6 (7 mg, 0.03 mmol), and the mixture was stirred at 80° C. for 3 hours. The reaction mixture was allowed to cool, and then extracted with ethyl acetate. The organic layer was washed with water and then with a saturated aqueous solution of sodium chloride, and dried over sodium sulfate. Subsequently, the solvent was distilled off, and the resulting residue was recrystallized from a mixture of ethyl acetate-hexane to obtain 83 mg (yield 77%) of the desired compound as a colorless powdery crystal.

Melting point: 84-85° C.

IR (KBr) cm$^{-1}$: 3465, 3276, 2926, 1664, 1505.

$^1$H-NMR (CDCl$_3$) δ: 1.35-1.53 (8H, m), 1.72-1.77 (2H, m), 1.80-1.87 (2H, m), 2.42 (2H, t, J=7.3 Hz), 2.63 (3H, s), 3.31 (2H, t, J=7.4 Hz), 7.06 (1H, dd, J=8.0, 4.7 Hz), 7.21-7.30 (3H, m), 7.43 (1H, dd, J=7.0, 0.6 Hz), 7.59 (1H, dd, J=7.6, 0.6 Hz), 8.25 (1H, d, J=4.7 Hz), 8.31 (1H, d, J=7.8 Hz).

EIMS m/z (relative intensity): 429 (M$^+$), 297 (100).

| Elemental analysis: as C$_{22}$H$_{27}$N$_3$O$_2$S$_2$ | | | |
|---|---|---|---|
| calculated: | C, 61.51; | H, 6.33; | N, 9.78; | S, 14.93. |
| found: | C, 61.51; | H, 6.28; | N, 9.64; | S, 14.99. |

Example 3 (Compound No. 15 in Table)

Production of 6-(benzothiazol-2-ylthio)-N-(2-methylthio-3-pyridyl)hexanamide

The reaction and the treatment were conducted in the same manner as in Example 1 except that 2-mercaptobenzothiazole was used instead of 2-mercaptobenzoxazole to obtain the desired compound as a colorless needle crystal.

Melting point: 118-119° C.

IR (KBr) cm$^{-1}$: 3429, 3265, 1654, 1522, 1508.

$^1$H-NMR (CDCl$_3$) δ: 1.57-1.65 (2H, m), 1.83 (2H, quint, J=7.4 Hz), 1.91 (2H, quint, J=7.4 Hz), 2.46 (2H, t, J=7.4 Hz), 2.61 (3H, s), 3.38 (2H, t, J=7.4 Hz), 7.06 (1H, dd, J=8.1, 4.9 Hz), 7.25 (1H, br s), 7.29 (1H, m), 7.41 (1H, m), 7.75 (1H, m), 7.86 (1H, m), 8.25 (1H, d, J=4.9 Hz), 8.29 (1H, d, J=8.1 Hz).

EIMS m/z (relative intensity): 403 (M$^+$), 223 (100).

| Elemental analysis: as C$_{19}$H$_{21}$N$_3$OS$_3$ | | | |
|---|---|---|---|
| calculated: | C, 56.55; | H, 5.24; | N, 10.41; | S, 23.83. |
| found: | C, 56.69; | H, 5.30; | N, 10.24; | S, 23.77. |

Example 4 (Compound No. 18 in Table)

Production of 9-(benzothiazol-2-ylthio)-N-(2-methylthio-3-pyridyl)nonanamide

The reaction and the treatment were conducted in the same manner as in Example 2 except that 2-mercaptobenzothiazole was used instead of 2-mercaptobenzoxazole to obtain the desired compound as a colorless needle crystal.

Melting point: 107-108° C.

IR (KBr) cm$^{-1}$: 3448, 3256, 2923, 1656, 1525.

$^1$H-NMR (d6-DMSO) δ: 1.24-1.34 (6H, m), 1.36-1.43 (2H, m), 1.54-1.59 (2H, m), 1.69-1.77 (2H, m), 2.26 (2H, t, J=7.4 Hz), 2.40 (3H, s), 3.28 (2H, t, J=7.2 Hz), 7.01 (1H, dd, J=7.8, 4.6 Hz), 7.26 (1H, dt, J=8.1, 1.2 Hz), 7.36 (1H, dt, J=7.3, 1.2 Hz), 7.58 (1H, dd, J=7.8, 1.5 Hz), 7.74 (1H, d, J=8.1 Hz), 7.85 (1H, dd, J=7.3, 1.2 Hz), 8.21 (1H, dd, J=4.6, 1.5 Hz), 8.73 (1H, br s).

EIMS m/z (relative intensity): 445 (M$^+$), 297 (100).

| Elemental analysis: as C$_{22}$H$_{27}$N$_3$OS$_3$ | | | | |
|---|---|---|---|---|
| calculated: | C, 59.29; | H, 6.11; | N, 9.43; | S, 21.58. |
| found: | C, 59.12; | H, 6.02; | N, 9.25; | S, 21.62. |

Example 5 (Compound No. 25 in Table)

Production of 6-(benzimidazol-2-ylthio)-N-(2-methylthio-3-pyridyl)hexanamide

The reaction and the treatment were conducted in the same manner as in Example 1 except that 2-mercaptobenzimidazole was used instead of 2-mercaptobenzoxazole to obtain the desired compound as a pale yellow needle crystal.

Melting point: 121-123° C.

IR (KBr) cm$^{-1}$: 3386, 3276, 1658, 1511, 1398.

$^1$H-NMR (CDCl$_3$) δ: 1.52-1.60 (2H, m), 1.74-1.86 (4H, m), 2.42 (2H, t, J=7.2 Hz), 2.60 (3H, s), 3.32 (2H, t, J=7.2 Hz), 7.05 (1H, dd, J=8.1, 4.9 Hz), 7.18-7.19 (2H, m), 7.32 (1H, br s), 7.36 (1H, br s), 7.66 (1H, br s), 8.23-8.26 (2H, m), 9.84 (1H, br s).

EIMS m/z (relative intensity): 386 (M$^+$), 205 (100).

| Elemental analysis: as C$_{19}$H$_{22}$N$_4$OS$_2$ | | | | |
|---|---|---|---|---|
| calculated: | C, 59.04; | H, 5.74: | N, 14.49; | S, 16.59. |
| found: | C, 59.06; | H, 5.76; | N, 14.35; | S, 16.57. |

Example 6 (Compound No. 28 in Table)

Production of 9-(benzimidazol-2-ylthio)-N-(2-methylthio-3-pyridyl)nonanamide

The reaction and the treatment were conducted in the same manner as in Example 2 except that 2-mercaptobenzimidazole was used instead of 2-mercaptobenzoxazole to obtain the desired compound as a colorless powdery crystal.

IR (KBr) cm$^{-1}$: 3260, 2929, 2851, 1664, 1519, 1394.

$^1$H-NMR (CDCl$_3$) δ: 1.31-1.47 (6H, m), 1.57-1.61 (2H, m), 1.69-1.79 (4H, m), 2.42 (2H, t, J=7.2 Hz), 2.63 (3H, s), 3.32 (2H, t, J=7.4 Hz), 7.06 (1H, dd, J=8.1, 4.6 Hz), 7.18-7.23 (4H, m), 7.67 (1H, br s), 8.26 (1H, d, J=4.6 Hz), 8.30 (1H, d, J=7.8 Hz), 9.31 (1H, br s).

EIMS m/z (relative intensity): 428 (M$^+$), 164 (100).

Example 7 (Compound No. 158 in Table)

Production of 9-(benzoxazol-2-ylthio)-N-(4-methyl-2-methylthio-3-pyridyl)nonanamide The reaction and the treatment were conducted in the same manner as in Example 1 except that 2-chloro-4-methyl-3-nitropyridine was used instead of 2-chloro-3-nitropyridine to obtain 4-methyl-2-methylthio-3-nitropyridine. This nitropyridine (474 mg, 2.57 mmol) was dissolved in a mixed solvent of acetic acid (18 ml) and conc. hydrochloric acid (0.7 ml), and zinc (2.02 g, 30.88 mmol) was added thereto in small portions while being cooled with ice. After the mixture was stirred for 30 minutes, the reaction mixture was filtered, and the filtrate was neutralized with an aqueous solution of sodium hydrogencarbonate, and extracted with methylene chloride. The organic layer was washed with water and then with a saturated aqueous solution of sodium chloride, and dried over sodium sulfate. Subsequently, the solvent was distilled off to obtain 307 mg (yield 77%) of 3-amino-4-methyl-2-methylthiopyridine as a colorless crystal.

Triethylamine (302 mg, 2.99 mmol) was added to a chloroform (4 ml) solution of this aminopyridine (307 mg, 1.99 mmol), and a chloroform (4 ml) solution of 9-bromononanyl chloride (2.99 mmol) was then slowly added thereto dropwise while being cooled with ice. The mixture was stirred at room temperature for 3 hours. The reaction mixture was diluted with water, and extracted with ethyl acetate. The organic layer was washed with water and then with a saturated aqueous solution of sodium chloride, and dried over sodium sulfate. Thereafter, the solvent was distilled off, and the resulting crude product was purified through silica gel chromatography (silica gel 125 g, eluent-hexane:ethyl acetate=3:1→2:1) to obtain 261 mg (yield 35%) of 9-bromo-N-(4-methyl-2-methylthio-3-pyridyl)nonanamide as a colorless powdery crystal (melting point: 77 to 78° C.). To a DMF (5 ml) solution of this amide (114 mg, 0.31 mmol) and 2-mercaptobenzoxazole (46 mg, 0.31 mmol) were added 18-crown-6 (8 mg, 0.03 mmol) and potassium carbonate (51 mg, 0.37 mmol), and the mixture was stirred at 80° C. for 2 hours. The reaction mixture was diluted with water, and then extracted with ethyl acetate. The organic layer was washed with water and then with a saturated aqueous solution of sodium chloride, and dried over sodium sulfate. Subsequently, the solvent was distilled off, and the resulting crude product was purified through preparative thin-layer chromatography (eluent—chloroform:methanol=20:1) to obtain 89 mg (yield 66%) of the desired compound as a colorless powdery crystal.

Melting point: 91-92° C.

IR (KBr) cm$^{-1}$: 3433, 3268, 2924, 1518, 1496.

$^1$H-NMR (CDCl$_3$) δ: 1.36-1.53 (8H, m), 1.74-1.88 (4H, m), 2.21 (3H, s), 2.43 (2H, t, J=7.6 Hz), 2.53 (3H, s), 3.32 (2H, t, J=7.3 Hz), 6.63 (1H, br s), 6.90 (1H, d, J=5.1 Hz), 7.22-7.30 (1H, m), 7.43 (1H, dd, J=7.2, 1.4 Hz), 7.60 (1H, dd, J=7.6, 1.4 Hz), 8.24 (1H, d, J=4.9 Hz).

EIMS m/z (relative intensity): 443 (M$^+$, 100).

| Elemental analysis: as $C_{23}H_{29}N_3O_2S_2$ | | | |
|---|---|---|---|
| calculated: | C, 62.27; | H, 6.59; | N, 9.47; S, 14.45. |
| found: | C, 62.34; | H, 6.58: | N, 9.33; S, 14.44. |

Example 8 (Compound No. 168 in Table)

Production of 9-(benzothiazol-2-ylthio)-N-(4-methyl-2-methylthio-3-pyridyl)nonanamide The reaction and the treatment were conducted in the same manner as in Example 7 except that 2-mercaptobenzothiazole was used instead of 2-mercaptobenzoxazole to obtain the desired compound as a colorless powdery crystal.

Melting point: 88-90° C.

IR (KBr) cm$^{-1}$: 3449, 3271, 2925, 1657, 1425, 997.

$^1$H-NMR (CDCl$_3$) δ: 1.37-1.53 (8H, m), 1.73-1.87 (4H, m), 2.21 (3H, s), 2.43 (2H, t, J=7.6 Hz), 2.53 (3H, s), 3.35 (2H, t, J=7.3 Hz), 6.62 (1H, br s), 6.90 (1H, d, J=5.1 Hz), 7.23-7.31 (1H, m), 7.39-7.43 (1H, m), 7.75 (1H, dd, J=8.1, 0.5 Hz), 7.86 (1H, dd, J=8.1, 0.5 Hz), 8.24 (1H, d, J=5.1 Hz).

| Elemental analysis: as $C_{23}H_{29}N_3OS_3$ | | | |
|---|---|---|---|
| calculated: | C, 60.10; | H, 6.36: | N, 9.14. |
| found: | C. 59.99; | H, 6.36: | N, 9.00. |

Example 9 (Compound No. 275 in Table)

Production of 6-(benzoxazol-2-ylthio)-N-[2,6-bis(methylthio)-3-pyridyl]hexanamide The reaction and the treatment were conducted in the same manner as in Example 1 except that 2,6-dichloro-3-nitropyridine was used instead of 2-chloro-3-nitropyridine. This nitropyridine (800 mg, 3.70 mmol) was dissolved in a mixed solvent of acetic acid (100 ml) and conc. hydrochloric acid (5.6 ml), and zinc (2.90 g, 44.39 mmol) was added thereto in small portions while being cooled with ice. After the mixture was stirred for 30 minutes, the reaction mixture was filtered, and the filtrate was neutralized with an aqueous solution of sodium hydrogencarbonate, and extracted with methylene chloride. The organic layer was washed with water and then with a saturated aqueous solution of sodium chloride, and dried over sodium sulfate. Subsequently, the solvent was distilled off, and the resulting crude product was purified through silica gel chromatography (eluent:hexane:ethyl acetate=4:1) to obtain 301 mg (yield 44%) of 3-amino-2,6-bis(methylthio)pyridine as a pale yellow powdery crystal.

Triethylamine (196 mg, 1.94 mmol) was added to a THF (3 ml) solution of this aminopyridine (301 mg, 1.62 mmol), and a THF (1 ml) solution of 6-bromohexanoyl chloride (345 mg, 1.62 mmol) was then slowly added thereto dropwise while being cooled with ice, and the mixture was stirred at 0° C. for 3 hours. The reaction mixture was diluted with water, and extracted with ethyl acetate. The organic layer was washed with water and then with a saturated aqueous solution of sodium chloride, and dried over magnesium sulfate. Subsequently, the solvent was distilled off, and the resulting crude product was purified through silica gel chromatography (eluent—hexane:ethyl acetate=4:1) to obtain 453 mg (yield 77%) of 6-bromo-N-[2,6-bis(methylthio)-3-pyridyl]hexanamide as a colorless powdery crystal (melting point: 117 to 119° C.). To a DMF (4 ml) solution of this amide (100 mg, 0.28 mmol) and 2-mercaptobenzoxazole (42 mg, 0.28 mmol) were added 18-crown-6 (7 mg, 0.03 mmol) and potassium carbonate (46 mg, 0.33 mmol), and the mixture was stirred at 80° C. for 3 hours. The reaction mixture was diluted with water, and then extracted with ethyl acetate. The organic layer was washed with water and then with a saturated aqueous solution of sodium chloride, and dried over magnesium sulfate. Subsequently, the solvent was distilled off, and the resulting crude product was recrystallized from a mixture of ethyl acetate and hexane to obtain 83 mg (yield 70%) of the desired compound as a colorless powdery crystal.

Melting point: 125-126° C.

IR (KBr) cm$^{-1}$: 3436, 3253, 2937, 1653, 1519, 1505.

$^1$H-NMR (CDCl$_3$) δ: 1.57-1.65 (2H, m), 1.78-1.86 (2H, m), 1.88-1.95 (2H, m), 2.44 (2H, t, J=7.4 Hz), 2.57 (3H, s), 2.62 (3H, s), 3.33 (2H, t, J=7.3 Hz), 6.93 (1H, d, J=8.4 Hz), 7.02 (1H, br s), 7.21-7.30 (29, m), 7.43 (1H, dd, J=7.4, 1.7 Hz), 7.59 (1H, dd, J=7.4, 1.7 Hz), 8.01 (1H, d, J=8.4 Hz),

| Elemental analysis: as $C_{20}H_{23}N_3O_2S_3$ | | | |
|---|---|---|---|
| calculated: | C, 55.40; | H, 5.35: | N, 9.69. |
| found: | C, 55.53; | H, 5.38: | N, 9.68. |

Example 10 (Compound No. 455 in Table)

Production of 6-(benzoxazol-2-ylthio)-N-(6-methyl-2-methylthio-3-pyridyl)hexanamide The reaction and the treatment were conducted in the same manner as in Example 1 except that 2-chloro-6-methyl-3-nitropyridine was used instead of 2-chloro-3-nitropyridine to obtain 6-methyl-2-methylthio-3-nitropyridine. This nitropyridine (921 mg, 5.0 mmol) was dissolved in a mixed solvent of acetic acid (40 ml) and conc. hydrochloric acid (1.75 ml), and zinc (3.81 g, 60 mmol) was added thereto in small portions while being cooled with ice. After the mixture was stirred for 30 minutes, the reaction mixture was filtered, and the filtrate was neutralized with an aqueous solution of sodium hydrogencarbonate, and extracted with methylene chloride. The organic layer was washed with water and then with a saturated aqueous solution of sodium chloride, and dried over sodium sulfate. Subsequently, the solvent was distilled off to obtain 685 mg (yield 88%) of 3-amino-6-methyl-2-methylthiopyridine as a yellow oil.

Triethylamine (475 mg, 4.7 mmol) was added to a chloroform (10 ml) solution of this aminopyridine (601 mg, 3.9 mmol), and 6-bromohexanoyl chloride (944 mg, 4.29 mmol) was then slowly added thereto dropwise while being cooled with ice, and the mixture was stirred at room temperature for 12 hours. The reaction mixture was diluted with water, and extracted with methylene chloride. The organic layer was washed with water and then with a saturated aqueous solution of sodium chloride, and dried over magnesium sulfate. Subsequently, the solvent was distilled off, and the resulting crude product was purified through silica gel chromatography (silica gel 50 g, eluent—hexane:ethyl acetate=10:1→5:1) to obtain 773 mg (yield 59%) of 6-bromo-N-(6-methyl-2-methylthio-3-pyridyl)hexanamide as a colorless crystal (melting point: 98 to 99° C.). To a DMF (2 ml) solution of this amide (133 mg, 0.4 mmol) and 2-mercaptobenzoxazole (67 mg, 0.44 mmol) were added 18-crown-6 (11 mg, 0.04 mmol) and potassium carbonate (67 mg, 0.44 mmol), and the mixture was stirred at 80° C. for 90 minutes. The reaction mixture was diluted with water, and extracted with ethyl acetate. The organic layer was washed with water and then with a saturated aqueous solution of sodium chloride, and dried over sodium sulfate. Subsequently, the solvent was distilled off, and the resulting crude product was purified through silica gel chromatography (silica gel 20 g, eluent-hexane:acetone=5:1→5:3) to obtain 125 mg (yield 78%) of the desired compound as a colorless needle crystal.

Melting point: 140-141° C.

IR (KBr) cm$^{-1}$: 3437, 3267, 1654, 1528, 1506.

$^1$H-NMR (CDCl$_3$) δ: 1.57-1.65 (2H, m),. 1.82 (2H, quint, J=7.4 Hz), 1.91 (2H, quint, J=7.4 Hz), 2.44 (2H, t, J=7.4 Hz), 2.48 (3H, s), 2.60 (3H, s), 3.33 (2H, t, J=7.4 Hz), 6.90 (1H, d, J=8.1 Hz), 7.21-7.30 (2H, m), 7.43 (1H, m), 7.59 (1H, m), 8.13 (1H, d, J=8.1 Hz).

EIMS m/z (relative intensity): 401 (M$^+$), 203 (100).

| Elemental analysis: as C$_{20}$H$_{23}$N$_3$O$_2$S$_2$ | | | |
|---|---|---|---|
| calculated: | C, 59.82; | H, 5.77: | N, 10.46. |
| found: | C, 59.90; | H, 5.84: | N, 10.32. |

Example 11 (Compound No. 458 in table)

Production of 9-(benzoxazol-2-ylthio)-N-(6-methyl-2-methylthio-3-pyridyl)nonanamide Triethylamine (607 mg, 6.0 mmol) was added to a chloroform (10 ml) solution of 3-amino-6-methyl-2-methylthiopyridine (685 mg, 4.44 mmol), and a chloroform (3 ml) solution of 9-bromononanyl chloride (1,281 mg, 5 mmol) was then slowly added thereto dropwise while being cooled with ice. The mixture was stirred at room temperature for 17 hours. The reaction mixture was diluted with water, and then extracted with ethyl acetate. The organic layer was washed with water and then with a saturated aqueous solution of sodium chloride, and dried over sodium sulfate. Subsequently, the solvent was distilled off, and the resulting crude product was purified through silica gel chromatography (silica gel 75 g, eluent—hexane:ethyl acetate=10:1→4:1) to obtain 433 mg (yield 27%) of 9-bromo-N-(6-methyl-2-methylthio-3-pyridyl)nonanamide as a colorless crystal (melting point: 80 to 82° C.).

To a DMF (1.5 ml) solution of this amide (131 mg, 0.35 mmol) and 2-mercaptobenzoxazole (58 mg, 0.385 mmol) were added 18-crown-6 (,9 mg, 0.035 mmol) and potassium carbonate (58 mg, 0.42 mmol), and the mixture was stirred at 80° C. for 3 hours. The reaction mixture was diluted with water, and then extracted with ethyl acetate. The organic layer was washed with water and then with a saturated aqueous solution of sodium chloride, and dried over sodium sulfate. Subsequently, the solvent was distilled off, and the resulting crude product was purified through silica gel chromatography (silica gel 30 g, eluent—hexane:ethyl acetate=4:1→3:1) to obtain 123 mg (yield 79%) of the desired compound as a colorless needle crystal.

Melting point: 99-100° C.

IR (KBr) cm$^{-1}$: 3421, 3235, 2924, 1655, 1528, 1497, 1455.

$^1$H-NMR (CDCl$_3$) δ: 1.32-1.42 (6H, m), 1.43-1.51 (2H, m), 1.70-1.78 (2H, m), 1.83 (2H, quint, J=-7.4 Hz), 2.40 (2H, t, J=7.4 Hz), 2.48 (3H, s), 2.61 (3H, s), 3.31 (2H, t, J=7.4 Hz), 6.90 (1H, d, J=8.1 Hz), 7.21-7.30 (3H, m), 7.43 (1H, m), 7.60 (1H, m), 8.15 (1H, d, J=8.1 Hz).

EIMS m/z (relative intensity): 443 (M$^+$), 311 (100).

Example 12 (Compound No. 465 in Table)

Production of 6-(benzothiazol-2-ylthio)-N-(6-methyl-2-methylthio-3-pyridyl)hexanamide The reaction and the treatment were conducted in the same manner as in Example 10 except that 2-mercaptobenzothiazole was used instead of 2-mercaptobenzoxazole to obtain the desired compound as a colorless needle crystal.

Melting point: 122-123° C.

IR (KBr) cm$^{-1}$: 3438, 3290, 1656, 1515, 1431.

$^1$H-NMR (CDCl$_3$) δ: 1.57-1.65 (2H, m), 1.82 (2H, quint, J=7.4 Hz), 1.90 (2H, quint, J=7.4 Hz), 2.44 (2H, t, J=7.4 Hz), 2.48 (3H, s), 2.60 (3H, s), 3.37 (2H, t, J=7.4 Hz), 6.90 (1H, d, J=8.3 Hz), 7.22(1H, br s) 7.29 (1H, m), 7.41 (1H, m), 7.75 (1H, m), 7.86 (1H, m), 8.13 (1H, J=8.3 Hz).

EIMS m/z (relative intensity): 417 (M$^+$), 168 (100).

| Elemental analysis: as C$_{20}$H$_{23}$N$_3$OS$_3$ | | | |
|---|---|---|---|
| calculated: | C, 57.52; | H, 5.55: | N, 10.06. |
| found: | C, 57.65; | H, 5.63: | N, 9.97. |

Example 13 (Compound No. 468 in Table)

Production of 9-(benzothiazol-2-ylthio)-N-(6-methyl-2-methylthio-3-pyridyl)nonanamide The reaction and the treatment were conducted in the same manner as in Example 11 except that 2-mercaptobenzothiazole was used instead of 2-mercaptobenzoxazole to obtain the desired compound as a colorless needle crystal.

Melting point: 104-105° C.

IR (KBr) cm$^{-1}$: 3280, 2924, 1662, 1527, 1428.

$^1$H-NMR (CDCl$_3$) δ: 1.32-1.41 (6H, m), 1.43-1.51 (2H, m), 1.70-1.77 (2H, m), 1.82 (2H, quint, J=7.4 Hz), 2.40 (2H, t, J 7.4 Hz), 2.48 (3H, s), 2.61 (3H, s), 3.34 (2H, t, J=7.4 Hz), 6.90 (1H, d, J=8.1 Hz), 7.22 (1H, br s) 7.29 (1H, m), 7.41 (1H, m), 7.76 (1H, m), 7.86 (1H, m), 8.15 (1H, d, J=8.1 Hz), EIMS m/z (relative intensity): 459 (M$^+$), 293 (100).

| Elemental analysis: as C$_{23}$H$_{29}$N$_3$OS$_3$ | | | |
|---|---|---|---|
| calculated: | C, 60.10; | H, 6.36: | N, 9.14. |
| found: | C, 60.17; | H, 6.40: | N, 9.11. |

Example 14 (Compound No. 475 in Table)

Production of 6-(benzimidazol-2-ylthio)-N-(6-methyl-2-methylthio-3-pyridyl )hexanamide The reaction and the treatment were conducted in the same manner as in Example 10 except that 2-mercaptobenzimidazole was used instead of 2-mercaptobenzoxazole to obtain the desired compound as a colorless crystal.

Melting point: 138-140° C.

IR (KBr) cm$^{-1}$: 3385, 3244, 1668, 1509, 1440.

¹H-NMR (CDCl₃) δ: 1.53-1.61 (2H, m), 1.78 (2H, quint, J=7.6 Hz), 1.82 (2H, quint, J=7.6 Hz), 2.41 (2H, t, J=7.6 Hz), 2.48 (3H, s), 2.59 (3H, s), 3.31 (2H, t, J=7.6 Hz), 6.88 (1H, d, J 8.3 Hz), 7.16-7.23 (2H, m), 7.31-7.32 (2H, m), 7.67 (1H, m), 8.08 (1H, d, J=8.3 Hz), 9.72 (1H, br s).
EIMS m/z (relative intensity): 400 (M⁺), 164 (100).

| Elemental analysis: as $C_{20}H_{24}N_4OS_2$ | | | |
|---|---|---|---|
| calculated: | C, 59.97; | H, 6.04: | N, 13.99. |
| found: | C, 60.08; | H, 6.08: | N, 13.94. |

Example 15 (Compound No. 478 in Table

Production of 9-(benzimidazol-2-ylthio)-N-(6-methyl-2-methylthio-3-pyridyl)nonanamide The reaction and the treatment were conducted in the same manner as in Example 11 except that 2-mercaptobenzimidazole was used instead of 2-mercaptobenzoxazole to obtain the desired compound as a colorless needle crystal.
Melting point: 73-75° C.
IR (KBr) cm⁻¹: 3254, 2926, 1663, 1515, 1438.
¹H-NMR (CDCl₃) δ: 1.27-1.43 (8H, m), 1.68-1.78 (4H, m), 2.40 (2H, t, J=7.4 Hz), 2.48 (3H, s), 2.60 (3H, s), 3.31 (2H, t, J=7.4 Hz), 6.89 (1H, d, J=8.1 Hz), 7.17-7.20 (2H, m), 7.31-7.33 (2H, m), 7.67 (1H, m), 8.13 (1H, d, J=8.1 Hz), 9.69 (1H, br s).

Example 16 (Compound No. 781 in Table)

Production of 2-(benzoxazol-2-ylthio)-N-[2,4-bis(methylthio)-6-methyl-3-pyridyl]acetamide Triethylamine (274 mg, 2.71 mmol) was added to a chloroform (10 ml) solution of 3-amino-2,4-bis(methylthio)-6-methylpyridine (492 mg, 2.46 mmol), and bromoacetyl bromide (521 mg, 2.58 mmol) was then slowly added thereto dropwise while being cooled with ice. The mixture was stirred at room temperature for 2 hours. The reaction mixture was diluted with water, and then extracted with methylene chloride. The organic layer was washed with 1N hydrochloric acid, water, an aqueous solution of sodium hydrogencarbonate, water and a saturated aqueous solution of sodium chloride in this order, and dried over sodium sulfate. Subsequently, the solvent was distilled off, and the resulting crude product was purified through silica gel chromatography (silica gel 25 g, eluent—hexane:acetone=7:1→5:1→3:1) to obtain 100 mg (yield 13%) of 2-bromo-N-[2,4-bis(methylthio)-6-methyl-3-pyridyl]acetamide as a colorless crystal (melting point: 171 to 172° C.).
Potassium carbonate (46 mg, 0.33 mmol) was added to an acetonitrile (5 ml) solution of this amide (96 mg, 0.3 mmol) and 2-mercaptobenzoxazole (45 mg, 0.3 mmol), and the mixture was stirred at room temperature for 90 minutes. The reaction mixture was diluted with water, and then extracted with ethyl acetate. The organic layer was washed with water and then with a saturated aqueous solution of sodium chloride, and dried over sodium sulfate. Subsequently, the solvent was distilled off, and the resulting crude product was purified through silica gel chromatography (silica gel 10 g, eluent—hexane:acetone=5:2) to obtain 88 mg (yield 75%) of the desired compound as a colorless crystal.
Melting point: 203-205° C.

IR (KBr) cm⁻¹: 3437, 3238, 1669, 1509, 1454.
¹H-NMR (CDCl₃) δ: 2.31 (3H, s), 2.41 (3H, s), 2.46 (3H, s), 4.10 (2H, s), 6.61 (1H, s), 7.28-7.33 (2H, m), 7.49 (1H, m), 7.60 (1H, m), 8.77 (1H, br s).
EIMS m/z (relative intensity): 391 (M⁺), 227 (100).

| Elemental analysis: as $C_{17}H_{17}N_3O_2S_3$ | | | |
|---|---|---|---|
| calculated: | C, 52.15; | H, 4.38; | N, 10.73. |
| found: | C, 52.14; | H, 4.44; | N, 10.57. |

Example 17 (Compound No. 783 in Table)

Production of 4-(benzoxazol-2-ylthio)-N-[2,4-bis(methylthio)-6-methyl-3-pyridyl]butanamide Triethylamine (206 mg, 2.04 mmol) was added to a THF (6 ml) solution of 3-amino-2,4-bis(methylthio)-6-methylpyridine (341 mg, 1.70 mmol), and 4-bromobutanoyl chloride (379 mg, 2.04 mmol) was then slowly added thereto dropwise while being cooled with ice. The mixture was stirred at room temperature for 2 hours. The reaction mixture was diluted with water, and then extracted with ethyl acetate. The organic layer was washed with water and then with a saturated aqueous solution of sodium chloride, and dried over sodium sulfate. Subsequently, the solvent was distilled off, and the resulting crude product was purified through silica gel chromatography (silica gel 75 g, eluent—hexane:acetone=5:1→3:1) to obtain 390 mg (yield 66%) of 4-bromo-N-[2,4-bis(methylthio)-6-methyl-3-pyridyl]butanamide as a colorless crystal (melting point: 139 to 140° C.).
To a DMF (2 ml) solution of this amide (105 mg, 0.3 mmol) and 2-mercaptobenzoxazole (50 mg, 0.33 mmol) were added 18-crown-6 (8 mg, 0.03 mmol) and potassium carbonate (50 mg, 0.36 mmol), and the mixture was stirred at 80° C. for 3 hours. The reaction mixture was diluted with water, and then extracted with ethyl acetate. The organic layer was washed with water and then with a saturated aqueous solution of sodium chloride, and dried over sodium sulfate. Subsequently, the solvent was distilled off, and the resulting crude product was purified through preparative thin-layer chromatography (eluent—hexane:ethyl acetate=3:2, eluted twice) to obtain 67 mg (yield 53%) of the desired compound as a colorless needle crystal.
Melting point: 149-150° C.
IR (KBr) cm⁻¹: 3437, 3248, 1667, 1503, 1455.
¹H-NMR (d6-DMSO) δ: 2.13 (2H, quint, J=7.2 Hz), 2.37 (3H, s), 2.38 (3H, s), 2.44 (3H, s), 2.49 (2H, t, J=7.2 Hz), 3.43 (2H, t, J=7.2 Hz), 6.88 (1H, s), 7.30-7.37 (2H, m), 7.64-7.68 (2H, m), 9.45 (1H, br s).
EIMS m/z (relative intensity): 419 (M⁺, 100).

| Elemental analysis: as $C_{19}H_{21}N_3O_2S_3$ | | | |
|---|---|---|---|
| calculated: | C, 54.39; | H, 5.04; | N, 10.01. |
| found: | C, 54.58; | H, 5.08; | N, 9.98. |

Example 18 (Compound No. 785 in table)

Production of 6-(benzoxazol-2-ylthio)-N-[2,4-bis(methylthio)-6-methyl-3-pyridyl]hexanamide The reaction and the treatment were conducted in the same manner as in Example 17 except that 6-bromohexanoyl chloride was used instead of 4-bromobutanoyl chloride to obtain the desired compound as a colorless powdery crystal.

Melting point: 120-121° C.

IR (KBr) cm$^{-1}$: 3433, 3235, 1662, 1502, 1455.

$^1$H-NMR (d6-DMSO) δ: 1.44-1.54 (2H, m), 1.58-1.68 (2H, m), 1.72-1.82 (2H, m), 2.18-2.27 (2H, m), 2.32 (3H, s), 2.34 (3H, s), 2.37 (3H, s), 3.27 (2H, t, J=7.2 Hz), 6.78 (1H, s), 7.19-7.26 (2H, m), 7.47-7.53 (2H, m), 8.74 (1H, br s).

EIMS m/z (relative intensity): 446 (M$^+$−1), 200 (100).

| Elemental analysis: as $C_{21}H_{25}N_3O_2S_3$ | | | |
|---|---|---|---|
| calculated: | C, 56.35; | H, 5.63: | N, 9.39; | S, 21.49. |
| found: | C, 56.42; | H, 5.62: | N, 9.26; | S, 21.39. |

Example 19 (Compound No. 788 in Table)

Production of 9-(benzoxazol-2-ylthio)-N-[2,4-bis(methylthio)-6-methyl-3-pyridyl]nonanamide The reaction and the treatment were conducted in the same manner as in Example 17 except that 9-bromononanoyl chloride was used instead of 4-bromobutanoyl chloride to obtain the desired compound as a colorless powdery crystal.

Melting point: 123-124° C.

IR (KBr) cm$^{-1}$: 3461, 3246, 1671, 1504, 1454.

$^1$H-NMR (d6-DMSO) δ: 1.26-1.46 (8H, m), 1.53-1.63 (2H, m), 1.72-1.83 (2H, m), 2.24 (2H, t, J=7.3 Hz), 2.37 (3H, s), 2.38 (3H, s), 2.43 (3H, s), 3.31-3.41 (2H, m), 6.86 (1H, s), 7.27-7.34 (2H, m), 7.58-7.66 (2H, m), 9.26 (1H, br s).

EIMS m/z (relative intensity): 489 (M$^+$, 100).

| Elemental analysis: as $C_{24}H_{31}N_3O_2S_3$ | | | |
|---|---|---|---|
| calculated: | C, 58.86; | H, 6.38: | N, 8.58; | S, 19.64. |
| found: | C, 58.94; | H, 6.37: | N, 8.44; | S, 19.55. |

Example 20 (Compound No. 793 in Table)

Production of 4-(benzothiazol-2-ylthio)-N-[2,4-bis(methylthio)-6-methyl-3-pyridyl]butanamide The reaction and the treatment were conducted in the same manner as in Example 17 except that 2-mercaptobenzothiazole was used instead of 2-mercaptobenzoxazole to obtain the desired compound as a colorless crystal.

Melting point: 131-133° C.

IR (KBr) cm$^{-1}$: 3435, 3250, 1665, 1509, 1428.

$^1$H-NMR (d6-DMSO) δ: 2.11 (2H, quint, J=7.2 Hz), 2.37 (3H, s), 2.38 (3H, s), 2.44 (3H, s), 2.49 (2H, t, J=7.2 Hz), 3.46 (2H, t, J=7.2 Hz), 6.88 (1H, s), 7.37 (1H, m), 7.47 (1H, m), 7.87 (1H, m), 8.02 (1H, m), 9.45 (1H, s).

EIMS m/z (relative intensity): 435 (M$^+$), 168 (100).

| Elemental analysis: as $C_{19}H_{21}N_3OS_4$ | | | |
|---|---|---|---|
| calculated: | C, 52.39; | H, 4.86: | N, 9.65. |
| found: | C, 52.39; | H, 4.84: | N, 9.56. |

Example 21 (Compound No. 795 in Table)

Production of 6-(benzothiazol-2-ylthio)-N-[2,4-bis(methylthio)-6-methyl-3-pyridyl]hexanamide The reaction and the treatment were conducted in the same manner as in Example 18 except that 2-mercaptobenzothiazole was used instead of 2-mercaptobenzoxazole to obtain the desired compound as a pale yellow crystal.

Melting point: 123-125° C.

IR (KBr) cm$^{-1}$: 3433, 3258, 2923, 1661, 1429

$^1$H-NMR (d6-DMSO) δ: 1.49-1.58 (6H, m), 1.67 (2H, quint, J=7.2 Hz), 1.83 (2H, quint, J=7.2 Hz), 2.29 (2H, t, J=7.2 Hz), 2.38 (3H, s), 2.39 (3H, s), 2.45 (3H, s), 3.38 (2H, t, J=7.2 Hz), 6.68 (1H, s), 7.36 (1H, td, J=8.0, 1.0 Hz), 7.46 (1H, td, J=8.0, 1.0 Hz), 7.86 (1H, dd, J=8.0, 1.0 Hz), 8.01 (1H, br d, J=8.0 Hz), 9.31 (1H, s).

EIMS m/z (relative intensity): 463 (M$^+$), 201 (100).

| Elemental analysis: as $C_{21}H_{25}N_3OS_4$ | | | |
|---|---|---|---|
| calculated: | C, 54.40; | H, 5.43: | N, 9.06; | S, 27.66. |
| found: | C, 54.42; | H, 5.45: | N, 8.79; | S, 27.68. |

Example 22 (Compound No. 798 in Table)

Production of 9-(benzothiazol-2-ylthio)-N-[2,4-bis(methylthio)-6-methyl-3-pyridyl]nonanamide The reaction and the treatment were conducted in the same manner as in Example 19 except that 2-mercaptobenzothiazole was used instead of 2-mercaptobenzoxazole to obtain the desired compound as a colorless powdery crystal.

Melting point: 126-127° C.

IR (KBr) cm$^-$: 3440, 3252, 2924, 1661, 1430.

$^1$H-NMR (d6-DMSO) δ: 1.31-1.52 (8H, m), 1.59-1.68 (2H, m), 1.77-1.85 (2H, m), 2.23-2.33 (2H, m), 2.40 (3H, s), 2.42 (3H, s), 2.45 (3H, s), 3.36 (2H, t, J=7.2 Hz), 6.86 (1H, s), 7.34 (1H, dt, J=7.8, 1.2 Hz), 7.44 (1H, dt, J=7.8, 1.2 Hz), 7.83 (1H, d, J=8.3 Hz), 7.93 (1H, dt, J=7.8, 0.6 Hz), 8.78 (1H, br s).

EIMS m/z (relative intensity): 504 (M$^+$−1), 200 (100).

| Elemental analysis: as $C_{24}H_{31}N_3OS_4$ | | | |
|---|---|---|---|
| calculated: | C, 57.00; | H, 6.18: | N, 8.31; | S, 25.36. |
| found: | C, 57.08; | H, 6.17: | N, 8.15; | S, 25.41. |

Example 23 (Compound No. 803 in Table)

Production of 4-(benzimidazol-2-ylthio)-N-[2,4-bis(methylthio)-6-methyl-3-pyridyl]butanamide The reaction and the treatment were conducted in the same manner as in Example 17 except that 2-mercaptobenzimidazole was used instead of 2-mercaptobenzoxazole to obtain the desired compound as a pale yellow needle crystal.

Melting point: 177-179° C.

IR (KBr) cm$^{-1}$: 3421, 3147, 1659, 1645, 1438.

$^1$H-NMR (d6-DMSO) δ: 2.06 (2H, quint, J=7.2 Hz), 2.38 (3H, s), 2.39 (3H, s), 2.44 (3H, s), 2.46 (2H, t, J=7.2 Hz), 3.36 (2H, t, J=7.2 Hz), 6.88 (1H, s), 7.09-7.13 (2H, m), 7.34-7.52 (2H, m), 9.48 (1H, s), 12.54 (1H, br s).

EIMS m/z (relative intensity): 418 (M$^+$), 150 (100).

Example 24 (Compound No. 805 in table)

Production of 6-(benzimidazol-2-ylthio)-N-[2,4-bis (methylthio)-6-methyl-3-pyridyl]hexanamide The reaction and the treatment were conducted in the same manner as in Example 18 except that 2-mercaptobenzimidazole was used instead of 2-mercaptobenzoxazole to obtain the desired compound as a colorless crystal.

Melting point: 139-141° C.

IR (KBr) cm$^{-1}$: 3433, 3244, 2924, 1659, 1437.

$^1$H-NMR (d6-DMSO) δ: 1.47-1.56 (2H, m), 1.65 (2H, quint, J=7.2 Hz), 1.76 (2H, quint, J=7.2 Hz), 2.28 (2H, t, J=7.2 Hz), 2.38 (3H, s), 2.39 (3H, s), 2.44 (3H, s), 3.29 (2H, t, J=7.2 Hz), 6.68 (1H, s), 7.08-7.13 (2H, m), 7.36 (1H, m), 7.50 (1H, m), 9.30 (1H, s), 12.50 (1H, br s)

EIMS m/z (relative intensity): 446 (M$^+$), 200 (100).

Example 25 (Compound No. 808 in table)

Production of 9-(benzimidazol-2-ylthio)-N-[2,4-bis (methylthio)-6-methyl-3-pyridyl]nonanamide The reaction and the treatment were conducted in the same manner as in Example 19 except that 2-mercaptobenzimidazole was used instead of 2-mercaptobenzoxazole to obtain the desired compound as a colorless powdery crystal.

IR (KBr) cm$^{-1}$: 3146, 2925, 2854, 1660, 1523, 1437.

$^1$H-NMR (d6-DMSO) δ: 1.25-1.44 (8H, m), 1.53-1.61 (2H, m), 1.65-1.74 (2H, m), 2.24 (2H, t, J=7.3 Hz), 2.37 (3H, s), 2.38 (3H, s), 2.43 (3H, s), 3.26 (2H, t, J=7.1 Hz), 6.86 (1H, s), 7.07-7.12 (2H, m), 7.32-7.37 (1H, m), 7.46-7.54 (1H, m), 9.26 (1H, s).

EIMS m/z (relative intensity): 488 (M$^+$), 150 (100).

Example 26 (Compound No. 811 in table)

Production of 2-(benzoxazol-2-ylthio)-N-[2,4-bis (ethylthio)-6-methyl-3-pyridyl]acetamide Ethanethiol (1.55 g, 25 mmol) was added dropwise to an ethanol (50 ml) solution of sodium ethoxide (1.27 g, 25 mmol) while being cooled with ice, and the mixture was stirred for 30 minutes. While being cooled with ice, a DMF (40 ml) solution of 2,4-dichloro-6-methyl-3-nitropyridine (2.1 g, 10 mmol) was slowly added thereto dropwise. After the mixture was stirred for 2 hours, the reaction mixture was extracted with ethyl acetate. The organic layer was washed with water and then with a saturated aqueous solution of sodium chloride, and dried over sodium sulfate. Subsequently, the solvent was distilled off to obtain 2.45 g (yield 95%) of 2,4-bis(ethylthio)-6-methyl-3-nitropyridine as a yellow needle crystal.

This nitropyridine (775 mg, 3 mmol) was dissolved in a mixed solvent of acetic acid (30 ml) and conc. hydrochloric acid (1.5 ml), and zinc (4 g, 60 mmol) was added thereto in small portions while being cooled with ice. After the mixture was stirred for 10 minutes, the reaction mixture was filtered, and the filtrate was neutralized with a sodium hydroxide aqueous solution, and extracted with ethyl acetate. The organic layer was washed with water and then with a saturated aqueous solution of sodium chloride, and dried over sodium sulfate. Subsequently, the solvent was distilled off to obtain 590 mg (yield 86%) of 3-amino-2,6-bis(ethylthio)-6-methylpyridine as a yellow oil. Triethylamine (304 mg, 3 mmol) was added to a THF (10 ml) solution of this aminopyridine (590 mg, 2.6 mmol), and bromoacetyl bromide (606 mg, 3 mmol) was then slowly added thereto dropwise while being cooled with ice. The mixture was stirred at room temperature for 1 hour. The reaction mixture was filtered, and the filtrate was concentrated. Then, the residue was purified through silica gel chromatography (silica gel 60 g, eluent—hexane:acetone=10:1→5:1) to obtain 410 mg (yield 45%) of 2-bromo-N-[2,4-bis(ethylthio)-6-methyl-3-pyridyl]acetamide as a light brown needle crystal. Potassium carbonate (46 mg, 0.33 mmol) was added to an acetonitrile (3 ml) solution of this amide (105 mg, 0.3 mmol) and 2-mercaptobenzoxazole (45 mg, 0.3 mmol), and the mixture was stirred at room temperature for 2 hours. The reaction mixture was extracted with ethyl acetate. The organic layer was washed with water and then with a saturated aqueous solution of sodium chloride, and dried over magnesium sulfate. Subsequently, the solvent was distilled off, and the resulting crude product was purified through preparative thin-layer chromatography (eluent—hexane:ethyl acetate=3:1) to obtain 70 mg (yield 56%) of the desired compound as a colorless needle crystal.

Melting point: 143-145° C.

IR (KBr) cm$^{-1}$: 3429, 3224, 1673, 1509, 1454.

$^1$H-NMR (CDCl$_3$) δ: 1.17 (3H, t, J=7.3 Hz), 1.20 (3H, t, J=7.5 Hz), 2.43 (3H, s), 2.81 (2H, q, J=7.3 Hz), 3.04 (2H, q, J=7.5 Hz), 4.11 (2H, s), 6.63 (1H, s), 7.25-7.33 (2H, m), 7.48 (1H, m), 7.61 (1H, m), 8.63 (1H, br s).

EIMS m/z (relative intensity): 419 (M$^+$), 268 (100).

| Elemental analysis: as $C_{19}H_{21}N_3O_2S_3$ | | | |
| --- | --- | --- | --- |
| calculated: | C, 54.39; | H, 5.04: | N, 10.01. |
| found: | C, 54.39; | H, 5.05: | N, 10.00. |

Example 27 (Compound No. 815 in Table)

Production of 6-(benzoxazol-2-ylthio)-N-[2,4-bis (ethylthio)-6-methyl-3-pyridyl]hexanamide The reaction and the treatment were conducted in the same manner as in Example 26 except that 6-bromohexanoyl chloride was used instead of bromoacetyl bromide to obtain 6-bromo-N-[2,4-bis(ethylthio)-6-methyl-3-pyridyl]hexanamide. To a DMF (2 ml) solution of this amide (122 mg, 0.3 mmol) and 2-mercaptobenzoxazole (45 mg, 0.3 mmol) were added potassium carbonate (46 mg, 0.33 mmol) and 18-crown-6 (8 mg, 0.03 mmol), and the mixture was stirred at 80° C. for 1.5 hours. The reaction mixture was allowed to cool, and then extracted with ethyl acetate. The organic layer was washed with water and then with a saturated aqueous solution of sodium chloride, and dried over sodium sulfate. Subsequently, the solvent was distilled off, and the resulting residue was purified through preparative thin-layer chromatography (eluent—hexane:acetone=5:2) to obtain 65 mg (yield 46%) of the desired compound as a light brown needle crystal.

Melting point: 100-103° C.

IR (KBr) cm$^{-1}$: 3233, 2928, 1668, 1504, 1455.

$^1$H-NMR (d6-DMSO) δ: 1.26 (3H, t, J=7.3 Hz), 1.27 (3H, t, J=7.3 Hz), 1.58 (2H, m), 1.70 (2H, m), 1.85 (2H, m), 2.32 (2H, m), 2.43 (3H, s), 2.94 (2H, q, J=7.3 Hz), 3.07 (2H, q, J=7.3 Hz), 3.35 (2H, t, J=7.3 Hz), 6.89 (1H, s), 7.26-7.34 (2H, m), 7.54-7.62 (2H, m), 8.77 (1H, br s).

EIMS m/z (relative intensity): 475 (M$^+$, 100).

| Elemental analysis: as $C_{23}H_{29}N_3O_2S_3$ | | | |
|---|---|---|---|
| calculated: | C, 58.08; | H, 6.14; | N, 8.83; | S, 20.22. |
| found: | C, 58.07; | H, 6.13; | N, 8.66; | S, 20.27. |

Example 28 (Compound No. 818 in table)

Production of 9-(benzoxazol-2-ylthio)-N-[2,4-bis(ethylthio)-6-methyl-3-pyridyl]nonanamide The reaction and the treatment were conducted in the same manner as in Example 27 except that 9-bromononanoyl chloride was used instead of 6-bromohexanoyl bromide to obtain the desired compound as a colorless needle crystal.

Melting point: 84-87° C.

IR (KBr) cm$^{-1}$: 3252, 2923, 1665, 1501, 1455.

$^1$H-NMR (d6-DMSO) δ: 1.26 (3H, t, J=7.3 Hz), 1.27 (3H, t, J=7.3 Hz), 1.28-1.52 (8H, m), 1.63 (2H, m), 1.82 (2H, quint, J=7.2 Hz), 2.26 (2H, m), 2.43 (3H, s), 2.94 (2H, q, J=7.3 Hz), 3.07 (2H, q, J=7.3 Hz), 3.34 (2H, t, J=7.2 Hz), 6.88 (1H, s), 7.26-7.34 (2H, m), 7.54-7.62 (2H, m), 8.72 (1H, br s).

EIMS m/z (relative intensity): 517 (M$^+$), 367 (100).

| Elemental analysis: as $C_{26}H_{35}N_3O_2S_3$ | | | |
|---|---|---|---|
| calculated: | C, 60.31; | H, 6.81; | N, 8.12. |
| found: | C, 60.52; | H, 6.85; | N, 7.85. |

Example 29 (Compound No. 821 in Table)

Production of 2-(benzothiazol-2-ylthio)-N-[2,4-bis(ethylthio)-6-methyl-3-pyridyl]acetamide The reaction and the treatment were conducted in the same manner as in Example 26 except that 2-mercaptobenzothiazole was used instead of 2-mercaptobenzoxazole to obtain the desired compound as a colorless needle crystal.

Melting point: 119-120° C.

IR (KBr) cm$^{-1}$: 3453, 3254, 1672, 1510, 1428.

$^1$H-NMR (CDCl$_3$) δ: 1.20 (3H, t, J=7.4 Hz), 1.22 (3H, t, J=7.4 Hz), 2.42 (3H, s), 2.82 (2H, q, J=7.4 Hz), 3.06 (2H, q, J=7.4 Hz), 4.18 (2H, s), 6.63 (1H, s), 7.33 (1H, m), 7.42 (1H, m), 7.77 (1H, m), 7.91 (1H, m), 8.95 (1H, br s).

EIMS m/z (relative intensity): 435 (M$^+$), 148 (100).

| Elemental analysis: as $C_{19}H_{21}N_3OS_4$ | | | |
|---|---|---|---|
| calculated: | C, 52.39; | H, 4.86; | N, 9.65. |
| found: | C, 52.40; | H, 4.86; | N, 9.53. |

Example 30 (Compound No. 825 in Table)

Production of 6-(benzothiazol-2-ylthio)-N-[2,4-bis(ethylthio)-6-methyl-3-pyridyl]hexanamide The reaction and the treatment were conducted in the same manner as in Example 27 except that 2-mercaptobenzothiazole was used instead of 2-mercaptobenzoxazole to obtain the desired compound as a colorless needle crystal.

Melting point: 81-83° C.

IR (KBr) cm$^{-1}$: 3150, 2927, 1647, 1524, 1428.

$^1$H-NMR (d6-DMSO) δ: 1.25 (3H, t, J=7.3 Hz), 1.26 (3H, t, J=7.3 Hz), 1.57 (2H, m), 1.69 (2H, m), 1.84 (2H, m), 2.29 (2H, m), 2.42 (3H, s), 2.93 (2H, q, J=7.3 Hz), 3.05 (2H, q, J=7.3 Hz), 3.36 (2H, t, J=7.3 Hz), 6.87 (1H, s), 7.33 (1H, m), 7.43 (1H, m), 7.82 (1H, m), 7.92 (1H, m), 8.77 (1H, br s).

EIMS m/z (relative intensity): 491 (M$^+$), 168 (100).

| Elemental analysis: as $C_{23}H_{29}N_3OS_4$ | | | |
|---|---|---|---|
| calculated: | C, 56.18; | H, 5.94; | N, 8.55; | S, 26.08. |
| found: | C, 56.19; | H, 5.91; | N, 8.43; | S, 26.06. |

Example 31 (Compound No. 828 in Table)

Production of 9-(benzothiazol-2-ylthio)-N-[2,4-bis(ethylthio)-6-methyl-3-pyridyl]nonanamide The reaction and the treatment were conducted in the same manner as in Example 28 except that 2-mercaptobenzothiazole was used instead of 2-mercaptobenzoxazole to obtain the desired compound as a colorless needle crystal.

Melting point: 88-92° C.

IR (KBr) cm$^{-1}$: 3433, 3241, 2928, 1668, 1510.

$^1$H-NMR (d6-DMSO) δ: 1.25 (3H, t, J=7.3 Hz), 1.26 (3H, t, J=7.3 Hz), 1.28-1.54 (8H, m), 1.62 (2H, m), 1.80 (2H, quint, J=7.2 Hz), 2.24 (2H, m), 2.42 (3H, s), 2.93 (2H, q, J=7.3 Hz), 3.05 (2H, q, J=7.3 Hz), 3.35 (2H, t, J=7.2 Hz), 6.87 (1H, s), 7.33 (1H, m), 7.43 (1H, m), 7.81 (1H, m), 7.92 (1H, m), 8.72 (1H, br s).

Example 32 (Compound No. 831 in Table)

Production of 2-(benzimidazol-2-ylthio)-N-[2,4-bis(ethylthio)-6-methyl-3-pyridyl]acetamide The reaction and the treatment were conducted in the same manner as in Example 26 except that 2-mercaptobenzimidazole was used instead of 2-mercaptobenzoxazole to obtain the desired compound as a colorless needle crystal.

Melting point: 182-183° C.

IR (KBr) cm$^{-1}$: 3148, 2928, 1674, 1524, 1412.

$^1$H-NMR (d6-DMSO) δ: 1.21 (3H, t, J=7.3 Hz), 1.21 (3H, t, J=7.3 Hz), 2.41 (3H, s), 2.90 (2H, q, J=7.3 Hz), 3.03 (2H, q, J=7.3 Hz), 4.15 (2H, br s), 6.87 (1H, s), 7.08-7.12 (2H, m), 7.39-7.44 (2H, m).

EIMS m/z (relative intensity): 418 (M$^+$), 357 (100).

| Elemental analysis: as $C_{19}H_{22}N_4OS_3$ | | | |
|---|---|---|---|
| calculated: | C, 54.52; | H, 5.30; | N, 13.38. |
| found: | C, 54.44; | H, 5.30; | N, 13.16. |

Example 33 (Compound No. 835 in Table)

Production of 6-(benzimidazol-2-ylthio)-N-[2,4-bis(ethylthio)-6-methyl-3-pyridyl]hexanamide The reaction and the treatment were conducted in the same manner as in Example 27 except that 2-mercaptobenzimidazole was used instead of 2-mercaptobenzoxazole to obtain the desired compound as a colorless needle crystal.

Melting point: 139-142° C.
IR (KBr) cm$^{-1}$: 3433, 3143, 2928, 1660, 1510.
$^1$H-NMR (CDCl$_3$) δ: 1.25 (3H, t, J=7.3 Hz), 1.26 (3H, t, J=7.3 Hz), 1.54 (2H, m), 1.68 (2H, m), 1.77 (2H, m), 2.28 (2H, m), 2.42 (3H, s), 2.92 (2H, q, J=7.3 Hz), 3.05 (2H, q, J=7.3 Hz), 3.27 (2H, t, J=7.2 Hz), 6.87 (1H, s), 7.05-7.11 (2H, m), 7.27-7.52 (2H, m), 8.75 (1H, br s), 12.05 (1H, br s).

Example 34 (Compound No. 838 in Table)

Production of 9-(benzimidazol-2-ylthio)-N-[2,4-bis(ethylthio)-6-methyl-3-pyridyl]nonanamide The reaction and the treatment were conducted in the same manner as in Example 28 except that 2-mercaptobenzimidazole was used instead of 2-mercaptobenzoxazole to obtain the desired compound as a colorless needle crystal.

Melting point: 76-78° C.
IR (KBr) cm$^{-1}$: 3104, 2928, 2854, 1658, 1526.
$^1$H-NMR (d6-DMSO) δ: 1.25 (3H, t, J=7.3 Hz), 1.26 (3H, t, J=7.3 Hz), 1.28-1.49 (8H, m), 1.61 (2H, m), 1.73 (2H, quint, J=7.2 Hz), 2.24 (2H, m), 2.42 (3H, s), 2.92 (2H, q, J=7.3 Hz), 3.05 (2H, q, J=7.3 Hz), 3.26 (2H, t, J=7.2 Hz), 6.87 (1H, s), 7.05-7.10 (2H, m), 7.24-7.54 (2H, m), 8.71 (1H, br s) 12.05 (1H, br s).

Example 35 (Compound No. 841 in Table)

Production of 2-(benzoxazol-2-ylthio)-N-[2,4-bis(isopropylthio)-6-methyl-3-pyridyl]acetamide To a 2-propanol (50 ml)-solution of sodium isopropoxide (2.05 g, 25 mmol) was added dropwise 2-propanethiol (1.90, 25 mmol) while being cooled with ice, and the mixtrue was stirred for 30 minutes. While being cooled with ice, a DMF (40 ml) solution of 2,4-dichloro-6-methyl-3-nitropyridine (2.07 g, 10 mmol) was slowly added thereto dropwise. After the mixture was stirred for 2 hours, the reaction mixture was extracted with ethyl acetate. The organic layer was washed with water and then with a saturated aqueous solution of sodium chloride, and dried over sodium sulfate. Subsequently, the solvent was distilled off to obtain 2.77 g (yield 97%) of 2,4-bis(isopropylthio)-6-methyl-3-nitropyridine as a yellow needle crystal.

This nitropyridine (1.08 g, 3.77 mmol) was dissolved in a mixed solvent of acetic acid (35 ml) and conc. hydrochloric acid (1.6 ml), and zinc (2.96 g, 45.25 mmol) was added thereto in small portions while being cooled with ice. After the mixture was stirred for 1 hour, the reaction mixture was filtered, and the filtrate was neutralized with an aqueous solution of sodium hydrogencarbonate, and extracted with chloroform. The organic layer was washed with water and then with a saturated aqueous solution of sodium chloride, and dried over sodium sulfate. Subsequently, the solvent was distilled off, and the resulting residue was purified through silica gel column chromatography (eluent—hexane:ethyl acetate=30:1→10:1) to obtain 774 mg (yield 80%) of 3-amino-2,4-bis(isopropylthio)-6-methylpyridine as a yellow oil. Triethylamine (336 mg, 3.32 mmol) was added to a THF (10 ml) solution of this aminopyridine (774 mg, 3.02 mmol), and bromoacetyl bromide (732 mg, 3.62 mmol) was then slowly added thereto dropwise while being cooled with ice, and the mixture was stirred for 17 hours. The reaction mixture was filtered, and the filtrate was concentrated. Then, the residue was purified through silica gel chromatography (eluent—hexane:ethyl acetate=10:1) to obtain 595 mg (yield 52%) of 2-bromo-N-[2,4-bis(isopropylthio)-6-methyl-3-pyridyl]acetamide as a colorless powdery crystal. sodium hydrogencarbonate (29 mg, 0.35 mmol) was added to an acetonitrile (5 ml) solution of this amide (132 mg, 0.35 mmol) and 2-mercaptobenzoxazole (53 mg, 0.35 mmol), and the mixture was stirred at room temperature for 28 hours. The reaction mixture was extracted with ethyl acetate. The organic layer was washed with water and then with a saturated aqueous solution of sodium chloride, and dried over magnesium sulfate. Subsequently, the solvent was distilled off, and the resulting crude product was purified through preparative thin-layer chromatography (eluent—hexane:benzen=6:1) to obtain 69 mg (yield 44%) of the desired compound as a colorless powdery crystal.

Melting point: 151-152° C.
IR (KBr) cm$^{-1}$: 3404, 2967, 1743, 1637, 1360.
$^1$H-NMR (CDCl$_3$) δ: 1.37-1.40 (12H, m), 2.52 (3H, s), 3.58 (1H, sept, J=6.8 Hz), 4.06 (2H, s), 4.11 (1H, sept, J=6.8 Hz), 6.01 (1H, s), 6.81-6.86 (2H, m), 6.92 (1H, dd, J=8.1, 1.3 Hz), 7.00-7.07 (2H, m).

Example 36 (Compound No. 845 in Table)

Production of 6-(benzoxazol-2-ylthio)-N-[2,4-bis(isopropylthio)-6-methyl-3-pyridyl]hexanamide The reaction and the treatment were conducted in the same manner as in Example 35 except that 6-bromohexanoyl chloride was used instead of bromoacetyl bromide to obtain 6-bromo-N-[2,4-bis(isopropylthio)-6-methyl-3-pyridyl]hexanamide. To a DMF (4 ml) solution of this amide (100 mg, 0.23 mmol) and 2-mercaptobenzoxazole (35 mg, 0.23 mmol) were added potassium carbonate (38 mg, 0.28 mmol) and 18-crown-6 (6 mg, 0.02 mmol), and the mixture was stirred at 80° C. for 2.5 hours. The reaction mixture was allowed to cool, and then extracted with ethyl acetate. The organic layer was washed with water and then with a saturated aqueous solution of sodium chloride, and dried over sodium sulfate. Subsequently, the solvent was distilled off, and the resulting residue was purified through preparative thin-layer chromatography (eluent—hexane:ethyl acetate=3:1) to obtain 92 mg (yield 79%) of the desired compound as a colorless powdery crystal.

Melting point: 98-100° C.
IR (KBr) cm$^{-1}$: 3135, 2961, 1648, 1498, 1454, 1133.
$^1$H-NMR (d6-DMSO) δ: 1.32 (6H, d, J=6.8 Hz), 1.35 (6H, d, J=6.8 Hz), 1.55-1.64 (2H, m), 1.65-1.75 (2H, m), 1.82-1.92 (2H, m), 2.23-2.36 (2H, m), 2.46 (3H, s), 3.38 (2H, t, J=7.1 Hz), 3.59 (1H, sept, J=6.8 Hz), 3.93 (1H, sept, J=6.8 Hz), 6.96 (1H, s), 7.29-7.37 (2H, m), 7.57-7.64 (2H, m), 8.95 (1H, br s).

Example 37 (Compound No. 1237 in Table)

Production of 6-(oxazolo[4,5-b]pyridin-2-ylthio)-N-[2,4-bis(methylthio)-6-methyl-3-pyridyl]hexanamide To a DMF (4 ml) solution of 6-bromo-N-[2,4-bis(methylthio)-6-methyl-3-pyridyl]hexanamide (100 mg, 0.27 mmol) and 2-mercaptoxazolo[4,5-b]pyridine (40 mg, 0.27 mmol) were added 18-crown-6 (7 mg, 0.03 mmol) and potassium carbonate (40 mg, 0.29 mmol), and the mixture was stirred at 80° C. for 4 hours. The reaction mixture was diluted with water, and then extracted with ethyl acetate. The organic layer was washed with water and then with a saturated aqueous solution of sodium chloride, and dried over magnesium sulfate. Subsequently, the solvent was distilled off, and the resulting crude product was purified through preparative thin-layer chromatography (eluent—hexane:acetone=2:1) to obtain 85 mg (yield 72%) of the desired compound as a colorless powdery crystal.

Melting point: 132-133° C.

IR (KBr) cm$^{-1}$: 3435, 3243, 2923, 1655, 1493, 1404.

$^1$H-NMR (d6-DMSO) δ: 1.53-1.63(2H,m), 1.65-1.76(2H, m), 1.83-1.93(2H,m), 2.27-2.35(2H,m), 2.40(3H,s),2.42(3H, s),2.45(3H,s), 3.40(2H,t,J=7.3Hz), 6.86(1H,S), 7.30(1H,dd, J=8.1,4.9Hz), 7.97(1H,dd,J=8.1,1.3HZ), 8.42(1H,dd,J=4.9, 1.3HZ), 8.83(1H,br s).

EIMS m/z (relative intensity): 447 (M$^+$−1), 400(100).

| Elemental analysis: as $C_{20}H_{24}N_4O_2S_3$ | | | |
|---|---|---|---|
| calculated: | C, 53.55; | H, 5.39; | N, 12.59; | S, 21.44. |
| found: | C, 53.72; | H, 5.39; | N, 12.41; | S, 21.51. |

Example 38 (Compound No. 1238 in Table)

Production of 6-(7-methoxycarbonylbenzoxazol-2-ylthio)-N-[2,4-bis(methylthio)-6-methyl-3-pyridyl]hexanamide The reaction and the treatment were conducted in the same manners as in Example 37 except that 7-methoxycarbonyl-2-mercaptobenzoxazole was used instead of 2-mercaptoxazolo[4,5-b]pyridine to obtain the desired compound as a colorless powdery crystal.

Melting point: 141-142° C.

IR (KBr) cm$^{-1}$: 3425, 3236, 2923, 1726, 1667, 1509.

$^1$H-NMR (d6-DMSO) δ: 1.54-1.63(2H,m), 1.67-1.76(2H, m), 1.84-1.93(2H,m), 2.28-2.35(2H,m), 2.40(3H,s), 2.42(3H,s), 2.45(3H,s), 3.39(2H,t,J=7.1Hz), 3.95(3H,s), 6.86 (1H,s), 7.44(1H,t,J=7.8Hz), 7.81(1H,dd,J=7.8,1.2Hz), 7.85 (1H,dd,J=7.8,1.2Hz), 8.82(1H,br s).

EIMS m/z (relative intensity): 504 (M$^+$−1), 167(100).

| Elemental analysis: as $C_{23}H_{27}N_3O_4S_3$ | | | |
|---|---|---|---|
| calculated: | C, 54.63; | H, 5.38; | N, 8.31; | S, 19.02. |
| found: | C, 54.70; | H, 5.37; | N, 8.27; | S, 19.15. |

Example 39 (Compound No. 1240 in Table)

Production of 9-(7-methoxycarbonylbenzoxazol-2-ylthio)-N-[2,4-bis(methylthio)-6-methyl-3-pyridyl]nonanamide To a DMF (4 ml) solution of 9-bromo-N-[2,4-bis(methylthio)-6-methyl-3-pyridyl]nonanamide (90 mg, 0.22 mmol) and 7-methoxycarbonyl-2-mercaptobenzoxazole (45 mg, 0.22 mmol) were added 18-crown-6 (6 mg, 0.02 mmol) and potassium carbonate (36 mg, 0.26 mmol), and the mixture was stirred at 80° C. for 4 hours. The rdaction mixture was diluted with water, and then extracted with ethyl acetate. The organic layer was washed with water and then with a saturated aqueous solution of sodium chloride, and dried over magnesium sulfate. Subsequently, the solvent was distilled off, and the resulting crude product was recrystallized from a mixture of ethyl acetate and hexane to obtain 84 mg (yield 72%) of the desired compound as a colorless powdery crystal.

Melting point: 126-128° C.

IR (KBr) cm$^{-1}$: 3231, 2924, 1720, 1657, 1508, 1297

$^1$H-NMR (d6-DMSO) δ: 1.27-1.47(8H,m), 1.54-1.62(2H, m), 1.74-1.85(2H,m), 2.24(2H,t,J=7.3 Hz), 2.37(3H,s),2.38 (3H,s),2.43(3H,s), 3.31-3.41(2H,m), 3.91(3H,s), 6.86(1H,s), 7.45(1H,t,J=7.8 Hz), 7.81(1H,dd,J=7.8,1.0 Hz), 7.91(1H,dd, J=7.8,1.0 Hz), 9.26(1H,s).

EIMS m/z (relative intensity): 546(M$^+$−1), 500(100).

| Elemental analysis: as $C_{26}H_{33}N_3O_4S_3$ | | | |
|---|---|---|---|
| calculated: | C, 57.01; | H, 6.07; | N, 7.67; | S, 17.56. |
| found: | C, 57.10; | H, 5.95; | N, 7.67; | S, 17.60. |

Examples 40 (Compound No. 151 in Table)

Production of 2-(benzoxazol-2-ylthio)-N-(4-methyl-2-methylthio-3-pyridyl)acetamide The reaction and the treatment were conducted in the same manner as in Example 16 except that 3-amino-4-methyl-2-methylthiopyridine was used instead of 3-amino-2,4-bis(methylthio)-6-methylpyridine to obtain the desired compound as a colorless needle crystal.

Melting point: 146-148° C.

IR (KBr) cm$^{-1}$: 3437, 3245, 1671, 1659, 1507, 1454.

$^1$H-NMR (CDCl$_3$) δ: 2.17 (3H, s), 2.42 (3H, s), 4.11 (2H, s), 6.87 (1H, d, J=4.9 Hz), 7.28-7.34 (2H, m), 7.50 (1H, m), 7.61 (1H, m), 8.23 (1H, d, J=4.9 Hz), 8.88 (1H, br s).

EIMS m/z (relative intensity): 345 (M$^+$, 100).

| Elemental analysis: as $C_{16}H_{15}N_3O_2S_2$ | | | |
|---|---|---|---|
| calculated: | C, 55.63; | H, 4.38; | N, 12.16; | S, 18.56. |
| found: | C, 55.66; | H, 4.46; | N, 12.02; | S, 18.55. |

Example 41 (Compound No. 155 in Table)

Production of 6-(benzoxazol-2-ylthio)-N-(4-methyl-2-methylthio-3-pyridyl)hexanamide The reaction and the treatment were conducted in the same manner as in Example 18 except that 3-amino-4-methyl-2-methylthiopyridine was used instead of 3-amino-2,4-bis(methylthio)-6-methylpyridine to obtain the desired compound as a colorless needle crystal.

Melting point: 122-124° C.

IR (KBr) cm$^{-1}$: 3437, 3245, 1660, 1521, 1507, 1133.

$^1$H-NMR (d$_6$-DMSO) δ: 1.49-1.56 (2H, m), 1.68 (2H, quint, J=7.4 Hz), 1.84 (2H, quint, J=7.4 Hz), 2.09 (3H, s), 2.33 (2H, t, J=7.4 Hz), 2.40 (3H, s), 3.36 (2H, t, J=7.4 Hz), 7.02 (1H, d, J=4.9 Hz), 7.29-7.36 (2H, m), 7.61-7.66 (2H, m),8.24 (1H, d, J=4.9 Hz), 9.40 (1H, br s).

EIMS m/z (relative intensity): 401 (M$^+$, 100).

| Elemental analysis: as $C_{20}H_{23}N_3O_2S_2$ | | | | |
|---|---|---|---|---|
| calculated: | C, 59.82; | H, 5.77; | N, 10.46; | S, 15.97. |
| found: | C, 59.93; | H, 5.89; | N, 10.34; | S, 15.99. |

Example 42 (Compound No. 365 in Table)

Production of 6-(benzoxasole-2-ylthio)-N-(6-methoxy-2-methylthio-3-pyridyl)hexanamide A methanol (100 ml) solution of 2-chloro-6-methoxy-3-nitropyridine (2.0 g, 10.4 mmol) was added dropwise to a methanol (20 ml) solution of sodium thiomethoxide (805 mg, 10.9 mmol) while being cooled with ice, and the temperature thereof was raised to the room temperature and the mixed solution was stirred for 17 hours and the precipitated crystal was filtered to obtain 1.26 g (yield 59%) of 6-methoxy-2-methylthio-3-nitropyridine as a yellow powdery crystal, This nitropyridine (400 mg, 2.0 mmol) was dissolved in a mixed solvent of acetic acid (20 ml) and conc. hydrochloric acid (0.5 ml), and zinc (1.57 g, 24.0 mmol) was added thereto in small portions while being cooled with ice for 5 minutes. After the mixture was stirred for 40 minutes at the room temperature, the reaction mixture was filtered, and the filtrate was neutralized with an aqueous solution of sodium hydrogencarbonate, and extracted with methylene chloride. The organic layer was washed with water and then with a saturated aqueous solution of sodium chloride, and dried over sodium sulfate. Thereafter, the solvent was distilled off, and the resulting crude product was purified through silica gel chromatography (eluent—hexane:ethyl acetate=6:1→4:1) to obtain 264 mg (yield 78%) of 3-amino-6-methoxy-2-methylthiopyridine as a pale brown powdery crystal.

And then the reaction and the treatment were conducted in the same manner as. in Example 18 except that 3-amino-6-methoxy-2-methylthiopyridine was used instead of 3-amino-2,4-bis(methlthio)-6-methylpyridine to obtain the desired compound as a colorless powdery crystal.

Melting point: 102-104° C.
IR (KBr) cm$^{-1}$: 3430, 3224, 2940, 1652, 1591.
$^1$H-NMR (CDCl$_3$) δ: 1.61 (2H, quint, J=7.4 Hz), 1.82 (2H, quint, J=7.4 Hz), 1.92 (2H, quint, J=7.4 Hz), 2.42 (2H, t, J=7.4 Hz), 2.59 (3H, s), 3,134 (2H, t, J=7.4 Hz), 3.94 (3H, s), 6.47 (1H, d, J=8.5 Hz), 6.91 (1H, br s), 7.23 (1H, td, J=7.7, 1.5 Hz), 7.27 (1H, td, J=7.7, 1.5 Hz), 7.43 (1H, dd, J=7.7, 1.5 Hz), 7.58 (1H, dd, J=7.7, 1.5 Hz), 7.93 (1H, d, J=8.5 Hz).
EIMS m/z (relative intensity): 417 (M$^+$), 171 (100).

Example 43 (Compound No. 451 in Table)

Production of 2-(benzoxazol-2-ylthio)-N-(6-methylthio-3-pyridyl)acetamide

The reaction and the treatment were conducted in the same manner as in Example 16 except that 3-amino-6-methyl-2-methylthiopyridine was used instead of 3-amino-2,4-bis(methylthio)-6-methylpyridine to obtain the desired compound as a colorless needle crystal.

Melting point: 180-181° C.
IR (KBr) cm$^{-1}$: 3437, 3254, 1661, 1534, 1509, 1135.
$^1$H-NMR (CDCl$_2$) δ: 2.46 (3H, s), 2.50 (3H, s), 4.10 (2H, s), 6.87 (2H, d, J=8.1 Hz), 7.26-7.34 (2H, m), 7.48 (1H, m), 7.62 (1H, m), 8.12 (2H, d, J=8.1 Hz), 9.27 (1H, br s).
EIMS m/z (relative intensity): 345 (M$^+$), 298 (100).

| Elemental analysis: as $C_{16}H_{15}N_3O_2S_2$ | | | | |
|---|---|---|---|---|
| calculated: | C, 55.63; | H, 4.38; | N, 12.16; | S, 18.56. |
| found: | C, 55.62; | H, 4.40; | N, 12.10; | S, 18.50. |

Example 44 (Compound No. 461 in table)

Production of 2-(benzothiazol-2-ylthio)-N-(6-methyl-2-methylthio-3-pyridyl)acetamide The reaction and the treatment were conducted in the same manner as in Example 43 except that 2-mercaptobenzothiazole was used instead of 2-mercaptobenzoxazole to obtain the desired compound as a colorless needle crystal.

Melting Point: 175-176° C.
IR (KBr) cm$^{-1}$: 3437, 3248, 1656, 1532, 1430.
$^1$H-NMR (CDCl$_3$) δ: 2.45 (3H, s), 2.47 (3H, s), 4.18 (2H, s), 6.87 (1H, d, J=8.1 Hz), 7.34 (1H, m), 7.44 (1H, m), 7.77 (1H, m), 8.01 (1H, m), 8.07 (1H, d, J=8.1 Hz), 9.31 (1H, br s).
EIMS m/z (relative intensity): 361 (M$^+$), 210 (100).

| Elemental analysis: as $C_{16}H_{15}N_3OS_3$ | | | | |
|---|---|---|---|---|
| calculated: | C, 53.16; | H, 4.18; | N, 11.62; | S, 26.61. |
| found: | C, 53.23; | H, 4.25; | N, 11.55; | S, 26.67. |

Example 45 (Compound No. 471 in Table)

Production of 2-(benzimidazol-2-ylthio)-N-(6-methyl-2-methylthio-3-pyridyl)acetamide The reaction and the treatment were conducted in the same manner as in Example 43 except that 2-2-mercaptobenzimidazole was used instead of 2-mercaptobenzoxazole to obtain the desired compound as a colorless needle crystal.

Melting point: 192-193° C. (d.)
IR (KBr) cm$^{-1}$: 3420, 3249, 1667, 1550, 1438, 744.
$^1$H-NMR (CDCl$_3$) δ: 2.45 (3H, s), 2.50 (3H, s), 4.08 (2H, s), 6.84 (1H, d, J=8.1 Hz), 7.19-7.25 (2H, m), 7.35 (1H, m), 7-.73 (1H, m), 8.00 (1H, d, J=8.1 Hz), 9.95 (1H, br s), 10.00 (1H, br s).
EIMS m/z (relative intensity): 344 (M$^+$), 118 (100).

| Elemental analysis: as $C_{16}H_{16}N_4OS_2$ | | | | |
|---|---|---|---|---|
| calculated: | C, 55.79; | H, 4.68; | N, 16.27; | S, 18.62. |
| found: | C, 55.80; | H, 4.68; | N, 16.16; | S, 18.65. |

Example 46 (Compound No. 784 in table)

Production of 5-(benzoxazol-2-ylthio)-N-(2,4-bis(methylthio)-6-methyl-3-pyridyl)pentanamide The reaction and the treatment were conducted in the same manner as in Example 17 except that 5-bromopentqnoic acid chloride was used instead of 4-bromobutanoyl chloride to obtain the desired compound as a colorless needles crystal.

Melting point: 147-150° C.

IR (KBr) cm$^{-1}$: 3230, 1664, 1501, 1455, 1136.

$^1$H-NMR (d$_6$-DMSO) δ: 1.72-1.96 (4H, m), 2.3-6 (3H, s), 2.26-2.42 (2H, m), 2.39 (3H, s), 2.43 (3H, s), 3.36 (2H, t, J=7.2 Hz), 6.83 (1H, s), 7.23-7.33 (2H, m), 7.52-7.59 (2H, m), 8.74 (1H, br s).

EIMS m/z (relative intensity): 433 (M$^+$), 201 (100).

Example 47 (Compound No. 786 in table)

Production of 7-(benzoxazol-2-ylthio)-N-[2,4-bis(methylthio)-6-methyl-3-pyridyl]heptanamide The reaction and the treatment were conducted in the same manner as in Example 17 except that 7-bromoheptanonyl chloride was used instead of 4-bromobutanoyl chloride to obtain the desired compound as a colorless powdery crystal.

Melting point: 137-139° C.

IR (KBr) cm$^{-1}$: 3437, 3242, 2922, 2857, 1660, 1500, 1455, 1132.

$^1$H-NMR (d$_6$-DMSO) δ: 1.41-1.54 (4H, m), 1.60-1.70 (2H, m), 1.81 (2H, quint, J=7.1 Hz), 2.26-2.32 (2H, m), 2.38 (3H, s), 2.40 (3H, s), 2.43 (3H, s), 3.33 (2H, t, J=7.1 Hz), 6.81 (1H, s), 7.27 (1H, td, J=7.6, 1.7 Hz), 7.30 (1H, td, J=7.6, 1.7 Hz), 7.54-7.60 (2H, m), 8.79 (1H, br s).

EIMS m/z (relative intensity): 461 (M$^+$), 200 (100).

Example 48 (Compound No. 787 in Table)

Production of 8-(benzoxazol-2-ylthio)-N-[2,4-bis(methylthio)-6-methyl-3-pyridyl]octanamide The reaction and the treatment were conducted in the same manner as in Example 17 except that 8-bromooctanoyl chloride was used instead of 4-bromobutanonyl chloride to obtain the desired compound as a colorless prism crystal.

Melting point: 119-122° C.

IR (KBr) cm$^{-1}$: 3435, 3248, 2923, 2856, 1660, 1501, 1454, 1131.

$^1$H-NMR (d$_6$-DMSO) δ: 1.33-1.52 (6H, m), 1.58-1.69 (2H, m), 1.81 (2H, quint, J=7.1 Hz), 2.26-2.32 (2H, m), 2.38 (3H, s), 2.41 (3H, s), 2.44 (3H, s), 3.33 (2H, t, J=7.1 Hz), 6.84 (1H, s), 7.27 (1H, td, J=7.6, 1.7 Hz), 7.30 (1H, td, J=7.6, 1.7 Hz), 7.54-7.60 (2H, m), 8.77 (1H, br s).

EIMS m/z (relative intensity): 475 (M$^+$), 200 (100).

Example 49 (Compound No. 791 in Table)

Production of 2-(benzothiazol-2-ylthio)-N-[2,4-bis(methylthio)-6-methyl-3-pyridyl)acetamide An acetonitrile solution (6 ml) of 2-bromo-N-[2,4-bis(methylthio)-3-pyridyl]acetamide (64 mg, 0.2 mmol) was added to an acetonitrile solution (1 ml) of sodium hydrogencarbonate (17 mg, 0.2 mmol) and 2-mercaptobenzothiazole (34 mg, 0.2 mmol), and the mixed solution was stirred for 48 hours at the room temperature. And the solution of reaction mixture was concentrated under reduced pressure, and the residue was extraxted with ethyl acetate after dilluting with water. The organic layer was washed with water and then with a saturated aqueous solution of sodium chloride, and dried over sodium sulfate. Thereafter, the solvent was distilled off, and the resulting crude product was purified through preparative thin layer chromatography (eluent—chloroform:methanol=20:1) to obtain 46 mg (yield 33%) as a colorless needle crystal.

Melting point: 178-179° C.

IR (KBr) cm$^{-1}$: 3437, 3246, 1665, 1564, 1497, 1430.

$^1$H-NMR (CDCl$_3$) δ: 2.33 (3H, s), 2.44 (3H, s), 2.46 (3H, s), 4.17 (2H, s), 6.61 (1H, s), 7.33 (1H, m), 7.43 (1H, m), 7.78 (1H, m), 7.90 (1H, m), 9.,11 (1H, br s).

EIMS m/z (relative intensity): 407 (M$^+$), 209 (100).

| Elemental analysis: as C$_{17}$H$_{17}$N$_3$OS$_4$ | | | |
|---|---|---|---|
| calculated: | C, 50.10; | H, 4.20; | N, 10.31; | S, 31.46. |
| found: | C, 50.18; | H, 4.29; | N, 10.23; | S, 31.49. |

Example 50 (Compound No. 794 in Table)

Production of 5-(benzothiazol-2-ylthio)-N-(2,4-bis(methylthio)-6-methyl-3-pyridyl)pentanamide The reaction and the treatment were conducted in the same manner as in Example 46 except that 2-mercaptobenzothiazole was used instead of 2-mercaptobenzoxazole to obtain the desired compound as a colorless needle crystal.

Melting point: 121-123° C.

IR (KBr) cm$^{-1}$: 3437, 3240, 2923, 1664, 1515, 1456, 1428, 995.

$^1$H-NMR (d$_6$-DMSO) δ: 1.78-1.87 (2H, m), 1.88-1.96 (2H, m), 2.30-2.40 (2H, m), 2.38 (3H, s), 2.41 (3H, s), 2.45 (3H, s), 3.41 (2H, t, J=7.1 Hz), 6.85 (1H, s), 7.34 (1H, t, J=7.6 Hz), 7.45 (1H, t, J=7.6 Hz), 7.84 (1H, d, J=7.6 Hz), 7.94 (1H, d, J=7.6 Hz), 8.87 (1H, br s).

EIMS m/z (relative intensity): 449 (M$^+$), 201 (100).

Example 51 (Compound No. 796 in table)

Production of 7-(benzothiazol-2-ylthio)-N-[2,4-bis(methylthio)-6-methyl-3-pyridyl)heptamamide The reaction and the treatment were conducted in the same manner as in Example 47 except that 2-mercaptobenzothiazole was used instead of 2-mercaptobenzoxazole to obtain the desired compound as a colorless needle crystal.

Melting point: 129-130° C.

IR (KBr) cm$^{-1}$: 3436, 3245, 2922, 1661, 1506, 1428.

$^1$H-NMR (d$_6$-DMSO) δ: 1.44-1.54 (4H, m), 1.62-1.71 (2H, m), 1.83 (2H, quint, J=7.2 Hz), 2.13-2.33 (2H, m), 2.39 (3H, s), 2.42 (3H, s), 2.45 (3H, s), 3.37 (2H, t. J=7.2 Hz), 6.86 (1H, s), 7.34 (1H, td, J=7.8, 1.2 Hz), 7.45 (1H, td, J=7.8, 1.2 Hz), 7.84 (1H, dd, J=7.8, 1.2 Hz), 7.94 (1H, dd, J=7.8, 1.2 Hz), 8.81 (1H, br s).

EIMS m/z (relative intensity): 477 (M$^+$), 200 (100).

| Elemental analysis: as C$_{22}$H$_{27}$N$_3$OS$_4$ | | | |
|---|---|---|---|
| calculated: | C, 55.31; | H, 5.70; | N, 8.80. |
| found: | C, 55.41; | H, 5.71; | N, 8.64. |

Example 52 (Compound No. 797 in Table)

Production of 8-(benzthiazol-2-ylthio)-N-[2,4-bis(methylthio)-6-methyl-3-pyridyl)octanamide The reaction and the treatment were conducted in the same manner as in Example 48 except that 2-mercaptobenzothiazole was used instead of 2-mercaptobenzoxazole to obtain the desired compound as a colorless needle crystal.

Melting point: 104-108° C.

IR (KBr) cm$^{-1}$: 3242, 2925, 1665, 1508, 1459, 1428.

$^1$H-NMR (d$_6$-DMSO) δ: 1.30-1.51 (6H, m), 1.55-1.69 (2H, m), 1.81 (2H, quint, J=7.1 Hz), 2.23-2.29 (2H, m), 2.38 (3H, s), 2.41. (3H, s), 2.44 (3H, s), 3.35 (2H, t, J=7.2 Hz) 6.83 (1H, s), 7.32 (1H, m), 7.43 (1H, m), 7.81 (1H, m), 7.91 (1H, m), 8.76 (1H, br s).

EIMS m/z (relative intensity): 491 (M$^+$), 200 (100).

Example 53 (Compound No. 801 in table)

Production of 2-(benzimidazol-2-ylthio)-N-[2,4-bis (methylthio)-6-methyl-3-pyridyl)pentanamide The reaction and the treatment were conducted in the same manner as in Example 49 except that 2-mercaptobenzimidazole was used instead of 2-mercaptobenothiazole to obtain the desired compound as a colorless needle crystal.

Melting point: 235-237° C. (d.)

IR (KBr) cm$^{-1}$: 3429, 3243, 2978, 2923, 1661, 1505, 1439.

$^1$H-NMR (CDCl$_3$) δ: 2.35 (3H, s), 2.46 (3H, s), 2.47 (3H, s), 4.03 (2H, s), 6.63 (1H, s), 7.21 (1H, t, J=6.1 Hz), 7.22 (1H, t, J=6.1 Hz), 7.43-7.60 (2H, m), 9.43 (1H, br s).

EIMS m/z (relative intensity): 390 (M$^+$), 344 (100).

Example 54 (Compound No. 804 in Table)

Production of 5-(benzimidazol-2-ylthio)-N-[2,4-bis (methylthio)-6-methyl-3-pyridyl]pentanamide The reaction and the treatment were conducted in the same manner as in Example 46 except that 2-mercaptobenzimdazole was used instead of 2-mercaptobenoxazole to obtain the desired compound as a colorless needle crystal.

Melting point: 176-177° C.

$^1$H-NMR (d$_6$-DMSO) δ: 1.74-1.84 (4H, m), 2.26-2.35 (2H. m). 2.36 (3H, s), 2.39 (3H, s), 2.43 (3H, s), 3.26-3.36 (2H, m), 6.84 (1H, s), 7.04-7.13 (2H, m), 7.34-7.45 (2H, m), 8.84 (1H, br s), 12.06 (1H, br s).

EIMS m/z (relative intensity): 432 (M$^+$), 200 (100).

Example 55 (Compound No. 806 in Table)

Production of 7-(benzimidazol-2-ylthio)-N-[2,4-bis (methylthio)-6-methyl-3-pyridyl]heptanamide The reaction and the treatment were conducted in the same manner as in Example 47 except that 2-mercaptobenzimidazole was used instead of 2-mercaptobenzoxazole to obtain the desired compound as a colorless prism crystal.

Melting point: 189-192° C.

IR (KBr) cm$^{-1}$: 3139, 2925, 2854, 1668, 1561, 1523, 1435, 1401.

$^1$H-NMR (d$_6$-DMSO) δ: 1.39-1.52 (4H, m), 1.56-1.70 (2H, m), 1.75 (2H, quint, J=7.1 Hz), 2.28-2.34 (2H, m), 2.38 (3H, s), 2.40 (3H, s), 2.43 (3H, s), 3.27 (2H, t, J=7.1 Hz), 6.84 (1H, s), 7.07 (1H, t, J=7.1 Hz), 7.08(1H, t, J=7.1 Hz), 7.32 (1H, d, J=7.1 Hz), 7.46 (1H, d, J=7.1 Hz), 8.79 (1H, br s).

EIMS m/z (relative intensity): 460 (M$^+$), 150 (100).

Example 56 (Compound No. 807 in Table)

Production of 8-(benzimidazol-2-ylthio)-N-[2,4-bis (methylthio)-6-methyl-3-pyridyl]octanamide The reaction and the treatment were conducted in the same manner as in Example 48 except that 2-mercaptobenzimidazole was used instead of 2-mercaptobenzoxazole to obtain the desired compound as a colorless crystal.

Melting point: 186-187° C.

IR (KBr) cm$^{-1}$: 3430, 3222, 2925, 1661, 1564, 1522, 1437, 808.

$^1$H-NMR (d$_6$-DMSO) δ: 1.35-1.43 (4H, m), 1.47 (2H, quint, J=7.2 Hz), 1.60-1.68 (2H, m), 1.76 (2H, quint, J=7.2 Hz), 2.23-2.32 (2H, m), 2.40 (3H, s), 2.42 (3H, s), 2.45 (3H,s), 3.28 (2H, t, J=7.2 Hz), 6.89 (1H, s), 7.09 (1H, t, J=5.9 Hz), 7.09 (1H, t, J=5.9 Hz), 7.40 (1H, d, J=5.9 Hz), 7.41 (1H, d, J=5.9 Hz), 8.80 (1H, br s). 12.09 (1H, br s).

EIMS m/z (relative intensity): 474 (M$^+$), 150 (100).

Example 57 (Compound No. 813 in Table)

Production of 4-(benzoxazol-2-ylthio)-N-[2,4-bis (ethylthio)-6-methyl-3-pyridyl]butanamide The reaction and the treatment were conducted in the same manner as in Example 27 except that 4-bromobutanoyl chloride was used instead of 6-bromohexanoyl chloride to obtain the desired compound as a colorless crystal.

Melting point: 12.3-125° C.

IR (KBr) cm$^{-1}$: 3436, 3239, 2974, 2929, 1656, 1502, 1454, 1130.

$^1$H-NMR (d$_6$-DMSO) δ: 1.23-1.28 (6H, m),2.12-2.19 (2H, m), 2.43 (3H, s), 2.48-2.50 (2H,m), 2.93 (2H, q, J=7.1 Hz), 3.06 (2H, q, J=7.1 Hz), 3.41-3.48 (2H, m), 6.89 (3H, s), 7.29-7.34 (2H. m), 7.56-7.62 (2H, m), 8.96 (1H, br s).

EIMS m/z (relative intensity): 447 (M$^+$), 227 (100).

Example 58 (Compound No. 814 in Table)

Production of 5-(benzoxazol-2-ylthio)-N-[2,4-bis (ethylthio)-6-methyl-3-pyridyl]pentanamide The reaction and the treatment were conducted in the same manner as in Example 27 except that 5-bromopentanoyl chloride was used instead of 6-bromohexanoyl chloride to obtain the desired compound as a colorless needle crystal.

Melting point: 122-123° C.

$^1$H-NMR (d$_6$-DMSO) δ: 1.25 (3H, t, J=7.3 Hz), 1.26 (3H, t, J=7.3 Hz), 1.76-1.87 (2H, m), 1.87-1.97 (2H, m), 2.29-2.40 (2H, m), 2.43 (3H, s), 2.92 (2H, q, J=7.3 Hz), 3.05 (2H, q, J=7.3 Hz), 3.38 (2H, t, J=7.2 Hz), 6.88 (1H, s), 7.26-7.35 (2H, m), 7.55-7.60 (2H, m), 8.82 (1H, br s).

EIMS m/z (relative intensity): 461 (M$^+$), 227 (100).

Example 59 (Compound No. 816 in Table)

Production of 7-(benzoxazol-2-ylthio)-N-[2,4-bis (ethylthio)-6-methyl-3-pyridyl]heptanamide The reaction and the treatment were conducted in the same manner as in Example 27 except that 7-bromoheptanoyl chloride was used instead of 6-bromohexanoyl chloride to obtain the desired compound as a colorless needle crystal.

Melting point: 103-105° C.

IR (KBr) cm$^{-1}$: 3247, 1663, 1501, 1455.

$^1$H-NMR (d$_6$-DMSO) δ: 1.24 (3H, t, J=7.3 Hz), 1.25 (3H, t, J=7.3 Hz), 1.38-1.54 (4H, m), 1.57-1.72 (2H, m), 1.73-1.89 (2H, m), 2.19-2.32 (2H, m), 2.41 (3H, s), 2.92 (2H, q, J=7.3 Hz), 3.05 (2H, q, J=7.3 Hz), 3.33 (2H, t, J=7.1 Hz), 6.86 (1H, s), 7.24-7.32 (2H, m), 7.52-7.60 (2H, m), 8.65 (1H, br s).

EIMS m/z (relative intensity): 489 (M$^+$), 228 (100).

Example 60 (Compound No. 817 in Table)

Production of 8-(benzoxazol-2-ylthio)-N-[2,4-bis (ethylthio)-6-methyl-3-pyridyl]octanamide The reaction and the treatment were conducted in the same manner as in Example 27 except that 8-bromooctanoyl chloride was used instead of 6-bromohexanoyl chloride to obtain the desired compound as a colorless needle crystal.
Melting point: 82-84° C.
IR (KBr) cm$^{-1}$: 3449, 3245, 2932, 1669, 1500, 1455, 1132.
$^1$H-NMR (d$_6$-DMSO) δ: 1.26 (3H, t, J=7.3 Hz), 1.27 (3H, t, J=7.3 Hz), 1.37-1.42 (4H, m), 1.48 (2H, quint. J=7.2 Hz), 1.60-1.67 (2H, m), 1.82 (2H, quint. J=7.2 Hz), 2.24-2.30 (2H, m), 2.43 (3H, s), 2.94 (2H, q, J=7.3 Hz), 3.07 (2H, q, J=7.3 Hz), 3.34 (2H, t, J=7.2 Hz), 6.88 (1H, s), 7.27-7.33 (2H, m), 7.56-7.61 (2H, m), 8.73 (1H, br s).
EIMS m/z (relative intensity): 503 (M$^+$), 229 (100).

Example 61 (Compound No. 823 in table)

Production of 4-(benzothiazol-2-ylthio)-N-[2,4-bis (ethylthio)-6-methyl-3-pyridyl]butanamide The reaction and the treatment were conducted in the same manner as in Example 57 except that 2-mercaptobenzothiazole was used instead of 2-mercaptobenzoxazole to obtain the desired compound as a colorless powdery crystal.
Melting point: 119-120° C.
$^1$H-NMR (d$_6$-DMSO) δ: 1.25 (3H, t, J=7.4 Hz), 1.26 (3H, t, J=7.4 Hz), 2.07-2.23 (2H, m), 2.43 (3H, s), 2.45-2.55 (2H, m,), 2.93 (2H, q, J=7.4 Hz), 3.06 (2H, q, J=7.4 Hz), 3.41-3.54 (2H, m), 6.89 (1H, s), 7.35 (1H, t, J=8.1 Hz), 7.45 (1H, t, J=8.1 Hz), 7.83 (1H, d, J=8.1 Hz). 7.94 (1H, d, J=8.1 Hz), 8.95 (1H, br s).
EIMS m/z (relative intensity): 463 (M$^+$), 229 (100).

Example 62 (Compound No. 824 in Table)

Production of 5-(benzothiazol-2-ylthio)-N-[2,4-bis (ethylthio)-6-methyl-3-pyridyl]pentanamide The reaction and the treatment were conducted in the same manner as in Example 58 except that 2-mercaptobenzothiazole was used instead of 2-mercaptobenzoxazole to obtain the desired compound as a colorless needle crystal.
Melting point: 102-104° C.
$^1$H-NMR (d$_6$-DMSO) δ: 1.25 (3H, t, J=7.3 Hz), 1.26 (3H, t, J=7.3 Hz), 1.77-1.88 (2H, m), 1.88-2.00 (2H, m), 2.29-2.41 (2H, m), 2.43 (3H, s), 2.93 (2H, q, J=7.3 Hz), 3.06 (2H, q, J=7.3 Hz), 3.41 (2H, t, J=7.0 Hz), 6.89 (1H, s), 7.35 (1H, ddd, J=8.2, 7.2, 1.2 Hz), 7.45 (1H, ddd, J=8.2, 7.2, 1.2 Hz), 7.84 (1H, dd, J=8.2, 1.2 Hz), 7.94 (1H, dd, J=8.2, 1.2 Hz), 8.84 (1H, br s).
EIMS m/z (relative intensity): 477 (M$^+$), 229 (100).

Example 63 (Compound No. 826 in Table)

Production of 7-(benzothiazol-2-ylthio)-N-[2,4-bis (ethylthio)-6-methyl-3-pyridyl]heptanamide The reaction and the treatment were conducted in the same manner as in Example 59 except that 2-mercaptobenzothiazole was used instead of 2-mercaptobenzoxazole to obtain the desired compound as a colorless needle crystal.
Melting Point: 114-116° C.
IR (KBr) cm$^{-1}$: 3245, 1665, 1536, 1509, 1426.
$^1$H-NMR (d$_6$-DMSO) δ: 1.24 (3H, t, J=7.3 Hz), 1.25 (3H, t, J=7.3 Hz), 1.39-1.56 (4H, m), 1.58-1.71 (2H, m), 1.75-1.88 (2H, m), 2.19-2.31 (2H, m), 2.42 (3H, s), 2.92 (2H, q, J=7.3 Hz), 3.05 (2H, q, J=7.3 Hz), 3.35 (2H, t, J=7.2 Hz), 6.86 (1H, s), 7.32 (1H, td, J=7.6, 1.2 Hz), 7.42 (1H, td, J=7.6, 1.2 Hz), 7.81 (1H, dd, J=7.6, 1.2 Hz), 7.91 (1H, dd, J=7.6, 1.2 Hz), 8.67 (1H, br s).
EIMS m/z (relative intensity): 505 (M$^+$), 227 (100).

Example 64 (Compound No. 827 in Table)

Production of 8-(benzothiazol-2-ylthio)-N-[2,4-bis (ethylthio)-6-methyl-3-pyridyl]octanamide The reaction and the treatment were conducted in the same manner as in Example 60 except that 2-mercaptobenzothiazole was used instead of 2-mercaptobenzoxazole to obtain the desired compound as a colorless needle crystal.
Melting point: 94-96° C.
IR (KBr) cm$^{-1}$: 3433, 3243, 2929, 1669, 1511, 1428.
$^1$H-NMR (d$_6$-DMSO) δ: 1.26 (3H, t, J=7.3 Hz), 1.27 (3H, t, J=7.3 Hz), 1.37-1.43 (4H, m), 1.45-1.52 (2H, m), 1.57-1.68 (2H, m), 1.82 (2H, quint, J=7.2 Hz), 2.20-2.32 (2H, m), 2.43 (3H, s), 2.94 (2H, q, J=7.3 Hz), 3.07 (2H, q, J=7.3 Hz), 3.37 (2H, t, J=7.2 Hz), 6.88 (1H, s), 7.34 (1H, td, J=7.6, 1.1 Hz), 7.44 (1H, td, J=7.6, 1.1 Hz), 7.83 (1H, dd, J=7.6, 1.1 Hz), 7.93 (1H, dd, J=7.6, 1.1 Hz), 8.73 (1H, br s).
EIMS m/z (relative intensity): 519 (M$^+$), 227 (100).

Example 65 (Compound No. 833 in Table)

Production of 4-(benzimidazol-2-ylthio)-N-[2,4-bis (ethylthio)-6-methyl-3-pyridyl]butanamide The reaction and the treatment were conducted in the same manner as in Example 57 except that 2-mercaptobenzimidazole was used instead of 2-mercaptobenzoxazole to obtain the desired compound as a pale-yellow powdery crystal.
Melting point: 160-161° C.
$^1$H-NMR (d$_6$-DMSO) δ: 1.25 (3H, t, J 7.3 Hz), 1.26 (3H, t, J 7.3 Hz), 2.27-2.37 (2H, m), 2.44 (3H, s), 2.48-2.50 (2H, m), 2.93 (2H, q, J=7.3 Hz), 3.06 (2H, q, J=7.3 Hz), 3.34-3.46 (2H, m), 6.89 (1H, s), 7.05-7.14 (2H, m), 7.33 (1H, m), 7.46 (1H, m), 8.95 (1H, br s).
EIMS m/z (relative intensity): 446 (M$^+$), 195 (100).

Example 66 (Compound No. 834 in Table)

Production of 5-(benzimidazol-2-ylthio)-N-[2,4-bis (ethylthio)-6-methyl-3-pyridyl]pentanamide The reaction and the treatment were conducted in the same manner as in Example 58 except that 2-mercaptobenzimidazole was used instead of 2-mercaptobenzoxazole to obtain the desired compound as a colorless needle crystal.
Melting point: 163-165° C.
$^1$H-NMR (d$_6$-DMSO) δ: 1.23 (3H, t, J=7.3 Hz), 1.24 (3H, t, J=7.3 Hz), 1.74-1.88 (4H, m), 2.27-2.38 (2H, m), 2.41 (3H, s), 2.90 (2H, q, J=7.3 Hz), 3.03 (2H, q, J=7.3 Hz), 3.26-3.34 (2H, m), 6.86 (1H, s), 7.04-7.11 (2H, m), 7.32 (1H, m), 7.46 (1H, m), 8.79 (1H, br s).
EIMS m/z (relative intensity): 460 (M$^+$), 195 (100).

Example 67 (Compound No. 836 in Table)

Production of 7-(benzimidazol-2-ylthio)-N-[2,4-bis(ethylthio)-6-methyl-3-pyridyl]heptanamide The reaction and the treatment were conducted in the same manner as in Example 59 except that 2-mercaptobenzimidazole was used instead of 2-mercaptobenzoxazole to obtain the desired compound as a colorless needle crystal.

Melting point: 151-156° C.
IR (KBr) cm$^{-1}$: 3136, 3106, 1656, 1518, 1438. 1401, 1337, 1268.
$^1$H-NMR (d$_6$-DMSO) δ: 1.24 (3H, t, J=7.3 Hz), 1.25 (3H, t, J=7.3 Hz), 1.36-1.54 (4H, m), 1.55-1.82 (4H, m), 2.15-2.32 (2H, m), 2.41 (3H, s), 2.92 (2H, q, J=7.3 Hz), 3.05 (2H, q, J=7.3 Hz), 3.26 (2H, t, J=7.3 Hz), 6.86 (1H, s), 7.03-7.11 (2H, m), 7.34-7.44 (2H, m), 8.67 (1H, br s).
EIMS m/z (relative intensity): 488 (M$^+$), 151 (100).

Example 68 (Compound No. 837 in table)

Production of 8-(benzoimidazol-2-ylthio)-N-[2,4-bis(ethylthio)-6-methyl-3-pyridyl]octanamide The reaction and the treatment were conducted in the same manner as in Example 60 except that 2-mercaptobenzoimidazole was used instead of 2-mercaptobenzoxazole to obtain the desired compound as a colorless crystal.

Melting point: 166-168° C.
IR (KBr) cm$^{-1}$: 3427, 3147, 2928, 1660, 1560, 1526, 1437.
$^1$H-NMR (d$_6$-DMSO) δ: 1.26 (3H, t, J=7.3 Hz), 1.27 (3H, t, J=7.3 Hz), 1.36-1.41 (4H, m), 1.47 (2H, quint, J=7.2 Hz), 1.60-1.67 (2H, m), 1.75 (2H, quint, J=7.2 Hz), 2.22-2.32 (2H, m), 2.43 (3H, s), 2.94 (2H, q, J=7.3 Hz), 3.07 (2H, q, J=7.3 Hz), 3.28 (2H, t, J=7.2 Hz), 6.88 (1H, s), 7.08 (1H, t, J=5.9 Hz), 7.09 (1H, t, J=5.9 Hz), 7.40 (1H, d, J=5.9 Hz), 7.41 (1H, d. J=5.9 Hz), 8.73 (1H, br s).
EIMS m/z (relative intensity): 502 (M$^+$), 151 (100).

Example 69 (Compund No. 843 in Table)

Production of 4-(benzoxazol-2-ylthio)-N-[2,4-bis(isopropylthio)-6-methyl-3-pyridyl]butanamide The reaction and the treatment were conducted in the same manner as in Example 36 except that 4-bromobutanoyl chloride was used instead of 6-bromohexanoyl chloride to obtain the desired compound as a colorless needle crystal.

Melting point: 128-129° C.
IR (KBr) cm$^{-1}$: 3448, 3235, 2962, 1683, 1657, 1555, 1515, 1500, 1456, 1131.
$^1$H-NMR (d$_6$-DMSO) δ: 1.27 (6H, d, J=6.6 Hz), 1.30 (6H, d, J=6.8 Hz), 2.10-2.17 (2H, m), 2.42 (3H, s), 2.47-2.50 (2H, m), 3.39-3.47 (2H, m), 3.55 (1H, sept, J=6.6 Hz), 3.89 (1H, sept, J=6.8 Hz), 6.92 (1H, s), 7.28 (1H, td, J=7.3, 1.7 Hz), 7.30 (1H, td, J=7.3, 1.7 Hz), 7.56 (1H, dd, J=7.3, 1.7 Hz), 7.58 (1H, dd, J=7.3, 1.7 Hz), 8.90 (1H, br s).
EIMS m/z (relative intensity): 475 (M$^+$), 207 (100).

Example 70 (Compound No. 844 in table)

Production of 5-(benzoxazol-2-ylthio)-N-[2,4-bis(isopropylthio)-6-methyl-3-pyridyl]pentanamide The reaction and the treatment were conducted in the same manner as in Example 36 except that 5-bromopentanoyl chloride was used instead of 6-bromohexanoyl chloride to obtain the desired compound as a colorless prism crystal.

Melting point: 129-130° C.
IR (KBr) cm$^{-1}$: 3448, 3215, 3167, 2965, 1654, 1555, 1525, 1500, 1454, 1128.
$^1$H-NMR (d$_6$-DMSO) δ: 1.27 (6H, d, J=6.8 Hz), 1.30 (6H, d, J=6.8 Hz), 1.75-1.85 (2H, m), 1.86-1.96 (2H, m), 2.26-2.40 (2H, m), 2.42 (3H, s), 3.37 (2H, t, J=7.1 Hz), 3.54 (1H, sept, J=6.8 Hz), 3.88 (1H, sept, J=6.8 Hz), 6.91 (1H, s), 7.27 (1H, td, J=7.6, 1.7 Hz), 7.30 (1H, td, J=7.6, 1.7 Hz), 7.55 (1H, dd, J=7.6, 1.7 Hz), 7.58 (1H, dd, J=7.6, 1.7 Hz), 8.75 (1H, br s).
EIMS m/z (relative intensity): 489 (M$^+$), 221 (100).

Example 71 (Compound No. 846 in Table)

Production of 7-(benzoxazol-2-ylthio)-N-[2,4-bis(isopropylthio)-6-methyl-3-pyridyl]heptanamide The reaction and the treatment were conducted in the same manner as in Example 36 except that 7-bromoheptanoyl chloride was used instead of 6-bromohexanoyl chloride to obtain the desired compound as a colorless needle crystal.

Melting point: 76-78° C.
IR (KBr) cm$^{-1}$: 3436, 3265, 2929, 1663, 1503, 1455.
$^1$H-NMR (d$_6$-DMSO) δ: 1.29 (6H, d, J=6.8 Hz), 1.32 (6H, d, J=6.8 Hz), 1.43-1.54 (4H, m), 1.65 (2H, quint, J=7.2 Hz), 1.83 (2H, quint, J=7.2 Hz), 2.20-2.33 (2H, m), 2.43 (3H, s), 3.35 (2H, t, J=7.2 Hz), 3.56 (1H, sept, J=6.8 Hz), 3.90 (1H, sept, J=6.8 Hz), 6.93 (1H, s), 7.27-7.34 (2H, m), 7.56-7.61 (2H, m), 8.72 (1H, br s).
EIMS m/z (relative intensity): 517 (M$^+$), 249 (100).

Example 72 (Compound No. 847 in Table)

Production of 8-(benzoxazol-2-ylthio)-N-[2,4-bis(isopropylthio)-6-methyl-3-pyridyl]octanamide The reaction and the treatment were conducted in the same manner as in Example 36 except that 8-bromooctanoyl chloride was used instead of 6-bromohexanoyl chloride to obtain the desired compound as a colorless oil.

IR (KBr) cm$^{-1}$: 3241, 166.4, 1559, 1526, 1501, 1454.
$^1$H-NMR (d$_6$-DMSO) δ: 1.29 (6H, d, J=6.8 Hz), 1.31 (6H, d, J=6.8 Hz), 1.34-1.54 (6H, m), 1.55-1.69 (2H, m), 1.73-1.89 (2H, m), 2.15-2.28 (2H, m), 2.42 (3H, s), 3.27 (2H, t, J=7.3 Hz), 3.54 (1H, sept, J=6.8 Hz), 3.89 (1H, sept, J=6.8 Hz), 6.90 (1H, s), 7.24-7.32 (2H, m), 7.51-7.60 (2H, m), 8.59 (1H, br s).
EIMS m/z (relative intensity): 531 (M$^+$), 263 (100).

Example 73 (Compound No. 848 in Table

Production of 9-(benzoxazol-2-ylthio)-N-[2,4-bis(isopropylthio)-6-methyl-3-pyridyl]nonanamide The reaction and the treatment were conducted in the same manner as in Example 36 except that 9-bromononanoyl chloride was used instead of 6-bromohexanoyl chloride to obtain the desired compound as a pale yellow oil.

IR (Cap) cm$^{-1}$: 3243, 2962, 2927, 1668, 1558, 1505, 1455, 1130.
$^1$H-NMR (d$_6$-DMSO) δ: 1.28 (6H, d, J=6.8 Hz) 1.31 (6H, d, J=6.8 Hz) 1.28-1.50 (8H, m), 1.55-1.65 (2H, m), 1.80 (2H, quint, J=7.3 Hz), 2.17-2.27 (2H, m), 2.42 (3H, s), 3.32 (2H, t, J=7.3 Hz), 3.55 (1H, sept, J=6.8 Hz), 3.89 (1H, sept, J=6.8 Hz), 6.91 (1H, s), 7.27 (1H, td, J=7.3, 1.7 Hz), 7.30 (1H, td, J=7.3, 1.7 Hz), 7.54-7.60 (2H, m), 8.65 (1H, br s).
EIMS m/z (relative intensity): 545 (M$^+$), 277 (100).

Example 74 (Compound No. 851 in Table)

Production of 2-(benzothiazol-2-ylthio)-N-[2,4-bis(isopropylthio)-6-methyl-3-pyridyl]acetamide The reaction and the treatment were conducted in the same manner as in Example 49 except that 2-bromo-N-[2,4-bis(isopropylthio)-6-methy-3-pyridyl]acetamide was used instead of 2-bromo-N-2,4-bis(methylthio)-6-methyl-3-pyridyl]acetamide to obtain the desired compound as a colorless needle crystal.

Melting point: 117-118° C.

IR (KBr) cm$^{-1}$: 3431, 3179, 2967, 1660, 1559, 1526, 1428.

$^1$H-NMR (CDCl$_3$) δ: 1.19 (6H, d, J=6.7 Hz), 1.21 (6H, d, J=6.7 Hz), 2.41 (3H, s), 3.39 (1H, sept, J=6.7 Hz), 3.92 (1H, sept, J=6.7 Hz), 4.18 (2H, s), 6.68 (1H, s), 7.32 (1H, td, J=7.7, 1.2 Hz), 7.41 (1H, td, J=7.7, 1.2 Hz), 7.77 (1H, d, J=7.7 Hz), 7.91 (1H, d, J=7.7 Hz), 8.80 (1H, br s).

EIMS m/z (relative intensity): 463 (M$^+$), 180 (100).

| Elemental Analysis: as C$_{21}$H$_{25}$N$_3$OS$_4$ | | | | |
|---|---|---|---|---|
| Calculated: | C, 54.39; | H, 5.43; | N, 9.06; | S, 27.66. |
| Found: | C, 54.28; | H, 5.45; | N, 8.93; | S, 27.73. |

Example 75 (Compound No. 853 in Table)

Production of 4-(benzothiazol-2-ylthio)-N-[2,4-bis(isopropylthio)-6-methyl-3-pyridyl]butanamide The reaction and the treatment were conducted in the same manner as in Example 69 except that 2-mercaptobenzothiazole was used instead of 2-mercaptobenzoxazole to obtain the desired compound as a colorless powdery crystal.

Melting point: 116-117° C.

IR (KBr) cm$^{-1}$: 3450, 3257, 2962, 1667, 1557, 1510, 1457, 1429, 987.

$^1$H-NMR (d$_6$-DMSO) δ: 1.27 (6H, d, J=6.8 Hz), 1.30 (6H, d, J=6.8 Hz), 2.08-2.17 (2H, m), 2.42 (3H, s), 2.43-2.47 (2H, m), 3.45 (2H, t, J=7.1 Hz), 3.55 (1H, sept, J=6.8 Hz), 3.89 (1H, sept, J=6.8 Hz), 6.92 (1H, s), 7.33 (1H, t, J=7.8 Hz), 7.43 (1H, t, J=7.8 Hz), 7.81 (1H, d, J=7.8 Hz), 7.92 (1H, d, J=7.8 Hz), 8.90 (1H, br s).

EIMS m/z (relative intensity): 491 (M$^+$), 69 (100).

Example 76 (Compound No. 854 in Table)

Production of 5-(benzothiazol-2-ylthio)-N-[2,4-bis(isopropylthio)-6-methyl-3-pyridyl]pentanamide The reaction and the treatment were conducted in the same manner as in Example 70 except that 2-mercaptobenzothiazole was used instead of 2-mercaptobenzoxazole to obtain the desired compound as a colorless powdery crystal.

Melting point: 107-109° C.

IR (KBr) cm$^{-1}$: 3441, 3215, 2963, 1656, 1557, 1523, 1460, 1429, 996.

$^1$H-NMR (d$_6$-DMSO) δ: 1.27 (6H, d, J 6.8 Hz), 1.30 (6H, d, J=6.8 Hz), 1.76-1.85 (2H, m), 1.86-1.96 (2H, m), 2.26-2.40 (2H, m), 2.42 (3H, s), 3.39 (2H, t, J=7.1 Hz), 3.54 (1H, sept, J=6.8 Hz), 3.89 (1H, sept, J=6.8 Hz), 6.91 (1H, s), 7.33 (1H, td, J=8.1, 1.2 Hz), 7.43 (1H, td, J=8.1, 1.2 Hz), 7.82 (1H, dd, J=8.1, 1.2 Hz), 7.92 (1H, dd, J=8.1, 1.2 Hz), 8.75 (1H, br s).

EIMS m/z (relative intensity): 505 (M$^+$), 221 (100).

Example 77 (Compound No. 855 in Table)

Production of 6-(benzothiazol-2-ylthio)-N-[2,4-bis(isopropylthio)-6-methyl-3-pyridyl]hexanamide The reaction and the treatment were conducted in the same manner as in Example 36 except that 2-mercaptobenzothiazole was used instead of 2-mercaptobenzoxazole to obtain the desired compound as a colorless crystal.

Melting point: 84-86° C.

IR (KBr) cm$^{-1}$: 3436, 3212, 2961, 2925, 1655, 1555, 1522, 1428.

$^1$H-NMR (d$_6$-DMSO) δ: 1.30 (6H, d, J=6.6 Hz), 1.33 (6H, d, J=6.8 Hz), 1.54-1.62 (2H, m), 1.65-1.73 (2H, m), 1.85 (2H, quint, J=7.0 Hz), 2.22-2.33 (2H, m), 2.43 (3H, s), 3.38 (2H, t, J=7.0 Hz), 3.57 (1H, sept, J=6.6 Hz), 3.91 (1H, sept, J=6.8 Hz), 6.93 (1H, s), 7.34 (1H, t, J=7.8 Hz), 7.44 (1H, t, J=7.8 Hz), 7.83 (1H, d, J=7.8 Hz), 7.93 (1H, d, J=7.8 Hz), 8.73 (1H, br s).

EIMS m/z (relative intensity): 519 (M$^+$), 235 (100).

Example 78 (Compound No. 856 in Table)

Production of 7-(benzothiazol-2-ylthio)-N-[2,4-bis(isopropylthio)-6-methyl-3-pyridyl]heptanamide The reaction and the treatment were conducted in the same manner as in Example 71 except that 2-mercaptobenzothiazole was used instead of 2-mercaptobenzoxazole to obtain the desired compound as a colorless crystal.

Melting point: 74-76° C.

IR (KBr) cm$^{-1}$: 3436, 3200, 3158, 2961, 2928, 1654, 1525, 1427.

$^1$H-NMR (d$_6$-DMSO) δ: 1.29 (6H, d, J=6.6 Hz), 1.32 (6H, d, J=6.8 Hz), 1.43-1.55 (4H, m), 1.65 (2H, quint, J=7.2 Hz), 1.83 (2H, quint, J=7.2 Hz), 2.22-2.33 (2H, m), 2.43 (3H, s), 3.37 (2H, t, J=7.2 Hz), 3.56 (1H, sept, J=6.6 Hz), 3.90 (1H, sept, J=6.8 Hz), 6.93 (1H, s), 7.34 (1H, td, J=7.7, 1.2 Hz), 7.44 (1H, td, J=7.7, 1.2 Hz), 7.83 (1H, dd, J=7.7, 1.2 Hz), 7.94 (1H, dd, J=7.7, 1.2 Hz), 8.68 (1H, br s).

EIMS m/z (relative intensity): 533 (M$^+$), 249 (100).

Example 79 (Compound No. 857 in Table)

Production of 8-(benzothiazol-2-ylthio)-N-[2,4-bis(isopropylthio)-6-methyl-3-pyridyl]octanamide The reaction and the treatment were conducted in the same manner as in Example 72 except that 2-mercaptobenzothiazole was used instead of 2-mercaptobenzoxazole to obtain the desired compound as a colorless neddle crystal.

Melting point: 107-108° c.

IR (KBr) cm$^{-1}$: 3239, 1664. 1559, 1526, 1456, 1428.

$^1$H-NMR (d$_6$-DMSO) δ: 1.29 (6H, d, J=6.8 Hz), 1.31 (6H, d, J=6.8 Hz), 1.34-1.54 (6H, m), 1.55-1.70 (2H, m), 1.73-1.88 (2H, m), 2.15-2.29 (2H, m), 2.42 (3H, s), 3.35 (2H, t, J=7.3 Hz), 3.54 (1H, sept, J=6.8 Hz), 3.89 (1H, sept, J=6.8 Hz), 6.90 (1H, s), 7.31 (1H, t, J=7.8 Hz), 7.42 (1H, t, J=7.8 Hz), 7.81 (1H, d, J=7.8 Hz), 7.90 (1H, d, J=7.8 Hz), 8.59 (1H, br s).

EIMS m/z (relative intensity): 547 (M$^+$), 263 (100).

Example 80 (Compound No. 858 in Table)

Production of 9-(benzothiazol-2-ylthio)-N-[2,4-bis(isopropylthio)-6-methyl-3-pyridyl]nonanamide The reaction and the treatment were conducted in the same manner as in Example 73 except that 2-mercaptobenzothiazole was used instead of 2-mercaptobenzoxazole to obtain the desired compound as a pale yellow oil.

IR (Cap) cm$^{-1}$: 3243, 2962, 2927, 1668, 1559, 1526, 1456.

$^1$H-NMR (d$_6$-DMSO) δ: 1.28 (6H, d, J=6.8 Hz), 1.31 (6H, d, J=6.8 Hz), 1.28-1.50 (8H, m), 1.55-1.65 (2H, m), 1.80 (2H, quint, J=7.0 Hz), 2.17-2.27 (2H, m), 2.42 (3H, s), 3.34 (2H, t, J=7.0 Hz), 3.55 (1H, sept, J=6.8 Hz), 3.89 (1H, sept, J=6.8 Hz), 6.91 (1H, s), 7.32 (1H, td, J=7.1, 1.2 Hz), 7.43 (1H, td, J=7.1, 1.2 Hz), 7.81 (1H, dd, J=7.1, 1.2 Hz), 7.91 (1H, dd, J=7.1, 1.2 Hz), 8.65 (1H, br s).

EIMS m/z (relative intensity): 561 (M$^+$), 277 (100).

Example 81 (Compound No. 861 in Table)

Production of 2-(benzimidazol-2-ylthio)-N-[2,4-bis(isopropylthio)-6-methyl-3-pyridyl]acetamide The reaction and the treatment were conducted in the same manner as in Example 53 except that 2-bromo-N-[2,4-bis(isopropylthio)-6-methylpyridyl]acetamide was used instead of 2-bromo-N-[2,4-bis(methylthio)-6-methylpyridyl]acetamide to obtain the desired compound as a colorless needle crystal.

Melting point: 223-224° C.

IR (KBr) cm$^{-1}$: 3437, 3138, 3106, 2960, 1668, 1534, 1414.

$^1$H-NMR (CDCl$_3$) δ: 1.22 (6H, d, J=6.8 Hz), 1.25 (6H, d, J=6.8 Hz), 2.42 (3H, s), 3.41 (1H, sept, J=6.8 Hz), 3.95 (1H, sept, J=6.8 Hz), 4.05 (2H, s), 6.69 (1H, s), 7.18 (1H, t, J=6.1 Hz), 7.19 (1H, t, J=6.1 Hz), 7.34 (1H, br s), 7.62 (1H, br s), 9.33 (1H, br s), 10.61 (1H, br s).

EIMS m/z (relative intensity): 446 (M$^+$), 371 (100).

| Elemental analysis: as C$_{21}$H$_{26}$N$_4$OS$_3$ | | | |
|---|---|---|---|
| calculated: | C, 56.47; | H, 5.87; | N, 12.54. |
| found: | C, 56.42; | H, 5.87; | N, 12.56. |

Example 82 (Compound No. 863 in Table)

Production of 4-(benzomidazol-2-ylthio)-N-[2,4-bis(isopropylthio)-6-methyl-3-pyridyl]butanamide The reaction and the treatment were conducted in the same manner as in Example 69 except that 2-mercaptobenzimidazole was used instead of 2-mercaptobenzoxazole to obtain the desired compound as a pale-yellow powdery crystal.

Melting point: 209-211° C.

IR (KBr) cm$^{-1}$: 3480, 3196, 2963, 1664, 1557, 1529, 1428.

$^1$H-NMR (d$_6$-DMSO) δ: 1.25 (6H, d, J=6.8 Hz), 1.28 (6H, d, J=6.8 Hz), 2.04 (2H, quint, J=7.1 Hz), 2.43 (3H, s), 2.44 (2H, t, J=7.1 Hz), 3.36 (2H, t, J=7.1 Hz), 3.61 (1H, sept, J=6.8 Hz), 3.86 (1H, sept, J=6.8 Hz), 6.96 (1H, s), 7.09 (1H, dd, J=7.3, 5.4 Hz), 7.12 (1H, dd, J=7.3, 5.4 Hz), 7.35 (1H, m), 7.49 (1H, m), 9.38 (1H, s), 12.53 (1H, s).

EIMS m/z (relative intensity): 474 (M$^+$), 207 (100).

Example 83 (Compound No. 864 in Table)

Production of 5-(benzimidazol-2-ylthio)-N-[2,4-bis(isopropylthio)-6-methyl-3-pyridyl]pentanamide The reaction and the treatment were conducted in the same manner as in Example 70 except that 2-mercaptobenimidazole was used instead of 2-mercaptobenzoxazole to obtain the desired compound as a colorless powdery crystal.

Melting point: 175-176° C.

IR (KBr) cm$^{-1}$: 3447, 3195, 2965, 1663, 1557, 1526, 1428, 1400.

$^1$H-NMR (d$_6$-DMSO) δ: 1.28 (6H, d, J=6.8 Hz), 1.30 (6H, d, J=6.8 Hz), 1.75-1.90 (4H, m), 2.26-2.38 (2H, m)., 2.42 (3H, s), 3.30 (2H, t, J=7.1 Hz), 3.54 (1H, sept, J=6.8 Hz), 3.88 (1H, sept, J=6.8 Hz), 6.91 (1H, s), 7.07 (1H, t, J=6.1 Hz), 7.08 (1H, t, J=6.1 Hz), 7.32 (1H, d, J=6.1 Hz), 7.46 (1H, d, J=6.1 Hz), 8.72 (1H, br s).

EIMS m/z (relative intensity): 488 (M$^+$), 221 (100).

Example 84 (Compound No. 865 in Table)

Production of 6-(benzimidazol-2-ylthio)-N-[2,4-bis(isopropylthio)-6-methyl-3-pyridyl]hexanamide The reaction and the treatment were conducted in the same manner as in Example 36 except that 2-mercaptobenzimidazole was used instead of 2-mercaptobenzoxazole to obtain the desired compound as a colorless powdery crystal.

Melting point: 175-176° C.

$^1$H-NMR (d$_6$-DMSO) δ: 1.30 (6H, d, J=6.7 Hz), 1.32 (6H, d, J=6.7 Hz), 1.47-1.61 (2H, m), 1.62-1.72 (2H, m), 1.73-1.84 (2H, m), 2.18-2.35 (2H, m), 2.43 (3H, s), 3.21-3.33 (2H, m), 3.55 (1H, sept, J=6.7 Hz), 3.90 (1H, sept, J=6.7 Hz), 6.92 (1H, s), 7.03-7.12 (2H, m), 7.33 (1H, m), 7.47 (1H, m), 8.75 (1H, br s), 12.05 (1H, br s).

EIMS m/z (relative intensity): 502 (M$^+$), 235 (100).

Example 85 (Compound No. 866 in Table)

Production of 7-(benzoimidazol-2-ylthio)-N-[2,4-bis(isopropylthio)-6-methyl-3-pyridyl]heptanamide The reaction and the treatment were conducted in the same manner as in Example 71 except that 2-mercaptobenzoimidazole was used instead of 2-mercaptobenzoxazole to obtain the desired compound as a pale-yellow needle crystal.

Melting point: 118-121° C.

IR (KBr) cm$^{-1}$: 3393, 3219, 2963, 2928, 1663, 1559, 1526, 1439.

$^1$H-NMR (d$_6$-DMSO) δ: 1.29 (6H, d, J=6.6 Hz), 1.32 (6H, d, J=6.8 Hz), 1.41-1.53 (4H, m), 1.64 (2H, quint, J=7.2 Hz), 1.76 (2H, quint, J=7.2 Hz), 2.18-2.33 (2H, m), 2.43 (3H, s), 3.28 (2H, t, J=7.2 Hz), 3.56 (1H, sept, J=6.6 Hz), 3.90 (1H, sept, J=6.8 Hz), 6.93 (1H, s), 7.08 (1H, t, J=5.9 Hz), 7.09 (1H, t, J=5.9 Hz), 7.40 (1H, d, J=5.9 Hz), 7.41 (1H, d, J=5.9 Hz), 8.86 (1H, br s).

EIMS m/z (relative intensity): 516 (M$^+$), 399 (100).

Example 86 (Compound No. 867 in Table)

Production of 8-(benzimidazol-2-ylthio)-N-[2,4-bis(isopropylthio)-6-methyl-3-pyridyl]octanamide The reaction and the treatment were conducted in the same manner as in Example 72 except that 2-mercaptobenzimidazole was used instead of 2-mercaptobenzoxazole to obtain the desired compound as a colorless powdery crystal.

Melting point: 176-171° C.
IR (KBr) cm$^{-1}$: 3158, 2963, 2930, 1665, 1559, 1526, 1508, 1429.
$^1$H-NMR (d$_6$-DMSO) δ: 1.28 (6H, d, J=6.8 Hz), 1.31 (6H, d, J=6.8 Hz) 1.32-1.50 (6H, m), 1.56-1.66 (2H, m), 1.74 (2H, quint, J=7.3 Hz), 2.17-2.27 (2H, m), 2.42 (3H, s), 3.26 (2H, t, J=7.3 Hz), 3.54 (1H, sept, J=6.8 Hz), 3.89 (1H, sept, J=6.8 Hz), 6.91 (1H, s), 7.05-7.10 (2H, m), 7.32 (1H, m), 7.45 (1H, m), 8.65 (1H, br s).
EIMS m/z (relative intensity): 530 (M$^+$), 413 (100).

Example 87 (Compound No. 868 in Table)

Production of 9-(benzimidazol-2-ylthio)-N-[2,4-bis(isopropylthio)-6-methyl-3-pyridyl]nonanamide The reaction and the treatment were conducted in the same manner as in Example 73 except that 2-mercaptobenzimidazole was used instead of 2-mercaptobenzoxazole to obtain the desired compound as a pale brown powdery crystal.

Melting point: 112-114° C.
IR (KBr) cm$^{-1}$: 3435, 3185, 2927, 1660, 1558, 1526, 1437.
$^1$H-NMR (d$_6$-DMSO) δ: 1.28 (6H, d, J 6.8 Hz) 1.31 (6H, d, J=6.8 Hz) 1.28-1.48 (8H, m), 1.52-1.65 (2H, m), 1.73 (2H, quint, J=7.1 Hz), 2.18-2.28 (2H, m), 2.42 (3H, s), 3.25 (2H, t, J=7.1 Hz), 3.55 (1H, sept, J=6.8 Hz), 3.89 (1H, sept, J=6.8 Hz), 6.91 (1H, s), 7.07 (1H, t, J=6.1 Hz), 7.08 (1H, t, J=6.1 Hz), 7.32 (1H, d, J=6.1 Hz), 7.46 (1H, d, J=6.1 Hz), 8.80 (1H, br s), 12.05 (1H, br s).
EIMS m/z (relative intensity): 544 (M$^+$), 151 (100).

Example 88 (Compound No. 1145 in Table)

Production of 6-(benzoxazole-2-ylthio)-N-[2-methyl-4,6-bis(methylthio)-5-pyrimidyl]hexanamide 4,6-Dihydroxy-2-methylpyrimidine (1.0 g, 7.9 mmol) was added gradualy to ice-cooled fuming nitric acid (3 ml) stirring. The mixture was stirred for 2 hours cooling with ice and for 1 hour at the room temperature, and then the precipitated crystal was filtered and dried to obtain 207 mg (yield 15%) of 4,6-dihydroxy-2-methy-5-nitropyrimidine.

This nitropyrimidine (205 mg, 1.2 mmol) was dissolved in phosphoryl chloride (1 ml) and diethylaniline (0.3 ml, 1.9 mmol) was added thereto, and the mixture was stirred for 1 hour at 100° C. and for 1 hour at 120° C. The reaction solution was added to ice and then extracted with ethyl acetate. The organic layer was washed with water add then with a saturated aqueous solution of sodium chloride, and dried over magnesium sulfate. Thereafter, the solvent was distilled off, and the resulting crude product was purified through silica gel chromatography (eluent—hexane:ethyl acetate=20:1) to obtain 194 mg (yield 77%) of 4,6-dichloro-2-methyl-5-nitropyrimidine as a colorless needle crystal.

And then a methanol (10 mml) solution of 4,6-dichloro-2-methyl-5-nitropyrimidine (1.0 g. 4.81 mmol) was added dropwise to a methanol (10 ml) solution of sodium thiomethoxide (780 mg, 10.6 mmol) while being cooled with ice, and after the mixture was stirred for 1 hour while being cooled with ice, water added to the reaction mixture and the mixture was extracted with ethyl acetate. The organic layer was washed with water and then with a saturated aqueous solution of sodium chloride, and dried over magnesium sulfate. Thereafter, the solvent was distilled off, and the resulting crude product was recrystalized with ethyl acetate-hexan to obtain 609 mg (yield 55%) of 4,6-bis(methylthio)-2-methyl-5-nitropyrimidine.

Potassium carbonate (119 mg, 0.865 mmol) and pratinum dioxide (40mg, 0.18 mmol) were added to ethanol (100 ml) solution of this nitropyrimidine (100 mg, 0.43 mmol) and stirred in hydrogen. After 1.5 hours, the reaction mixture was filtered, the fltrate was distilled off, and the resulting crude product was purified through silica gel chromatography (eluent—hexane:ethyl acetate=6:1) to obtain 66 mg (yield 76%) of 5-amino-4,6-bis(methylthio)-2-methylpyrimidine.

And then the reaction and the treatment were conducted in the same manner as in Example 18 except that 5-amino-4,6-bis(methylthio)-2-methylthiopyrimidine was used instead of 3-amino-2,4-bis(methlthio)-6-methylpyridine to obtain the desired compound as a colorless powdery crystal.

Melting point: 148-151° C.
IR (KBr) cm$^{-1}$: 3440, 3245, 2929, 1660, 1530.
$^1$H-NMR (CDCl$_3$) δ:
1.43-1.55 (2H, m), 1.57-1.69 (2H, m),
1.72-1.84 (2H,m),
2.14-2.29 (2H, m), 2.38 (6H, s), 2.48 (3H, m),
3.28 (2H, t, J=7.3 Hz), 7.21 (1H, td, J=7.4, 1.7 Hz),
7.24 (1H, td, J=7.4, 1.7 Hz), 7.49 (1H, dd, J=7.4 Hz),
7.51 (1H, dd, J=7.4, 1.7 Hz), 8.91 (1H, br s).
EIMS m/z (relative intensity): 448 (M$^+$, 100).

Example 89 Compound No. 1247 in Table

Production of 2-(7-trifluoromethylbenzoxazol-2-ylthio)-N-[2,4-bis(methylthio)-6-methyl-3-pyridyl]acetamide The reaction and the treatment were conducted in the same manner as in Example 49 except that 2-mercapto-7-trifluoromethylbenzoxazole was used instead of 2-mercaptobenzoxazole to obtain the desired compound as a colorless needle crystal.

Melting point: 207-209° C.
IR (KBr) cm$^{-1}$: 3435, 3235, 1673, 1509, 1433, 1329, 1130.
$^1$H-NMR (CDCl$_3$) δ:
2.32 (3H, s), 2.41 (3H, s), 2.48 (3H, s), 4.14 (2H,s),
6.81 (1H, s), 7.41 (1H, t, J=7.8 Hz),
7.52 (1H, d, J=7.8 Hz), 7.79 (1H, d, J=7.8 Hz),
8.46 (1H, br s).
EIMS m/z (relative intensity): 459 (M$^+$), 227 (100).

| Elemental analysis: as $C_{18}H_{16}F_3N_3O_2S_3$ | | | |
|---|---|---|---|
| Calculated: | C, 47.05; | H, 3.51; | N, 9.14. |
| Found: | C, 46.84; | H, 3.66; | N, 9.03. |

Example 90 Compound No. 1250 in Table

Production of 5-(7-trifluoromethylbenzoxazol-2-ylthio)-N-[2,4-bis(methylthio)-6-methyl-3-pyridyl]pentanamide The reaction and the treatment were conducted in the same manner as in Example 46 except that 2-mercapto-7-trifluoromethylbenzoxazole was used instead of 2-mercaptobenzoxazole to obtain the desired compound as a colorless crystal.

Melting point: 179-180° C.

¹H-NMR (d₆-DMSO) δ:
1.75-1.87 (2H, m), 1.87-2.00 (2H, m),
2.37 (3H, s), 2.39 (3H, s), 2.30-2.39 (2H, m),
2.43 (3H, s), 3.36-3.46 (2H, m), 6.84 (1H, s),
7.50 (1H, t, J=7.9 Hz), 7.59 (1H, d, J=7.9 Hz),
7.89 (1H, d, J=7.9 Hz), 8.85 (1H, br s).
EIMS m/z (relative intensity): 501 (M⁺), 200 (100).

Example 91 Compound No. 1252 in Table

Production of 7-(7-trifluoromethylbenzoxazol-2-ylthio)-N-[2,4-bis(methylthio)-6-methyl-3-pyridyl]heptanamide The reaction and the treatment were conducted in the same manner as in Example 47 except that 2-mercapto-7-trifluoromethylbenzoxazole was used instead of 2-mercaptobenzoxazole to obtain the desired compound as a colorless needle crystal.
Melting point: 129-131° C.
IR (KBr) cm⁻¹: 3247, 1662, 1505, 1435, 1337, 1128.
¹H-NMR (d₆-DMSO) δ:
1.40-1.55 (4H, m), 1.60-1.71 (2H, m),
1.80-1.89 (2H,m),
2.20-2.34 (2H, m), 2.38 (3H, s), 2.40 (3H, s),
2.44 (3H, s), 3.37 (2H, t, J=7.1 Hz), 6.84 (1H, s),
7.49 (1H, t, J=7.8 Hz), 7.58 (1H, d, J=7.8 Hz),
7.88 (1H, d, J=7.8 Hz), 8.78 (1H, br s).
EIMS m/z (relative intensity): 529 (M⁺), 200 (100).

Example 92 Compound No. 1253 in Table

Production of 8-(7-trifluoromethylbenzoxazol-2-ylthio)-N-[2,4-bis(methylthio)-6-methyl-3-pyridyl]octanamide The reaction and the treatment were conducted in the same manner as in Example 48 except that 2-mercapto-7-trifluoromethylbenzoxazole was used instead of 2-mercaptobenzoxazole to obtain the desired compound as a colorless powdery crystal.
Melting point: 115-116° C.
¹H-NMR (d₆-DMSO) δ:
1.40-1.54 (6H, m), 1.56-1.72 (2H, m),
1.85 (2H, quint, J=7.0 Hz), 2.18-2.36 (2H, m),
2.40 (3H, s),,2.43 (3H, s), 2.46 (3H, s), 3.38 (2H, t, J=7.3 Hz),
6.86 (1H, s), 7.51 (1H, t, J=7.5 Hz), 7.60 (1H, d, J=7.5 Hz),
7.90 (1H, d, J=7.5 Hz), 8.16 (1H, br s).
EIMS m/z (relative intensity): 543 (M⁺), 200 (100).

Example 93 Compound No. 1260 in Table

Production of 5-(5-chloro-7-isopropyl-4-methylbenzoxazol-2-ylthio)-N-[2,4-bis(methylthio)-6-methyl-3-pyridyl]pentanamide The reaction and the treatment were conducted in the same manner as in Example 46 except that 5-chloro-7-isopropyl-2-mercapto-4-metylbenzoxazole was used instead of 2-mercaptobenzoxazole to obtain the desired compound as a colorless needle crystal.
Melting point: 155-156° C.
¹H-NMR.(d₆-DMSO) δ:
1.31 (6H, d, J=7.1 Hz), 1.72-1.85 (2H, m), 1.85-1.98 (2H, m),
2.36 (3H, s), 2.39 (3H, s), 2.32-2.40 (2H, m),
2.43 (3H, s), 2.46 (3H, s), 3.22 (1H, sept, J=7.1 Hz),
3.31-3.42 (2H, m), 6.84 (1H, s), 7.13 (1H, s), 8.73 (1H, br s).
EIMS m/z (relative intensity): 525 (M⁺:³⁷Cl), 523 (M⁺: ³⁵Cl), 200 (100).

Example 94 Compound No. 1262 in Table

Production of 7-(5-chloro-7-isopropyl-4-methylbenzoxazol-2-ylthio)-N-[2,4-bis(methylthio)-6-methyl-3-pyridyl]heptanamide The reaction and the treatment were conducted in the same manner as in Example 47 except that 5-chloro-7-isopropyl-2-mercapto-4-metylbenzoxazole was used instead of 2-mercaptobenzoxazole to obtain the desired compound as a colorless prism crystal.
Melting point: 129-131° C.
IR (KBr) cm⁻¹: 3413, 3241, 2964, 2924, 1655, 1567, 1505, 1490, 1435, 1149.
¹H-NMR (d₆-DMSO) δ:
1.31 (6H, d, J=7.1 Hz), 1.40-1.55 (4H, m),
1.56-1.70 (2H, m),
1.83 (2H, quint, J=7.1 Hz), 2.30 (2H, t, J=7.1 Hz),
2.38 (3H, s), 2.40 (3H, s), 2.41 (3H, s), 2.46 (3H,s),
3.21 (1H, sept, J=7.1 Hz), 3.34 (2H, t, J=7.1 Hz),
6.84 (1H, s), 7.14 (1H, s), 8.51 (1H, br s).
EIMS m/z (relative intensity): 553 (M⁺:³⁷Cl), 551 (M⁺: ³⁵Cl), 200 (100).

Example 95 Compound No. 1260 in Table

Production of 8-(5-chloro-7-isopropyl-4-methylbenzoxazol-2-ylthio)-N-[2,4-bis(methylthio)-6-methyl-3-pyridyl]octanamide The reaction and the treatment were conducted in the same manner as in Example 48 except that 5-chloro-7-isopropyl-2-mercapto-4-methylbenzoxazole was used instead of 2-mercaptobenzoxazole to obtain the desired compound as a colorless needle crystal.
Melting point: 128-131° C.
IR (KBr) cm⁻: 3423, 3231, 2929, 1662, 1504, 1489.
¹H-NMR (d₆-DMSO) δ:
1.32 (6H, d, J 7.0 Hz), 1.38-1.43 (4H, m),
1.49 (2H, quint, J=7.2 Hz), 1.60-1.69 (2H, m),
1.84 (2H, quint, J=7.2 Hz), 2.23-2.33 (2H, m),
2.40 (3H, s),
2.42 (3H, s), 2.45 (3H, s), 2.47 (3H, s),
3.23 (1H, sept, J=7.0 Hz), 3.35 (1H, t, J=7.2 Hz),
6.86 (1H, s), 7.15 (1H, s), 8.78 (1H, br s).
EIMS m/z (relative intensity): 567 (M⁺;³⁷Cl), 565 (M⁺; ³⁵Cl), 200 (100).

Example 96 Compound No. 1267 in Table

Production of 2-(7-trifluoromethylbenzoxazol-2-ylthio)-N-[2,4-bis(ethylthio)-6-methyl-3-pyridyl]acetamide The reaction and the treatment were conducted in the same manner as in Example 89 except that 3-amino-2,4-bis(ethylthio)-6-methylpyridine was used instead of 3-amino-2,4-bis(methylthio)-6-methylpyridine to obtain the desired compound as a colorless prism crystal.
Melting point: 182-183° C.
IR (KBr) cm⁻¹: 3435, 3244, 1663, 1508, 1432, 1332.

¹H-NMR (CDCl₃) δ:
1.16 (3H, t, J=7.4 Hz), 1.20 (3H, t, J=7.4 Hz),
2.42 (3H, s), 2.81 (2H, q, J=7.4 Hz),
3.03 (2H, q, J=7.4 Hz), 4.14(2H,s),
6.63 (1H, s), 7.40 (1H, t, J=7.8 Hz),
7.52 (1H, d, J=7.8 Hz),
7.68 (1H, d, J=7.8 Hz), 8.34 (1H, br s).
EIMS m/z (relative intensity): 487 (M⁺), 235 (100).

| Elemental Analysis: $C_{20}H_{20}F_3N_3O_2S_3$ | | | | |
|---|---|---|---|---|
| Calculated: | 'C, 49.27; | H, 4.13; | N, 8.62; | F, 11.69. |
| Found: | C, 49.41; | H, 4.20; | N, 8.62; | F, 11.59. |

Example 97 Compound No. 1269 in Table

Production of 4-(7-trifluoromethylbenzoxazol-2-ylthio)-N-[2,4-bis(ethylthio)-6-methyl-3-pyridyl]butanamide The reaction and the treatment were conducted in the same manner as in Example 57 except that 2-mercapto-7-trifluoromethylbenzoxazole was used instead of 2-mercaptobenzoxazole to obtain the desired compound as a colorless powdery crystal.

Melting point: 148-150° C.
IR (KBr) cm⁻¹: 3439, 3256, 2975, 2929, 1656, 1509, 1433, 1332, 1125.
¹H-NMR (d₆-DMSO) δ:
1.23 (3H, t, J=7.3 Hz), 1.24 (3H, t, J=7.3 Hz),
2.04-2.22 (2H, m), 2.42 (3H, s),
2.47-2.48 (2H, m), 2.92 (2H, q, J=7.3 Hz),
3.04 (2H, q, J=7.3 Hz), 3.42-3.51 (2H, m),
6.87(1H,s),
7.51 (1H, t, J=7.8 Hz) 7.59 (1H, d, J=7.8 Hz),
7.89 (1H, d, J=7.8 Hz), 8.95 (1H, br s).
EIMS m/z (relative intensity): 515 (M⁺), 227 (100).

Example 98 Compound No. 1270 in Table

Production of 5-(7-trifluoromethylbenzoxazol-2-ylthio)-N-[2,4-bis(ethylthio)-6-methyl-3-pyridyl]pentanamide The reaction and the treatment were conducted in the same manner as in Example 58 except that 2-mercapto-7-trifluoromethylbenzoxazole was used instead of 2-mercaptobenzoxazole to obtain the desired compound as a colorless powdery crystal.

Melting point: 155-156° C.
¹H-NMR (d₆-DMSO) δ:
1.20-1.30 (6H, m), 1.73-2.05 (4H, m),
2.30-2.41 (2H, m), 2.42 (3H, s),
2.85-3.00 (2H, m), 3.01-3.09 (2H, m),
3.37-3.48 (2H, m), 6.88 (1H, s),
7.51 (1H, t, J=7.5 Hz), 7.60 (1H, d, J=7.5 Hz),
7.90 (1H, d, J=7.5 Hz), 8.75 (1H, br s).
EIMS m/z (relative intensity): 529 (M⁺), 227 (100).

Example 99 Compound No. 1272 in Table

Production of 7-(7-trifluoromethylbenzoxazol-2-ylthio)-N-[2,4-bis(ethylthio)-6-methyl-3-pyridyl]heptanamide The reaction and the treatment were conducted in the same manner as in Example 59 except that 2-mercapto-7-trifluoromethylbenzoxazole was used instead of 2-mercaptobenzoxazole to obtain the desired compound as a colorless needle crystal.

Melting point: 127-128° C.
IR (KBr) cm⁻¹: 3448, 1659. 1506, 1336, 1128. 1116.
¹H-NMR (d₆-DMSO) δ:
1.24 (3H, t, J=7.3 Hz), 1.25 (3H, t, J=7.3 Hz),
1.39-1.56 (4H, m), 1.56-1.72 (2H, m),
1.78-1.91 (2H, m), 2.19-2.33 (2H, m),
2.42 (3H, s), 2.92 (2H, q, J=7.3 Hz),
3.05 (2H, q, J=7.3 Hz), 3.37 (2H, t, J=7.2 Hz),
6.86 (1H, s), 7.49 (1H, t, J=7.9 Hz),
7.58 (1H, d, J=7.9 Hz),
7.88 (1H, d, J=7.9 Hz), 8.67 (1H, br s).
EIMS m/z (relative intensity): 557 (M⁺), 227 (100).

Example 100 Compound No. 1273 in Table

Production of 8-(7-trifluoromethylbenzoxazol-2-ylthio)-N-[2,4-bis(ethylthio)-6-methyl-3-pyridyl]octanamide The reaction and the treatment were conducted in the same manner as in Example 60 except that 2-mercapto-7-trifluoromethylbenzoxazole was used instead of 2-mercaptobenzoxazole to obtain the desired compound as a colorless crystal.

Melting point: 99-100° C.
IR (KBr) cm⁻¹: 3425, 3245, 2923, 1655, 1509, 1433, 1332, 1125.
¹H-NMR (d₆-DMSO) δ:
1.26 (3H, t, J=7.3 Hz), 1.27 (3H,.t, J=7.3 Hz),
1.38-1.43 (4H, m), 1.49 (2H, quint, J=7.2 Hz),
1.60-1.68 (2H, m), 1.85 (2H, quint, J=7.2 Hz),
2.20-2.30 (2H, m), 2.43 (3H, s),
2.94 (2H, q, J=7.3 Hz),
3.06 (2H, q, J=7.3 Hz), 3.38 (2H, t, J=7.2 Hz),
6.88 (1H, s), 7.51 (1H, t, J=7.8 Hz),
7.60 (1H, d, J=7.8 Hz),
7.90 (1H, d, J=7.8 Hz), 8.73 (1H. br s).
EIMS m/z (relative intensity): 571 (M⁺), 227 (100).

Example 101 Compound No. 1274 in Table

Production of 9-(7-trifluoromethylbenzoxazol-2-ylthio)-N-[2,4-bis(ethylthio)-6-methyl-3-pyridyl]nonanamide The reaction and the treatment were conducted in the same manner as in Example 28 except that 2-mercapto-7-trifluoromethylbenzoxazole was used instead of 2-mercaptobenzoxazole to obtain the desired compound as a colorless powdery crystal.

Melting point: 115-116° C.
¹H-NMR (d6-DMSO) δ:
1.26 (3H, t, J=7.2 Hz), 1.27 (3H, t, J 7.2 Hz),
1.31-1.55 (8H, m), 1.57-1.69 (2H, m),
1.84 (2H, quint, J=6.9 Hz), 2.18-2.34 (2H, m),
2.43 (3H, s), 2.94 (2H, q, J=7.2 Hz), 3.06 (2H, q, J=7.2 Hz),
3.37 (2H, t, J=7.3 Hz), 6.88 (1H, s),
7.51 (1H, t, J=8.4 Hz),
7.61 (1H, d, J=8.4 Hz), 7.90 (1H, d, J=8.4 Hz),
8.73 (1H, br s).
EIMS m/z (relative intensity): 585 (M$^+$), 227 (100).

Example 102 Compound No. 1279 in Table

Production of 4-(5-chloro-7-isopropyl-4-methylbenzoxazol-2-ylthio)-N-[2,4-bis(ethylthio)-6-methyl-3-pyridyl]butanamide The reaction and the treatment were conducted in the same manner as in Example 57 except that 5-chloro-7-isopropyl-2-mercapto-4-methylbenzoxazole was used instead of 2-mercaptobenzoxazole to obtain the desired compound as a colorless needle crystal.

Melting point: 122-123° C.
IR (KBr) cm$^{-1}$: 3258, 1665, 1502, 1145.
$^1$H-NMR (d$_6$-DMSO) δ:
1.23 (3H, t, J=7.3 Hz), 1.24 (3H, t, J=7.3 Hz),
1.31 (6H, d, J=6.8 Hz), 2.15 (2H, t, J=7.0 Hz),
2.42 (3H, s), 2.46 (3H, s), 2.47-2.50 (2H, m),
2.92 (2H, q, J=7.3 Hz),
3.04 (2H, q, J=7.3 Hz), 3.22 (1H, sept, J=6.8 Hz),
3.43 (2H, t, J=7.0 Hz), 6.87 (1H, s), 7.14(1H, s),
8.83 (1H, br s).
EIMS m/z (relative intensity): 559 (M$^+$:$^{37}$Cl), 557 (M$^+$: $^{35}$Cl), 227 (100).

Example 103 Compound No. 1280 in Table

Production of 5-(5-chloro-7-isopropyl-4-methylbenzoxazol-2-ylthio)-N-[2,4-bis(ethylthio)-6-methyl-3-pyridyl]pentanamide The reaction and the treatment were conducted in the same manner as in Example 58 except that 5-chloro-7-isopropyl-2-mercapto-4-methylbenzoxazole was used instead of 2-mercaptobenzoxazole to obtain the desired compound as a colorless powdery crystal.

Melting point: 141-142° C.
$^1$H-NMR (d6-DMSO) δ:
1.25(3H, t, J=7.4 Hz), 1.26 (3H, t, J=7.4 Hz),
1.32 (6H, d, J=6.9 Hz), 1.75-1.86 (2H, m),
1.87-2.00 (2H, m), 2.30-2.40 (2H, m), 2.43 (3H,s),
2.45-2.52 (3H, s), 2.92 (2H, q, J=7.4 Hz),
3.04 (2H, q, J=7.4 Hz), 3.23 (1H, sept, J=6.9 Hz),
3.33-3.43 (2H, m), 6.88 (1H, s), 7.15 (1H, s), 8.82 (1H, br s).
EIMS m/z (relative intensity): 553 (M$^+$;$^{37}$Cl), 551 (M$^+$; $^{35}$Cl), 227 (100).

Example 104 Compound No. 1282 in Table

Production of 7-(5-chloro-7-isopropyl-4-methylbenzoxazol-2-ylthio)-N-[2,4-bis(ethylthio)-6-methyl-3-pyridyl]heptanamide The reaction and the treatment were conducted in the same manner as in Example 59 except that 5-chloro-7-isopropyl-2-mercapto-4-methylbenzoxazole was used instead of 2-mercaptobenzoxazole to obtain the desired compound as a colorless prism crystal.

Melting point: 117-120° C.
IR (KBr) cm$^{-1}$: 3320, 1668, 1506, 1482, 1150.
$^1$H-NMR (d$_6$-DMSO) δ:
1.24 (3H, t, J=7.3 Hz), 1.25 (3H, t, J=7.3 Hz),
1.31 (6H, d, J=6.8 Hz), 1.39-1.57 (4H, m),
1.57-1.71 (2H, m),
1.77-1.89 (2H, m), 2.19-2.30 (2H, m), 2.42 (3H,s),
2.46 (3H, s), 2.92 (2H, q, J=7.3 Hz),
3.05 (2H, q, J=7.3 Hz),
3.21 (1H, sept, J=6.8 Hz), 3.33 (2H, t, J=7.2 Hz),
6.86 (1H, s), 7.13 (1H, s), 8.66 (1H, br s).
EIMS m/z (relative intensity): 581 (M$^+$:$^{37}$Cl), 579 (M$^+$: $^{35}$Cl), 227 (100).

Example 105 Compound No. 1283 in Table

Production of 8-(5-chloro-7-isopropyl-4-methylbenzoxazol-2-ylthio)-N-[2,4-bis(ethylthio)-6-methyl-3-pyridyl]octanamide The reaction and the treatment were conducted in the same manner as in Example 60 except that 5-chloro-7-isoprdpyl-2-mercapto-4-methylbenzoxazole was used instead of 2-mercaptobenzoxazole to obtain the desired compound as a colorless needle crystal.

Melting point: 82-84° C.
IR (KBr) cm$^{-1}$: 3435, 3259, 2929, 1655, 1504, 1490.
$^1$H-NMR (d$_6$-DMSO) δ:
1.26 (3H, t, J=7.3 Hz), 1.27 (3H, t, J=7.3 Hz),
1.32 (6H, d, J=6.8 Hz), 1.39-1.43 (4H, m),
1.49 (2H, quint, J=7.2 Hz), 1.60-1.68 (2H, m),
1.84 (2H, quint, J=7.2 Hz), 2.22-2.32 (2H, m), 2.43 (3H, s),
2.47 (3H, s), 2.94 (2H, q, J=7.3 Hz), 3.06 (2H, q, J=7.3 Hz),
3.22 (1H, sept, J=6.8 Hz), 3.35 (2H, t, J=7.2 Hz),
6.88 (1H, s), 7.15 (1H, s), 8.73 (1H, br s).
EIMS m/z (relative intensity): 595 (M$^+$;$^{37}$Cl), 593 (M$^+$; $^{35}$Cl), Example 106 Compound No. 1284 in Table Production of 9-(5-chloro-7-isopropyl-4-methylbenzoxazol-2-ylthio)-N-[2,4-bis(ethylthio)-6-methyl-3-pyridyl]nonanamide The reaction and the treatment were conducted in the same manner as in Example 28 except that 5-chloro-7-isopropyl-2-mercapto-4-methylbenzoxazole was used instead of 2-mercaptobenzoxazole to obtain the desired compound as a colorless powdery crystal.

Melting point: 93-94° C.
$^1$H-NMR (d$_6$-DMSO) δ:
1.27 (3H, t, J=7.3 Hz), 1.28 (3H, t, J 7.3 Hz),
1.32 (6H, d, J=7.0 Hz), 1.29-1.55 (8H, m),
1.56-1.69 (2H, m), 1.83 (2H, quint, J=6.9 Hz),
2.07-2.17 (2H, m), 2.43 (3H, s),
2.45-2.49 (3H, m), 2.94 (2H, q, J=7.3 Hz),
3.07 (2H, q, J=7.3 Hz), 3.22 (1H, sept, J=7.0 Hz),
3.34 (2H, t, J=7.3 Hz), 6.88 (1H, s), 7.15 (1H, s),
8.73 (1H, br s).
EIMS m/z (relative intensity): 609 (M$^+$;$^{37}$Cl), 607 (M$^+$; $^{35}$Cl), 229 (100).

Example 107 Compound No. 1287 in Table

Production of 2-(7-triffluoromethylbenzoxazol-2-ylthio)-N-[2,4-bis(isopropylthio)-6-methyl-3-pyridyl]acetamide The reaction and the treatment were conducted in the same manner as in Example 89 except that 2-bromo-N-[2,4-bis(isopropylthio)-6-methylpyridyl]amide was used instead of 2-bromo-[2,4-bis(methylthio)-6-methylpyridyl]acetamide to obtain the desired compound as a colorless needle crystal.

Melting point: 121-122° C.
IR (KBr) cm$^{-1}$: 3426, 3210, 2967, 1655, 1507, 1431, 1329.
$^1$H-NMR (CDCl$_3$) δ:
1.17 (6H, d, J=6.8 Hz), 1.19 (6H, d, J=6.8 Hz),
2.42 (3H, s),
3.39 (1H, sept, J=6.8 Hz), 3.90 (1H, sept, J=6.8 Hz),
4.13 (2H, s), 6.68 (1H, s), 7.41 (1H, t, J=7.9 Hz),
7.52 (1H, d, J=7.9 Hz), 7.80 (1H, d, J=7.9 Hz),
8.30 (1H, br s).
EIMS m/z (relative intensity): 515 (M$^+$), 181 (100).

| Elemental analysis: as C$_{22}$H$_{24}$F$_3$N$_3$O$_2$S$_3$ | | | | |
|---|---|---|---|---|
| Calculated: | C, 51.25; | H, 4.69; | N, 8.15; | F, 11.05. |
| Found: | C, 51.28; | H, 4.73; | N, 8.07; | F, 11.02. |

Example 108 Compound No. 1289 in Table

Production of 4-(7-trifluoromethylbenzoxazol-2-ylthio)-N-[2,4-bis(isopropylthio)-6-methyl-3-pyridyl]butanamide The reaction and the treatment were conducted in the same manner as in Example 69 except that 2-mercapto-7-trifluoromethylbenzoxazole was used instead of 2-mercaptobenzoxazole to obtain the desired compound as a colorless prism crystal.

Melting point: 135-136° C.
IR (KBr) cm$^{-1}$: 3446, 3255, 2968, 1660, 1559, 1531, 1504, 1491, 1433, 1139.
$^1$H-NMR (d$_6$-DMSO) δ:
1.27 (6H, d, J=6.8 Hz), 1.29 (6H, d, J=6.8 Hz),
2.13-2.21 (2H, m), 2.42 (3H, s),
2.47-2.50 (2H, m), 3.44-3.50 (2H, m),
3.55 (1H, sept, J=6.8 Hz), 3.88 (1H, sept, J=6.8 Hz),
6.92 (1H, s), 7.51 (1H, t, J=7.8 Hz),
7.59 (1H, d, J=7.8 Hz),
7.88 (1H, d, J=7.8 Hz), 8.91 (1H, br s).
EIMS m/z (relative intensity): 543 (M$^+$), 207 (100).

Example 109 Compound No. 1290 in Table

Production of 5-(7-trifluoromethylbenzoxazol-2-ylthio)-N-[2,4-bis(isopropylthio)-6-methyl-3-pyridyl]pentanamide The reaction and the treatment were conducted in the same manner as in Example 70 except that 2-mercapto-7-trifluoromethylbenzoxazole was used instead of 2-mercaptobenzoxazole to obtain the desired compound as a colorless needle crystal.

Melting point: 118-120° C.
IR (KBr) cm$^{-1}$: 3208, 3163, 1663, 1506, 1431, 1328, 1139.
$^1$H-NMR (d$_6$-DMSO) δ:
1.27 (6H, d, J=6.8 Hz), 1.30 (6H, d, J=6.8 Hz),
1.73-1.87 (2H, m), 1.87-2.01 (2H, m),
2.23-2.38 (2H, m), 2.41 (3H, s),
3.41 (2H, t, J=7.0 Hz), 3.54 (1H, sept, J=6.8 Hz),
3.88 (1H, sept, J=6.8 Hz), 6.91 (1H, s),
7.49 (1H, t, J=7.9 Hz),
7.58 (1H, d, J=7.9 Hz), 7.88 (1H, d, J=7.9 Hz).
8.67 (1H, br s).
EIMS m/z (relative intensity): 557 (M$^+$), 221 (100).

Example 110 Compound No. 1291 in Table

Production of 6-(7-trifluoromethylbenzoxazol-2-ylthio)-N-[2,4-bis(isopropylthio)-6-methyl-3-pyridyl]hexanamide The reaction and the treatment were conducted in the same manner as in Example 36 except that 2-mercapto-7-trifluoromethylbenzoxazole was used instead of 2-mercaptobenzoxazole to obtain the desired compound as a colorless needle crystal.

Melting point: 102-103° C.
IR (KBr) cm$^{-1}$: 3136, 1648, 1507, 1431, 1332, 1129.
$^1$H-NMR (d$_6$-DMSO) δ:
1.28 (6H, d, J=6.8 Hz), 1.31 (6H, d, J=6.8 Hz),
1.49-1.76 (4H, m), 1.77-1.94 (2H, m),
2.19-2.32 (2H, m), 2.42 (3H, s), 3.38 (2H, t, J=7.3 Hz),
3.55 (1H, sept, J=6.8 Hz), 3.89 (1H, sept, J=6.8 Hz),
6.91 (1H, s), 7.49 (1H, t, J=7.8 Hz), 7.58 (1H, d, J=7.8 Hz),
7.87 (1H, d, J=7.8 Hz), 8.62 (1H, br s).
EIMS m/z (relative intensity): 571 (M$^+$), 235 (100).

Example 111 Compound No. 1292 in Table

Production of 7-(7-trifluoromethylbenzoxazol-2-ylthio)-N-[2,4-bis(isopropylthio)-6-methyl-3-pyridyl]heptanamide The reaction and the treatment were conducted in the same manner as in Example 71 except that 2-mercapto-7-trifluoromethylbenzoxazole was used instead of 2-mercaptobenzothiazole to obtain the desired compound as a colorless crystal.

Melting point: 76-78° C.
IR (KBr) cm$^{-1}$: 3423, 3268, 2931, 1660, 1506, 1433, 1334.
$^1$H-NMR (d$_6$-DMSO) δ:
1.29 (6H, d, J=6.8 Hz), 1.31 (6H, d, J=6.8 Hz),
1.43-1.54 (4H, m), 1.61-1.69 (2H, m),
1.86 (2H, quint, J=7.2 Hz), 2.18-2.32 (2H, m),
2.43 (3H, s), 3.39 (2H, t, J=7.2 Hz),
3.56 (1H, sept, J=6.8 Hz),
3.90 (1H, sept, J=6.8 Hz), 6.93 (1H, s),
7.51 (1H, dd, J=8.1, 7.8 Hz), 7.60 (1H, d, J=7.8 Hz),
7.90 (1H, d, J=8.1 Hz), 8.68 (1H, br s).
EIMS m/z (relative intensity): 585 (M$^+$), 249 (100).

Example 112 Compound No. 1293 in Table

Production of 8-(7-trifluoromethylbenzoxazol-2-ylthio)-N-[2,4-bis(isopropylthio)-6-methyl-3-pyridyl]octanamide The reaction and the treatment were conducted in the same manner as in Example 72 except that 2-mercapto-7-trifluoromethylbenzoxazole was used instead of 2-mercaptobenzoxazole to obtain the desired compound as a pale yellow oil.

IR (Cap) cm$^{-1}$: 3246, 2964, 2930, 1664, 1559, 1506, 1432.
$^1$H-NMR (d$_6$-DMSO) δ:
1.28 (6H, d, J=6.8 Hz), 1.30 (6H, d, J=6.8 Hz),
1.32-1.50 (6H, m), 1.56-1.66 (2H, m),
1.83 (2H, quint, J=7.1 Hz), 2.17-2.27 (2H, m),
2.42 (3H, s), 3.36 (2H, t, J=7.1 Hz),
3.55 (1H, sept, J=6.8 Hz),
3.89 (1H, sept, J=6.8 Hz),
6.91 (1H, s), 7.50 (1H, t, J=7.8 Hz),
7.59 (1H, d, J=7.8 Hz),
7.88 (1H, d, J=7.8 Hz), 8.65 (1H, br s).
EIMS m/z (relative intensity): 599 (M$^+$), 263 (100)

Example 113 Compound No. 1294 in Table

Production of 9-(7-trifluoromethylbenzoxazol-2-ylthio)-N-[2,4-bis(isopropylthio)-6-methyl-3-pyridyl]nonanamide The reaction and the treatment were conducted in the same manner as in Example 73 except that 2-mercapto-7-trifluoromethylbenzoxazole was used instead of 2-mercaptobenzoxazole to obtain the desired compound as a pale-yellow powdery crystal.
Melting point: 97-98° C.
IR (KBr) cm$^{-1}$: 3446, 3266, 2928, 1661, 1560, 1506, 1335, 1127.
$^1$H-NMR (d$_6$-DMSO) δ:
1.28 (6H, d, J=6.6 Hz), 1.30 (6H, d, J 6.8 Hz)
1.28-1.51 (8H, m), 1.55-1.64 (2H, m),
1.83 (2H, quint, J=7.3 Hz), 2.20-2.30 (2H, m),
2.42 (3H, s), 3.36 (2H, t, J=7.3 Hz),
3.55 (1H, sept, J=6.6 Hz), 3.89 (1H, sept, J=6.8 Hz),
6.91 (1H, s), 7.50 (1H, t, J=7.8 Hz),
7.59 (1H, d, J=7.8 Hz),
7.89 (1H, d, J=7.8 Hz), 8.71 (1H, br s).
EIMS m/z (relative intensity): 613 (M$^+$), 277 (100).

Example 114 Compound No. 1299 in Table

Production of 4-(5-chloro-7-isopropyl-4-methylbenzoxazol-2-ylthio)-N-[2,4-bis(isopropylthio)-6-methyl-3-pyridyl]butanamide The reaction and the treatment were conducted in the same manner as in Example 69 except that 5-chloro-2-mercapto-4-methylbenzoxazole was used instead of 2-mercaptobenzoxazole to obtain the desired compound as a colorless needle crystal.
Melting point: 141-143° C.
$^1$H-NMR (d$_6$-DMSO) δ:
1.27 (6H, d, J=6.8 Hz), 1.29 (6H, d, J=6.8 Hz),
1.31 (6H, d, J=6.8 Hz), 2.03-2.21 (2H, m),
2.42 (3H, s), 2.43-2.50 (5H, m),
3.22 (1H, sept, J=6.8 Hz),
3.38-3.48 (2H, m), 3.55 (1H, sept, J=6.8 Hz),
3.88 (1H, sept, J=6.8 Hz), 6.92 (1H, s), 7.14 (1H,s),
8.87 (1H, br s).
EIMS m/z (relative intensity): 567 (M$^+$:$^{37}$Cl), 565 (M$^+$:$^{35}$Cl), 207 (100).

Example 115 Compound No. 1300 in Table

Production of 5-(5-chloro-7-isopropyl-4-methylbenzoxazol-2-ylthio)-N-[2,4-bis(isopropylthio)-6-methyl-3-pyridyl]pentanamide The reaction and the treatment were conducted in the same manner as in Example 70 except that 5-chloro-7-isopropyl-2-mercapto-4-methylbenzoxazole was used instead of 2-mercaptobenzoxazole to obtain the desired compound as a colorless needle crystal.
Melting point: 143-145° C.
IR (KBr) cm$^{-1}$: 3231, 2924, 1720, 1657, 1508, 1297
$^1$H-NMR (d6-DMSO) δ:
1.27 (6H, d, J=6.8 Hz), 1.29 (6H, d, J=6.8 Hz),
1.31 (6H, d, J=6.8 Hz), 1.73-1.85 (2H, m),
1.85-1.98 (2H, m),
2.25-2.37 (2H, m), 2.41 (3H, s),
2.43-2.50 (3H, s), 3.21 (1H, sept, J=6.8 Hz),
3.37 (2H, t, J=7.2 Hz), 3.54 (1H, sept, J=6.8 Hz),
3.88 (1H, sept, J=6.8 Hz), 6.92 (1H, s), 7.14 (1H,s),
8.76 (1H, br s).
EIMS m/z (relative intensity): 581 (M$^+$:$^{37}$Cl), 579 (M$^+$:$^{35}$Cl, 100)

Example 116 Compound No. 1301 in Table

Production of 6-(5-chloro-7-isopropyl-4-methylbenzoxazol-2-ylthio)-N-[2,4-bis(isopropylthio)-6-methyl-3-pyridyl]hexanamide The reaction and the treatment were conducted in the same manner as in Example 36 except that 5-chloro-7-isopropyl-2-mercapto-4-methylbenzoxazole was used instead of 2-mercaptobenzoxazole to obtain the desired compound as a colorless needle crystal.
Melting point: 99-101° C.
IR (KBr) cm$^{-1}$: 3413, 3224, 2964, 1663, 1506, 1148.
$^1$H-NMR (d6-DMSO) δ:
1.29 (6H, d, J=6.8 Hz), 1.32 (12H, d, J=6.8 Hz),
1.54-1.62 (2H, m), 1.70 (2H, quint, J=7.1 Hz),
1.87 (2H, quint, J=7.1 Hz), 2.22-2.33 (2H, m),
2.43 (3H, s), 2.48 (3H, s),
3.23 (1H, sept, J=6.8 Hz), 3.36 (2H, t, J=7.1 Hz),
3.57 (1H, sept, J=6.8 Hz), 3.90 (1H, sept, J=6.8 Hz),
6.93 (1H, s), 7.15 (1H, s), 8.72 (1H, br s).
EIMS m/z (relative intensity): 595 (M$^+$;$^{37}$Cl), 593 (M$^+$:$^{35}$Cl), 518 (100)

Example 117 Compound No. 1302 in Table

Production of 7-(5-chloro-7-isopropyl-4-methylbenzoxazol-2-ylthio)-N-[2,4-bis(isopropylthio)-6-methyl-3-pyridyl]heptanamide The reaction and the treatment were conducted in the same manner as in Example 71 except that 5-chloro-7-isopropyl-2-mercapto-4-methylbenzoxazole was used instead of 2-mercaptobenzoxazole to obtain the desired compound as a colorless needle crystal.
Melting point: 91-93° C.
IR (KBr) cm$^{-1}$: 3436, 3213, 3169, 2962, 2929, 1666, 1505, 1152.
$^1$H-NMR (d$_6$-DMSO) δ:
1.29 (6H, d, J=6.8 Hz), 1.31 (6H, d, J=6.8 Hz),
1.31 (6H, d, J=6.8 Hz), 1.40-1.52 (4H, m),
1.60-1.68 (2H, m), 1.85 (2H, quint, J=7.1 Hz), 2.17-2.32 (2H, m), 2.43 (3H, s),
2.47 (3H, s), 3.22 (1H, sept, J=6.8 Hz),
3.35 (2H, t, J=7.1 Hz),
3.56 (1H, sept, J=6.8 Hz), 3.90 (1H, sept, J=6.8 Hz),
6.93 (1H, s), 7.15 (1H, s), 8.67 (1H, br s).
EIMS m/z (relative intensity): 609 (M$^+$;$^{37}$Cl), 607 (M$^+$; $^{35}$Cl), 532 (100).

Example 118 Compound No. 1303 in Table

Production of 8-(5-chloro-7-isopropyl-4-methylbenzoxazol-2-ylthio)-N-[2,4-bis(isopropylthio)-6-methyl-3-pyridyl]octanamide The reaction and the treatment were conducted in the same manner as in Example 72 except that 5-chloro-7-isopropyl-2-mercapto-4-methylbenzoxazole was used instead of 2-mercaptobenzoxazole to obtain the desired compound as a pale yellow oil.
IR (Cap) cm$^{-1}$: 3242, 2964, 2928, 1668, 1559, 1506, 1148.
$^1$H-NMR (d$_6$-DMSO) δ:
1.28 (6H, d, J=6.6 Hz), 1.31 (12H, d, J=6.8 Hz),
1.32-1.50 (6H, m), 1.57-1.67 (2H, m),
1.82 (2H, quint, J=7.1 Hz), 2.17-2.27 (2H, m),
2.42 (3H, s), 2.46 (3H, s), 3.21 (1H, sept, J=6.8 Hz),
3.33 (2H, t, J=7.1 Hz), 3.55 (1H, sept, J=6.6 Hz),
3.89 (1H, sept, J=6.8 Hz), 6.91 (1H, s),
7.14 (1H, s), 8.65 (1H, br s).
EIMS m/z (relative intensity): 623 (M$^+$;$^{37}$Cl), 621 (M$^+$: $^{35}$Cl) 546 (100).

Example 119 Compound No. 1304 in Table

Production of 9-(5-chloro-7-isopropyl-4-methylbenzoxazol-2-ylthio)-N-[2,4-bis(isopropylthio)-6-methyl-3-pyridyl]nonanamide The reaction and the treatment were conducted in the same manner as in Example 73 except that 5-chloro-7-isopropyl-2-mercapto-4-methylbenzoxazole was used instead of 2-mercaptobenzoxazole to obtain the desired compound as a pale yellow oil.
IR (Cap) cm$^{-1}$: 3249, 2961, 2926, 1667, 1563, 1505.
$^1$H-NMR (d$_6$-DMSO) δ:
1.28 (6H, d, J=6.8 Hz), 1.30 (12H, d, J=7.1 Hz)
1.28-1.50 (8H, m), 1.55-1.65 (2H, m),
1.81 (2H, quint, J=7.1 Hz), 2.17-2.27 (2H, m),
2.41 (3H, s), 2.46 (3H, s), 3.21 (1H, sept, J=7.1 Hz),
3.32 (2H, t, J=7.1 Hz), 3.54 (1H, sept, J=6.8 Hz),
3.89 (1H, sept, J=7.1 Hz), 6.91 (1H, s),
7.14 (1H, s), 8.65 (1H, br s).
EIMS m/z (relative intensity): 637 (M$^+$;$^{37}$Cl), 635 (M$^+$: $^{25}$Cl) 560 (100).

Example 120 Compound No. 1317 in Table

Production of 2-(7-methansulfonylbenzoxazol-2-ylthio)-N-[2,4-bis(ethylthio)-6-methyl-3-pyridyl]acetamide The reaction and the treatment were conducted in the same manner as in Example 96 except that 2-mercapto-7-methansulfonylbenzoxazole was used instead of 2-mercapto-7-trifluoromethylbenzoxazole to obtain the desired compound as a colorless needle crystal.
Melting point: 159-162° C.

IR (KBr) cm$^{-1}$: 3449, 3271, 2966, 2928, 1678, 1508, 1315, 1118.
$^1$H-NMR (CDCl$_3$) δ:
1.14 (3H, t, J=7.3 Hz), 1.20 (3H, t, J=7.3 Hz),
2.43 (3H, s),
2.82 (2H, q, J=7.3 Hz), 3.01 (2H, q, J=7.3 Hz),
3.27 (2H, s),
4.15 (2H, s), 6.63 (1H, s), 7.49 (1H, t, J=7.9 Hz),
7.83 (1H, dd, J=7.9, 1.2 Hz), 7.90 (1H, dd, J=7.9, 1.2 Hz),
8.17 (1H, br s).
EIMS m/z (relative intensity): 497 (M$^+$), 311 (100).

| Elemental analysis: as C$_{20}$H$_{23}$N$_3$O$_4$S$_4$ | | | |
|---|---|---|---|
| Calculated: | C, 48.27; | H, 4.66; | N, 8.44; | S, 25.77. |
| Found: | C, 48.36; | H, 4.66; | N, 8.31; | S, 25.76. |

Example 121 Compound No. 1327 in Table

Production of 2- (7-methansulfonylbenzoxazol-2-ylthio)-N-[2,4-bis(isopropylthio)-6-methyl-3-pyridyl]acetamide The reaction and the treatment were conducted in the same manner as in Example 74 except that 2-mercapto-7-methansulfonylbenzoxazole was used instead of 2-mercaptobenzothiazole to obtain the desired compound as a pale yellow amorphous.
IR (KBr) cm$^{-1}$: 3435, 3337, 2965, 2926, 1695, 1506, 1424, 1319, 1117.
$^1$H-NMR (CDCl$_3$) δ:
1.16 (6H, d, J=6.8 Hz), 1.21 (6H, d, J=6.8 Hz),
2.42 (3H, s),
3.26 (3H, s), 3.40 (1H, sept, J=6.8 Hz),
3.90 (1H, sept, J=6.8 Hz), 4.15 (2H, s), 6.68 (1H,s),
7.49 (1H, t, J=7.9 Hz), 7.83 (1H, dd, J=7.9, 1.0 Hz),
7.90 (1H, dd, J=7.9, 1.0 Hz), 8.11 (1H, br s).
EIMS m/z (relative intensity): 525 (M$^+$), 339 (100).

Example 122 Compound No. 1341 in Table

Production of 6-(benzoxasole-2-ylthio)-N-(4-methyl-2-(methylthio)-5-pyridyl)hexanamide A methanol (8 mml) solution of 2-dichloro-4-methyl-5-nitropyrimidine (2.0 g. 10.4 mmol) was added dropwise to a methanol (8 ml) solution of sodium thiomethoxide (436 mg, 5.9 mmol) while being cooled with ice, and after the mixture was stirred for 15 hours while raising its temperature to the room temperature, water added to the reaction mixture and the mixture was extracted with ethyl acetate. The organic layer was washed with water and then with a saturated aqueous solution of sodium chloride, and dried over sodium sulfate. Thereafter, the solvent was distilled off, and the resulting crude product was recrystalized with ethyl acetate-hexan to obtain 1.02 g (yield 98%) of 4-methyl-2-methylthio-5-nitropyridine as a pale-yellow needle crystal.
This nitropyridine (497 mg, 2.7 mmol) was dissolved in a mixed solvent of acetic acid (15 ml) and conc. hydrochloric acid (0.5 ml), and zinc (2.12 g, 32.4 mmol) was added thereto in small portions while being cooled with ice for 5 minutes. After the mixture was stirred for 30 minutes at the room temperature, the reaction mixture was filtered, and the filtrate was neutralized with an aqueous solution of sodium hydrogencarbonate, and extracted with methylene chloride. The organic layer was washed with water and then with a saturated aqueous solution of sodium chloride, and dried over sodium sulfate. Thereafter, the solvent was distilled off, and the resulting crude product was purified through silica gel chromatography (eluent—hexane:ethyl acetate=1:1) to obtain 352 mg (yield 85%) of 5-amino-4-methyl-2-methylthiopyridine as a pale-yellow powdery crystal.

And then the reaction and the treatment were conducted in the same manner as in Example 18 except that 5-amino-4-methyl-2-methylthiopyridine was used instead of 3-amino-2,4-bis(methlthio)-6-methylpyridine to obtain the desired compound as a colorless powdery crystal.

Melting point: 125-127° C.
IR (KBr) cm$^{-1}$: 3433, 3284, 2930, 1654, 1598.
$^1$H-NMR (CDCl$_3$) δ:
1.61 (2H, quint, J=7.4 Hz),
1.83 (2H, quint, J=7.4 Hz),
1.92 (2H, quint, J=7.4 Hz), 2.19 (3H, s),
2.43 (2H, t, J=7.4 Hz), 2.54 (3H, s),
3.33 (2H, t, J=7.4 Hz),
6.92 (1H, br s), 7.03 (1H, s),
7.24 (1H, td, J=7.7, 1.7 Hz),
7.28 (1H, td, J=7.7, 1.7 Hz),
7.43 (1H, dd, J=7.7, 1.7 Hz),
7.57 (1H, dd, J=7.7, 1.7 Hz), 8.57 (1H, s).
EIMS m/z (relative intensity): 401 (M$^+$), 69 (100).

Example 123 Compound No. 1371 in Table

Production of 6-(benzoxasole-2-ylthio)-N-(5-methylthio-2-pyridyl)hexanamide

After conc. sulfuric acid (50 ml) was cooled with ice, 30% aqueous solution of hydrogen peroxide (25 ml) was dropped thereto stirring, and then conc. sulfuric acid (50 ml) solution of 2-amino-5-chloropyridine (5.0 g, 38.9 mmol) was dropped thereto further and stirred for 48 hours at the room temperature. The reaction mixture was added into ice and filtered. The residue was recrystallized with ethanol to obtain 4.38 g (yield 71 %) of 5-chloro-2-nitoropyriine as a colorless powdery crystal.

A methanol (40 mml) solution of 5-chloro-2-nitropyridine (2.0 g. 12.6 mmol) was added dropwise to a methanol (20 ml) solution of sodium thiomethoxide (1.02 g, 13.9 mmol) while being cooled with ice, and after the mixture was stirred for 13 hours while raising its temperature to the room temperature, water added to the reaction mixture and the mixture was extracted with ethyl acetate. The organic layer was washed with water and then with a saturated aqueous solution of sodium chloride, and dried over magnesium sulfate. Thereafter, the solvent was distilled off, and the resulting crude product was recrystalized with ethyl acetate-hexane to obtain 972 mg (yield 45%) of 5-methylthio-2-nitropyridine.

This nitropyridine (300 mg, 1.8 mmol) was dissolved in a mixed solvent of acetic acid (7 ml) and conc. hydrochloric acid (0.5 ml), and zinc (692 g, 10.6 mmol) was added thereto in small portions while being cooled with ice for 5 minutes. After the mixture was stirred for 30 minutes at the room temperature, the reaction mixture was filtered, and the filtrate was neutralized with an aqueous solution of sodium hydrogencarbonate, and extracted with methylene chloride. The organic layer was washed with water and then with a saturated aqueous solution of sodium chloride, and dried over sodium sulfate. Thereafter, the solvent was distilled off, and the resulting crude product was purified through silica gel chromatography (eluent—hexane:ethyl acetate=1:1→chloroform:methanol=20:1) to obtain 158 mg (yield 64%) of 2-amino-5-methylthiopyridine as a pale-yellow powdery crystal.

And then the reaction and the treatment were conducted in the same manner as in Example 18 except that 2-amino-5-methylthiopyridine was used instead of 3-amino-2,4-bis(methlthio)-6-methylpyridine to obtain the desired compound as a colorless powdery crystal.

Melting point: 83-85° C.
IR (KBr) cm$^-$: 3246, 2930, 1684, 1576, 1522.
$^1$H-NMR (CDCl$_3$) δ:
1.59 (2H, quint, J=7.4 Hz),
1.81 (2H, quint, J=7.4 Hz),
1.90 (2H, quint, J=7.4 Hz), 2.42 (2H, t, J 7.4 Hz),
2.48 (3H, s), 3.32 (2H, t, J=7.4 Hz),
7.23 (1H, td, J=7.4, 1.4 Hz),
7.28 (1H, td, J=7.4, 1.4 Hz),
7.43 (1H, dd, J=7.4, 1.4 Hz),
7.59 (1H, dd, J=7.4, 1.4 Hz),
7.64 (1H, dd, J=8.6, 2.5 Hz), 7.82 (1H, br s),
8.15 (1H, d, J=8.6 Hz), 8.18 (1H, d, J=2.5 Hz).
EIMS m/z (relative intensity): 387 (M$^+$, 100).

Example 124 Compound No. 1401 in Table

Production of 6-(benzoxazol-2-ylthio)-N-[2,4,6-tris(methylthio)-5-pyrimidyl]hexanamide The reaction and the treatment were conducted in the same manner as in Example 88 except that 4,6-dihydroxy-2-methylthiopyrimidine was used instead of 4,6-dihydroxy-2-methylpyrimidine to obtain the desired compound as a colorless powdery crystal.

Melting point: 149-153° C.
IR (KBr) cm$^{-1}$: 3448, 3247, 2926, 1667, 1496.
$^1$H-NMR (CDCl$_3$) δ:
1.46-1.62 (2H, m), 1.63-1.76 (2H, m),
1.77-1.91 (2H, m), 2.20-2.36 (2H, m),
2.46 (9H, s), 3.36 (2H, t, J=7.1 Hz),
7.22-7.35 (2H, m), 7.51-7.62 (2H, m),
9.02 (1H, bras).
EIMS m/z (relative intensity): 480 (M$^+$, 100).

Example 125 Compound No. 1427 in Table

Production of 2-(7-methoxycarbonylbenzoxazol-2-ylthio)-N-[2,4-bis(ethylthio)-6-methyl-3-pyridyl]acetamide The reaction and the treatment were conducted in the same manner as in Example 26 except that 2-mercapto-7-methoxycarbonylbenzoxazole was used instead of 2-mercaptobenzoxasole to obtain the desired compound as a colorless needle crystal.

Melting point: 168-169° C.
IR (KBr) cm$^{-1}$: 3433, 3257, 1727, 1677, 1513, 1297, 1120.
$^1$H-NMR (CDCl$_3$) δ:
1.16 (3H, t, J=7.4 Hz), 1.19 (3H, t, J=7.4 Hz),
2.42 (3H, s), 2.80 (2H, q, J=7.4 Hz),
3.03 (2H, q, J=7.4 Hz), 4.00 (3H, s),
4.12 (2H, s), 6.63 (1H, s),
7.38 (1H, dd, J=8.1,7.8 Hz),
7.80 (1H, dd, J=8.1, 1.2 Hz),
7.92 (1H, dd, J=7.8, 1.2 Hz),
8.48 (1H, br s).
EIMS m/z (relative intensity): 477 (Me), 323 (100).

| Elemental analysis: as $C_{21}H_{23}N_3O_4S_3$ | | | | |
|---|---|---|---|---|
| Calculated: | C, 52.81; | H, 4.85; | N, 8.80; | S, 20.14. |
| Found: | C, 52.90; | H, 4.91; | N, 8.73; | S, 20.12. |

Example 126 Compound No. 1428 in Table

Production of 2-(oxazolo[4,5-b]pyridine-2-ylthio)-N-[2,4-bis(ethylthio)-6-methyl-3-pyridyl]acetamide The reaction and the treatment were conducted in the same manner as in Example 49 except that 2-mercaptoxazolo[4,5-b]pyridine was used instead of 2-mercaptobenzoxasole to obtain the desired compound as a colorless crystal.
IR (KBr) cm$^{-1}$: 34,60, 3167, 2972, 1685, 1561.
$^1$H-NMR (CDCl$_3$) δ:
1.14 (3H, t, J=7.4 Hz), 1.21 (3H, t, J=7.4 Hz),
2.42 (3H, s), 2.82 (2H, q, J 7.4 Hz),
3.02 (2H, q, J=7.4 Hz), 4.16 (2H, s), 6.62 (1H, s),
7.25 (1H, dd, J=8.3, 5.1 Hz),
7.78 (1H, dd, J=8.3, 1.2 Hz),
8.40 (1H, br s), 8.49 (1H, dd, J=5.1, 1.2 Hz).
EIMS m/z (relative intensity): 420 (M$^+$, 100).

Example 127 Compound No. 1257 in Table

Production of 2-(5-chloro-7-isopropyl-4-methylbenzoxazol-2-ylthio)-N-[2,4-bis(methylthio)-6-methyl-3-pyridyl]acetamide The reaction and the treatment were conducted in the same manner as in Example 49 except that 5-chloro-7-isopropyl-2-mercapto4-methylbenzoxazole was used instead of 2-mercaptobenzothiazole to obtain the desired compound as a colorless powdery crystal.
EIMS m/z (relative intensity): 481 (M$^+$), 210 (100).

Example 128 Compound No. 1277 in Table

Production of 2-(5-chloro-7-isopropyl-4-methylbenzoxazol-2-ylthio)-N-[2,4-bis(ethylthio)-6-methyl-3-pyridyl]acetamide The reaction and the treatment were conducted in the same manner as in Example 127 except that 3-amino-2,4-bis(isopropylthio)-6-methylpyridine was used instead of 3-amino-2,4-bis(methylthio)-6-methylpyridine to obtain the desired compound as a colorless powdery crystal.
EIMS m/z (relative intensity): 511 (M$^+$;$^{37}$Cl), 509 (M$^+$; $^{35}$Cl), 235 (100).

Example 129 Compound No. 1297 in Table

Production of 2-(5-chloro-7-isopropyl-4-methylbenzoxazol-2-ylthio)-N-[2,4-bis(isopropylthio)-6-methyl-3-pyridyl]acetamide The reaction and the treatment were conducted in the same manner as in Example 127 except that 3-amino-2,4-bis(isopropylthio)-6-methylpyridine was used instead of 3-amino-2,4-bis(methylthio)-6-methylpyridine to obtain the desired compound as a colorless powdery crystal.
EIMS m/z (relative intensity): 539 (M$^+$;$^{37}$Cl), 537 (M$^+$; $^{35}$Cl), 223 (100).

The invention claimed is:

1. A compound represented by the formula (I)

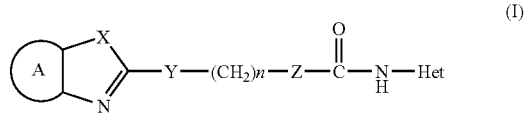

wherein

represents a divalent residue of benzene, cyclohexane or naphthalene, or a group:

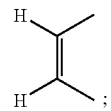

wherein the divalent residue is optionally substituted with an alkyl group having from 1 to 6 carbon atoms, an alkoxy group having 1 to 6 carbon atoms, an alkylthio group having 1 to 6 carbon atoms, an alkylsulfonyl group having 1 to 6 carbon atoms, an alkylcarbonyl group having 1 to 6 carbon atoms, a halogen atom, an amino group, an amino group substituted with an alkyl group having 1 to 6 carbon atoms, an aryl group, an aralkyl group or an alkylenedioxy group, Het represents a 2,4-substituted-pyridin-3-yl group wherein each substituent at the 2 and 4 positions of the pyridine ring is an alkyl group having 1 to 3 carbon atoms, an alkoxy group having 1 to 3 carbon atoms or an alkylthio group having 1 to 3 carbon atoms, and the 2,4-substituted-pyridin-3-yl group is optionally substituted with an alkyl group having 1 to 6 carbon atoms at 6 position of the pyridine ring;

X represents —NH—;

Y represents —NR$_4$—, an oxygen atom, a sulfur atom, a sulfoxide or a sulfone;

Z represents a single bond;

R$_4$ represents a hydrogen atom, a lower alkyl group or an aryl group; and n is an integer of from 2 to 15 or a salt thereof.

2. The compound according to claim 1, which are represented by the formula (IA)

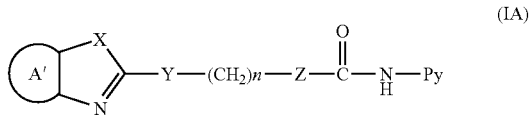

wherein

represents a divalent residue of benzene;
wherein the divalent residue is optionally substituted with an alkyl group having from 1 to 6 carbon atoms, an alkoxy group having 1 to 6 carbon atoms, an alkylthio group having 1 to 6 carbon atoms, an alkylsulfonyl group having 1 to 6 carbon atoms, an alkylcarbonyl group having 1 to 6 carbon atoms, a halogen atom, an amino group, an amino group substituted with an alkyl group having 1 to 6 carbon atoms, an aryl group, an aralkyl group or an alkylenedioxy group, Py represents a 2,4-substituted-pyridin-3-yl group wherein each substituent at the 2 and 4 positions of the pyridine ring is an alkyl group having 1 to 3 carbon atoms, an alkoxy group having 1 to 3 carbon atoms or an alkylthio group having 1 to 3 carbon atoms, and the 2,4-substituted-pyridin-3-yl group is optionally substituted with an alkyl group having 1 to 6 carbon atoms at 6 position of the pyridine ring;

X represents —NH—;

Y represents —NR$_4$,-, an oxygen atom, a sulfur atom, a sulfoxide or a sulfone;

Z represents a single bond;

$_4$, represents a hydrogen atom, a lower alkyl group or an aryl group; and n is an integer of from 2 to 15 or a salt thereof.

3. The compound according to claim 1, which are represented by the formula (III)

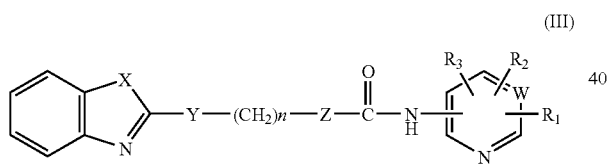

(III)

wherein, W represents =CH—;

X represents —NH—;

Y represents —NR$_4$—, an oxygen atom, a sulfur atom, a sulfoxide or a sulfone;

Z represents a single bond;

$R_1$ and $R_2$, are the same or different, and each represents a lower alkyl group having 1 to 3 carbon atoms, a lower alkoxy group having 1 to 3 carbon atoms, a lower alkylthio group having 1 to 3 carbon atoms at the 2 and 4 positions of the pyridine ring;

$R_3$ represents a hydrogen atom, a lower alkyl group having 1 to 6 carbon atoms at the 6 position of the pyridine ring;

$R_4$, represents a hydrogen atom, a lower alkyl group or an aryl group; and n is an integer of from 2 to 15 or a salt thereof.

4. A pharmaceutical composition comprising a pharmaceutically acceptable carrier and one or more compound(s) selected from the compounds represented by the formula (I)

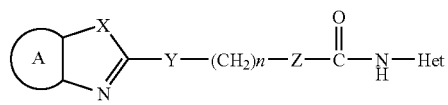

(I)

wherein

represents a divalent residue of benzene, cyclohexane or naphthalene, or a group:

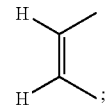

wherein the divalent residue is optionally substituted with an alkyl group having from 1 to 6 carbon atoms, an alkoxy group having 1 to 6 carbon atoms, an alkylthio group having 1 to 6 carbon atoms, an alkylsulfonyl group having 1 to 6 carbon atoms, an alkylcarbonyl group having 1 to 6 carbon atoms, a halogen atom, an amino group, an amino group substituted with an alkyl group having 1 to 6 carbon atoms, an aryl group, an aralkyl group or an alkylenedioxy group, Het represents a 2,4-substituted-pyridin-3-yl group wherein each substituent at the 2 and 4 positions of the pyridine ring is an alkyl group having 1 to 3 carbon atoms, an alkoxy group having 1 to 3 carbon atoms or an alkylthio group having 1 to 3 carbon atoms, and the 2,4-substituted-pyridin-3-yl group is optionally substituted with an alkyl group having 1 to 6 carbon atoms at 6 position of the pyridine ring;

X represents —NH—;

Y represents —NR$_4$—, an oxygen atom, a sulfur atom, a sulfoxide or a sulfone;

Z represents a single bond;

R$_4$, represents a hydrogen atom, a lower alkyl group or an aryl group; and n is an integer of from 2 to 15, or a salt thereof.

5. A pharmaceutical composition comprising a pharmaceutically acceptable carrier and one or more compound(s) according to claim 3.

6. A pharmaceutical composition comprising a pharmaceutically acceptable carrier and one or more compound(s) according to claim 2.

* * * * *